United States Patent
Burgdorf et al.

(10) Patent No.: US 12,371,430 B2
(45) Date of Patent: Jul. 29, 2025

(54) 5-MORPHOLIN-4-YL-PYRAZOLO[4,3-B] PYRIDINE DERIVATIVES

(71) Applicant: Merck Patent GmbH, Darmstadt (DE)

(72) Inventors: Lars Burgdorf, Frankfurt am Main (DE); Christos Tsaklakidis, Heidelberg (DE)

(73) Assignee: Merck Patent GmbH, Darmstadt (DE)

( * ) Notice: Subject to any disclaimer, the term of this patent is extended or adjusted under 35 U.S.C. 154(b) by 772 days.

(21) Appl. No.: 17/274,043

(22) PCT Filed: Sep. 4, 2019

(86) PCT No.: PCT/EP2019/073520
§ 371 (c)(1),
(2) Date: Mar. 5, 2021

(87) PCT Pub. No.: WO2020/049017
PCT Pub. Date: Mar. 12, 2020

(65) Prior Publication Data
US 2021/0355123 A1 Nov. 18, 2021

(30) Foreign Application Priority Data
Sep. 7, 2018 (EP) ..................... 18193083

(51) Int. Cl.
*C07D 471/04* (2006.01)
*C07D 519/00* (2006.01)

(52) U.S. Cl.
CPC ......... *C07D 471/04* (2013.01); *C07D 519/00* (2013.01)

(58) Field of Classification Search
CPC ..... C07D 471/04; C07D 519/00; A61P 29/00; A61P 31/04; A61P 35/00
See application file for complete search history.

(56) References Cited

U.S. PATENT DOCUMENTS

| 8,536,375 B2 | 9/2013 | Engell |
| 10,729,680 B2 | 8/2020 | Ulrich |
| 2011/0053923 A1 | 3/2011 | Foote et al. |

FOREIGN PATENT DOCUMENTS

| JP | 2010111624 A | * | 5/2010 | |
| WO | 10073034 A1 | | 7/2010 | |
| WO | WO-2017109476 A1 | * | 6/2017 | ............. A61P 35/00 |
| WO | 2017121684 A1 | | 7/2017 | |
| WO | 18121684 A1 | | 7/2018 | |

OTHER PUBLICATIONS

Kusakabe K. JP-2010111624-A. English Translation. 2010 (Year: 2010).*
Lin, Guo-Qiang, Qi-Dong You, and Jie-Fei Cheng. "Chiral drugs." Chemistry and Biological Action. Wiley, ed 1 (2011). (Year: 2011).*
Healy, A. M., et al. Advanced Drug Delivery Reviews 117 (2017) 25-46 (Year: 2017).*
Biswas, H., et al. Int. J. Mol. Sci. 2023, 24, 11684. 2023 (Year: 2023).*
International Search Report PCT/EP2019/073520 dated Oct. 22, 2019 (pp. 1-3).

* cited by examiner

Primary Examiner — Eric Olson
Assistant Examiner — Samuel L Galster
(74) Attorney, Agent, or Firm — Csaba Henter; MILLEN, WHITE, ZELANO & BRANIGAN

(57) ABSTRACT

Compounds of the formula Ia and Ib

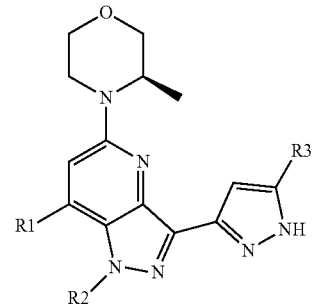

Ia

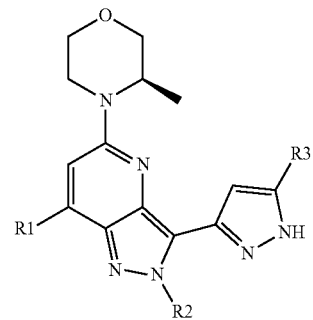

Ib in which $R^1$, $R^2$ and $R^3$ have the meanings indicated in claim 1, are inhibitors of ATR, and can be employed for the treatment of diseases such as cancer.

20 Claims, No Drawings

5-MORPHOLIN-4-YL-PYRAZOLO[4,3-B] PYRIDINE DERIVATIVES

BACKGROUND OF THE INVENTION

The invention had the object of finding novel compounds having valuable properties, in particular those which can be used for the preparation of medicaments.

The present invention relates to 5-Morpholin-4-yl-pyrazolo[4,3-b]pyridine derivatives which inhibit ATR (Ataxia telangiectasia mutated and Rad3-related kinase). The compounds of this invention are therefore useful in treating diseases such as cancer.

The present invention also provides methods for preparing these compounds, pharmaceutical compositions comprising these compounds, and methods of treating diseases utilizing pharmaceutical compositions comprising these compounds.

The chemical entities of the present invention are inhibitors of ATR and have a number of therapeutic applications, particularly in the treatment of cancer.

Cancers are the consequence of uncontrolled cell growth of a wide variety of different tissues. In many cases the new cells penetrate into existing tissue, or they metastasize into remote organs. Cancers occur in a wide variety of organs and often progress in a manner specific to the tissue. The term "cancer" as a generic term therefore describes a large group of defined diseases of different organs, tissue and cell types.

In 2008, over 12 million people worldwide were diagnosed with cancer. In the same year, approx. 7.5 million deaths were assumed to be a consequence of these diseases (Globocan 2008 Report). In the USA alone, in 2012, more than 1.6 million new cases and more than 500 000 deaths were predicted from cancers. The majority of these new cases relate to cancers of the colon (~100 000), lung (~230 000), breast (~230 000) and prostate (~240 000) (American Cancer Society, Cancer Facts and Figures 2012).

Many current cancer treatments, including chemotherapeutic agents and ionizing radiation, induce DNA damage and replication fork stalling, thereby activating cell cycle checkpoint pathways and leading to cell cycle arrest. A variety of studies have shown that this response is an important mechanism that helps cancer cells survive the treatments. These findings have prompted the development of agents targeting DNA damage response signalling pathways.

ATR is a member of phosphatidylinositol kinase-related kinase (PIKK) protein family, and is activated by a wide variety of DNA damage events. In particular, ATR is essential to coordinate the response to replicative stress (RS), which stands for the pathological accumulation of single stranded DNA (ssDNA). The recombinogenic nature of ssDNA leads to chromosomal rearrangements that are a hallmark of cancer. In response to RS, ATR triggers arrest of the cell cycle in the S and G2/M stages by phosphorylation of CHK1.

ATR can prevent cancer development, as the ATR checkpoint response might limit the expansion of precancerous cells undergoing RS as a result of oncogene activation. Moreover, because the ATR-CHK1 checkpoint pathway serves to ensure cell survival after RS, a normal and robust ATR-CHK1 checkpoint may be a mechanism of resistance to chemotherapy and may allow cancer cells to survive with high endogenous levels of RS.

Inhibition of ATR-CHK1 pathway components could potentially enhance the effectiveness of replication inhibitors. In addition, ATR inhibition may be particularly toxic for cells with high levels of RS, such as those expressing oncogenes or lacking tumour suppressors. In these cells, strong limitation of ATR activity (for example, by use of an ATR inhibitor) would generate lethal amounts of RS leading to cell death.

A potential advantage of sensitizing cells in this way would be the capacity to lower the doses of the replication inhibitors. This would result in reduced toxicity to haematological and gastrointestinal organ systems among others, if the normal cells are not sensitized to the same extent. Specificity of the replication inhibitor for causing cancer cell death may be assisted by the fact that untransformed cells have more robust S and G2 checkpoints than tumour cells. For example, many cancers have mutations in p53 or other components of the p53 pathway, leading to reliance on the S and G2 checkpoints to arrest the cell cycle and provide for repair and survival. Inhibition of the S and G2 checkpoints may then preferentially kill these p53 deficient tumour cells.

The listing or discussion of an apparently prior-published document in this specification should not necessarily be taken as an acknowledgement that the document is part of the state of the art or is common general knowledge.

There is a lack of potent inhibitors of ATR. Therefore, a need exists for chemical entities that selectively inhibit ATR for clinical use or for further study of the ATR response.

It has been found that the compounds according to the invention and salts thereof have very valuable pharmacological properties while being well tolerated.

The host or patient can belong to any mammalian species, for example a primate species, particularly humans; rodents, including mice, rats and hamsters; rabbits; horses, cows, dogs, cats, etc. Animal models are of interest for experimental investigations, providing a model for treatment of human disease.

The susceptibility of a particular cell to treatment with the compounds according to the invention can be determined by in vitro tests. Typically, a culture of the cell is combined with a compound according to the invention at various concentrations for a period of time which is sufficient to allow active agents such as anti IgM to induce a cellular response such as expression of a surface marker, usually between about one hour and one week. In vitro testing can be carried out using cultivated cells from blood or from a biopsy sample. The amount of surface marker expressed is assessed by flow cytometry using specific antibodies recognising the marker.

The dose varies depending on the specific compound used, the specific disease, the patient status, etc. A therapeutic dose is typically sufficient considerably to reduce the undesired cell population in the target tissue while the viability of the patient is maintained. The treatment is generally continued until a considerable reduction has occurred, for example an at least about 50% reduction in the cell burden, and may be continued until essentially no more undesired cells are detected in the body.

PRIOR ART

Other bicyclic heterocyclic compounds for the treatment of cancer have been described in WO 2013/130660 A1 and in WO 2017/121684 A1.

SUMMARY OF THE INVENTION

The invention relates to compounds of the formula Ib and Ib

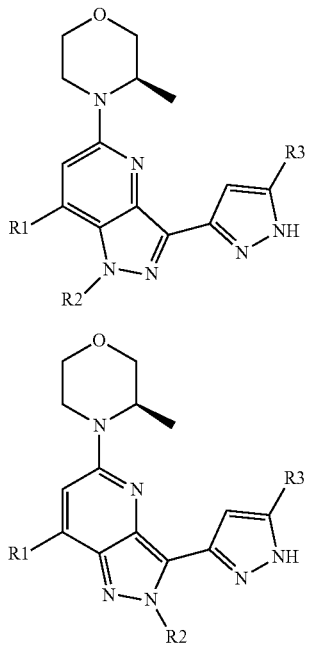

Ia

Ib in which

R¹ denotes H, Het, Ar, $(CH_2)_nOH$, 1-methylsulfonyl-cycloprop-1-yl, $CONH_2$, CONHA, $CONA_2$, Cyc, OA or $CH(A)SO_2A$, R² denotes H, A, $(CH_2)_nAr$, $(CH_2)_nCyc$ or $(CH_2)_nHet$, R³ denotes H or A, Het denotes a mono- or bicyclic aromatic, unsaturated or saturated heterocycle having 1 to 4 N, O and/or S atoms, which may be unsubstituted or mono-, di- or trisubstituted by $NH_2$, NHA, $NA_2$, COOH, COOA, $CONH_2$, CONHA, $CONA_2$, $CONHA_2$, CN, OH, $(CH_2)_n Ar^1$, $O(CH_2)_n Ar^1$, A, SOA, $SO_2A$, Hal, =NH and/or =O, Ar denotes phenyl, napthyl or biphenyl, each of which is unsubstituted or mono-, di- or trisubstituted by $NH_2$, NHA, $NA_2$, COOH, COOA, $CONH_2$, CONHA, $CONA_2$, NHCOA, CHO, COA, $SO_3H$, $SO_2NH_2$, $O(CH_2)_pNH_2$, $(CH_2)_nHet^1$, $O(CH_2)_nHet^1$, $(CH_2)_nAr^1$, $O(CH_2)_nAr^1$, $O(CH_2)_pCONH_2$, $O(CH_2)_pNHCOA$, Hal, SOA, S(=O, =NH)A, $SO_2A$, A, CN and/or $(CH_2)_n$OH, Ar¹ denotes phenyl which is unsubstituted or mono-, di- or trisubstituted by Hal, A, OH and/or OA, Het¹ denotes a mono- or bicyclic aromatic, unsaturated or saturated heterocycle having 1 to 4 N, O and/or S atoms, which may be unsubstituted or mono-, di- or trisubstituted by Hal, A, COOA, $NH_2$, NHA and/or $NA_2$, A denotes unbranched or branched alkyl having 1-6 C-atoms, in which 1-7H atoms may be replaced by OH, F, Cl and/or Br and/or in which one or two non-adjacent $CH_2$ groups may be replaced by O and/or NH groups, Cyc denotes cyclic alkyl with 3, 4, 5, 6 or 7 C-atoms, Hal denotes F, Cl, Br or I, n denotes 0, 1, 2, 3 or 4, p denotes 1, 2, 3 or 4, and pharmaceutically acceptable salts, tautomers and stereoisomers thereof, including mixtures thereof in all ratios.

The invention also relates to the optically active forms (stereoisomers), the enantiomers, the racemates, the diastereomers and the hydrates and solvates of these compounds.

By reciting compounds of formula Ia or Ib showing stereochemistry information and also reciting stereoisomers thereof or racemates, etc., the formula Ia* or Ib* are meant that are as follow:

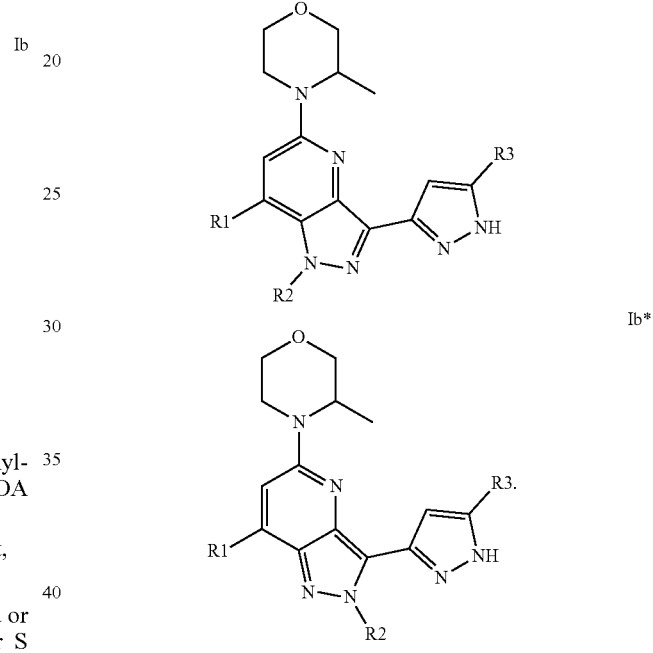

Ia*

Ib*

Moreover, the invention relates to pharmaceutically acceptable derivatives of compounds of formula Ib and Ib.

The term solvates of the compounds is taken to mean adductions of inert solvent molecules onto the compounds which form owing to their mutual attractive force. Solvates are, for example, mono- or dihydrates or alkoxides.

It is understood, that the invention also relates to the solvates of the salts.

The term pharmaceutically acceptable derivatives is taken to mean, for example, the salts of the compounds according to the invention and also so-called prodrug compounds.

As used herein and unless otherwise indicated, the term "prodrug" means a derivative of a compound of formula I that can hydrolyze, oxidize, or otherwise react under biological conditions (in vitro or in vivo) to provide an active compound, particularly a compound of formula I. Examples of prodrugs include, but are not limited to, derivatives and metabolites of a compound of formula I that include biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. In certain embodiments, prodrugs of compounds with carboxyl functional groups are the lower alkyl esters of the carboxylic acid. The carboxylate esters are conveniently formed by esterifying any of the carboxylic acid moieties present on the molecule. Prodrugs can typically be prepared using well-known methods, such as those described by Burger's Medicinal Chemistry and Drug Discovery 6th ed. (Donald J. Abraham ed., 2001, Wiley) and Design and Application of Prodrugs (H. Bundgaard ed., 1985, Harwood Academic Publishers Gmfh).

The expression "effective amount" denotes the amount of a medicament or of a pharmaceutical active ingredient which causes in a tissue, system, animal or human a biological or medical response which is sought or desired, for example, by a researcher or physician.

In addition, the expression "therapeutically effective amount" denotes an amount which, compared with a corresponding subject who has not received this amount, has the following consequence:

improved treatment, healing, prevention or elimination of a disease, syndrome, condition, complaint, disorder or side-effects or also the reduction in the advance of a disease, complaint or disorder.

The expression "therapeutically effective amount" also encompasses the amounts which are effective for increasing normal physiological function.

The invention also relates to the use of mixtures of the compounds of the formula Ib and Ib, for example mixtures of two diastereomers, for example in the ratio 1:1, 1:2, 1:3, 1:4, 1:5, 1:10, 1:100 or 1:1000.

These are particularly preferably mixtures of stereoisomeric compounds.

"Tautomers" refers to isomeric forms of a compound that are in equilibrium with each other. The concentrations of the isomeric forms will depend on the environment the compound is found in and may be different depending upon, for example, whether the compound is a solid or is in an organic or aqueous solution.

Above and below, the radicals $R^1$, $R^2$ and $R^3$ have the meanings indicated for the formula I, unless explicitly stated otherwise.

A denotes alkyl, this is unbranched (linear) or branched, and has 1, 2, 3, 4, 5, 6, 7 or 8 C atoms. A preferably denotes methyl, ethyl, propyl, isopropyl, butyl, isobutyl, sec-butyl or tert-butyl, furthermore also pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl, 1,1,2- or 1,2,2-trimethylpropyl, furthermore preferably, for example, trifluoromethyl.

A very particularly preferably denotes alkyl having 1, 2, 3, 4, 5 or 6 C atoms, preferably methyl, ethyl, propyl, isopropyl, butyl, isobutyl, sec-butyl, tert-butyl, pentyl, hexyl, trifluoromethyl, pentafluoroethyl or 1,1,1-trifluoroethyl.

Moreover, A denotes preferably $CH_2OCH_3$, $CH_2CH_2OH$ or $CH_2CH_2OCH_3$.

$R^3$ preferably denotes H or $CH_3$, most preferably H.

Cyc denotes cycloprolyl, cyclobutyl, cyclopentyl, cyclohexyl or cycloheptyl.

The heterocyclic substituent pyridyl=pyridinyl.

Irrespective of further substitutions, Het denotes, for example, 2- or 3-furyl, 2- or 3-thienyl, 1-, 2- or 3-pyrrolyl, 1-, 2, 4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, furthermore preferably 1,2,3-triazol-1-, -4- or -5-yl, 1,2,4-triazol-1-, -3- or 5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 3- or 4-pyridazinyl, pyrazinyl, 1-, 2-, 3-, 4-, 5-, 6- or 7-indolyl, 4- or 5-isoindolyl, indazolyl, 1-, 2-, 4- or 5-benzimidazolyl, 1-, 3-, 4-, 5-, 6- or 7-benzopyrazolyl, 2-, 4-, 5-, 6- or 7-benzoxazolyl, 3-, 4-, 5-, 6- or 7-benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 2-, 3-, 4-, 5-, 6-, 7- or 8-quinolyl, 1-, 3-, 4-, 5-, 6-, 7- or 8-isoquinolyl, 3-, 4-, 5-, 6-, 7- or 8-cinnolinyl, 2-, 4-, 5-, 6-, 7- or 8-quinazolinyl, 5- or 6-quinoxalinyl, 2-, 3-, 5-, 6-, 7- or 8-2H-benzo-1,4-oxazinyl, pyrrolopyridinyl, purinyl, further preferably 1,3-benzodioxol-5-yl, 1,4-benzodioxan-6-yl, 2,1,3-benzothiadiazol-4- or -5-yl, 2,1,3-benzoxadiazol-5-yl, azabicyclo[3.2.1]-octyl or dibenzofuranyl.

The heterocyclic radicals may also be partially or fully hydrogenated.

Irrespective of further substitutions, Het can thus also denote, for example, 2,3-dihydro-2-, -3-, -4- or -5-furyl, 2,5-dihydro-2-, -3-, -4- or 5-furyl, tetrahydro-2- or -3-furyl, 1,3-dioxolan-4-yl, tetrahydro-2- or -3-thienyl, 2,3-dihydro-1-, -2-, -3-, -4- or -5-pyrrolyl, 2,5-dihydro-1-, -2-, -3-, -4- or -5-pyrrolyl, 1-, 2- or 3-pyrrolidinyl, tetrahydro-1-, -2- or -4-imidazolyl, 2,3-dihydro-1-, -2-, -3-, -4- or -5-pyrazolyl, tetrahydro-1-, -3- or -4-pyrazolyl, 1,4-dihydro-1-, -2-, -3- or -4-pyridyl, 1,2,3,4-tetrahydro-1-, -2-, -3-, -4-, -5- or -6-pyridyl, 1-, 2-, 3- or 4-piperidinyl, 2-, 3- or 4-morpholinyl, tetrahydro-2-, -3- or -4-pyranyl, 1,4-dioxanyl, 1,3-dioxan-2-, -4- or -5-yl, hexahydro-1-, -3- or -4-pyridazinyl, hexahydro-1-, -2-, -4- or -5-pyrimidinyl, 1-, 2- or 3-piperazinyl, 1,2,3,4-tetrahydro-1-, -2-, -3-, -4-, -5-, -6-, -7- or -8-quinolyl, 1,2,3,4-tetra-hydro-1-, -2-, -3-, -4-, -5-, -6-, -7- or -8-isoquinolyl, 2-, 3-, 5-, 6-, 7- or 8-3,4-dihydro-2H-benzo-1,4-oxazinyl, furthermore preferably 2,3-methylenedioxyphenyl, 3,4-methylenedioxyphenyl, 2,3-ethylenedioxyphenyl, 3,4-ethylenedioxyphenyl, 3,4-(difluoromethylenedioxy)phenyl, 2,3-dihydro-benzofuran-5- or 6-yl, 2,3-(2-oxomethylenedioxy)phenyl or also 3,4-dihydro-2H-1,5-benzodioxepin-6- or -7-yl, furthermore preferably 2,3-dihydrobenzofuranyl, 2,3-dihydro-2-oxo-furanyl, 3,4-dihydro-2-oxo-1H-quinazolinyl, 2,3-dihydrobenzoxazolyl, 2-oxo-2,3-dihydrobenzoxazolyl, 2,3-dihydrobenzimidazolyl, 1,3-dihydroindole, 2-oxo-1,3-dihydroindole or 2-oxo-2,3-dihydrobenzimidazolyl.

Irrespective of further substitutions, $Het^1$ denotes, for example, 2- or 3-furyl, 2- or 3-thienyl, 1-, 2- or 3-pyrrolyl, 1-, 2, 4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, furthermore preferably 1,2,3-triazol-1-, -4- or -5-yl, 1,2,4-triazol-1-, -3- or 5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 3- or 4-pyridazinyl, pyrazinyl, 1-, 2-, 3-, 4-, 5-, 6- or 7-indolyl, 4- or 5-isoindolyl, indazolyl, 1-, 2-, 4- or 5-benzimidazolyl, 1-, 3-, 4-, 5-, 6- or 7-benzopyrazolyl, 2-, 4-, 5-, 6- or 7-benzoxazolyl, 3-, 4-, 5-, 6- or 7-benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 2-, 3-, 4-, 5-, 6-, 7- or 8-quinolyl, 1-, 3-, 4-, 5-, 6-, 7- or 8-isoquinolyl, 3-, 4-, 5-, 6-, 7- or 8-cinnolinyl, 2-, 4-, 5-, 6-, 7- or 8-quinazolinyl, 5- or 6-quinoxalinyl, 2-, 3-, 5-, 6-, 7- or 8-2H-benzo-1,4-oxazinyl, pyrrolopyridinyl, purinyl, further preferably 1,3-benzodioxol-5-yl, 1,4-benzodioxan-6-yl, 2,1,3-benzothiadiazol-4- or -5-yl, 2,1,3-benzoxadiazol-5-yl, azabicyclo[3.2.1]-octyl or dibenzofuranyl.

The heterocyclic radicals may also be partially or fully hydrogenated.

Irrespective of further substitutions, Het$^1$ can thus also denote, for example, 2,3-dihydro-2-, -3-, -4- or -5-furyl, 2,5-dihydro-2-, -3-, -4- or 5-furyl, tetrahydro-2- or -3-furyl, 1,3-dioxolan-4-yl, tetrahydro-2- or -3-thienyl, 2,3-dihydro-1-, -2-, -3-, -4- or -5-pyrrolyl, 2,5-dihydro-1-, -2-, -3-, -4- or -5-pyrrolyl, 1-, 2- or 3-pyrrolidinyl, tetrahydro-1-, -2- or -4-imidazolyl, 2,3-dihydro-1-, -2-, -3-, -4- or -5-pyrazolyl, tetrahydro-1-, -3- or -4-pyrazolyl, 1,4-dihydro-1-, -2-, -3- or -4-pyridyl, 1,2,3,4-tetrahydro-1-, -2-, -3-, -4-, -5- or -6-pyridyl, 1-, 2-, 3- or 4-piperidinyl, 2-, 3- or 4-morpholinyl, tetrahydro-2-, -3- or -4-pyranyl, 1,4-dioxanyl, 1,3-dioxan-2-, -4- or -5-yl, hexahydro-1-, -3- or -4-pyridazinyl, hexahydro-1-, -2-, -4- or -5-pyrimidinyl, 1-, 2- or 3-piperazinyl, 1,2,3,4-tetrahydro-1-, -2-, -3-, -4-, -5-, -6-, -7- or -8-quinolyl, 1,2,3,4-tetrahydro-1-, -2-, -3-, -4-, -5-, -6-, -7- or -8-isoquinolyl, 2-, 3-, 5-, 6-, 7- or 8-3,4-dihydro-2H-benzo-1,4-oxazinyl, furthermore preferably 2,3-methylenedioxyphenyl, 3,4-methylenedioxyphenyl, 2,3-ethylenedioxyphenyl, 3,4-ethylenedioxyphenyl, 3,4-(difluoromethylenedioxy)phenyl, 2,3-dihydrobenzofuran-5- or 6-yl, 2,3-(2-oxomethylenedioxy)phenyl or also 3,4-dihydro-2H-1,5-benzodioxepin-6- or -7-yl, furthermore preferably 2,3-dihydrobenzofuranyl, 2,3-dihydro-2-oxofuranyl, 3,4-dihydro-2-oxo-1H-quinazolinyl, 2,3-dihydrobenzoxazolyl, 2-oxo-2,3-dihydrobenzoxazolyl, 2,3-dihydrobenzimidazolyl, 1,3-dihydroindole, 2-oxo-1,3-dihydroindole or 2-oxo-2,3-dihydrobenzimidazolyl.

Ar denotes, for example, phenyl, o-, m- or p-tolyl, o-, m- or p-ethylphenyl, o-, m- or p-propylphenyl, o-, m- or p-isopropylphenyl, o-, m- or p-tert-butylphenyl, o-, m- or p-hydroxyphenyl, o-, m- or p-nitrophenyl, o-, m- or p-aminophenyl, o-, m- or p-(N-methylamino)phenyl, o-, m- or p-(N-methylaminocarbonyl)phenyl, o-, m- or p-acetamidophenyl, o-, m- or p-methoxyphenyl, o-, m- or p-ethoxyphenyl, o-, m- or p-ethoxycarbonylphenyl, o-, m- or p-(N,N-dimethylamino)-phenyl, o-, m- or p-(N,N-dimethylaminocarbonyl)phenyl, o-, m- or p-(N-ethylamino)phenyl, o-, m- or p-(N,N-diethylamino)phenyl, o-, m- or p-fluorophenyl, o-, m- or p-bromophenyl, o-, m- or p-chlorophenyl, o-, m- or p-(methylsulfonamido)phenyl, o-, m- or p-(methylsulfonyl)phenyl, o-, m- or p-cyanophenyl, o-, m- or p-carboxyphenyl, o-, m- or p-methoxycarbonylphenyl, o-, m- or p-aminosulfonylphenyl, o-, m- or p-(benzylamino)phenyl furthermore preferably 2,3-, 2,4-, 2,5-, 2,6-, 3,4- or 3,5-difluorophenyl, 2,3-, 2,4-, 2,5-, 2,6-, 3,4- or 3,5-dichlorophenyl, 2,3-, 2,4-, 2,5-, 2,6-, 3,4- or 3,5-dibromophenyl, 2,4- or 2,5-dinitrophenyl, 2,5- or 3,4-dimethoxyphenyl, 3-nitro-4-chlorophenyl, 3-amino-4-chloro-, 2-amino-3-chloro-, 2-amino-4-chloro-, 2-amino-5-chloro- or 2-amino-6-chlorophenyl, 2-nitro-4-N,N-dimethylamino- or 3-nitro-4-N,N-dimethylaminophenyl, 2,3-diaminophenyl, 2,3,4-, 2,3,5-, 2,3,6-, 2,4,6- or 3,4,5-trichlorophenyl, 2,4,6-trimethoxyphenyl, 2-hydroxy-3,5-dichlorophenyl, p-iodophenyl, 3,6-dichloro-4-aminophenyl, 4-fluoro-3-chlorophenyl, 2-fluoro-4-bromophenyl, 2,5-difluoro-4-bromophenyl, 3-bromo-6-methoxyphenyl, 3-chloro-6-methoxyphenyl, 3-chloro-4-acetamidophenyl, 3-fluoro-4-methoxyphenyl, 3-amino-6-methylphenyl, 3-chloro-4-acetamidophenyl or 2,5-dimethyl-4-chlorophenyl.

Het preferably denotes 1H-pyrrolo[2,3-b]pyridinyl, 1H-pyrrolo[2,3-c]pyridinyl, indolyl, benzimidazolyl, imidazolyl, 1,2,3,4-tetrahydroisoquinolyl, pyridyl, pyrimidinyl, triazolyl, pyrazolyl, quinolyl, isoquinolyl, quinazolinyl, furanyl, tetrahydrofuranyl, pyranyl, 3,6-dihydro-2H-pyranyl, tetrahydropyranyl, 3,6-dihydro-2H-thiopyranyl or hexahydro-thiopyranyl, each of which is unsubstituted or mono-, di- or trisubstituted by A, SOA, SO$_2$A, Hal and/or =O.

Ar preferably denotes phenyl, which is unsubstituted or mono-, di- or trisubstituted by SOA, S(=O, =NH)A, SO$_2$A, A, CN and/or (CH$_2$)$_n$OH.

Throughout the invention, all radicals which occur more than once may be identical or different, i.e. are independent of one another.

The compounds of the formula Ib and Ib may have one or more chiral centres and can therefore occur in various stereoisomeric forms. The formula Ib and Ib encompasses all these forms.

Accordingly, the invention relates, in particular, to the compounds of the formula Ib and Ib in which at least one of the said radicals has one of the preferred meanings indicated above. Some preferred groups of compounds may be expressed by the following sub-formulae Iaa and Iba to Iad and Ibd, which conform to the formula Ia and Ib and in which the radicals not designated in greater detail have the meaning indicated for the formula Ia and Ib, but in which in Iaa and Iba Het denotes 1H-pyrrolo[2,3-b]pyridinyl, 1H-pyrrolo[2,3-c]pyridinyl, indolyl, benzimidazolyl, imidazolyl, 1,2,3,4-tetrahydroisoquinolyl, pyridyl, pyrimidinyl, triazolyl, pyrazolyl, quinolyl, isoquinolyl, quinazolinyl, furanyl, tetrahydrofuranyl, pyranyl, 3,6-dihydro-2H-pyranyl, tetrahydropyranyl, 3,6-dihydro-2H-thiopyranyl or hexahydro-thiopyranyl, each of which is unsubstituted or mono-, di- or trisubstituted by A, SOA, SO$_2$A, Hal and/or =O;

in Iab and Ibb Ar denotes phenyl, which is unsubstituted or mono-, di- or trisubstituted by SOA, S(=O, =NH)A, SO$_2$A, A, CN and/or (CH$_2$)$_n$OH;

in Iac and Ibc R$^3$ denotes H or methyl;

in Iad and Ibd R$^1$ denotes H, Het, Ar, (CH$_2$)$_n$OH, 1-methylsulfonyl-cycloprop-1-yl, CONH$_2$, CONHA, CONA$_2$, Cyc, OA or CH(A)SO$_2$A;

R$^2$ denotes H, A, (CH$_2$)$_n$Ar, (CH$_2$)$_n$Cyc or (CH$_2$)$_n$Het, R$^3$ denotes H or A, Het denotes 1H-pyrrolo[2,3-b]pyridinyl, 1H-pyrrolo[2,3-c]pyridinyl, indolyl, benzimidazolyl, imidazolyl, 1,2,3,4-tetrahydroisoquinolyl, pyridyl, pyrimidinyl, triazolyl, pyrazolyl, quinolyl, isoquinolyl, quinazolinyl, furanyl, tetrahydrofuranyl, pyranyl, 3,6-dihydro-2H-pyranyl, tetrahydropyranyl, 3,6-dihydro-2H-thiopyranyl or hexahydro-thiopyranyl, each of which is unsubstituted or mono-, di- or trisubstituted by A, SOA, SO$_2$A, Hal and/or =O, Ar denotes phenyl, which is unsubstituted or mono-, di- or trisubstituted by SOA, S(=O, =NH)A, SO$_2$A, A, CN and/or (CH$_2$)$_n$OH, A denotes unbranched or branched alkyl having 1-6 C-atoms, in which 1-7H atoms may be replaced by OH, F, Cl and/or Br and/or in which one or two non-adjacent CH$_2$ groups may be replaced by O and/or NH groups, Cyc denotes cyclic alkyl with 3, 4, 5, 6 or 7 C-atoms, Hal denotes F, Cl, Br or I, n denotes 0, 1, 2, 3 or 4, and pharmaceutically acceptable salts, tautomers and stereoisomers thereof, including mixtures thereof in all ratios.

Most preferred compounds according to the invention are examples 1, 26, 42 and 61.

The compounds of the formula Ib and Ib and also the starting materials for their preparation are, in addition, prepared by methods known per se, as described in the literature (for example in the standard works, such as Houben-Weyl, Methoden der organischen Chemie [Methods of Organic Chemistry], Georg-Thieme-Verlag, Stuttgart), to be precise under reaction conditions which are known and suitable for the said reactions. Use can also be made here of variants known per se which are not mentioned here in greater detail.

Pharmaceutical Salts and Other Forms

The said compounds according to the invention can be used in their final non-salt form. On the other hand, the present invention also encompasses the use of these compounds in the form of their pharmaceutically acceptable salts, which can be derived from various organic and inorganic acids and bases by procedures known in the art. Pharmaceutically acceptable salt forms of the compounds of the formula Ib and Ib are for the most part prepared by conventional methods. If the compound of the formula Ib and Ib contains a carboxyl group, one of its suitable salts can be formed by reacting the compound with a suitable base to give the corresponding base-addition salt. Such bases are, for example, alkali metal hydroxides, including potassium hydroxide, sodium hydroxide and lithium hydroxide; alkaline earth metal hydroxides, such as barium hydroxide and calcium hydroxide; alkali metal alkoxides, for example potassium ethoxide and sodium propoxide; and various organic bases, such as piperidine, diethanolamine and N-methylglutamine. The aluminium salts of the compounds of the formula Ib and Ib are likewise included. In the case of certain compounds of the formula Ib and Ib, acid-addition salts can be formed by treating these compounds with pharmaceutically acceptable organic and inorganic acids, for example hydrogen halides, such as hydrogen chloride, hydrogen bromide or hydrogen iodide, other mineral acids and corresponding salts thereof, such as sulfate, nitrate or phosphate and the like, and alkyl- and monoarylsulfonates, such as ethanesulfonate, toluenesulfonate and benzenesulfonate, and other organic acids and corresponding salts thereof, such as acetate, trifluoroacetate, tartrate, maleate, succinate, citrate, benzoate, salicylate, ascorbate and the like. Accordingly, pharmaceutically acceptable acid-addition salts of the compounds of the formula Ib and Ib include the following: acetate, adipate, alginate, arginate, aspartate, benzoate, benzenesulfonate (besylate), bisulfate, bisulfite, bromide, butyrate, camphorate, camphorsulfonate, caprylate, chloride, chlorobenzoate, citrate, cyclopentanepropionate, digluconate, dihydrogenphosphate, dinitrobenzoate, dodecylsulfate, ethanesulfonate, fumarate, formate, galacterate (from mucic acid), galacturonate, glucoheptanoate, gluconate, glutamate, glycerophosphate, hemisuccinate, hemisulfate, heptanoate, hexanoate, hippurate, hydrochloride, hydrobromide, hydroiodide, 2-hydroxyethanesulfonate, iodide, isethionate, isobutyrate, lactate, lactobionate, malate, maleate, malonate, mandelate, metaphosphate, methanesulfonate, methylbenzoate, monohydrogenphosphate, 2-naphthalenesulfonate, nicotinate, nitrate, oxalate, oleate, palmoate, pectinate, persulfate, phenylacetate, 3-phenylpropionate, phosphate, phosphonate, phthalate, but this does not represent a restriction.

Furthermore, the base salts of the compounds according to the invention include aluminium, ammonium, calcium, copper, iron(III), iron(II), lithium, magnesium, manganese (III), manganese(II), potassium, sodium and zinc salts, but this is not intended to represent a restriction. Of the above-mentioned salts, preference is given to ammonium; the alkali metal salts sodium and potassium, and the alkaline earth metal salts calcium and magnesium. Salts of the compounds of the formula Ib and Ib which are derived from pharmaceutically acceptable organic non-toxic bases include salts of primary, secondary and tertiary amines, substituted amines, also including naturally occurring substituted amines, cyclic amines, and basic ion exchanger resins, for example arginine, betaine, caffeine, chloroprocaine, choline, N,N'-dibenzylethylenediamine (benzathine), dicyclohexylamine, diethanolamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lidocaine, lysine, meglumine, N-methyl-D-glucamine, morpholine, piperazine, piperidine, polyamine resins, procaine, purines, theobromine, triethanolamine, triethylamine, trimethylamine, tripropylamine and tris(hydroxymethyl)methylamine (tromethamine), but this is not intended to represent a restriction.

Compounds of the present invention which contain basic nitrogen-containing groups can be quaternised using agents such as ($C_1$-$C_4$)alkyl halides, for example methyl, ethyl, isopropyl and tert-butyl chloride, bromide and iodide; di($C_1$-$C_4$)alkyl sulfates, for example dimethyl, diethyl and diamyl sulfate; ($C_{10}$-$C_{18}$)alkyl halides, for example decyl, dodecyl, lauryl, myristyl and stearyl chloride, bromide and iodide; and aryl($C_1$-$C_4$)alkyl halides, for example benzyl chloride and phenethyl bromide. Both water- and oil-soluble compounds according to the invention can be prepared using such salts.

The above-mentioned pharmaceutical salts which are preferred include acetate, trifluoroacetate, besylate, citrate, fumarate, gluconate, hemisuccinate, hippurate, hydrochloride, hydrobromide, isethionate, mandelate, meglumine, nitrate, oleate, phosphonate, pivalate, sodium phosphate, stearate, sulfate, sulfosalicylate, tartrate, thiomalate, tosylate and tromethamine, but this is not intended to represent a restriction.

Particular preference is given to hydrochloride, dihydrochloride, hydrobromide, maleate, mesylate, phosphate, sulfate and succinate.

The acid-addition salts of basic compounds of the formula Ib and Ib are prepared by bringing the free base form into contact with a sufficient amount of the desired acid, causing the formation of the salt in a conventional manner. The free base can be regenerated by bringing the salt form into contact with a base and isolating the free base in a conventional manner. The free base forms differ in a certain respect from the corresponding salt forms thereof with respect to certain physical properties, such as solubility in polar solvents; for the purposes of the invention, however, the salts otherwise correspond to the respective free base forms thereof.

As mentioned, the pharmaceutically acceptable base-addition salts of the compounds of the formula I are formed with metals or amines, such as alkali metals and alkaline earth metals or organic amines. Preferred metals are sodium, potassium, magnesium and calcium. Preferred organic amines are N,N'-dibenzylethylenediamine, chloroprocaine, choline, diethanolamine, ethylenediamine, N-methyl-D-glucamine and procaine.

The base-addition salts of acidic compounds according to the invention are prepared by bringing the free acid form into contact with a sufficient amount of the desired base, causing the formation of the salt in a conventional manner. The free acid can be regenerated by bringing the salt form into contact with an acid and isolating the free acid in a conventional manner. The free acid forms differ in a certain respect from the corresponding salt forms thereof with respect to certain physical properties, such as solubility in polar solvents; for the purposes of the invention, however, the salts otherwise correspond to the respective free acid forms thereof.

If a compound according to the invention contains more than one group which is capable of forming pharmaceutically acceptable salts of this type, the invention also encompasses multiple salts. Typical multiple salt forms include, for example, bitartrate, diacetate, difumarate, dimeglumine, diphosphate, disodium and trihydrochloride, but this is not intended to represent a restriction.

With regard to that stated above, it can be seen that the expression "pharmaceutically acceptable salt" in the present connection is taken to mean an active ingredient which comprises a compound of the formula Ib and Ib in the form of one of its salts, in particular if this salt form imparts improved pharmacokinetic properties on the active ingredient compared with the free form of the active ingredient or any other salt form of the active ingredient used earlier. The pharmaceutically acceptable salt form of the active ingredient can also provide this active ingredient for the first time with a desired pharmacokinetic property which it did not have earlier and can even have a positive influence on the pharmacodynamics of this active ingredient with respect to its therapeutic efficacy in the body.

Isotopes

There is furthermore intended that a compound of the formula Ib and Ib includes isotope-labelled forms thereof. An isotope-labelled form of a compound of the formula Ib and Ib is identical to this compound apart from the fact that one or more atoms of the compound have been replaced by an atom or atoms having an atomic mass or mass number which differs from the atomic mass or mass number of the atom which usually occurs naturally. Examples of isotopes which are readily commercially available and which can be incorporated into a compound of the formula Ib and Ib by well-known methods include isotopes of hydrogen, carbon, nitrogen, oxygen, phosphorus, fluorine and chlorine, for example $^2H$, $^3H$, $^{13}O$, $^{14}O$, $^{15}N$, $^{18}O$, $^{17}O$, $^{31}P$, $^{32}P$, $^{35}S$, $^{18}F$ and $^{36}Cl$, respectively. A compound of the formula Ia and Ib or a pharmaceutically acceptable salt of either which contains one or more of the above-mentioned isotopes and/or other isotopes of other atoms is intended to be part of the present invention. An isotope-labelled compound of the formula Ia and Ib can be used in a number of beneficial ways. For example, an isotope-labelled compound of the formula Ia and Ib into which, for example, a radioisotope, such as $^3H$ or $^{14}C$, has been incorporated is suitable for medicament and/or substrate tissue distribution assays. These radioisotopes, i.e. tritium ($^3H$) and carbon-14 ($^{14}C$), are particularly preferred owing to simple preparation and excellent detectability. Incorporation of heavier isotopes, for example deuterium ($^2H$), into a compound of the formula Ib and Ib has therapeutic advantages owing to the higher metabolic stability of this isotope-labelled compound. Higher metabolic stability translates directly into an increased in vivo half-life or lower dosages, which under most circumstances would represent a preferred embodiment of the present invention. An isotope-labelled compound of the formula Ib and Ib can usually be prepared by carrying out the procedures dis-closed in the synthesis schemes and the related description, in the example part and in the preparation part in the present text, replacing a non-isotope-labelled reactant by a readily available isotope-labelled reactant.

Deuterium ($^2H$) can also be incorporated into a compound of the formula Ia and Ib for the purpose in order to manipulate the oxidative metabolism of the compound by way of the primary kinetic isotope effect. The primary kinetic isotope effect is a change of the rate for a chemical reaction that results from exchange of isotopic nuclei, which in turn is caused by the change in ground state energies necessary for covalent bond formation after this isotopic exchange. Exchange of a heavier isotope usually results in a lowering of the ground state energy for a chemical bond and thus cause a reduction in the rate in rate-limiting bond breakage. If the bond breakage occurs in or in the vicinity of a saddle-point region along the coordinate of a multi-product reaction, the product distribution ratios can be altered substantially. For explanation: if deuterium is bonded to a carbon atom at a non-exchangeable position, rate differences of $k_M/k_D$=2-7 are typical. If this rate difference is successfully applied to a compound of the formula Ib and Ib that is susceptible to oxidation, the profile of this compound in vivo can be drastically modified and result in improved pharmacokinetic properties.

When discovering and developing therapeutic agents, the person skilled in the art attempts to optimise pharmacokinetic parameters while retaining desirable in vitro properties. It is reasonable to assume that many compounds with poor pharmacokinetic profiles are susceptible to oxidative metabolism. In vitro liver microsomal assays currently available provide valuable information on the course of oxidative metabolism of this type, which in turn permits the rational design of deuterated compounds of the formula I with improved stability through resistance to such oxidative meta-bolism. Significant improvements in the pharmacokinetic profiles of compounds of the formula I are thereby obtained, and can be expressed quantitatively in terms of increases in the in vivo half-life (t½), concentration at maximum therapeutic effect ($C_{max}$), area under the dose response curve (AUC), and F; and in terms of reduced clearance, dose and materials costs.

The following is intended to illustrate the above: a compound of the formula Ia and Ib which has multiple potential sites of attack for oxidative metabolism, for example benzylic hydrogen atoms and hydrogen atoms bonded to a nitrogen atom, is prepared as a series of analogues in which various combinations of hydrogen atoms are replaced by deuterium atoms, so that some, most or all of these hydrogen atoms have been replaced by deuterium atoms. Half-life determinations enable favourable and accurate determination of the extent of the extent to which the improvement in resistance to oxidative metabolism has improved. In this way, it is deter-mined that the half-life of the parent compound can be extended by up to 100% as the result of deuterium-hydrogen exchange of this type.

Deuterium-hydrogen exchange in a compound of the formula Ib and Ib can also be used to achieve a favourable modification of the metabolite spectrum of the starting compound in order to diminish or eliminate undesired toxic metabolites. For example, if a toxic metabolite arises through oxidative carbon-hydrogen (C—H) bond cleavage, it can reasonably be assumed that the deuterated analogue will greatly diminish or eliminate production of the unwanted metabolite, even if the particular oxidation is not a rate-determining step. Further information on the state of the art with respect to deuterium-hydrogen exchange may be found, for example in Hanzlik et al., J. Org. Chem. 55, 3992-3997, 1990, Reider et al., J. Org. Chem. 52, 3326-3334, 1987, Foster, Adv. Drug Res. 14, 1-40, 1985, Gillette et al, Biochemistry 33(10) 2927-2937, 1994, and Jarman et al. Carcinogenesis 16(4), 683-688, 1993.

The invention furthermore relates to medicaments comprising at least one compound of the formula Ib and Ib and/or pharmaceutically acceptable salts, solvates and stereoisomers thereof, including mixtures thereof in all ratios, and optionally excipients and/or adjuvants.

Pharmaceutical formulations can be administered in the form of dosage units which comprise a predetermined amount of active ingredient per dosage unit. Such a unit can comprise, for example, 0.5 mg to 1 g, preferably 1 mg to 700 mg, particularly preferably 5 mg to 100 mg, of a compound according to the invention, depending on the condition treated, the method of administration and the age, weight and condition of the patient, or pharmaceutical formulations can be administered in the form of dosage units which comprise a predetermined amount of active ingredient per dosage unit. Preferred dosage unit formulations are those which comprise a daily dose or part-dose, as indicated above, or a corresponding fraction thereof of an active ingredient. Furthermore, pharmaceutical formulations of this type can be prepared using a process which is generally known in the pharmaceutical art.

Pharmaceutical formulations can be adapted for administration via any desired suitable method, for example by oral (including buccal or sublingual), rectal, nasal, topical (including buccal, sublingual or transdermal), vaginal or parenteral (including subcutaneous, intramuscular, intravenous or intradermal) methods. Such formulations can be prepared using all processes known in the pharmaceutical art by, for example, combining the active ingredient with the excipient(s) or adjuvant(s).

Pharmaceutical formulations adapted for oral administration can be administered as separate units, such as, for example, capsules or tablets; powders or granules; solutions or suspensions in aqueous or non-aqueous liquids; edible foams or foam foods; or oil-in-water liquid emulsions or water-in-oil liquid emulsions.

Thus, for example, in the case of oral administration in the form of a tablet or capsule, the active-ingredient component can be combined with an oral, non-toxic and pharmaceutically acceptable inert excipient, such as, for example, ethanol, glycerol, water and the like. Powders are prepared by comminuting the compound to a suitable fine size and mixing it with a pharmaceutical excipient comminuted in a similar manner, such as, for example, an edible carbohydrate, such as, for example, starch or mannitol. A flavour, preservative, dispersant and dye may likewise be present.

Capsules are produced by preparing a powder mixture as described above and filling shaped gelatine shells therewith. Glidants and lubricants, such as, for example, highly disperse silicic acid, talc, magnesium stearate, calcium stearate or polyethylene glycol in solid form, can be added to the powder mixture before the filling operation. A disintegrant or solubiliser, such as, for example, agar-agar, calcium carbonate or sodium carbonate, may likewise be added in order to improve the availability of the medicament after the capsule has been taken.

In addition, if desired or necessary, suitable binders, lubricants and disintegrants as well as dyes can likewise be incorporated into the mixture. Suitable binders include starch, gelatine, natural sugars, such as, for example, glucose or beta-lactose, sweeteners made from maize, natural and synthetic rubber, such as, for example, acacia, tragacanth or sodium alginate, carboxymethylcellulose, polyethylene glycol, waxes, and the like. The lubricants used in these dosage forms include sodium oleate, sodium stearate, magnesium stearate, sodium benzoate, sodium acetate, sodium chloride and the like. The disintegrants include, without being restricted thereto, starch, methylcellulose, agar, bentonite, xanthan gum and the like. The tablets are formulated by, for example, preparing a powder mixture, granulating or dry-pressing the mixture, adding a lubricant and a disintegrant and pressing the entire mixture to give tablets. A powder mixture is prepared by mixing the compound comminuted in a suitable manner with a diluent or a base, as described above, and optionally with a binder, such as, for example, carboxymethylcellulose, an alginate, gelatine or polyvinylpyrrolidone, a dissolution retardant, such as, for example, paraffin, an absorption accelerator, such as, for example, a quaternary salt, and/or an absorbant, such as, for example, bentonite, kaolin or dicalcium phosphate. The powder mixture can be granulated by wetting it with a binder, such as, for example, syrup, starch paste, acadia mucilage or solutions of cellulose or polymer materials and pressing it through a sieve. As an alternative to granulation, the powder mixture can be run through a tabletting machine, giving lumps of non-uniform shape, which are broken up to form granules. The granules can be lubricated by addition of stearic acid, a stearate salt, talc or mineral oil in order to prevent sticking to the tablet casting moulds. The lubricated mixture is then pressed to give tablets. The compounds according to the invention can also be combined with a free-flowing inert excipient and then pressed directly to give tablets without carrying out the granulation or dry-pressing steps. A transparent or opaque protective layer consisting of a shellac sealing layer, a layer of sugar or polymer material and a gloss layer of wax may be present. Dyes can be added to these coatings in order to be able to differentiate between different dosage units.

Oral liquids, such as, for example, solution, syrups and elixirs, can be prepared in the form of dosage units so that a given quantity comprises a prespecified amount of the compound. Syrups can be prepared by dissolving the compound in an aqueous solution with a suitable flavour, while elixirs are prepared using a non-toxic alcoholic vehicle. Suspensions can be formulated by dispersion of the compound in a non-toxic vehicle. Solubilisers and emulsifiers, such as, for example, ethoxylated isostearyl alcohols and polyoxyethylene sorbitol ethers, preservatives, flavour additives, such as, for example, peppermint oil or natural sweeteners or saccharin, or other artificial sweeteners and the like, can likewise be added.

The dosage unit formulations for oral administration can, if desired, be encapsulated in microcapsules. The formulation can also be prepared in such a way that the release is extended or retarded, such as, for example, by coating or embedding of particulate material in polymers, wax and the like.

The compounds of the formula Ib and Ib and pharmaceutically salts, tautomers and stereoisomers thereof can also be administered in the form of liposome delivery systems, such as, for example, small unilamellar vesicles, large unilamellar vesicles and multilamellar vesicles. Liposomes can be formed from various phospholipids, such as, for example, cholesterol, stearylamine or phosphatidylcholines.

The compounds of the formula Ib and Ib and the salts, tautomers and stereoisomers thereof can also be delivered using monoclonal antibodies as individual carriers to which the compound molecules are coupled. The compounds can also be coupled to soluble polymers as targeted medicament carriers. Such polymers may encompass polyvinylpyrrolidone, pyran copolymer, polyhydroxypropylmethacrylamidophenol, polyhydroxyethylaspartamidophenol or polyethylene oxide polylysine, substituted by palmitoyl radicals. The compounds may furthermore be coupled to a class of biodegradable polymers which are suitable for achieving controlled release of a medicament, for example polylactic acid, poly-epsilon-caprolactone, polyhydroxybutyric acid, polyorthoesters, polyacetals, polydihydroxypyrans, polycyanoacrylates and crosslinked or amphipathic block copolymers of hydrogels.

Pharmaceutical formulations adapted for transdermal administration can be administered as independent plasters for extended, close contact with the epidermis of the recipient. Thus, for example, the active ingredient can be delivered from the plaster by iontophoresis, as described in general terms in Pharmaceutical Research, 3(6), 318 (1986).

Pharmaceutical compounds adapted for topical administration can be formulated as ointments, creams, suspensions, lotions, powders, solutions, pastes, gels, sprays, aerosols or oils.

For the treatment of the eye or other external tissue, for example mouth and skin, the formulations are preferably applied as topical ointment or cream. In the case of formulation to give an ointment, the active ingredient can be employed either with a paraffinic or a water-miscible cream base. Alternatively, the active ingredient can be formulated to give a cream with an oil-in-water cream base or a water-in-oil base.

Pharmaceutical formulations adapted for topical application to the eye include eye drops, in which the active ingredient is dissolved or suspended in a suitable carrier, in particular an aqueous solvent.

Pharmaceutical formulations adapted for topical application in the mouth encompass lozenges, pastilles and mouthwashes.

Pharmaceutical formulations adapted for rectal administration can be administered in the form of suppositories or enemas.

Pharmaceutical formulations adapted for nasal administration in which the carrier substance is a solid comprise a coarse powder having a particle size, for example, in the range 20-500 microns, which is administered in the manner in which snuff is taken, i.e. by rapid inhalation via the nasal passages from a container containing the powder held close to the nose. Suitable formulations for administration as nasal spray or nose drops with a liquid as carrier substance encompass active-ingredient solutions in water or oil.

Pharmaceutical formulations adapted for administration by inhalation encompass finely particulate dusts or mists, which can be generated by various types of pressurised dispensers with aerosols, nebulisers or insufflators.

Pharmaceutical formulations adapted for vaginal administration can be administered as pessaries, tampons, creams, gels, pastes, foams or spray formulations.

Pharmaceutical formulations adapted for parenteral administration include aqueous and non-aqueous sterile injection solutions comprising antioxidants, buffers, bacteriostatics and solutes, by means of which the formulation is rendered isotonic with the blood of the recipient to be treated; and aqueous and non-aqueous sterile suspensions, which may comprise suspension media and thickeners. The formulations can be administered in single-dose or multi-dose containers, for example sealed ampoules and vials, and stored in freeze-dried (lyophilised) state, so that only the addition of the sterile carrier liquid, for example water for injection purposes, immediately before use is necessary. Injection solutions and suspensions prepared in accordance with the recipe can be prepared from sterile powders, granules and tablets.

It goes without saying that, in addition to the above particularly mentioned constituents, the formulations may also comprise other agents usual in the art with respect to the particular type of formulation; thus, for example, formulations which are suitable for oral administration may comprise flavours.

A therapeutically effective amount of a compound of the formula Ib and Ib depends on a number of factors, including, for example, the age and weight of the animal, the precise condition that requires treatment, and its severity, the nature of the formulation and the method of administration, and is ultimately determined by the treating doctor or vet. However, an effective amount of a compound according to the invention is generally in the range from 0.1 to 100 mg/kg of body weight of the recipient (mammal) per day and particularly typically in the range from 1 to 10 mg/kg of body weight per day. Thus, the actual amount per day for an adult mammal weighing 70 kg is usually between 70 and 700 mg, where this amount can be administered as a single dose per day or usually in a series of part-doses (such as, for example, two, three, four, five or six) per day, so that the total daily dose is the same. An effective amount of a salt or solvate or of a physiologically functional derivative thereof can be determined as the fraction of the effective amount of the compound according to the invention per se. It can be assumed that similar doses are suitable for the treatment of other conditions mentioned above.

A combined treatment of this type can be achieved with the aid of simultaneous, consecutive or separate dispensing of the individual components of the treatment. Combination products of this type employ the compounds according to the invention.

The invention furthermore relates to medicaments comprising at least one compound of the formula Ib and Ib and/or pharmaceutically acceptable salts, tautomers and stereoisomers thereof, including mixtures thereof in all ratios, and at least one further medicament active ingredient.

The invention also relates to a set (kit) consisting of separate packs of
  (a) an effective amount of a compound of the formula Ib and Ib and/or pharmaceutically acceptable salts, tautomers and stereoisomers thereof, including mixtures thereof in all ratios, and
  (b) an effective amount of a further medicament active ingredient.

The set comprises suitable containers, such as boxes, individual bottles, bags or ampoules. The set may, for example, comprise separate ampoules, each containing an effective amount of a compound of the formula I and/or pharmaceutically acceptable salts, tautomers and stereoisomers thereof, including mixtures thereof in all ratios,
and an effective amount of a further medicament active ingredient in dissolved or lyophilised form.

"Treating" as used herein, means an alleviation, in whole or in part, of symptoms associated with a disorder or disease, or slowing, or halting of further progression or worsening of those symptoms, or prevention or prophylaxis of the disease or disorder in a subject at risk for developing the disease or disorder.

The term "effective amount" in connection with a compound of formula Ia and Ib can mean an amount capable of alleviating, in whole or in part, symptoms associated with a disorder or disease, or slowing or halting further progression or worsening of those symptoms, or preventing or providing prophylaxis for the disease or disorder in a subject having or at risk for developing a disease disclosed herein, such as inflammatory conditions, immunological conditions, cancer or metabolic conditions.

In one embodiment an effective amount of a compound of formula Ib and Ib is an amount that inhibits ATR in a cell, such as, for example, in vitro or in vivo. In some embodiments, the effective amount of the compound of formula (I) inhibits tankyrase in a cell by 10%, 20%, 30%, 40%, 50%, 60%, 70%, 80%, 90% or 99%, compared to the activity of ATR in an untreated cell. The effective amount of the compound of formula Ib and Ib, for example in a pharmaceutical composition, may be at a level that will exercise the desired effect; for example, about 0.005 mg/kg of a subject's body weight to about 10 mg/kg of a subject's body weight in unit dosage for both oral and parenteral administration.

Use

The present compounds are suitable as pharmaceutical active ingredients for mammals, especially for humans. in the treatment of cancer.

The present invention encompasses the use of the compounds of the formula Ib and Ib and/or pharmaceutically acceptable salts, tautomers and stereoisomers thereof for the preparation of a medicament for the treatment or prevention of cancer.

Moreover, the present invention encompasses the compounds for use of the formula Ib and Ib and/or pharmaceutically acceptable salts, tautomers and stereoisomers thereof for treatment or prevention of cancer, Also encompassed is the use of the compounds of the formula Ib and Ib and/or pharmaceutically acceptable salts, tautomers and stereoisomers thereof for the preparation of a medicament for the treatment or prevention of an ATR-induced disease or an ATR-induced condition in a mammal, in which to this method a therapeutically effective amount of a compound according to the invention is administered to a sick mammal in need of such treatment. The therapeutic amount varies according to the specific disease and can be determined by the person skilled in the art without undue effort.

The present invention specifically relates to compounds of the formula Ia and Ib and pharmaceutically acceptable salts, tautomers and stereoisomers thereof, including mixtures thereof in all ratios, for the use for the treatment of diseases in which the inhibition, regulation and/or modulation inhibition of ATR plays a role.

The present invention specifically relates to compounds of the formula Ia and Ib and pharmaceutically acceptable salts, tautomers and stereoisomers thereof, including mixtures thereof in all ratios, for the use for the inhibition of ATR.

Representative cancers that compounds of formula Ib and Ib are useful for treating or preventing include, but are not limited to, cancer of the head, neck, eye, mouth, throat, esophagus, bronchus, larynx, pharynx, chest, bone, lung, colon, rectum, stomach, prostate, urinary bladder, uterine, cervix, breast, ovaries, testicles or other reproductive organs, skin, thyroid, blood, lymph nodes, kidney, liver, pancreas, brain, central nervous system, solid tumors and blood-borne tumors.

Preferably, the present invention relates to a method wherein the disease is a cancer.

Particularly preferable, the present invention relates to a method wherein the disease is a cancer, wherein administration is simultaneous, sequential or in alternation with administration of at least one other active drug agent.

The disclosed compounds of the formula Ib and Ib can be administered in combination with other known therapeutic agents, including anticancer agents. As used here, the term "anticancer agent" relates to any agent which is administered to a patient with cancer for the purposes of treating the cancer.

The anti-cancer treatment defined above may be applied as a monotherapy or may involve, in addition to the herein disclosed compounds of formula I, conventional surgery or radiotherapy or medicinal therapy. Such medicinal therapy, e.g. a chemotherapy or a targeted therapy, may include one or more, but preferably one, of the following anti-tumor agents:

Alkylating Agents
such as altretamine, bendamustine, busulfan, carmustine, chlorambucil, chlormethine, cyclophosphamide, dacarbazine, ifosfamide, improsulfan, tosilate, lomustine, melphalan, mitobronitol, mitolactol, nimustine, ranimustine, temozolomide, thiotepa, treosulfan, mechloretamine, carboquone;
apaziquone, fotemustine, glufosfamide, palifosfamide, pipobroman, trofosfamide, uramustine, TH-302[4], VAL-083[4];

Platinum Compounds
such as carboplatin, cisplatin, eptaplatin, miriplatine hydrate, oxaliplatin, lobaplatin, nedaplatin, picoplatin, satraplatin;
lobaplatin, nedaplatin, picoplatin, satraplatin;

DNA Altering Agents
such as amrubicin, bisantrene, decitabine, mitoxantrone, procarbazine, trabectedin, clofarabine;
amsacrine, brostallicin, pixantrone, laromustine[1,3];

Topoisomerase Inhibitors
such as etoposide, irinotecan, razoxane, sobuzoxane, teniposide, topotecan; amonafide, belotecan, elliptinium acetate, voreloxin;

Microtubule Modifiers
such as cabazitaxel, docetaxel, eribulin, ixabepilone, paclitaxel, vinblastine, vincristine, vinorelbine, vindesine, vinflunine;
fosbretabulin, tesetaxel;

Antimetabolites
such as asparaginase[3], azacitidine, calcium levofolinate, capecitabine, cladribine, cytarabine, enocitabine, floxuridine, fludarabine, fluorouracil, gemcitabine, mercaptopurine, methotrexate, nelarabine, pemetrexed, pralatrexate, azathioprine, thioguanine, carmofur;
doxifluridine, elacytarabine, raltitrexed, sapacitabine, tegafur[2,3], trimetrexate;

Anticancer Antibiotics
such as bleomycin, dactinomycin, doxorubicin, epirubicin, idarubicin, levamisole, miltefosine, mitomycin C, romidepsin, streptozocin, valrubicin, zinostatin, zorubicin, daunorubicin, plicamycin; aclarubicin, peplomycin, pirarubicin;

Hormones/Antagonists
such as abarelix, abiraterone, bicalutamide, buserelin, calusterone, chlorotrianisene, degarelix, dexamethasone, estradiol, fluocortolone fluoxymesterone, flutamide, fulvestrant, goserelin, histrelin, leuprorelin, megestrol, mitotane, nafarelin, nandrolone, nilutamide, octreotide, prednisolone, raloxifene, tamoxifen, thyrotropin alfa, toremifene, trilostane, triptorelin, diethylstilbestrol;
acolbifene, danazol, deslorelin, epitiostanol, orteronel, enzalutamide[1,3];

Aromatase Inhibitors
such as aminoglutethimide, anastrozole, exemestane, fadrozole, letrozole, testolactone;
formestane;

Small Molecule Kinase Inhibitors
such as crizotinib, dasatinib, erlotinib, imatinib, lapatinib, nilotinib, pazopanib, regorafenib, ruxolitinib, sorafenib, sunitinib, vandetanib, vemurafenib, bosutinib, gefitinib, axitinib;

afatinib, alisertib, dabrafenib, dacomitinib, dinaciclib, dovitinib, enzastaurin, nintedanib, lenvatinib, linifanib, linsitinib, masitinib, midostaurin, motesanib, neratinib, orantinib, perifosine, ponatinib, radotinib, regorafenib, rigosertib, tepotinib, tipifarnib, tivantinib, tivozanib, trametinib, pimasertib, brivanib alaninate, cediranib, apatinib[4], cabozantinib S-malate[1,3], ibrutinib[1,3], icotinib[4], buparlisib[2], cipatinib[4], cobimetinib[1,3], idelalisib[1,3], fedratinib[1], XL-647[4];

Photosensitizers
such as methoxsalen[3];
porfimer sodium, talaporfin, temoporfin;

Antibodies
such as alemtuzumab, besilesomab, brentuximab vedotin, cetuximab, denosumab, ipilimumab, ofatumumab, panitumumab, rituximab, tositumomab, trastuzumab, bevacizumab, pertuzumab[2,3];
catumaxomab, elotuzumab, epratuzumab, farletuzumab, mogamulizumab, necitumumab, nimotuzumab, obinutuzumab, ocaratuzumab, oregovomab, ramucirumab, rilotumumab, siltuximab, tocilizumab, zalutumumab, zanolimumab, matuzumab, dalotuzumab[1,2,3], onartuzumab[1,3], racotumomab[1], tabalumab[1,3], EMD-525797[4], avelumab, nivolumab[1,3];

Cytokines
such as aldesleukin, interferon alfa[2], interferon alfa2a[3], interferon alfa2b[2,3]; celmoleukin, tasonermin, teceleukin, oprelvekin[1,3], recombinant interferon beta-1a[4];

Drug Conjugates
such as denileukin diftitox, ibritumomab tiuxetan, iobenguane I123, prednimustine, trastuzumab emtansine, estramustine, gemtuzumab, ozogamicin, aflibercept;
cintredekin besudotox, edotreotide, inotuzumab ozogamicin, naptumomab estafenatox, oportuzumab monatox, technetium (99mTc) arcitumomab[1,3], vintafolide[1,3];

Vaccines
such as sipuleucel[3]; vitespen[3], emepepimut-S[3], oncoVAX[4], rindopepimut[3], troVax[4], MGN-1601[4], MGN-1703[4];

Miscellaneous
alitretinoin, bexarotene, bortezomib, everolimus, ibandronic acid, imiquimod, lenalidomide, lentinan, metirosine, mifamurtide, pamidronic acid, pegaspargase, pentostatin, sipuleucel[3], sizofiran, tamibarotene, temsirolimus, thalidomide, tretinoin, vismodegib, zoledronic acid, vorinostat; celecoxib, cilengitide, entinostat, etanidazole, ganetespib, idronoxil, iniparib, ixazomib, lonidamine, nimorazole, panobinostat, peretinoin, plitidepsin, pomalidomide, procodazol, ridaforolimus, tasquinimod, telotristat, thymalfasin, tirapazamine, tosedostat, trabedersen, ubenimex, valspodar, gendicine[4],
picibanil[4], reolysin[4], retaspimycin hydrochloride[1,3], trebananib[2,3], virulizin[4], carfilzomib[1,3], endostatin[4], immucothel[4], belinostat[3], MGN-1703[4];

PARP Inhibitors
Olaparib, Veliparib.

[1] Prop. INN (Proposed International Nonproprietary Name)
[2] Rec. INN (Recommended International Nonproprietary Names)
[3] USAN (United States Adopted Name)
[4] no INN.

The following abbreviations refer respectively to the definitions below: aq (aqueous), h (hour), g (gram), L (liter), mg (milligram), MHz (Megahertz), min. (minute), mm (millimeter), mmol (millimole), mM (millimolar), m.p. (melting point), eq (equivalent), mL (milliliter), L (microliter), ACN (acetonitrile), AcOH (acetic acid), CDCl$_3$ (deuterated chloroform), CD$_3$OD (deuterated methanol), CH$_3$CN (acetonitrile), c-hex (cyclohexane), DCC (dicyclohexyl carbodiimide), DCM (dichloromethane), DIC (diisopropyl carbodiimide), DIEA (diisopropylethyl-amine), DMF (dimethylformamide), DMSO (dimethylsulfoxide), DMSO (deuterated dimethylsulfoxide), EDC (1-(3-dimethylamino-propyl)-3-ethylcarbodiimide), ESI (Electro-spray ionization), EtOAc (ethyl acetate), Et$_2$O (diethyl ether), EtOH (ethanol), HATU (dimethylamino-([1,2,3]triazolo[4,5-b]pyridin-3-yloxy)-methylene]-dimethyl-ammonium hexafluorophosphate), HPLC (High Performance Liquid Chromatography), i-PrOH (2-propanol), K$_2$CO$_3$ (potassium carbonate), LC (Liquid Chromatography), MeOH (methanol), MgSO$_4$ (magnesium sulfate), MS (mass spectrometry), MTBE (Methyl tert-butyl ether), NaHCO$_3$ (sodium bicarbonate), NaBH$_4$ (sodium borohydride), NMM (N-methyl morpholine), NMR (Nuclear Magnetic Resonance), PyBOP (benzotriazole-1-yl-oxy-tris-pyrrolidino-phosphonium hexafluorophosphate), RT (room temperature), Rt (retention time), SPE (solid phase extraction), TBTU (2-(1-H-benzotriazole-1-yl)-1,1,3,3-tetramethyluromium tetrafluoroborate), TEA (triethylamine), TFA (trifluoroacetic acid), THF (tetrahydrofuran), TLC (Thin Layer Chromatography), UV (Ultraviolet).

Above and below, all temperatures are indicated in ° C. In the following examples, "conventional work-up" means: water is added if necessary, the pH is adjusted, if necessary, to values between 2 and 10, depending on the constitution of the end product, the mixture is extracted with ethyl acetate or dichloromethane, the phases are separated, the organic phase is dried over sodium sulfate and evaporated, and the residue is purified by chromatography on silica gel and/or by crystallisation. Rf values on silica gel; eluent: ethyl acetate/methanol 9:1.

$^1$H NMR was recorded on Bruker DPX-300, DRX-400, AVII-400 or on a 500 MHz spectrometer, using residual signal of deuterated solvent as internal reference. Chemical shifts ($\delta$) are reported in ppm relative to the residual solvent signal ($\delta$=2.49 ppm for $^1$H NMR in DMSO). $^1$H NMR data are reported as follows: chemical shift (multiplicity, coupling constants, and number of hydrogens). Multiplicity is abbreviated as follows: s (singlet), d (doublet), t (triplet), q (quartet), m (multiplet), br (broad).

LC-MS

LCMS data provided in the examples are given with retention time, purity and/or mass in m/z. The results were obtained as followed: Mass spectrum: LC/MS Waters ZMD (ESI) or Hewlett Packard System of the HP 1100 series (Ion source: Electrospray (positive mode) or Waters Acquity H Class SQD; Scan: 100-1000 m/z; Fragmentation-voltage: 60 V; Gas-temperature: 300° C., DAD: 220 nm. Flow rate: 2.4 ml/Min. The used splitter reduced the flow rate after the DAD for the MS to 0.75 ml/Min; Column: Chromolith Speed ROD RP-18e 50-4.6; Solvent: LiChrosolv-quality from the company Merck KGaA or as mentioned in the method.

Method A: Shimadzu LCMS-2020 Column: Poroshell HPH—C18, 3.0*50 mm, 2.7 μm; Mobile Phase A: water/5 mM NH4HCO3, Mobile Phase B: Acetonitrile; Flow rate: 1.2 mL/min; Gradient: 10% B to 95% B in 2.1 min, hold 0.6 min; 254 nm Method B: Shimadzu LCMS-2020 Column: Shim-pack XR-ODS, 3.0*50 mm, 2.2 μm; Mobile Phase A: Water/

0.05% TFA, Mobile Phase B: ACN/0.05% TFA; Flow rate: 1.2 mL/min; Gradient: 5% B to 100% B in 3.8 min, hold 1.0 min; 254 nm Method C: Waters Acquity H-Class-SQD; column: BEH C-18 2.1-50 1.7 μm; column temp.: 40° C.; detection: 220 nm; eluent A: water+0.1% HCOOH; eluent B: acetonitrile+0.08% HCOOH; flow: 0.9 ml/min; gradient: 0 min 4% B, in 1 min up to 100% B, till 1.3 min 100% B, till 1.4 min to 4% B, till 2 min 4% B Method D: Shimadzu LCMS-2020 Column: Ascentis Express C18, 3.0*50 mm, 2.7 μm; Mobile Phase A: Water/0.05% TFA, Mobile Phase: ACN/0.05% TFA; Flow Rate: 1.5 mL/min; Gradient: 5% B to 100% B in 2.1 min, hold 0.7 min; 254 nm Method E: Shimadzu LCMS-2020 Column: Shim-pack XR-ODS, 3.0*50 mm, 2.2 μm; Mobile Phase A: Water/0.05% TFA, Mobile Phase B: ACN/0.05% TFA; Flow rate: 1.2 mL/min; Gradient: 5% B to 100% B in 2.0 min, hold 0.7 min; 254 nm Method F: Agilent 1200-6120B; Chromolith Performance RP18e, 100 mm length, inner diameter 3 mm; wavelength 220 nm; gradient: 4.2 min; flow: 2 ml/min 99:01 to 0:100; Water+0.1% (Vol.) TFA: Acetonitrile+0.1% (Vol.) TFA; 0.0 to 0.2 min: 99:01; 0.2 to 3.8 min: 99:01 to 0:100; 3.8 to 4.2 min: 0:100

Method G: Shimadzu LCMS-2020, $LC_2OADXR$, Column: Kinetex EVO C18, 3.0*50 mm, 2.6 μm; Mobile Phase A: water/5 mM $NH_4HCO_3$, Mobile Phase B: ACN; Flow rate: 1.3 mL/min; Gradient: 10% B to 95% B in 2.1 min, hold 0.6 min; 254 nm Method H: Shimadzu LCMS-2020 Column: Poroshell HPH—C18, 3.0*50 mm, 2.7 μm; Mobile Phase A: water/5 mM $NH_4HCO_3$, Mobile Phase B: Acetonitrile; Flow rate: 1.3 mL/min; Gradient: 10% B to 95% B in 2.1 min, hold 0.6 min; 254 nm Method I: Shimadzu LCMS-2020 Column: Poroshell HPH—C18, 3.0*50 mm, 2.7 μm; Mobile Phase A: water/5 mM $NH_4HCO_3$, Mobile Phase B: Acetonitrile; Flow rate: 1.3 mL/min; Gradient: 10% B to 95% B in 4.0 min, hold 0.8 min; 254 nm Method J: Shimadzu LCMS-2020 Column: Shim-pack XR-ODS, 3.0*50 mm, 2.2 μm; Mobile Phase A: Water/0.05% TFA, Mobile Phase B: ACN/0.05% TFA; Flow rate: 1.2 mL/min; Gradient: 5% B to 100% B in 1.1 min, hold 0.6 min; 254 nm Method K: Waters Acquity H-Class-SQD; column: kinetex EVO C18 2.1-50 1.7 μm; column temp.: 40° C.; detection: 220 nm; eluent A: water+0.1% HCOOH; eluent B: acetonitrile+0.08% HCOOH; flow: 0.9 ml/min; gradient: 0 min 4% B, in 1 min up to 100% B, till 1.3 min 100% B, till 1.4 min to 4% B, till 2 min 4% B Method L: Shimadzu LCMS-2020 Column: CORTECS C18+ 100A, 2.1*50 mm, 2.7 μm; Mobile phase A: Water/0.1% FA, Mobile phase B: Acetonitrile/0.1% FA; Flow rate: 1.0 mL/min; Gradient: 10% B to 100% B in 1.1 min, hold 0.5 min; 254 nm Method M: Shimadzu LCMS-2020 Column: Ascentis Express C18, 3.0*50 mm, 2.7 μm; Mobile Phase A: Water/0.05% TFA, Mobile Phase: ACN/0.05% TFA; Flow Rate: 1.5 mL/min; Gradient: 5% B to 100% B in 2.0 min, hold 0.7 min; 254 nm Method N: Shimadzu LCMS-2020 Column: Shim-pack XR-ODS, 3.0*50 mm, 2.2 μm; Mobile Phase A: Water/0.05% TFA, Mobile Phase B: MeOH; Flow rate: 0.82 mL/min; Gradient: 30% B to 100% B in 6.2 min, hold 1.1 min; 254 nm Method O: Shimadzu LCMS-2020 Column: kinetex EVO C18 3.0-50 2.6 μm; Mobile Phase A: Water/5 mM $NH_4HCO_3$, Mobile Phase B: Acetonitrile; Flow Rate: 1.2 mL/min; Gradient: 10% B to 95% B in 2.1 min, hold 0.6 min; 254 nm Method P: Shimadzu LCMS-2020 Column: Ascentis Express C18, 3.0*50 mm, 2.7 μm; Mobile Phase A: Water/0.05% TFA, Mobile Phase: ACN/0.05% TFA; Flow Rate: 1.5 mL/min; Gradient: 5% B to 100% B in 1.2 min, hold 0.5 min; 254 nm Method Q: Waters Acquity H-Class-SQD; column: CORTECS C18 2.1-50 1.6 μm; column temp.: 30° C.; detection: 220 nm; eluent A: water+0.05% HCOOH; eluent B: acetonitrile+0.04% HCOOH; flow: 0.9 ml/min; gradient: 2% B to 100% B in 1.0 min, hold 0.3 min Method R: Waters Acquity H-Class-SQD; column: kinetex EVO C18 2.1-50 1.7 μm; column temp.: 30° C.; detection: 220 nm; eluent A: water+0.05% HCOOH; eluent B: acetonitrile+0.04% HCOOH; flow: 0.9 ml/min; gradient: 1% B to 99% B in 1.0 min, hold 0.3 min Method S: Shimadzu LCMS-2020 Column: kinetex EVO C18 3.0-50 2.6 μm; Mobile Phase A: Water/0.04% $NH_4OH$, Mobile Phase B: Acetonitrile; Flow Rate: 1.2 mL/min; Gradient: 10% B to 95% B in 2.1 min, hold 0.6 min; 254 nm Method T: Shimadzu LCMS-2020 Column: kinetex EVO C18 3.0-50 2.6 μm; Mobile Phase A: Water/0.04% $NH_4OH$, Mobile Phase B: Acetonitrile; Flow Rate: 1.2 mL/min; Gradient: 10% B to 95% B in 1.2 min, hold 0.5 min; 254 nm Method U: Shimadzu LCMS-2020 Column: Shim-pack XR-ODS, 3.0*50 mm, 2.2 μm; Mobile Phase A: Water/0.05% TFA, Mobile Phase B: ACN/0.05% TFA; Flow rate: 1.2 mL/min; Gradient: 5% B to 100% B in 4.2 min, hold 0.8 min; 254 nm Method V: Agilent 1200-6120B; Column: waters sunfire C18, 3100 mm, 5 μm; gradient: 4.3 min; flow: 1.3 ml/min 99:01 to 0:100; Water+0.1% (Vol.) TFA: Acetonitrile+0.1% (Vol.) TFA; 0.0 to 0.2 min: 99:01; 0.2 to 3.8 min: 99:01 to 0:100; 3.8 to 4.3 min: 0:100

Method W: Shimadzu LCMS-2020 Column: CORTECS C18+100A, 2.1*50 mm, 2.7 um; Mobile phase A: Water/0.1% FA, Mobile phase B: Acetonitrile/0.1% FA; Flow rate: 1.0 mL/min; Gradient: 10% B to 100% B in 2.0 min, hold 0.6 min; 254 nm Method X: Shimadzu LCMS-2020 Column: Ascentis Express C18, 3.0*50 mm, 2.7 μm; Mobile Phase A: Water/0.05% TFA, Mobile Phase: ACN/0.05% TFA; Flow Rate: 1.5 mL/min; Gradient: 5% B to 100% B in 3.0 min, hold 1.5 min; 254 nm Preparative column chromatography was done by Teledyne Isco Combi Flash Rf, silica gel cartridge with one of the following solvent systems Method A: dichloromethane/methanol 10:1
Method B: (ethyl acetate/petroleum ether 2:3)
Method C: (ethyl acetate/petroleum ether 3:7)
Method D: (n-Heptane/EtOAc).
Method E: ethyl acetate/petroleum ether 1:1
Method F: ethyl acetate/PE 1:10
Method G: ethyl acetate/petroleum ether 1:5
Method H: dichloromethane/methanol 2:3
Method I: ethyl acetate/PE 4:1
Method J: EA/PE 10:1
Method K: $CH_3CN/H2O$ 3:7
Method L: DCM-MeOH-gradient
Method M: n-heptane/EtOAc gradient
Method N: n-heptane/EtOAc/MeOH gradient
Method O: DCM/MeOH gradient
Method P: ethyl acetate/petroleum ether gradient Preparative HPLC was performed on a Agilent 1200. Column: Chromolith prep RP 18e Merck KGaA. Mobile phase: 0.1% formic acid in water/0.1% formic acid in acetonitrile. Alternative methods were:

Method A: 1 min 99% A. In 2.5 min from 99% A to 100% B. Followed by 1.5 min 100% B and 1 min 99% A. Column Chromolith SpeedRod RP-18e; 50-4.6 mm; detection 220 nM (Solvent A: $H_2O$ (0.1% TFA), Solvent B: ACN (0.1% TFA)

Method B: 2#-AnalyseHPLC-SHIMADZU(HPLC-10)): Column, XBridge Shield RP18 OBD Column, 5 um, 19*150 mm; mobile phase, Water (0.05% $NH_3H_2O$) and ACN (20% ACN up to 39% in 8 min); Detector, UV 254 nm Method C: 2#-AnalyseHPLC-SHIMADZU(HPLC-10)): Column, XBridge Prep C18 OBD Column, 19??150 mm 5 um; mobile phase, Water (10 MMOL/L $NH_4HCO_3$+0.1% $NH_3·H_2O$) and ACN (25.0% ACN up to 46.0% in 8 min); Detector, UV 254 nm.

Method D: 2#-AnalyseHPLC-SHIMADZU(HPLC-10)): Column, XBridge Prep C18 OBD Column, 19*150 mm 5 um; mobile phase, Water (10 MMOL/L $NH_4HCO_3$+0.1% $NH_3·H_2O$) and ACN (31% ACN up to 53% in 8 min); Detector, UV 254/220 nm Method E: 2#-AnalyseHPLC-SHIMADZU(HPLC-10)): Column, XBridge Shield RP18 OBD Column, 5 um, 19*150 mm; mobile phase, Water (10 MMOL/L $NH_4HCO_3$+0.1% $NH_3·H_2O$) and ACN (22% ACN up to 58% in 9 min); Detector, uv 254 nm Method F: 2#-AnalyseHPLC-SHIMADZU(HPLC-10)): Column, XBridge Prep C18 OBD Column, 19??150 mm 5 um; mobile phase, Water (10 MMOL/L $NH_4HCO_3$+0.1% $NH_3·H_2O$) and ACN (45.0% ACN up to 65.0% in 8 min); Detector, uv 254 nm Method G: 2#-AnalyseHPLC-SHIMADZU(HPLC-10)): Column, XBridge Shield RP18 OBD Column, 5 um, 19*150 mm; mobile phase, Water (10 MMOL/L $NH_4HCO_3$+0.1% $NH_3·H_2O$) and ACN (20.0% ACN up to 35.0% in 10 min); Detector, uv 254 nm Method H: 2#-AnalyseHPLC-SHIMADZU(HPLC-10)): Column, XBridge Prep C18 OBD Column, 19??150 mm 5 um; mobile phase, and (60% up to 62% in 10 min); Detector, uv 254 nm.

Method I: Chiral-Prep-HPLC ( ): Column, mobile phase, Detector, 20 mg product was obtained which Alpha degree C.

Method J: 2#SHIMADZU (HPLC-01)): Column, XBridge Shield RP18 OBD Column, 5 um, 19*150 mm; mobile phase, Water (10 MMOUL $NH_4HCO_3$+0.1% $NH_3·H_2O$) and ACN (10% ACN up to 33% in 7 min); Detector, uv 254 nm Method K: 2#-AnalyseHPLC-SHIMADZU(HPLC-10)): Column, XBridge Shield RP18 OBD Column, 5 um, 19*150 mm; mobile phase, Water (10 MMOL/L $NH_4HCO_3$+0.1% $NH_3·H_2O$) and ACN (10% ACN up to 35% in 8 min); Detector, UV 254 nm Method L: 2#-AnalyseHPLC-SHIMADZU(HPLC-10)): Column, XBridge Shield RP18 OBD Column, 5 um, 19*150 mm; mobile phase, Water (10 MMOL/L $NH_4HCO_3$+0.1% $NH_3·H_2O$) and ACN (18.0% ACN up to 53.0% in 8 min); Detector, uv 254 nm Method M: 2#-AnalyseHPLC-SHIMADZU(HPLC-10)): Column, XBridge Shield RP18 OBD Column, 5 um, 19*150 mm; mobile phase, Water (10 MMOL/L $NH_4HCO_3$+0.1% $NH_3·H_2O$) and ACN (18.0% ACN up to 60.0% in 9 min); Detector, uv 254 nm Method N: 2#-AnalyseHPLC-SHIMADZU(HPLC-10)): Column, XBridge Prep C18 OBD Column, 19150 mm 5 um; mobile phase, Water (10 MMOUL $NH_4HCO_3$+0.1% $NH_3·H_2O$) and ACN (25% ACN up to 41% in 8 min); Detector, UV 254 nm.

Method O: 2#-AnalyseHPLC-SHIMADZU(HPLC-10)): Column, XBridge Prep OBD C18 Column, 19*250 mm, 5 um; mobile phase, Water (10 MMOUL $NH_4HCO_3$+0.1% $NH_3·H_2O$) and ACN (18% ACN up to 41% in 8 min); Detector, UV 254 nm.

Method P: (2#-AnalyseHPLC-SHIMADZU(HPLC-10)): Column, XBridge Prep C18 OBD Column, 19150 mm 5 um; mobile phase, Water (10 MMOUL $NH_4HCO_3$+0.1% $NH_3·H_2O$) and ACN (18% ACN up to 38% in 8 min); Detector, UV 254 nm.

Method Q: 2#-AnalyseHPLC-SHIMADZU(HPLC-10)): Column, XBridge Shield RP18 OBD Column, 5 um, 19*150 mm; mobile phase, Water (10 MMOL/L $NH_4HCO_3$+0.1% $NH_3·H_2O$) and ACN (20% PhaseB up to 60% in 9 min); Detector, uv 254 nm.

Method R: Waters Acquity H-Class-SQD; column: BEH C-18 2.1-50 1.7 µm; column temp.: 40° C.; detection: 220 nm; eluent A: water+0.1% HCOOH; eluent B: acetonitrile+ 0.08% HCOOH; flow: 0.9 ml/min; gradient: 0 min 4% B, in 1 min up to 100% B, till 1.3 min 100% B, till 1.4 min to 4% B till 2 min 4% B.

The microwave chemistry is performed on a single mode microwave reactor Emrys™ Optimiser from Personal Chemistry.

ATR/ATRIP Kinase Assay—Measurement of ATR/ATRIP Inhibition

The $IC_{50}$ value was determined by an ATR/ATRIP enzymatic assay. The assay comprises two steps: the enzymatic reaction and the detection step. First, a mixture of ATR/ATRIP protein (Ataxia Telangiectasia and Rad3-related protein/ATR interacting protein), the compound in question at different concentrations, p53 as substrate protein and adenosine triphosphate (ATP) are incubated in assay buffer. ATR phosporylates p53 at Ser15 and other residues. The amount of phosphorylated p53 is then detected using specific antibodies and the TR-FRET assay technology.

In detail: The ATR/ATRIP enzymatic assay is performed as a TR-FRET-(HTRF™, Cisbio Bioassays) based 384-well assay. In a first step, purified human recombinant ATR/ATRIP (human ATR, full length, GenBank ID: NM_001184.3, and human ATRIP, full length, GenBank ID AF451323.1, co-expressed in a mammalian cell line) is incubated in assay buffer for 15 minutes at 22° C. with test compound at different concentrations or without test compound (as a negative control). The assay buffer contains 25 mM HEPES pH 8.0, 10 mM $Mg(CH_3COO)_2$, 1 mM $MnCl_2$, 0.1% BSA, 0.01% Brij® 35, and 5 mM dithiothreitol (DTT). An Echo 555 (Labcyte) is used for dispensing of compound solutions. Then, in a second step, purified human recombinant cmyc-tagged p53 (human p53, full length, GenBank ID: BC003596, expressed in Sf21 insect cells) and ATP are added and the reaction mixture is incubated for 25-35 minutes, typically 25 minutes, at 22° C. The pharmacologically relevant assay volume is 5 µl. The final concentrations in the assay during incubation of the reaction mixture are 0.3-0.5 nM, typically 0.3 nM, ATR/ATRIP, 50 nM p53, and 0.5 µM ATP. The enzymatic reaction is stopped by the addition of EDTA. The generation of phosphorylated p53 as a result of the ATR mediated reaction in the presence of ATP is detected by using specific antibodies [labeled with the fluorophores europium (Eu) as donor and d2 as acceptor (Cisbio Bioassays)] enabling FRET. For this purpose, 2 µl of antibody-containing stop solution (12.5 mM HEPES pH 8.0, 125 mM EDTA, 30 mM sodium chloride, 300 mM potassium fluoride, 0.006% Tween-20, 0.005% Brij® 35, 0.21 nM anti-phospho-p53(Ser15)-Eu antibody, 15 nM anti-cmyc-d2 antibody) are added to the reaction mixture. Following signal development for 2 h the plates are analyzed in an EnVision (PerkinElmer) microplate reader using the TRF mode with laser excitation. Upon excitation of the donor europium at 340 nm the emitted fluorescence light of the acceptor d2 at 665 nm as well as from the donor Eu at 615 nm are measured. The amount of phosphorylated p53 is directly proportional to the ratio of the amounts of emitted light i.e. the ratio of the relative fluorescence units (rfu) at 665 nm and 615 nm. Data are processed employing the Genedata Screener software. In particular, $IC_{50}$ values are determined in the usual manner by fitting a dose-response curve to the data points using nonlinear regression analysis.

$IC_{50}$=half maximal inhibitory concentration
ATP=Adenosine triphosphate
TR-FRET=Time-Resolved Fluorescence Resonance Energy Transfer
HTRF®=Homogeneous Time Resolved Fluorescence
HEPES=2-(4-(2-Hydroxyethyl)-1-piperazinyl)-ethane-sulfonic acid
$Mg(CH3COO)_2$=Magnesium acetate
$MnCl_2$=Manganese(II)-chloride
BSA=Bovine Serum Albumin
EDTA=Ethylendiamine Tetraacetate
TRF=Time Resolved Fluorescence $pCHK_1$ Cellular Assay Chk1 kinase acts downstream of ATR and has a key role in DNA damage checkpoint control. Activation of Chk1 involves phosphorylation of Ser317 and Ser345 (regarded as the preferential target for phosphorylation/activation by ATR) and occurs in response to blocked DNA replication and certain forms of genotoxic stress. Phosphorylation at Ser 345 serves to localize Chk1 to the nucleus following checkpoint activation.

This assay measures a decrease in phosphorylation of Chk1 (Ser 345) in HT29 colon adenocarcinoma cells following treatment with compound and hydroxyurea (which promotes fork stalling because of dNTP depletion) and using an immunocytochemical procedure and high content imaging.

For the assay HT29 cells are plated in culture medium (DMEM high Glucose (no phenol red), 2 mM Glutamax, 1 mM Pyruvate, 10% FCS into Greiner 384 well plates, black, µclear #781090 (2500 cells/well/30 µl) and incubated for at least 20 hours at 37° C., 10% CO2 and 90% rH. Diluted test compounds (1 nM-30 µM final) and hydroxyurea (3 mM final) are added simultaneously and cells are incubated for 4 h at 37° C. After fixation/prmeabilisation with 100% MeOH (−20° C. cold) and permeabilisation with 0.2% Triton X-100 a complete immunocytochemical procedure is performed using a specific anti-pChk1 antibody (Cell Signaling, #2348BF) and fluorescently labelled secondary antibody (Alexa Fluor® 488 goat anti-rabbit F(ab')2 fragment, Invitrogen A11070) and parallel nuclear staining for cell counting.

The nuclear localised pChk1 signal is detected on an ImageXpress Ultra confocal high content reader and reported as % positive cells (nuclei).

Kv11.1 (hERG) Ion Channel Activity

In this assay, a potential in vitro effect of test compounds on the Kv11.1 (hERG) ion channel current is investigated which mediates the rapidly activating, delayed rectifier cardiac potassium current (IKr). The assay is performed with a stable Kv11.1 (hERG) transfected human embryonic kidney cell line (HEK293) by whole cell patch clamp technique carried out at room temperature.

The Kv11.1 (hERG) ion channel blocker quinidine is used as reference compound. The effects of the test compounds and quinidine are normalized to the corresponding vehicle control. The whole cell recordings are carried out with an automated patch clamp device Patchliner™, Nanion Technologies, Munich). Hereby the Patch Clamp measurements run on silicate-coated chips with a hole of a defined diameter. Solutions, cell suspension and compounds are applied by a Teflon-laminated pipette needle through microfluidic silicate-laminated channels. Commercial patch clamp amplifiers ($EPC_{10}$, HEKA Elektronik Dr. Schulze GmbH, Germany) are used for the patch clamp recordings. HEK293 cells stably expressing the hERG gene are held at −80 mV. Steady-state inhibition of Kv11.1 (hERG) potassium current due to test/reference compound application is measured using a pulse pattern with fixed amplitudes: 51 ms/−80 mV, 500 ms/+40 mV, 500 ms/−40 mV, 200 ms/−80 mV. The hERG-specific voltage protocol is repeated at 10 s intervals. The leak current is subtracted by a P4 leak subtraction. Cells are resuspended in extracellular patch clamp solution (EC) and applied into the chip. After trapping the cell, the EC is exchanged by seal enhancer solution (SE) to improve the sealing procedure. When the whole cell configuration is attained, seal enhancer is washed out by the application of EC. The recording is started in EC for 1.5 min. Afterwards DMSO (vehicle control, 0.1% DMSO) is applied and the control current is measured for 3 min. Following control steady-state current, test compound is applied twice at the same concentration and the tail current is measured for 3.5 min each. For the determination of a concentration-relationship, the test compound is applied as a cumulative concentration-response curve and each concentration is measured for 5 min. The reference compound quinidine is treated in the same way. The effect on Kv11.1 (hERG) ion channel activity is judged from the tail current amplitude monitored at −40 mV (current of interest, COI). Results are calculated from the last recorded current traces. Changes in Kv11.1 (hERG) ion channel activity between control value, defined as 100% Kv11.1 (hERG) ion channel activity, application of test compound and application of quinidine is reported as percent change of control value of COI. An aliquot of test compound is collected for concentration verification during the recording. The sample is immediately measured by HPLC and the final compound concentration within the assay is calculated according to a calibration curve.

Pharmacological Data

TABLE 1

Inhibition ($IC_{50}$) of ATR-ATRIP; pCHK1 cellular assay; Kv11.1 (hERG) ion channel activity

| Compound No. | ATR-ATRIP $IC_{50}$ [M] | pCHK1 $IC_{50}$ [M] | hERG Ki (nM/% effect @ conc) |
|---|---|---|---|
| 1 | 2.3 | xxx | >30.000/−28% effect @ 30 µM |
| 2 | 0.8 | xxx | >10.000/−3% effect @ 10 µM |
| 3 | 0.9 | xxx | |
| 4 | 0.8 | xxx | >10.000/−12% effect @ 10 µM |
| 5 | 3.5 | xxx | >10.000/−22% effect @ 10 µM |
| 6 | 8.9 | xx | |
| 7 | 2.3 | xxx | >10.000/−16% effect @ 10 µM |
| 8 | 2.1 | xxxx | >10.000/−6% effect @ 10 µM |
| 9 | 4.1 | xxx | |
| 10 | 1.9 | xxx | |
| 11 | 0.9 | xxx | >10.000/−5% effect @ 10 µM |
| 12 | 0.8 | xx | |

TABLE 1-continued

Inhibition (IC$_{50}$) of ATR-ATRIP;
pCHK1 cellular assay;
Kv11.1 (hERG) ion channel activity

| Compound No. | ATR-ATRIP IC$_{50}$ [M] | pCHK1 IC$_{50}$ [M] | hERG Ki (nM/% effect @ conc) |
|---|---|---|---|
| 13 | 1.4 | xx | |
| 14 | 99.0 | x | |
| 15 | 0.6 | xxx | >10.000/−24% effect @ 10 μM |
| 16 | 67.0 | x | |
| 17 | 3.6 | xxx | >10.000/5% effect @ 10 μM |
| 18 | 6.2 | xx | >10.000/−14% effect @ 10 μM |
| 19 | 3.4 | xxx | >10.000/−6% effect @ 10 μM |
| 20 | 1.2 | xxx | >10.000/−11% effect @ 10 μM |
| 21 | 510.0 | | |
| 22 | 3.3 | xx | |
| 23 | 1.0 | xxx | |
| 24 | 28.0 | xx | |
| 25 | 4.3 | xxx | >10.000/−1% effect @ 10 μM |
| 26 | 0.8 | xxx | >30.000/−24% effect @ 30 μM |
| 27 | 10.0 | xx | |
| 28 | 5.3 | xx | |
| 29 | 5.4 | x | |
| 30 | 15.0 | xx | |
| 31 | 33.0 | xx | |
| 32 | 20.0 | x | |
| 33 | 16.0 | xx | |
| 34 | 6.1 | xxx | >10.000/−1% effect @ 10 μM |
| 35 | 0.5 | xxx | >10.000/−23% effect @ 10 μM |
| 36 | 0.6 | xxx | >10.000/−9% effect @ 10 μM |
| 37 | 7.9 | xx | |
| 38 | 4.3 | xx | |
| 39 | 7.9 | xx | |
| 40 | 50.6 | xx | >10.000/9% effect @ 10 μM |
| 41 | 1.3 | xxx | |
| 42 | 0.3 | xxxx | >30.000/−26% effect @ 30 μM |
| 43 | 3.9 | xx | |
| 44 | 4.2 | xx | |
| 45 | 1800.0 | | |
| 46 | 25.0 | x | |
| 47 | 89.0 | x | |
| 48 | 2.0 | xxx | >10.000/−32% effect @ 10 μM |
| 49 | 1.8 | xxx | >10.000/−18% effect @ 10 μM |
| 50 | 1.3 | xxxx | >10.000/−17% effect @ 10 μM |
| 51 | 1.2 | xx | |
| 52 | 1.4 | xxx | |
| 53 | 58.0 | x | |
| 54 | 2.2 | xxx | >10.000/−2% effect @ 10 μM |
| 55 | 0.7 | xxx | >10.000/−14% effect @ 10 μM |
| 56 | 25.0 | x | |
| 57 | 150.0 | x | |
| 58 | 10.0 | xx | |
| 59 | 21.0 | x | |
| 60 | 32.0 | x | |
| 61 | 0.6 | xxx | >30.000/−12% effect @ 30 μM |
| 62 | 22.0 | x | |
| 63 | 27.0 | xx | |
| 64 | 51.0 | x | |
| 65 | 5.8 | xx | |
| 66 | 1.9 | xxxx | |
| 67 | 0.8 | xxx | >10.000/−12% effect @ 10 μM |
| 68 | | xxx | >30.000/−35% effect @ 30 μM |
| 69 | | xxx | >30.000/−29% effect @ 30 μM |
| 70 | 2.2 | xxx | >10.000/−20% effect @ 10 μM |
| 71 | | xxx | >10.000/−16% effect @ 10 μM |
| 72 | | xxx | |
| 73 | 28.0 | xx | |
| 74 | 17.0 | | |
| 75 | 21.0 | xx | |
| 76 | 28.0 | xx | |
| 77 | 58.0 | x | |
| 78 | | xxx | >30.000/−12% effect @ 30 μM |
| 79 | | xxx | |
| 80 | | xx | |
| 81 | 3 | xx | |
| 82 | 0.8 | xx | |
| 83 | | x | |
| 84 | | xxx | |
| 85 | 21 | x | |

TABLE 1-continued

Inhibition (IC$_{50}$) of ATR-ATRIP;
pCHK1 cellular assay;
Kv11.1 (hERG) ion channel activity

| Compound No. | ATR-ATRIP IC$_{50}$ [M] | pCHK1 IC$_{50}$ [M] | hERG Ki (nM/% effect @ conc) |
|---|---|---|---|
| 86 | 24 | x | |
| 87 | 0.4 | xxx | |
| 88 | | x | |
| 89 | 0.9 | x | | pCHK1:

<10 nM = xxxx xxx: 10-100 nM xx: 100-1000 nM x: 1000-10000 nM

The compounds shown in Table 1 are particularly preferred compounds according to the invention.

Description of the Synthesis Scheme and Compound Examples:

In the following formulae "abs" means the absolute stereochemistry as indicated.

Azaindazole derivatives can be synthesized according to scheme 1.

Scheme 1: Synthesis route to azaindazole 10

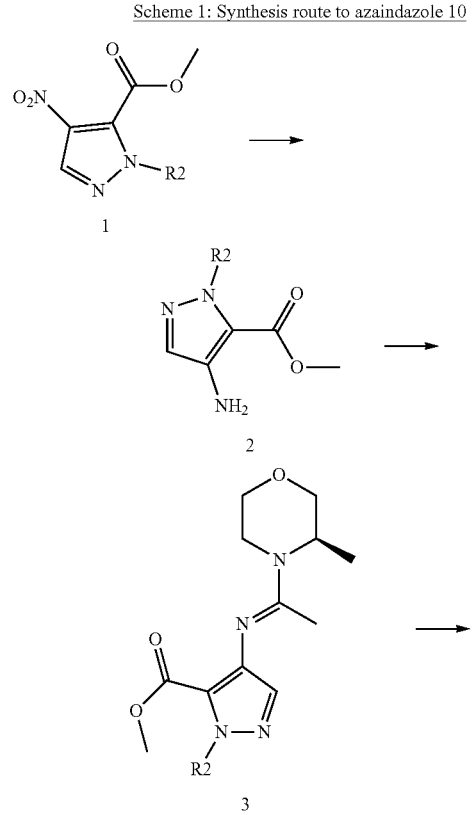

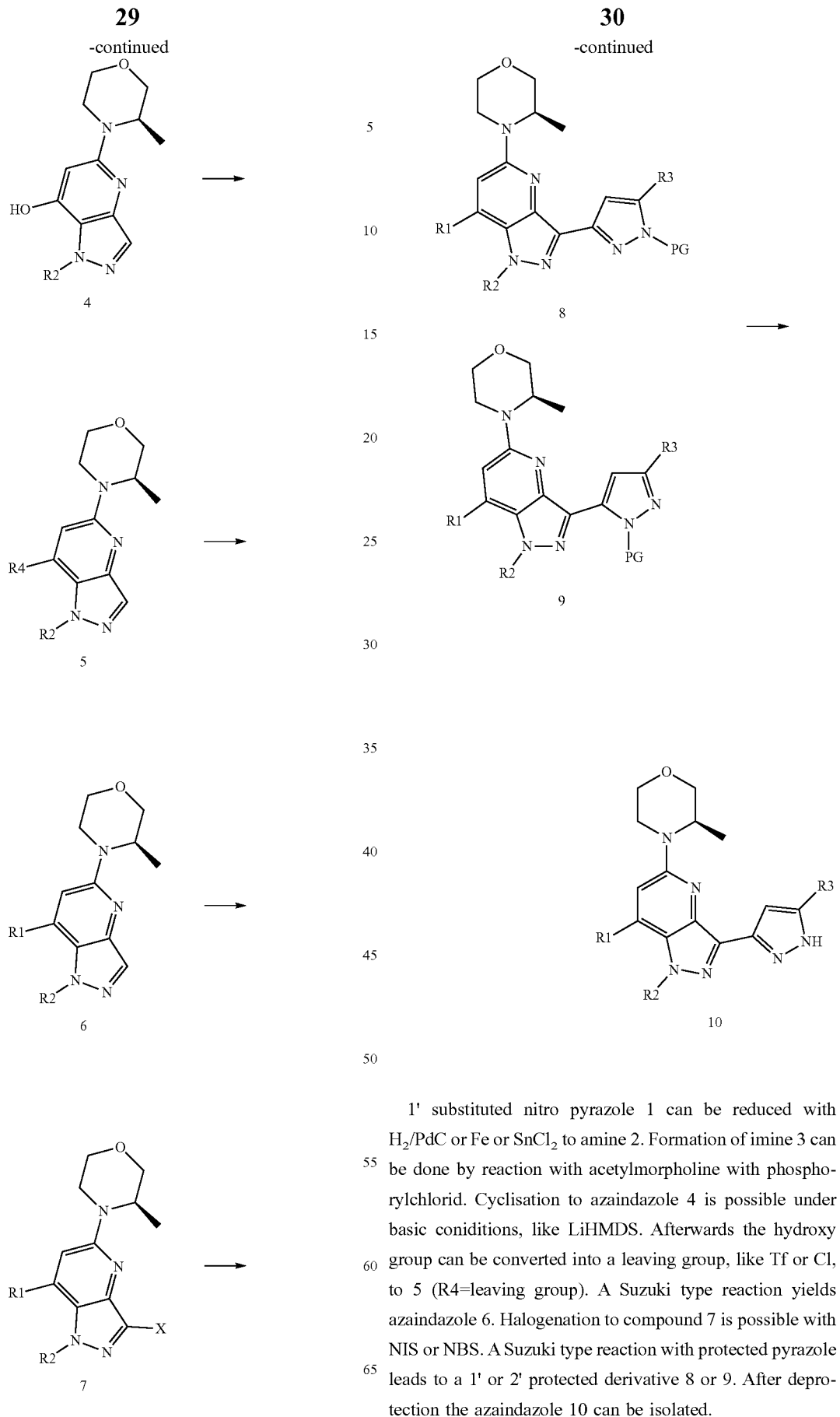

1' substituted nitro pyrazole 1 can be reduced with H₂/PdC or Fe or SnCl₂ to amine 2. Formation of imine 3 can be done by reaction with acetylmorpholine with phosphorylchlorid. Cyclisation to azaindazole 4 is possible under basic coniditions, like LiHMDS. Afterwards the hydroxy group can be converted into a leaving group, like Tf or Cl, to 5 (R4=leaving group). A Suzuki type reaction yields azaindazole 6. Halogenation to compound 7 is possible with NIS or NBS. A Suzuki type reaction with protected pyrazole leads to a 1' or 2' protected derivative 8 or 9. After deprotection the azaindazole 10 can be isolated.

Unsubstituted azaindazole derivatives can be synthesized according Scheme 2.

Scheme 2: Synthesis route to unsubstituted azaindazole 13

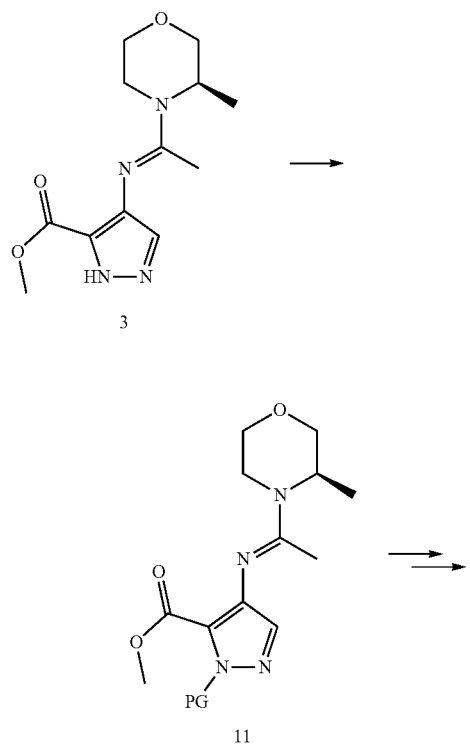

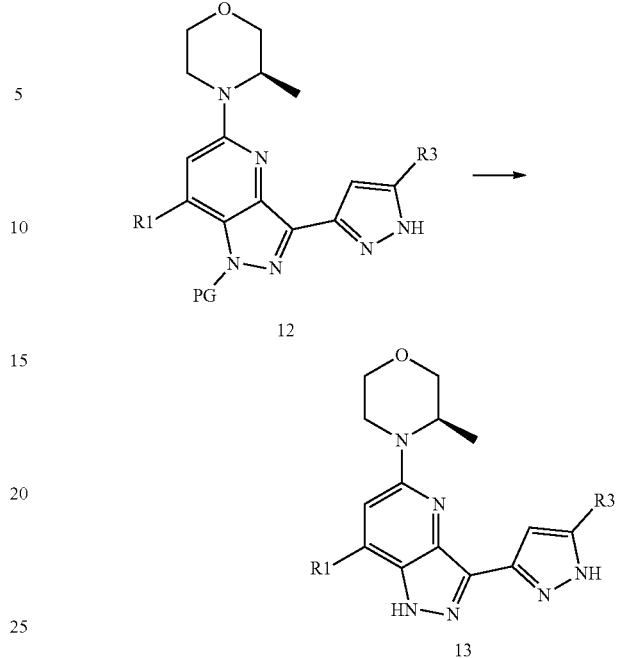

Starting from 3 (R2=H), a protecting group can be introduced at the azaindazole core to 11. The following steps are as described as in scheme 1. The protecting group can be removed in the last step from 12 to yield unsubstituted azaindazole 13.

An alternative route to azaindazole derivatives starting from pyridine derivatives is described in Scheme 3.

Scheme 3: Alternative synthesis route to Azaindazole 10

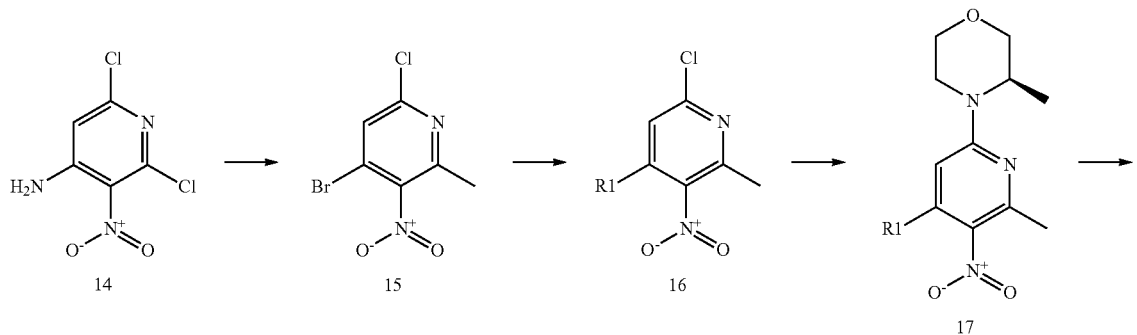

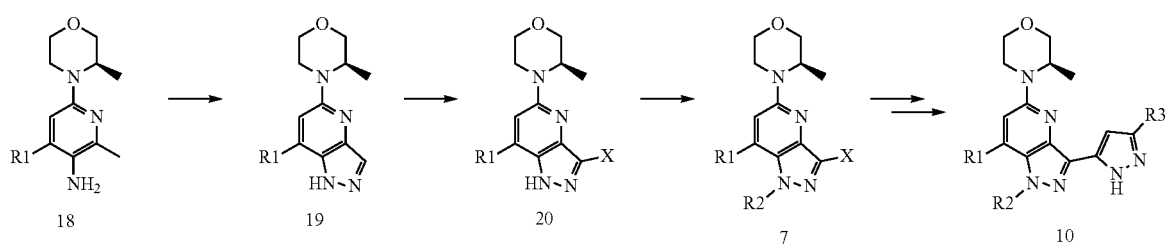

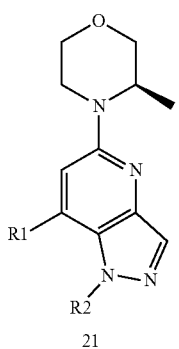

21

2,6-Dichloro-3-nitropyridin-4-amine 14 can be brominated under Sandmeyer conditions to 15. A Suzuki type reaction leads to 16. The methyl morpholine can be introduced to 17 under Buchwald conditions or via nucleophilic aromatic substitution under basic conditions. The nitro group can be reduced with $H_2$/PdC or Fe or $SnCl_2$ to amine 18. Cyclisation to 19 is possible with sodium nitrite in acetic acid. This compound can be halogenated with NBS, NIS, $Br_2$ or $I_2$ to 20 and alkylation to 7. Alternatively, 7 can be prepared from 19 by alkylation to 21 and halogenation with NBS or NIS. The steps from 7 to 10 are as described as in scheme 1.

Azaindazole derivatives can also be synthesized according Scheme 4.

Scheme 4: Alternative Suzuki type reaction to azaindazole 6 and subsequently to 10.

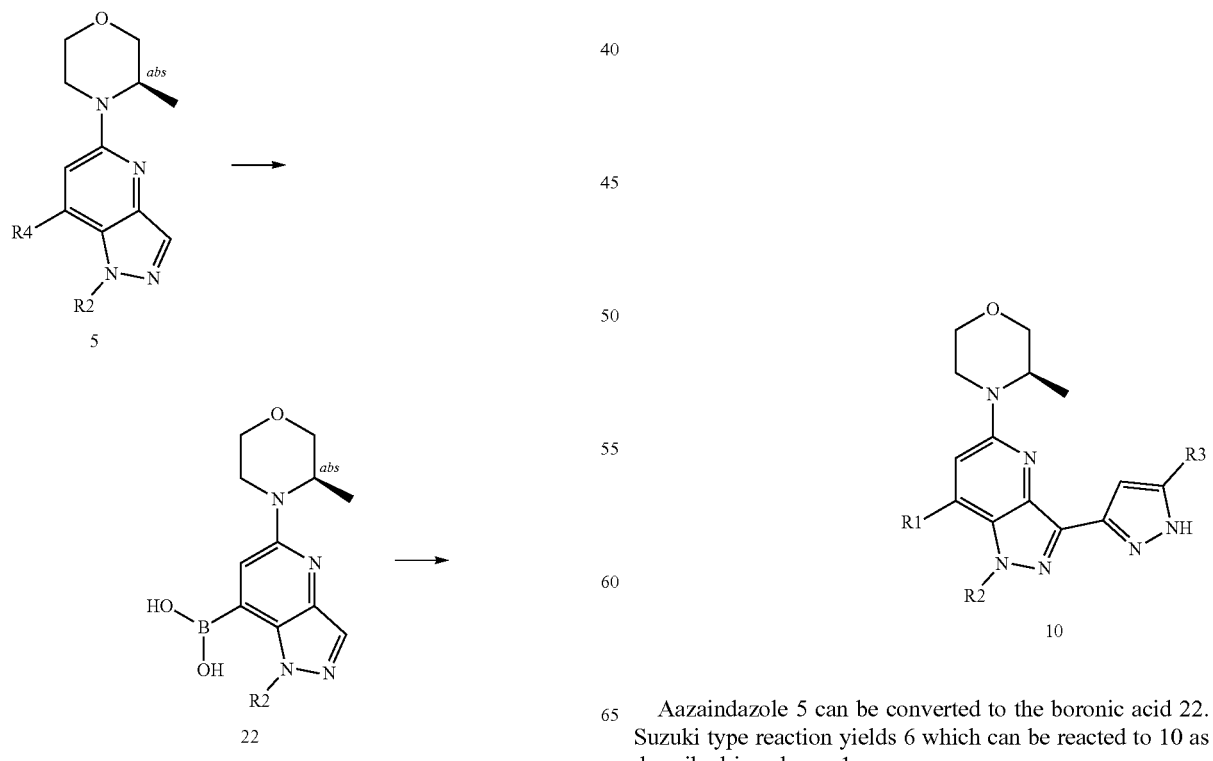

Aazaindazole 5 can be converted to the boronic acid 22. Suzuki type reaction yields 6 which can be reacted to 10 as described in scheme 1.

Azaindazole derivatives without a substitution at $R^1$ ($R^1$=H) can be synthesized according Scheme 5.

Scheme 5: Synthesis route to azaindazole 24

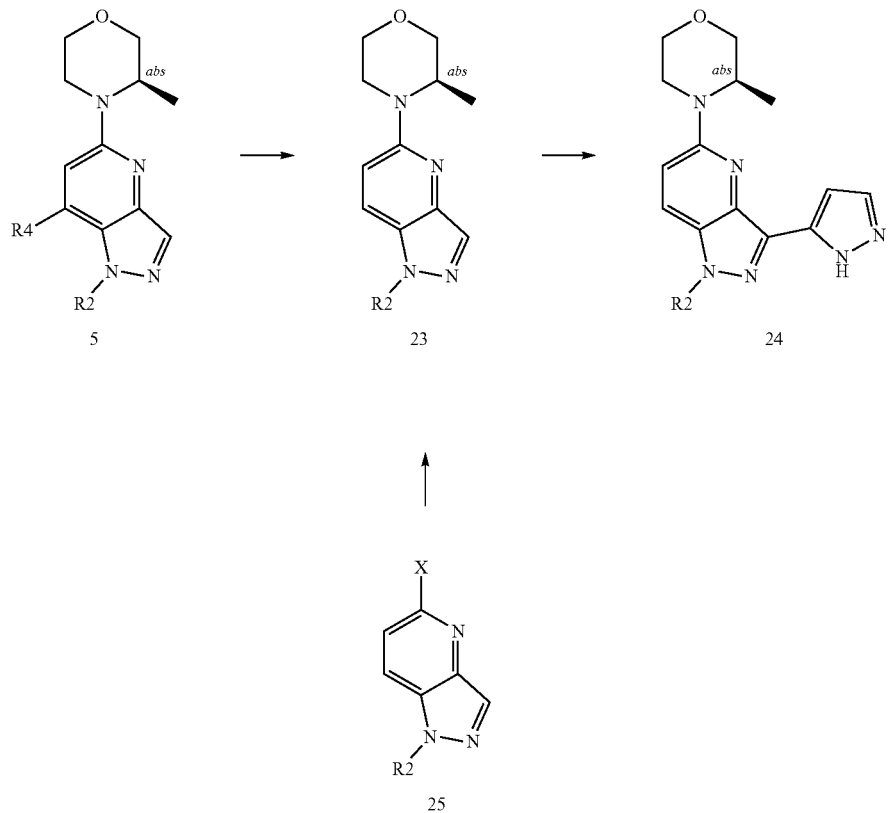

Starting from azaindazole 5 with $PdCl_2$ and a phosphine ligand, like dppf, azaindazole 23 can be prepared. Alternatively, azaindazole 25 can be reacted under Buchwald conditions to azaindazole 23. Reaction steps to 24 are as in scheme 1 described for the synthesis of azaindazole 10.

An alternative synthesis route to azaindazole 34 is described in scheme 6.

Scheme 6: Synthesis route to cyclopropyl azaindazole 35

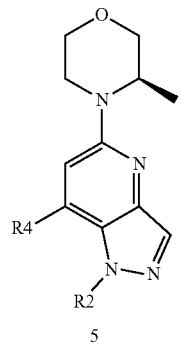

-continued

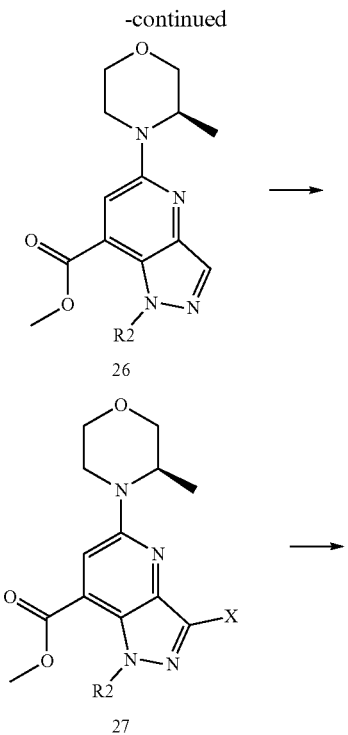

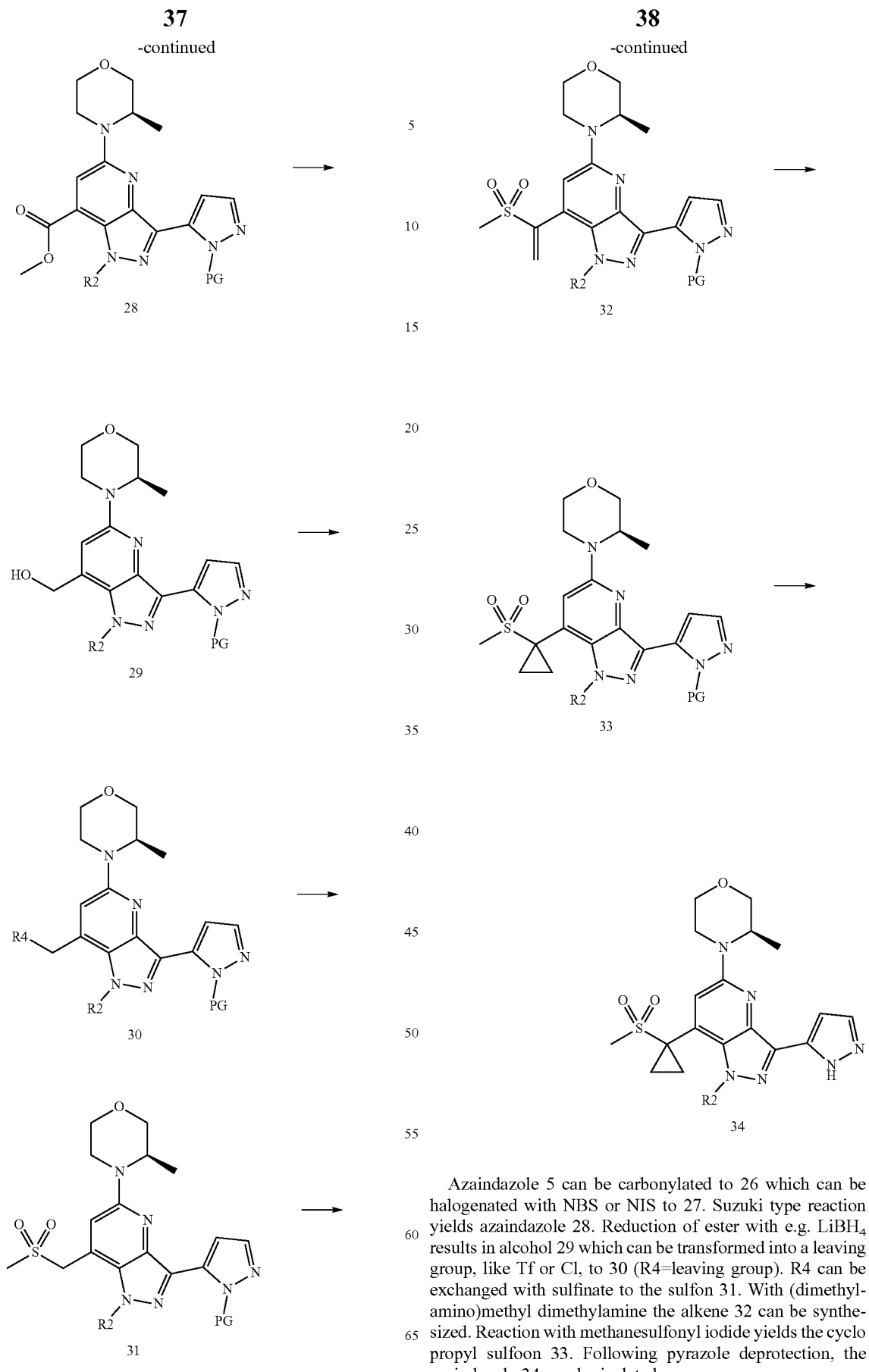

Azaindazole 5 can be carbonylated to 26 which can be halogenated with NBS or NIS to 27. Suzuki type reaction yields azaindazole 28. Reduction of ester with e.g. LiBH₄ results in alcohol 29 which can be transformed into a leaving group, like Tf or Cl, to 30 (R4=leaving group). R4 can be exchanged with sulfinate to the sulfon 31. With (dimethylamino)methyl dimethylamine the alkene 32 can be synthesized. Reaction with methanesulfonyl iodide yields the cyclo propyl sulfoon 33. Following pyrazole deprotection, the azaindazole 34 can be isolated.

Cyclopropyl azaindazole derivative 34 can alternatively be synthesized as described in scheme 7.

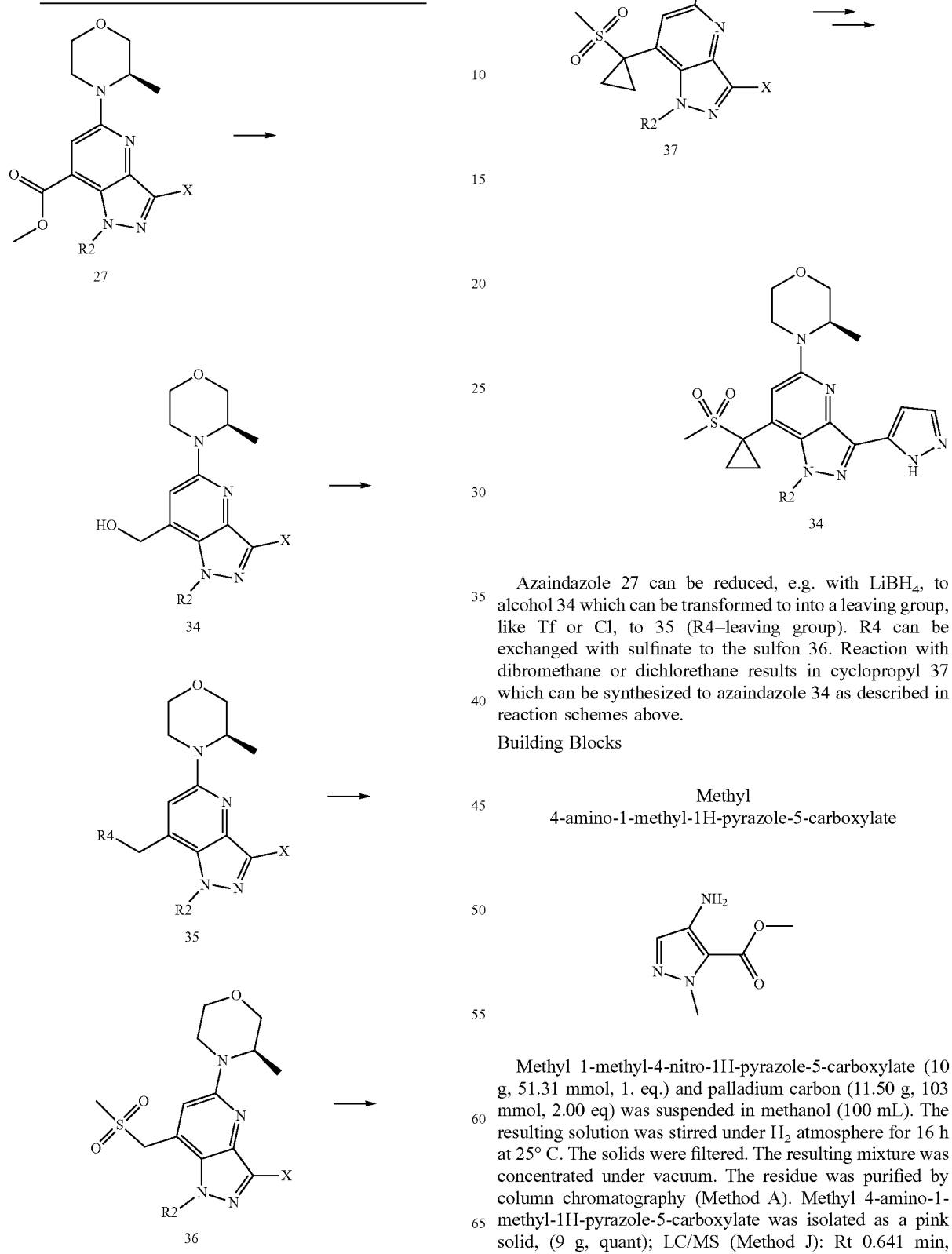

Azaindazole 27 can be reduced, e.g. with LiBH$_4$, to alcohol 34 which can be transformed to into a leaving group, like Tf or Cl, to 35 (R4=leaving group). R4 can be exchanged with sulfinate to the sulfon 36. Reaction with dibromethane or dichlorethane results in cyclopropyl 37 which can be synthesized to azaindazole 34 as described in reaction schemes above.

Building Blocks

Methyl 4-amino-1-methyl-1H-pyrazole-5-carboxylate

Methyl 1-methyl-4-nitro-1H-pyrazole-5-carboxylate (10 g, 51.31 mmol, 1. eq.) and palladium carbon (11.50 g, 103 mmol, 2.00 eq) was suspended in methanol (100 mL). The resulting solution was stirred under H$_2$ atmosphere for 16 h at 25° C. The solids were filtered. The resulting mixture was concentrated under vacuum. The residue was purified by column chromatography (Method A). Methyl 4-amino-1-methyl-1H-pyrazole-5-carboxylate was isolated as a pink solid, (9 g, quant); LC/MS (Method J): Rt 0.641 min, [MH]+156.1 m/z.

1-[(3R)-3-Methylmorpholin-4-yl]ethan-1-one

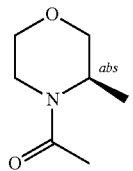

(3R)-3-Methylmorpholine (12 g, 112.71 mmol), potassium carbonate (86.08 g, 591.70 mmol, 5.25 eq) were dissolved in dichloromethane (280 mL) and stirred for 30 min at 0° C. To this was added acetyl chloride (32.60 g, 395 mmol, 3.50 eq.). The resulting solution was stirred for 16 h at 25° C. The solids were filtered out. The resulting mixture was concentrated under vacuum to obtain 1-[(3R)-3-methylmorpholin-4-yl]ethan-1-one as yellow oil (15 g, 88%);

LC/MS (Method J): Rt 1.151 min, [MH]+144.0 m/z.

Methyl 1-methyl-4-[(E)-{1-[(3R)-3-methylmorpholin-4-yl]ethylidene}amino]-1H-pyrazole-5-carboxylate

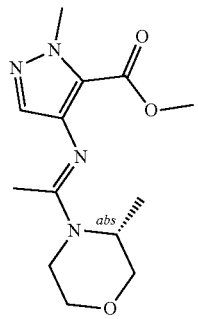 [SMILES: COC(=O)c1c(/N=C(\C)N2CCOC[C@H]2C)cnn1C]

Methyl 4-amino-1-methyl-1H-pyrazole-5-carboxylate (9 g, 52.21 mmol) and 1-[(3R)-3-methylmorpholin-4-yl]ethan-1-one (15 g, 94.28 mmol, 1.81 eq.) were dissolved in DCE (200 mL, 2.40 mol) and stirred at 0° C. for 0.5 h. To this was added phosphorylchlorid (40 g, 247.95 mmol, 4.75 eq.). The resulting solution was stirred for 16 h at 40° C. The reaction was then quenched by the addition of 20 mL of NH₄Cl. The resulting solution was extracted with ethyl acetate and the organic layers combined and concentrated under vacuum. The residue was purified by column chromatography (Method B). Methyl 1-methyl-4-[(E)-[1-[(3R)-3-methylmorpholin-4-yl]ethylidene]amino]-1H-pyrazole-5-carboxylate was isolated as a yellow solid (11 g, 68%); LC-MS (Method J) Rt: 0.664 min, [MH]+281.2.

1-methyl-5-[(3R)-3-methylmorpholin-4-yl]-1H-pyrazolo[4,3-b]pyridin-7-ol

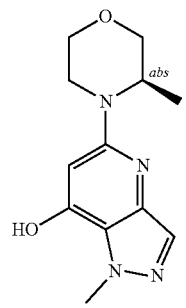 [SMILES: C[C@@H]1COCCN1c1cc(O)c2c(cnn2C)n1]

Methyl 1-methyl-4-[(E)-[1-[(3R)-3-methylmorpholin-4-yl]ethylidene]amino]-1H-pyrazole-5-carboxylate (11 g, 35.32 mmol, 1. eq.) was dissolved in DMF (300 mL). The solution was stirred for 30 min at 0° C. To this was added LiHMDS (100 mL, 6.19 mmol). The resulting solution was stirred for 1 h at 0° C. in a water/ice bath. The reaction was then quenched by the addition of aq. NH₄Cl. The resulting solution was extracted with ethyl acetate and the organic layers combined and dried over anhydrous sodium sulfate and concentrated under vacuum. The residue was purified by column chromatography (Method A) and re-crystallized by ethylaceate. 1-Methyl-5-[(3R)-3-methylmorpholin-4-yl]-1H-pyrazolo[4,3-b]pyridin-7-ol was obtained as a colorless solid (6 g, 68%);

LC/MS (Method B): Rt 1.458 min, [MH]+249.2.

1-Methyl-5-[(3R)-3-methylmorpholin-4-yl]-1H-pyrazolo[4,3-b]pyridin-7-yl trifluoromethane-sulfonate

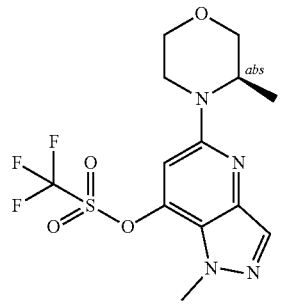 [SMILES: C[C@@H]1COCCN1c1cc(OS(=O)(=O)C(F)(F)F)c2c(cnn2C)n1]

1-Methyl-5-[(3R)-3-methylmorpholin-4-yl]-1H-pyrazolo[4,3-b]pyridin-7-ol (6 g, 21.75 mmol, 1.00 eq), DCM (700 mL), DIEA (20.26 g, 148.92 mmol, 3.16 eq.) and 1,1,1-trifluoro-N-phenyl-N-(trifluoromethane)sulfonylmethane-sulfonamide (37.39 g, 99.43 mmol, 2.11 eq.) were combined and stirred for 16 h at room temperature. The resulting mixture was concentrated under vacuum. The residue was purified by column chromatography (Method C). 1-Methyl-5-[(3R)-3-methylmorpholin-4-yl]-1H-pyrazolo[4,3-b]pyridin-7-yl trifluoromethane-sulfonate was isolated as yellow oil (18 g, 90%); LC/MS (Method L): Rt 0.978 min, [MH]+381.0.

Trifluoro-methanesulfonic acid 1-isopropyl-5-((R)-3-methyl-morpholin-4-yl)-1H-pyrazolo[4,3-b]pyridin-7-yl ester

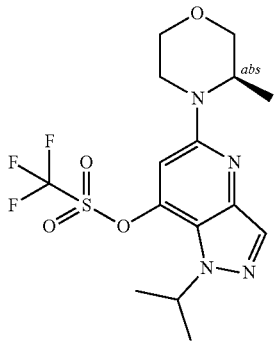 [SMILES: CC(C)n1ncc2nc(N3CCOC[C@H]3C)cc(OS(=O)(=O)C(F)(F)F)c21]

Trifluoro-methanesulfonic acid 1-isopropyl-5-((R)-3-methyl-morpholin-4-yl)-1H-pyrazolo[4,3-b]pyridin-7-yl ester building block was prepared analogously to above building blocks. Trifluoro-methanesulfonic acid 1-isopropyl-5-((R)-3-methyl-morpholin-4-yl)-1H-pyrazolo[4,3-b]pyridin-7-yl ester was isolated as brown solid (105 mg, 86%); LC/MS (Method F): Rt 2.781 min; [MH]+409.1 m/z.

4-Amino-2H-pyrazole-3-carboxylic acid methyl ester

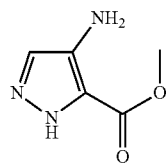

4-Nitro-2H-pyrazole-3-carboxylic acid methyl ester (3 g, 0.017 mol) and Pd—C 5% (0.75 g) were suspended in methanol (30 ml) and stirred under hydrogen for 14 h at RT. The suspension was filtered and the solvent removed under vacuo. 4-Amino-2H-pyrazole-3-carboxylic acid methyl ester was isolated as a pale pink solid (2.4 g, quant); LC/MS (Method F) Rt 0.363 min; [MNa]+164.1 m/z.

4-[1-((R)-3-Methyl-morpholin-4-yl)-eth-(E)-ylideneamino]-2H-pyrazole-3-carboxylic acid methyl ester

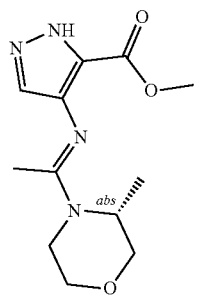 [SMILES: COC(=O)c1[nH]ncc1/N=C(\C)N1CCOC[C@H]1C]

1-((R)-3-Methyl-morpholin-4-yl)-ethanone (3.409 g; 23.808 mmol; 1.40 eq.) was dissolved in 1,2-dichloroethane (24 ml) and phosphoryl chloride (4.684 ml; 51.018 mmol; 3 eq.) was added dropwise. The brown solution was stirred for 30 minutes at RT and then 4-amino-2H-pyrazole-3-carboxylic acid methyl ester (2.400 g; 17.006 mmol; 1 eq.) was added and stirred at 80° C. for 2 hours. The reaction solution was evaporated to dryness. The residue was suspended in water (50 ml) and pH adjusted to 12 with aq NaOH (32%) and extracted with EtOAc. Combined organic phases were dried over sodium sulfate, filtered and evaporated to dryness. 4-[1-((R)-3-Methyl-morpholin-4-yl)-eth-(E)-ylideneamino]-2H-pyrazole-3-carboxylic acid methyl ester was isolated as yellow solid (5 g, quant); LC/MS (Method F): Rt 0.968 min; [MH]+267 m/z.

4-[1-((R)-3-Methyl-morpholin-4-yl)-eth-(E)-ylideneamino]-2-(2-trimethylsilanyl-ethoxymethyl)-2H-pyrazole-3-carboxylic acid methyl ester

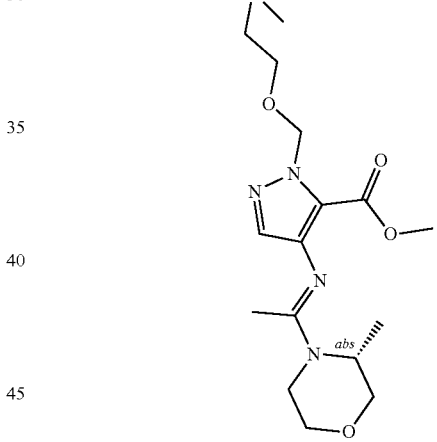

4-[1-((R)-3-Methyl-morpholin-4-yl)-eth-(E)-ylideneamino]-2H-pyrazole-3-carboxylic acid methyl ester (1 g; 3.755 mmol) was suspended in THF (20 ml) and triethylamine (781 µl; 5.633 mmol; 1.50 eq.) and 2-(trimethylsilyl)ethoxy-methyl chloride (731.084 µl; 4.131 mmol; 1.10 eq.) were added and stirred for 1 hours at RT. The solvent was removed under vacuo and extracted with EtOAc/water. The combined organic phases were dried over sodium sulfate and evaporated to dryness. The crude product was purified by column chromatography (Method D). 4-[1-((R)-3-Methyl-morpholin-4-yl)-eth-(E)-ylideneamino]-2-(2-trimethylsilanyl-ethoxymethyl)-2H-pyrazole-3-carboxylic acid methyl ester was isolated as colorless solid (580 mg, 38%); LC/MS (Method F): Rt 2.251 min, [MH]+397.2 m/z.

5-((R)-3-Methyl-morpholin-4-yl)-1-(2-trimethylsilanyl-ethoxymethyl)-1H-pyrazolo[4,3-b]pyridin-7-ol

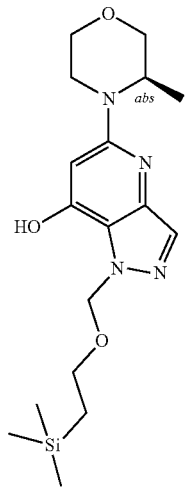

4-[1-((R)-3-Methyl-morpholin-4-yl)-eth-(E)-ylideneamino]-2-(2-trimethylsilanyl-ethoxymethyl)-2H-pyrazole-3-carboxylic acid methyl ester (200 mg; 0.494 mmol; 1, eq.) was dissolved in THF (3 ml) and lithium bis(trimethylsilyl)amide solution 1 M in THF (1.977 ml; 1.977 mmol; 4, eq.) was added and stirred at RT for 2 hours. To the reaction solution water (0.2 ml) was added and the solvent removed under vacuo. The residue was suspended in water (2 ml) and the pH adjusted to 7 with 2 N HCl and saturated ammmonium chloride solution and extracted with DCM. The combined organic phases were dried, filtered and evaporated. 5-((R)-3-Methyl-morpholin-4-yl)-1-(2-trimethylsilanyl-ethoxymethyl)-1H-pyrazolo[4,3-b]pyridin-7-ol was isolated as yellow solid (182 mg, 95%); LC/MS (Method F): Rt 2.28 min; [MH]+365.2 m/z.

Trifluoro-methanesulfonic acid 5-((R)-3-methyl-morpholin-4-yl)-1-(2-trimethylsilanyl-ethoxymethyl)-1H-pyrazolo[4,3-b]pyridin-7-yl ester

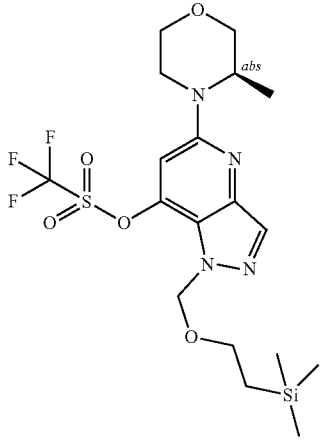 [SMILES: C[C@@H]1COCCN1c1cc(OS(=O)(=O)C(F)(F)F)c2c(cnn2COCC[Si](C)(C)C)n1]

5-((R)-3-Methyl-morpholin-4-yl)-1-(2-trimethylsilanyl-ethoxymethyl)-1H-pyrazolo[4,3-b]pyridin-7-ol (50 mg; 0.137 mmol; 1.0 eq.) was dissolved in DCM (1 ml) and triethylamine (34.226 μl; 0.247 mmol; 1.80 eq.) was added. The reaction mixture was cooled down to 5° C. and trifluoromethanesulfonic anhydride (41 μl; 0.247 mmol; 1.80 eq.) was added and stirred for 1 hour and allowed to warm to RT. The reaction solution was extracted with DCM and water and the combined organic phase washed with brine, dried over sodium sulfate, filtered and evaporated to dryness. Trifluoro-methanesulfonic acid 5-((R)-3-methyl-morpholin-4-yl)-1-(2-trimethylsilanyl-ethoxymethyl)-1H-pyrazolo[4,3-b]pyridin-7-yl ester was isolated as orange-brown solid (61 mg, 90%). LC/MS (Method F): Rt 3.006 min, [MH]+ 497.1 m/z.

EXAMPLES

Example 1

1-Methyl-5-((R)-3-methyl-morpholin-4-yl)-7-(6-methyl-pyridin-3-yl)-3-(1H-pyrazol-3-yl)-1H-pyrazolo[4,3-b]pyridine (1)

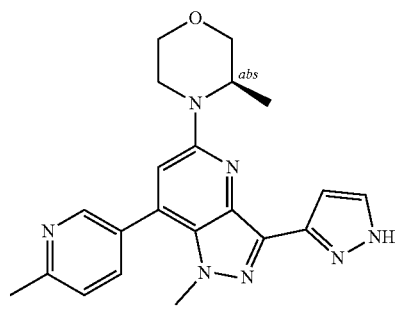 [SMILES: Cc1ccc(-c2cc(N3CCOC[C@H]3C)nc3c(-c4cc[nH]n4)nn(C)c23)cn1]

Building Block for Synthesis of Example 1: (3R)-3-methyl-4-[1-methyl-7-(6-methylpyridin-3-yl)-1H-pyrazolo[4,3-b]pyridin-5-yl]morpholine

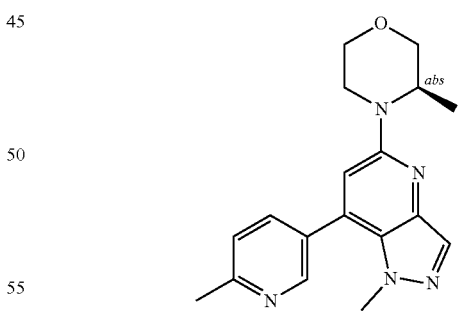

1-Methyl-5-[(3R)-3-methylmorpholin-4-yl]-1H-pyrazolo[4,3-b]pyridin-7-yl trifluoromethanesulfonat (1 g, 2.37 mmol, 1.0 eq.), (6-methylpyridin-3-yl)boronic acid (680 mg, 4.72 mmol, 1.99 eq.), Pd(dppf)Cl$_2$·CH$_2$Cl$_2$ (210 mg, 0.23 mmol, 0.10 eq.) and sodium carbonate (790 mg, 7.08 mmol, 2.99 eq.) were suspended in DMF (12 mL), water (3 mL). The final reaction mixture was heated to 100° C. for 1 h in the microwave. (3R)-3-Methyl-4-[1-methyl-7-(6-methylpyridin-3-yl)-1H-pyrazolo[4,3-b]pyridin-5-yl]morpholine was isolated as a yellow solid (600 mg, 70%).

47

Building Block for Synthesis of Example 1: (3R)-4-[3-bromo-1-methyl-7-(6-methylpyridin-3-yl)-1H-pyrazolo[4,3-b]pyridin-5-yl]-3-methylmorpholine

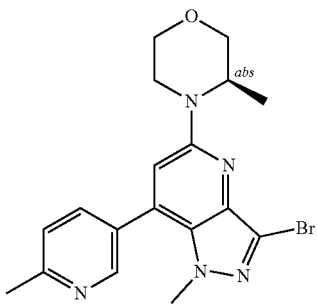 [SMILES: Cc1ccc(-c2cc(N3CCOC[C@H]3C)nc3c(Br)nn(C)c23)cn1]

(3R)-3-Methyl-4-[1-methyl-7-(6-methylpyridin-3-yl)-1H-pyrazolo[4,3-b]pyridin-5-yl]morpholine (12 g, 33.40 mmol, 1. eq.) and NBS (9.39 g, 50.12 mmol, 1.50 eq.) were dissolved in MeCN (480 mL) and stirred for 1 h at 25° C. The resulting mixture was concentrated under vacuum. The residue was purified by column chromatography (Method E). (3R)-4-[3-Bromo-1-methyl-7-(6-methylpyridin-3-yl)-1H-pyrazolo[4,3-b]pyridin-5-yl]-3-methylmorpholine was isolated as a yellow solid (15 g, 100%).

Building Block for Synthesis of Example 1: (3R)-3-methyl-4-[1-methyl-7-(6-methylpyridin-3-yl)-3-[1-(oxan-2-yl)-1H-pyrazol-3-yl]-1H-pyrazolo[4,3-b]pyridin-5-yl]morpholine

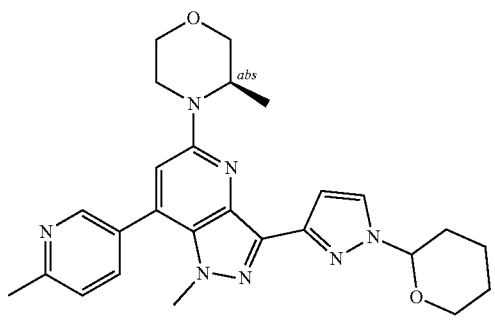 [SMILES: Cc1ccc(-c2cc(N3CCOC[C@H]3C)nc3c(-c4ccn(C5CCCCO5)n4)nn(C)c23)cn1]

(3R)-4-[3-Bromo-1-methyl-7-(6-methylpyridin-3-yl)-1H-pyrazolo[4,3-b]pyridin-5-yl]-3-methylmorpholine (1.20 g, 2.68 mmol, 1.0 eq.), 1-(oxan-2-yl)-3-(tetramethyl-1,3,2-dioxaborolan-2-yl)-1H-pyrazole (2.36 g, 8.06 mmol, 3 eq.), Pd(pph3)4 (340 mg, 0.26 mmol, 0.10 eq.) and sodium carbonate (900 mg, 8.07 mmol, 3 eq.) were suspended in tetrahydrofuran (12 mL), water (3 mL, 158.20 mmol, 58.93 eq.). The resulting solution was stirred for 1 h at 90° C. The resulting solution was extracted with ethyl acetate and the organic layers combined and concentrated under vacuum. The residue was purified by column chromatography (Method E). (3R)-3-Methyl-4-[1-methyl-7-(6-methylpyridin-3-yl)-3-[1-(oxan-2-yl)-1H-pyrazol-3-yl]-1H-pyrazolo[4,3-b]pyridin-5-yl]morpholine was isolated as a yellow solid (700 mg, 50%).

48

Example 1

1-Methyl-5-((R)-3-methyl-morpholin-4-yl)-7-(6-methyl-pyridin-3-yl)-3-(1H-pyrazol-3-yl)-1H-pyrazolo[4,3-b]pyridine (1)

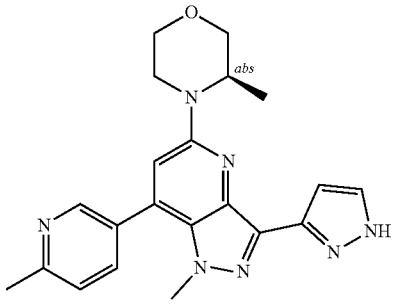 [SMILES: Cc1ccc(-c2cc(N3CCOC[C@H]3C)nc3c(-c4cc[nH]n4)nn(C)c23)cn1]

(3R)-3-Methyl-4-[1-methyl-7-(6-methylpyridin-3-yl)-3-[1-(oxan-2-yl)-1H-pyrazol-3-yl]-1H-pyrazolo[4,3-b]pyridin-5-yl]morpholine (10 g, 19.00 mmol, 1. eq.) was dissolved in methanolic HCl (200 mL). The resulting solution was stirred for 1 h at 25° C. The resulting solution was extracted with ethyl acetate and the organic layers combined and concentrated under vacuum. The crude product was purified by preparative HPLC. 1-Methyl-5-((R)-3-methyl-morpholin-4-yl)-7-(6-methyl-pyridin-3-yl)-3-(1H-pyrazol-3-yl)-1H-pyrazolo[4,3-b]pyridine was isolated as a yellow solid (2 g, 28%); melting point: 118-120° C.; $^1$H NMR (300 MHz, DMSO-$d_6$): δ12.81 (s, 1H), 8.63 (d, J=2.4 Hz, 1H), 7.88 (dd, J=7.9, 2.4 Hz, 1H), 7.62 (s, 1H), 7.41 (d, J=8.1 Hz, 1H), 7.00 (s, 1H), 6.89-6.81 (m, 1H), 4.46 (s, 1H), 4.07-3.90 (m, 2H), 3.72 (s, 1H), 3.62-3.48 (m, 1H), 3.23 (td, J=12.5, 11.7, 3.7 Hz, 1H), 3.01 (s, 1H), 2.58 (d, J=2.8 Hz, 4H), 2.02 (d, J=2.7 Hz, OH), 1.21 (dd, J=6.9, 2.6 Hz, 3H);

LC/MS (Method A) Rt 1.338 min, [MH]+390.0.

Example 2

5-((R)-3-Methyl-morpholin-4-yl)-7-(6-methyl-pyridin-3-yl)-3-(1H-pyrazol-3-yl)-1H-pyrazolo[4,3-b]pyridine (2)

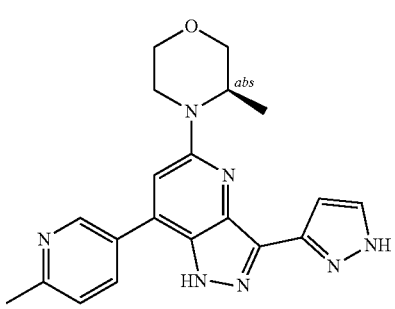 [SMILES: Cc1ccc(-c2cc(N3CCOC[C@H]3C)nc3c(-c4cc[nH]n4)n[nH]c23)cn1]

Building Block for Synthesis of Example 2:
6-chloro-2-methyl-3-nitropyridin-4-amine

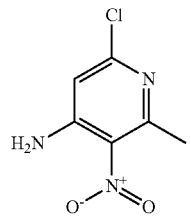

2,6-Dichloro-3-nitropyridin-4-amine (1 g, 4.33 mmol, 1. eq.), Pd(PPh₃)₄ (557 mg, 0.46 mmol, 0.11 eq.) and AlMe₃ (2.64 mL, 23.94 mmol, 5.53 eq.) were dissolved in DMF (15 mL) and stirred for 3 h at 70° C. The reaction was quenched by the addition of 50 mL of ice/salt. The solids were filtered out. The resulting solution was extracted with ethyl acetate and the organic layers combined and concentrated under vacuum. The residue was purified by column chromatography (Method B). 6-Chloro-2-methyl-3-nitropyridin-4-amine was isolated as a yellow solid (500 mg, 55%).

Building Block for Synthesis of Example 2:
4-bromo-6-chloro-2-methyl-3-nitropyridine

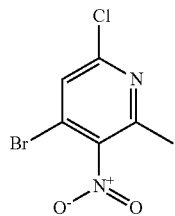

6-Chloro-2-methyl-3-nitropyridin-4-amine (1 g, 4.80 mmol, 1. eq.), CuBr₂ (1601.79 mg, 6.81 mmol, 1.42 eq.) and tBuONO (697.86 mg, 6.43 mmol, 1.34 eq.) were dissolved in MeCN (20 mL) and stirred for 2 h at 65° C. The pH value of the solution was adjusted to 2 with hydrogen chloride. The resulting solution was extracted with ethyl acetate and the organic layers combined and concentrated under vacuum. The residue was purified by column chromatography (Method F). 4-Bromo-6-chloro-2-methyl-3-nitropyridine was isolated as a yellow solid (1 g, 75%).

Building Block for Synthesis of Example 2:
6-chloro-2-methyl-4-(6-methylpyridin-3-yl)-3-nitropyridine

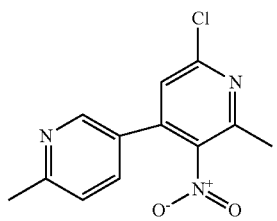

4-Bromo-6-chloro-2-methyl-3-nitropyridine (500 mg, 1.79 mmol, 1. eq.), (6-methylpyridin-3-yl)boronic acid (326.75 mg, 2.15 mmol, 1.20 eq.), Pd(pph₃)₂Cl₂ (130 mg, 0.18 mmol, 0.10 eq.) and sodium carbonate (604.65 mg, 5.42 mmol, 3.03 eq.) were dissolved in dioxane (2 mL), water (0.4 mL) and stirred for 3 h at 80° C. The resulting solution was extracted with ethyl acetate and the organic layers combined and concentrated under vacuum. The residue was purified by column chromatography (Method G). 6-Chloro-2-methyl-4-(6-methylpyridin-3-yl)-3-nitropyridine was isolated as a yellow solid (400 mg, 76%).

Building Block for Synthesis of Example 2: (3R)-3-methyl-4-[6-methyl-4-(6-methylpyridin-3-yl)-5-nitropyridin-2-yl]morpholine

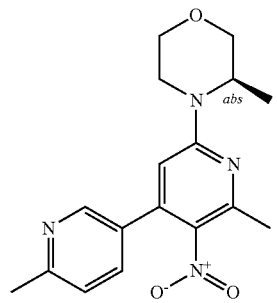

6-Chloro-2-methyl-4-(6-methylpyridin-3-yl)-3-nitropyridine (500 mg, 1.71 mmol, 1. eq.), (3R)-3-methylmorpholine (230.16 mg, 2.05 mmol, 1.20 eq.), DIPEA (696.53 mg, 5.12 mmol, 3 eq.) were dissolved in DMA (25 mL) and stirred for 16 h at 110° C. The resulting solution was extracted with ethyl acetate and the organic layers combined and concentrated under vacuum. (3R)-3-Methyl-4-[6-methyl-4-(6-methylpyridin-3-yl)-5-nitropyridin-2-yl]morpholine was isolated as crude product and used without further purification in the next step.

Building Block for Synthesis of Example 2:
2-methyl-6-[(3R)-3-methylmorpholin-4-yl]-4-(6-methylpyridin-3-yl)pyridin-3-amine

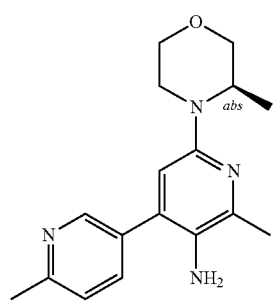

(3R)-3-Methyl-4-[6-methyl-4-(6-methylpyridin-3-yl)-5-nitropyridin-2-yl]morpholine (200 mg, 0.55 mmol, 1. eq.), Fe (170 mg, 2.89 mmol, 5.28 eq.) and NH₄Cl (170 mg, 3.02 mmol, 5.51 eq.) were dissolved in water (10 mL) and i-propanol (10 mL) and stirred for 5 h at 70° C. The solids were filtered out. The resulting solution was extracted with ethyl acetate and the organic layers combined and dried over anhydrous sodium sulfate and concentrated under vacuum. The residue was purified by column chromatography (Method H). 2-Methyl-6-[(3R)-3-methylmorpholin-4-yl]-4-(6-methylpyridin-3-yl)pyridin-3-amine was isolated as a yellow oil (70 mg, 38%).

Building Block for Synthesis of Example 2: (3R)-3-methyl-4-[7-(6-methylpyridin-3-yl)-1H-pyrazolo[4,3-b]pyridin-5-yl]morpholine

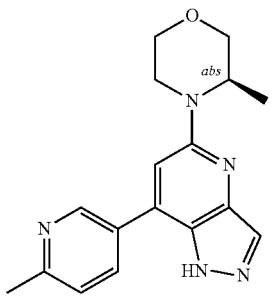

2-Methyl-6-[(3R)-3-methylmorpholin-4-yl]-4-(6-methylpyridin-3-yl)pyridin-3-amine (480 mg, 1.45 mmol, 1. eq.), and NaNO$_2$ (95.69 mg, 1.32 mmol, 0.91 eq.) were dissolved in AcOH (96 mL) and stirred for 2 h at 25° C. The resulting solution was extracted with ethyl acetate and the organic layers combined and dried over anhydrous sodium sulfate and concentrated under vacuum. The residue was purified by column chromatography (Method B). (3R)-3-Methyl-4-[7-(6-methylpyridin-3-yl)-1H-pyrazolo[4,3-b]pyridin-5-yl]morpholine was isolated as a yellow solid (100 mg, 20%).

Building Block for Synthesis of Example 2: (3R)-4-[3-iodo-7-(6-methylpyridin-3-yl)-1H-pyrazolo[4,3-b]pyridin-5-yl]-3-methylmorpholine

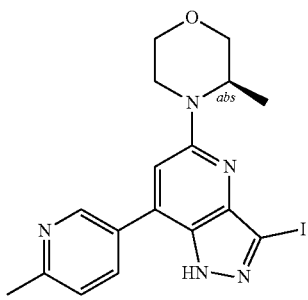 [SMILES: Cc1ccc(-c2cc(N3CCOC[C@H]3C)nc3c(I)n[nH]c23)cn1]

(3R)-3-Methyl-4-[7-(6-methylpyridin-3-yl)-1H-pyrazolo[4,3-b]pyridin-5-yl]morpholine (100 mg, 0.29 mmol, 1. eq.), potassium hydroxide (59.96 mg, 1.02 mmol, 3.49 eq.) and I2 (150.01 mg, 0.56 mmol, 1.93 eq.) were dissolved in methanol (10 mL) and stirred for 16 h at 25° C. The resulting solution was extracted with ethyl acetate and the organic layers combined and dried over sodium sulfate and concentrated under vacuum. The residue was purified by column chromatography (Method 1). (3R)-4-[3-Iodo-7-(6-methylpyridin-3-yl)-1H-pyrazolo[4,3-b]pyridin-5-yl]-3-methylmorpholine was isolated as a yellow solid (90 mg, 64%).

Building Block for Synthesis of Example 2: (3R)-3-methyl-4-[7-(6-methylpyridin-3-yl)-3-[1-(oxan-2-yl)-1H-pyrazol-3-yl]-1H-pyrazolo[4,3-b]pyridin-5-yl]morpholine

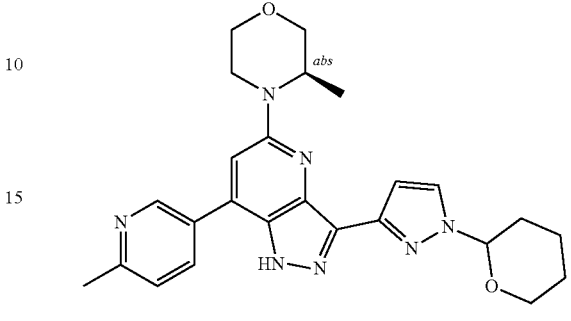

(3R)-4-[3-Iodo-7-(6-methylpyridin-3-yl)-1H-pyrazolo[4,3-b]pyridin-5-yl]-3-methylmorpholine (90 mg, 0.19 mmol, 1.0 eq.), 1-(oxan-2-yl)-3-(tetramethyl-1,3,2-dioxaborolan-2-yl)-1H-pyrazole (180 mg, 0.58 mmol, 3.13 eq.), Pd(PPh$_3$)$_4$ (27 mg, 0.02 mmol, 0.12 eq.), water (3 mL), tetrahydrofuran (12 mL) and sodium carbonate (65 mg, 0.58 mmol, 3.13 eq.) were combined and the resulting solution was stirred for 1 h at 80° C. The resulting solution was extracted with ethyl acetate and the organic layers combined and dried over anhydrous sodium sulfate and concentrated under vacuum. The residue was purified by column chromatography (Method B). (3R)-3-Methyl-4-[7-(6-methylpyridin-3-yl)-3-[1-(oxan-2-yl)-1H-pyrazol-3-yl]-1H-pyrazolo[4,3-b]pyridin-5-yl]morpholine was isolated as a yellow solid (75 mg, 77%).

Example 2

5-((R)-3-Methyl-morpholin-4-yl)-7-(6-methyl-pyridin-3-yl)-3-(1H-pyrazol-3-yl)-1H-pyrazolo[4,3-b]pyridine (2)

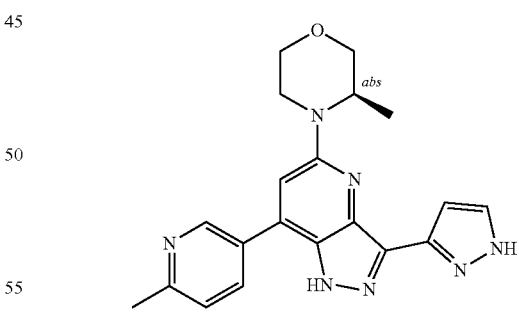

(3R)-3-Methyl-4-[7-(6-methylpyridin-3-yl)-3-[1-(oxan-2-yl)-1H-pyrazol-3-yl]-1H-pyrazolo[4,3-b]pyridin-5-yl]morpholine (70 mg, 0.14 mmol, 1. eq.) was dissolved in hydrogen chloride in methanol (3 mL) and stirred for 1 h at 25° C. The pH value of the solution was adjusted to 9 with sodium bicarbonate (0.5 mL mol/L). The resulting mixture was concentrated under vacuum. The crude product was purified by Prep-HPLC. 5-((R)-3-Methyl-morpholin-4-yl)-7-(6-methyl-pyridin-3-yl)-3-(1H-pyrazol-3-yl)-1H-pyrazolo[4,3-b]pyridine was isolated as a yellow solid (4 mg, 8%);

melting point 180-182° C.; $^1$H NMR (400 MHz, DMSO-d$_6$): δ13.31 (s, 1H), 8.89 (s, 1H), 8.12 (s, 1H), 7.65 (s, 1H), 7.46 (d, J=8.2 Hz, 1H), 7.14 (s, 1H), 7.07 (s, 1H), 4.54 (s, 1H), 4.08 (d, J=13.1 Hz, 1H), 3.99 (dd, J=11.3, 3.4 Hz, 1H), 3.80-3.66 (m, 2H), 3.54 (m, 1H), 3.25-3.13 (m, 1H), 2.57 (s, 3H), 1.18 (d, J=6.6 Hz, 3H);

LC/MS (Method B): Rt 1.544 min, [MH]+376.0.

Example 3

(3R)-3-Methyl-4-[3-(3-methyl-1H-pyrazol-5-yl)-7-(6-methylpyridin-3-yl)-1H-pyrazolo[4,3-b]pyridin-5-yl]morpholine (3)

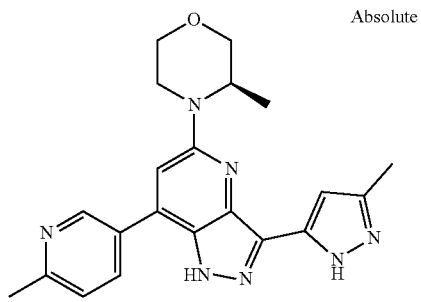

Absolute

Building Block for Synthesis of Example 3: 5-((R)-3-methyl-morpholin-4-yl)-7-(6-methyl-pyridin-3-yl)-3-[5-methyl-2-(tetrahydro-pyran-2-yl)-2H-pyrazol-3-yl]-1H-pyrazolo[4,3-b]pyridine

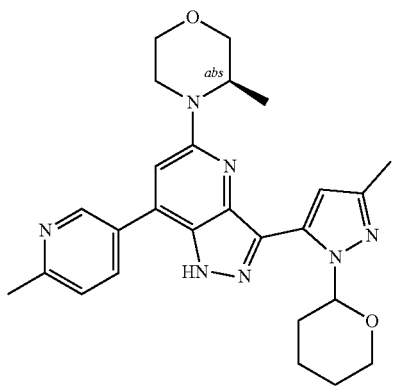

(3R)-4-[3-Iodo-7-(6-methylpyridin-3-yl)-1H-pyrazolo[4,3-b]pyridin-5-yl]-3-methylmorpholine (56 mg; 0.114 mmol; 0.789 eq.) and (3R)-4-[3-iodo-7-(6-methylpyridin-3-yl)-1H-pyrazolo[4,3-b]pyridin-5-yl]-3-methylmorpholine (15 mg; 0.031 mmol; 0.211 eq.) were dissolved in tetrahydrofuran (1.42 ml) and water (142.00 µl). 1-BOC-3-Methylpyrazole-5-boronic acid (49 mg; 0.217 mmol; 1.5 eq.), sodium carbonate (0.02 ml; 0.434 mmol; 3 eq.) and tetrakis(triphenyl-phosphine)-palladium(0) (20 mg; 0.017 mmol; 0.120 eq.) were added. The reaction suspension was stirred at 80° C. for 1 hour. 3-Methyl-1-(oxan-2-yl)-5-(tetramethyl-1,3,2-dioxaborolan-2-yl)-1H-pyrazole (66.67 mg; 0.217 mmol; 1.5 eq.) and tetrakis(triphenylphosphine)-palladium(0) (20.04 mg; 0.017 mmol; 0.120 eq.) were added and it was stirred at 80° C. for 1 hour. The solid was filtered off and the filtrate concentrated under reduced pressure. The product was purified by flash chromatography (n-heptane/EtOAc gradient) to yield 35 mg (47.9%) as a brown solid; LC/MS (Method C): Rt 0.946 min; [MH]+474.2.

Example 3

(3R)-3-Methyl-4-[3-(3-methyl-1H-pyrazol-5-yl)-7-(6-methylpyridin-3-yl)-1H-pyrazolo[4,3-b]pyridin-5-yl]morpholine (3)

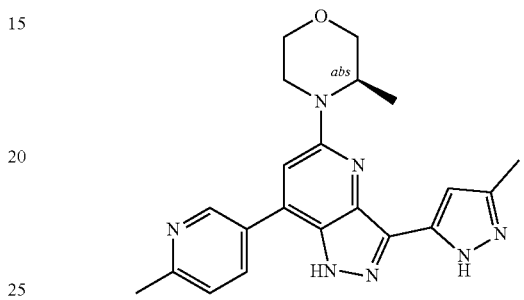

5-((R)-3-Methyl-morpholin-4-yl)-7-(6-methyl-pyridin-3-yl)-3-[5-methyl-2-(tetrahydro-pyran-2-yl)-2H-pyrazol-3-yl]-1H-pyrazolo[4,3-b]pyridine (35 mg; 0.069 mmol; 1 eq.) was dissolved in hydrogen chloride solution in dioxane (0.86 ml). The suspension was stirred at room temperature over 48 h. The reaction mixture was concentrated under reduced pressure and purified by flash chromatography (Method O). (3R)-3-Methyl-4-[3-(3-methyl-1H-pyrazol-5-yl)-7-(6-methylpyridin-3-yl)-1H-pyrazolo[4,3-b]pyridin-5-yl]morpholine was isolated as yellow solid (10 mg, 37%);

$^1$H NMR (400 MHz, DMSO-d$_6$/90° C.) δ9.09-9.04 (m, 1H), 8.37-8.32 (m, 1H), 7.53 (d, J=8.1 Hz, 1H), 7.16 (s, 1H), 6.78 (s, 1H), 4.56-4.49 (m, 1H), 4.10-4.03 (m, 1H), 4.01-3.96 (m, 1H), 3.76-3.71 (m, 2H), 3.58 (td, J=11.5, 3.1 Hz, 1H), 3.32-3.23 (m, 1H), 2.62 (s, 3H), 2.30 (s, 3H), 1.23 (d, J=6.7 Hz, 3H);

LC/MS (Method C): Rt 0.821 min; [MH]+390.2.

Example 4

1-Methyl-5-((R)-3-methyl-morpholin-4-yl)-7-(2-methyl-pyridin-3-yl)-3-(1H-pyrazol-3-yl)-1H-pyrazolo[4,3-b]pyridine (4)

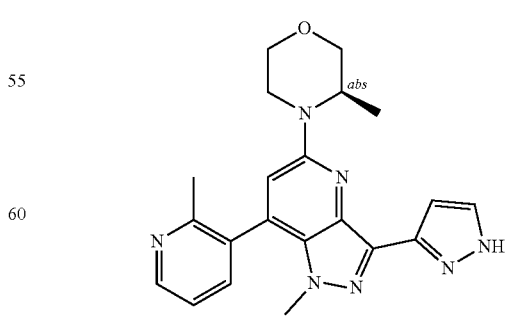

1-Methyl-5-((R)-3-methyl-morpholin-4-yl)-7-(2-methyl-pyridin-3-yl)-3-(1H-pyrazol-3-yl)-1H-pyrazolo[4,3-b]pyridine was prepared analogously to above examples and isolated as a yellow solid (160 mg, 36%), melting point 228-230° C.;

¹H NMR (300 MHz, DMSO-d₆): δ13.24 (s, 1H), 8.64 (dd, J=4.9, 1.7 Hz, 1H), 7.83 (dt, J=7.6, 2.1 Hz, 1H), 7.69 (s, 1H), 7.43 (dd, J=7.6, 4.9 Hz, 1H), 7.09 (s, 1H), 6.97 (s, 1H), 4.46 (s, 1H), 4.13-3.94 (m, 2H), 3.82-3.62 (m, 2H), 3.62-3.49 (m, 1H), 3.46 (s, 3H), 3.18 (td, J=12.7, 3.7 Hz, 1H), 2.33 (d, J=1.4 Hz, 3H), 1.20 (dd, J=6.7, 3.0 Hz, 3H);

LC/MS (Method D): Rt 0.782 min, [MH]+390.2.

Example 5

7-(4-Methanesulfinyl-phenyl)-1-methyl-5-((R)-3-methyl-morpholin-4-yl)-3-(1H-pyrazol-3-yl)-1H-pyrazolo[4,3-b]pyridine (5)

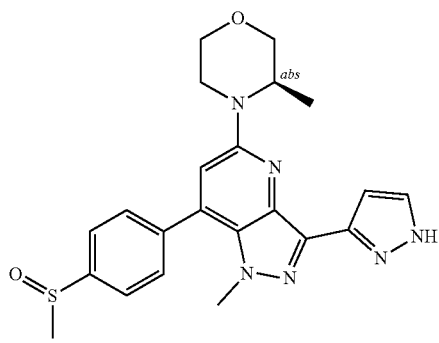 [SMILES: C[C@@H]1COCCN1c1cc(-c2ccc(S(C)=O)cc2)c2c(n1)c(-c1cc[nH]n1)nn2C]

7-(4-Methanesulfinyl-phenyl)-1-methyl-5-((R)-3-methyl-morpholin-4-yl)-3-(1H-pyrazol-3-yl)-1H-pyrazolo[4,3-b]pyridine was prepared analogously to above examples and isolated as a yellow solid (90 mg, 23%); melting point of 155-157° C.

¹H NMR (Methanol-d₄): δ7.89 (d, J=8.2 Hz, 2H), 7.78 (d, J=8.0 Hz, 2H), 7.68 (s, 1H), 7.12 (s, 1H), 6.89 (s, 1H), 4.47 (t, J=6.8 Hz, 1H), 4.04 (dd, J=11.3, 3.2 Hz, 2H), 3.82 (d, J=2.2 Hz, 2H), 3.73-3.62 (m, 4H), 3.38-3.32 (m, 1H), 2.65 (s, 1H), 1.29 (d, J=6.7 Hz, 3H);

LC/MS (Method B): Rt 1.993 min, [MH]+437.1.

Example 6

Imino(methyl)(4-{1-methyl-5-[(3R)-3-methylmorpholin-4-yl]-3-(1H-pyrazol-3-yl)-1H-pyrazolo[4,3-b]pyridin-7-yl}phenyl)-lambda6-sulfanone (6)

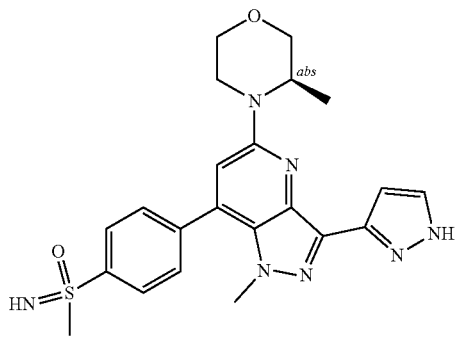 [SMILES: C[C@@H]1COCCN1c1cc(-c2ccc(S(C)(=N)=O)cc2)c2c(n1)c(-c1cc[nH]n1)nn2C]

Building Block for Synthesis of Example 6: 2,2,2-trifluoro-N-[methane(4-{1-methyl-5-[(3R)-3-methyl-morpholin-4-yl]-3-[1-(oxan-2-yl)-1H-pyrazol-3-yl]-1H-pyrazolo[4,3-b]pyridin-7-yl}benzene)sulfinylidene]acetamide

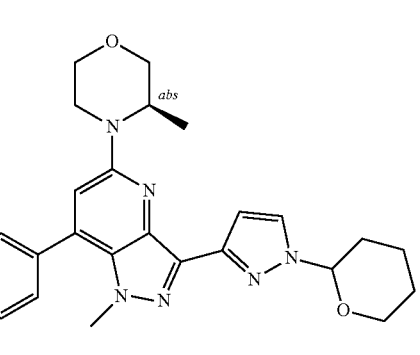

(3R)-4-[7-(4-Methanesulfinylphenyl)-1-methyl-3-[1-(oxan-2-yl)-1H-pyrazol-3-yl]-1H-pyrazolo[4,3-b]pyridin-5-yl]-3-methylmorpholine (70 mg, 0.12 mmol, 1. eq.), MgO (25.67 mg, 0.61 mmol, 5. eq.), dichloromethane (5 mL), Rh₂(OAc)₄ (5.63 mg, 0.01 mmol, 0.10 eq.) and phenyliodine diacetate (82.05 mg, 0.24 mmol, 2. eq.) were combined and the solution was stirred for 12 h at 25° C. The resulting mixture was concentrated under vacuum. 2,2,2-Trifluoro-N-[methane(4-[1-methyl-5-[(3R)-3-methylmorpholin-4-yl]-3-[1-(oxan-2-yl)-1H-pyrazol-3-yl]-1H-pyrazolo[4,3-b]pyridin-7-yl]benzene)sulfinylidene]acetamide was isolated as a yellow solid (70 mg, 74%) and used without further purification in the next step.

Building Block for Synthesis of Example 6: (3R)-4-(7-{4-[imino(methane)-sulfinyl]phenyl}-1-methyl-3-[1-(oxan-2-yl)-1H-pyrazol-3-yl]-1H-pyrazolo[4,3-b]pyridin-5-yl)-3-methylmorpholine 2,2,2-Trifluoro-N-[methane(4-[1-methyl-5-[(3R)-3-methylmorpholin-4-yl]-3-[1-(oxan-2-yl)-1H-pyrazol-3-yl]-1H-pyrazolo[4,3-b]pyridin-7-yl]benzene)-sulfinylidene]acetamide (70 mg, 0.08 mmol, 1.0 eq. 70%) in methanol (5 mL) and potassium carbonate (33.86 mg, 0.23 mmol, 3 eq.) were combined and the solution was stirred for 1 h at 25° C. The resulting mixture was concentrated under vacuum. (3R)-4-(7-[4-[Imino(methane)sulfinyl]phenyl]-1-methyl-3-[1-(oxan-2-yl)-1H-pyrazol-3-yl]-1H-pyrazolo[4,3-b]pyridin-5-yl)-3-methylmorpholine was isolated as a yellow solid (70 mg, quant) and used without further purification in the next step.

Example 6

Imino(methyl)(4-{1-methyl-5-[(3R)-3-methylmorpholin-4-yl]-3-(1H-pyrazol-3-yl)-1H-pyrazolo[4,3-b]pyridin-7-yl}phenyl)-lambda6-sulfanone (6)

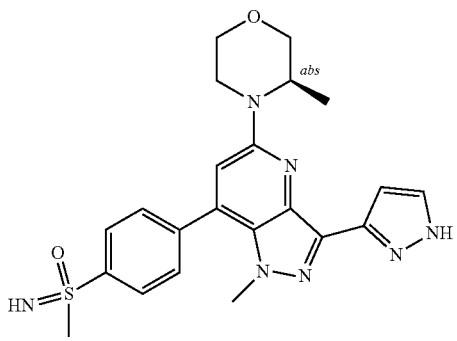 [SMILES: C[C@@H]1COCCN1c1cc(-c2ccc(S(C)(=N)=O)cc2)c2c(n1)c(-c1cc[nH]n1)nn2C]

(3R)-4-(7-[4-[imino(methane)sulfinyl]phenyl]-1-methyl-3-[1-(oxan-2-yl)-1H-pyrazol-3-yl]-1H-pyrazolo[4,3-b]pyridin-5-yl)-3-methylmorpholine (70 mg, 0.09 mmol, 1.0 eq. 70%) was dissolved in hydrogen chloride in dioxane (5 mL) and stirred for 1 h at 25° C. The resulting solution was extracted with ethyl acetate and the organic layers combined and dried over sodium sulfate and concentrated under vacuum. The crude product was purified by Prep-HPLC (Method B). Imino(methyl)(4-{1-methyl-5-[(3R)-3-methyl-morpholin-4-yl]-3-(1H-pyrazol-3-yl)-1H-pyrazolo[4,3-b]pyridin-7-yl}phenyl)-lambda6-sulfanone was isolated as a yellow solid (14 mg, 34%); melting point of 180° C.;

$^1$H NMR (300 MHz, DMSO-d$_6$) δ13.17 (br, 1H) 8.10 (d, J=8.4 Hz, 2H), 7.84 (d, J=8.4 Hz, 2H), 7.67 (s, 1H), 7.07 (d, J=1.9 Hz, 1H), 6.93 (s, 1H), 4.56-4.41 (m, 1H), 4.37 (s, 1H), 4.02 (ddd, J=24.4, 11.9, 3.1 Hz, 2H), 3.80-3.64 (m, 2H), 3.61 (s, 3H), 3.58-3.44 (m, 1H), 3.34-3.16 (m, 4H), 1.18 (d, J=6.5 Hz, 3H). LC/MS (Method B): Rt 1.857 min, [MH]+452.1.

Example 7

7-(4-Methanesulfonyl-phenyl)-1-methyl-5-((R)-3-methyl-morpholin-4-yl)-3-(1H-pyrazol-3-yl)-1H-pyrazolo[4,3-b]pyridine (7)

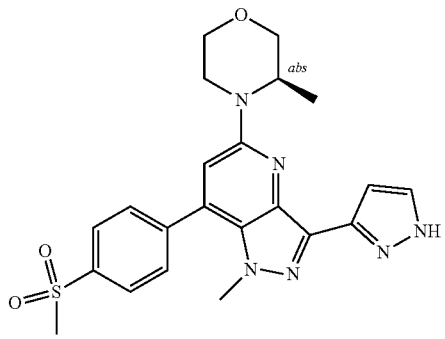 [SMILES: C[C@@H]1COCCN1c1cc(-c2ccc(S(C)(=O)=O)cc2)c2c(n1)c(-c1cc[nH]n1)nn2C]

7-(4-Methanesulfonyl-phenyl)-1-methyl-5-((R)-3-methyl-morpholin-4-yl)-3-(1H-pyrazol-3-yl)-1H-pyrazolo[4,3-b]pyridine was prepared analogously to above examples and was isolated as a yellow solid (18 mg, 31%); melting point of >300° C.;

$^1$H NMR (300 MHz, DMSO-d$_6$) δ13.09 (d, J=90.7 Hz, 1H), 8.28-7.99 (m, 2H), 7.71 (d, J=67.8 Hz, 1H), 7.04 (s, 1H), 6.96 (s, 1H), 4.46 (d, J=11.2 Hz, 1H), 4.18-3.92 (m, 2H), 3.81-3.64 (m, 2H), 3.64-3.44 (m, 4H), 3.32 (s, 4H), 3.24-3.04 (m, 1H), 1.18 (d, J=6.5 Hz, 3H);

LC/MS (Method F): Rt 1.298 min, [MH]+453.1.

Example 8

7-(6-Methanesulfinyl-2-methyl-pyridin-3-yl)-1-methyl-5-((R)-3-methyl-morpholin-4-yl)-3-(1H-pyrazol-3-yl)-1H-pyrazolo[4,3-b]pyridine (8)

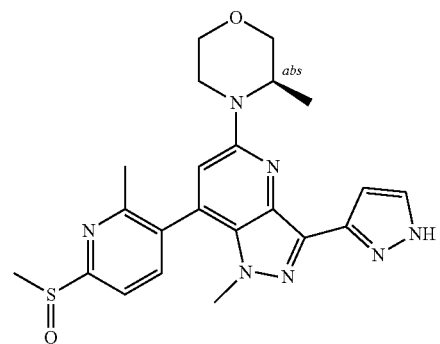 [SMILES: Cc1nc(S(C)=O)ccc1-c1cc(N2CCOC[C@H]2C)nc2c(-c3cc[nH]n3)nn(C)c12]

Building Block for Synthesis of Example 8: 3-bromo-2-methyl-6-(methylsulfanyl)pyridine

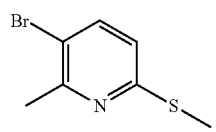

3-Bromo-6-fluoro-2-methylpyridine (3 g, 15.00 mmol, 1.0 eq.), DMF (300 mL) and (methylsulfanyl)sodium (1.44 g, 19.52 mmol, 1.30 eq.) were combined and stirred for 4 h at 0° C. The resulting solution was extracted with ethyl acetate and the organic layers combined and concentrated under vacuum. 3-Bromo-2-methyl-6-(methylsulfanyl)pyridine was isolated as yellow oil (2.5 g, 69%); LC/MS (Method J): Rt 1.324 min, [MH]+220.0.

Building Block for Synthesis of Example 8:
3-bromo-6-methanesulfinyl-2-methylpyridine

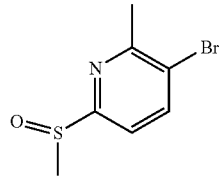

3-Bromo-2-methyl-6-(methylsulfanyl)pyridine (2.50 g, 10.32 mmol, 1.0 eq.), dichloromethane (200 mL) and m-CPBA (1.87 g, 10.29 mmol, 1.0 eq.) were combined and stirred for 2 h at 25° C. The resulting solution was extracted with ethyl acetate and the organic layers combined and dried over sodium sulfate and concentrated under vacuum. The residue was purified by column chromatography (Method J). 3-Bromo-6-methanesulfinyl-2-methylpyridine as yellow oil (1.8 g, 67%); LC/MS (Method J): Rt 0.937 min, [MH]+ 233.9.

Building Block for Synthesis of Example 8:
6-methanesulfinyl-2-methyl-3-(tetramethyl-1,3,2-dioxaborolan-2-yl)pyridine

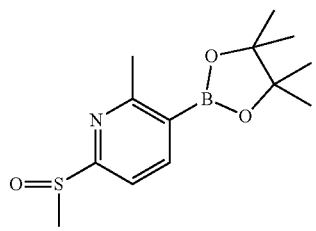 [SMILES: Cc1nc(S(C)=O)ccc1B1OC(C)(C)C(C)(C)O1]

3-Bromo-6-methanesulfinyl-2-methylpyridine (1.80 g, 6.92 mmol, 1.0 eq.), 4,4,5,5-tetramethyl-2-(tetramethyl-1,3,2-dioxaborolan-2-yl)-1,3,2-dioxaborolane (7.77 g, 29.07 mmol, 4.20 eq.), dioxane (120 mL, 1.35 mol, 194.47 eq.), CH₃COOK (3 g, 29.04 mmol, 4.19 eq.) and Pd(dppf)Cl₂·CH₂Cl₂ (820 mg, 0.90 mmol, 0.13 eq.) were combined 3 h at 25° C. The resulting solution was extracted with ethyl acetate and the organic layers combined and dried over sodium sulfate and concentrated under vacuum. The residue was purified by column chromatography (Method J). 6-Methanesulfinyl-2-methyl-3-(tetramethyl-1,3,2-dioxaborolan-2-yl)pyridine as yellow oil (1.8 g 83%); LC/MS (Method J): Rt 1.131 min [MH]+282.1.

Example 8

7-(6-Methanesulfinyl-2-methyl-pyridin-3-yl)-1-methyl-5-((R)-3-methyl-morpholin-4-yl)-3-(1H-pyrazol-3-yl)-1H-pyrazolo[4,3-b]pyridine (8)

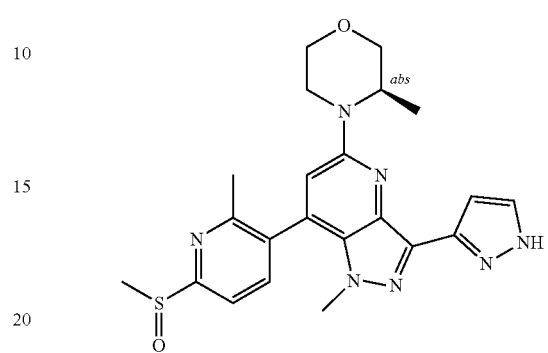

7-(6-Methanesulfinyl-2-methyl-pyridin-3-yl)-1-methyl-5-((R)-3-methyl-morpholin-4-yl)-3-(1H-pyrazol-3-yl)-1H-pyrazolo[4,3-b]pyridine was prepared analogously to above examples and was isolated as a yellow solid (150 mg, 41%); melting point 174-176° C.;
¹H NMR (300 MHz, CD₃O_D): δ8.05 (dd, J=7.9, 1.8 Hz, 1H), 7.94 (dd, J=7.9, 3.0 Hz, 1H), 7.64 (s, 1H), 7.08 (s, 1H), 6.90 (s, 1H), 4.44 (d, J=7.0 Hz, 1H), 4.09-3.96 (m, 2H), 3.80 (d, J=1.9 Hz, 2H), 3.64 (td, J=11.8, 3.1 Hz, 1H), 3.51 (s, 3H), 3.38-3.30 (m, OH), 2.93 (d, J=6.0 Hz, 3H), 2.40 (d, J=2.6 Hz, 3H), 1.27 (dd, J=6.7, 4.4 Hz, 3H);
LC/MS (Method E): Rt 1.199 min, [MH]+452.0.

Example 9

(3R)-4-(7-{6-[(S)-Methanesulfinyl]-2-methylpyridin-3-yl}-1-methyl-3-(1H-pyrazol-3-yl)-1H-pyrazolo[4,3-b]pyridin-5-yl)-3-methylmorpholine (9)

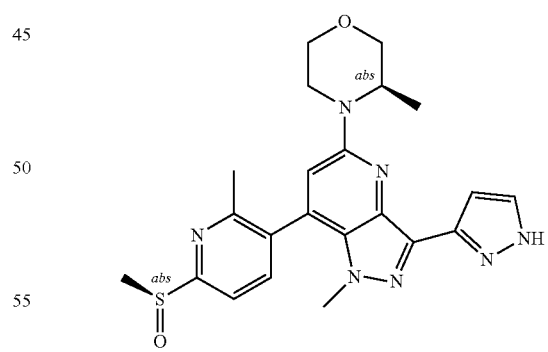

Diastereoisomers of (3R)-4-[7-(6-methanesulfinyl-2-methylpyridin-3-yl)-1-methyl-3-(1H-pyrazol-3-yl)-1H-pyrazolo[4,3-b]pyridin-5-yl]-3-methylmorpholine were separated by chiral chromatography (ChiralPak AS-H with solvent system CO₂: 2-propanol+0.5% DEA 60:40) to isolate (3R)-4-(7-{6-[(S)-methanesulfinyl]-2-methylpyridin-3-yl}-1-methyl-3-(1H-pyrazol-3-yl)-1H-pyrazolo[4,3-b]pyridin-5-yl)-3-methylmorpholine as a yellow solid (30 mg, 40%)

¹H NMR (500 MHz, DMSO-d₆): δ13.26-12.90 (m, 1H), 8.15-8.12 (m, 1H), 7.94-7.89 (m, 1H), 7.86-7.56 (m, 1H), 7.14-6.96 (m, 2H), 4.50-4.38 (m, 1H), 4.15-4.02 (m, 1H), 3.99 (dd, J=11.4, 3.6 Hz, 1H), 3.77-3.72 (m, 1H), 3.71-3.67 (m, 1H), 3.54 (td, J=11.8, 3.0 Hz, 1H), 3.49-3.44 (m, 3H), 3.21-3.14 (m, 1H), 2.90-2.86 (m, 3H), 2.39-2.36 (m, 3H), 1.21-1.16 (m, 3H), LC/MS (Method F): Rt 2.017 min; [MH]+452.2.

Example 10

(3R)-4-(7-{6-[(R)-Methanesulfinyl]-2-methylpyridin-3-yl}-1-methyl-3-(1H-pyrazol-3-yl)-1H-pyrazolo[4,3-b]pyridin-5-yl)-3-methylmorpholine (10)

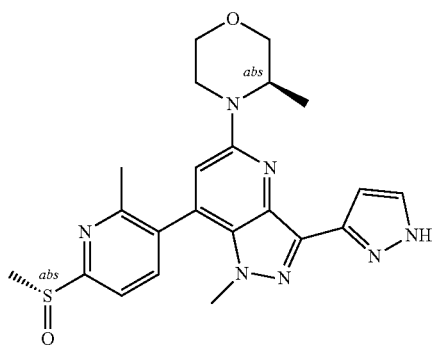 [SMILES: Cc1nc([S@@](C)=O)ccc1-c1cc(N2CCOC[C@H]2C)nc2c(-c3cc[nH]n3)nn(C)c12]

Diastereoisomers of (3R)-4-[7-(6-methanesulfinyl-2-methylpyridin-3-yl)-1-methyl-3-(1H-pyrazol-3-yl)-1H-pyrazolo[4,3-b]pyridin-5-yl]-3-methylmorpholine were separated by chiral chromatography (ChiralPak AS-H with solvent system CO₂: 2-propanol+0.5% DEA 60:40) to isolate (3R)-4-(7-{6-[(R)-methanesulfinyl]-2-methylpyridin-3-yl}-1-methyl-3-(1H-pyrazol-3-yl)-1H-pyrazolo[4,3-b]pyridin-5-yl)-3-methylmorpholine as yellow solid (33 mg, 44%);

¹H NMR (500 MHz, DMSO-d₆): δ13.25-12.90 (m, 1H), 8.16-8.11 (m, 1H), 7.93-7.89 (m, 1H), 7.86-7.55 (m, 1H), 7.14-6.97 (m, 2H), 4.51-4.38 (m, 1H), 4.13-4.02 (m, 1H), 3.98 (dd, J=11.4, 3.5 Hz, 1H), 3.77-3.72 (m, 1H), 3.69 (dd, J=11.3, 3.0 Hz, 1H), 3.54 (td, J=11.7, 3.0 Hz, 1H), 3.49-3.43 (m, 3H), 3.22-3.13 (m, 1H), 2.90-2.86 (m, 3H), 2.39-2.36 (m, 3H), 1.21-1.16 (m, 3H);

LC/MS (Method F): Rt 2.024 min; [MH]+452.

Example 11

(3R)-4-[7-(6-Methanesulfonyl-2-methylpyridin-3-yl)-1-methyl-3-(1H-pyrazol-3-yl)-1H-pyrazolo[4,3-b]pyridin-5-yl]-3-methylmorpholine (11)

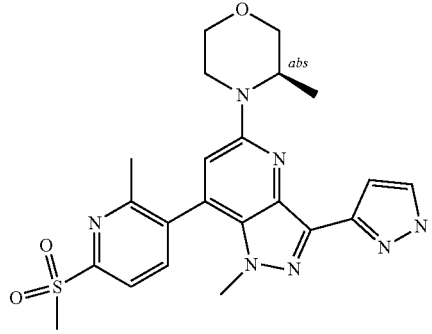 [SMILES: Cc1nc(S(C)(=O)=O)ccc1-c1cc(N2CCOC[C@H]2C)nc2c(-c3cc[nH]n3)nn(C)c12]

(3R)-4-[7-(6-Methanesulfinyl-2-methylpyridin-3-yl)-1-methyl-3-[1-(oxan-2-yl)-1H-pyrazol-3-yl]-1H-pyrazolo[4,3-b]pyridin-5-yl]-3-methylmorpholine (20 mg, 0.04 mmol, 1.0 eq.), methanol (0.1 mL), water (1.5 mL) and oxone (7.69 mg, 0.04 mmol, 1.23 eq.) were combined and stirred for 16 h at 25° C. The resulting mixture was concentrated under vacuum. The crude product was purified by Prep-HPLC (Method C). (3R)-4-[7-(6-Methanesulfonyl-2-methylpyridin-3-yl)-1-methyl-3-(1H-pyrazol-3-yl)-1H-pyrazolo[4,3-b]pyridin-5-yl]-3-methylmorpholine as a yellow solid (3 mg, 16%); melting point 276-278° C.; ¹H NMR (400 MHz, Methanol-d₄): δ8.12 (d, J=1.4 Hz, 2H), 7.71 (s, 1H), 7.16 (s, 1H), 6.95 (s, 1H), 4.49 (q, J=6.8, 6.2 Hz, 1H), 4.08 (dq, J=11.1, 3.9, 3.3 Hz, 2H), 3.90-3.82 (m, 2H), 3.69 (td, J=11.7, 3.1 Hz, 1H), 3.56 (d, J=1.2 Hz, 3H), 3.41-3.36 (m, 1H), 2.50 (d, J=3.8 Hz, 3H), 1.31 (d, J=4.9 Hz, 3H); LC/MS (Method G): Rt 1.213 min [MH]+468.2.

Example 12

7-(6-Methanesulfonyl-2-methyl-pyridin-3-yl)-5-((R)-3-methyl-morpholin-4-yl)-3-(1H-pyrazol-3-yl)-1H-pyrazolo[4,3-b]pyridine (12)

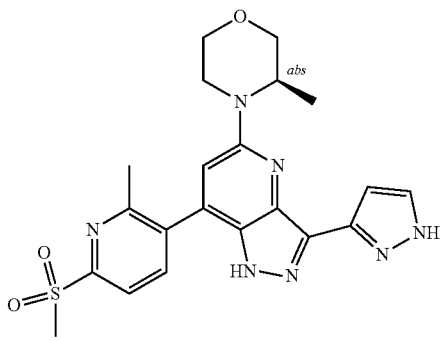 [SMILES: Cc1nc(S(C)(=O)=O)ccc1-c1cc(N2CCOC[C@H]2C)nc2c(-c3cc[nH]n3)n[nH]c12]

7-(6-Methanesulfonyl-2-methyl-pyridin-3-yl)-5-((R)-3-methyl-morpholin-4-yl)-3-(1H-pyrazol-3-yl)-1H-pyrazolo[4,3-b]pyridine was prepared analogously to above examples and was isolated as a light yellow solid (58 mg, 72%);

¹H NMR (400 MHz, DMSO-d₆): δ13.09 (s, 1H), 8.17 (d, J=7.8 Hz, 1H), 8.05 (d, J=7.9 Hz, 1H), 7.73-7.65 (m, 1H), 7.09 (d, J=2.2 Hz, 2H), 4.46 (d, J=7.3 Hz, 1H), 4.14-4.06 (m, 1H), 4.00 (dd, J=11.3, 3.5 Hz, 1H), 3.81-3.66 (m, 2H), 3.56 (td, J=11.7, 3.0 Hz, 1H), 3.32 (s, 3H), 3.20 (td, J=12.8, 3.8 Hz, 1H), 2.49 (s, 3H), 1.21 (d, J=6.6 Hz, 3H);

LC/MS (Method E): Rt 1.191; [MH]+454.0.

Example 13

(3R)-4-[7-(6-Methanesulfonyl-2-methylpyridin-3-yl)-3-(3-methyl-1H-pyrazol-5-yl)-1H-pyrazolo[4,3-b]pyridin-5-yl]-3-methylmorpholine (13)

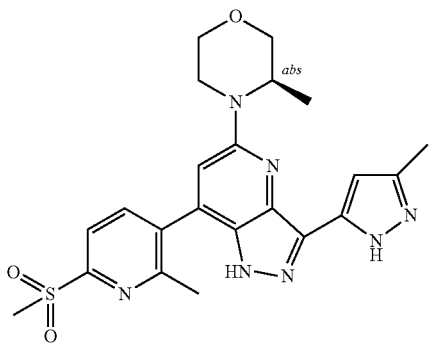

(3R)-4-[7-(6-Methanesulfonyl-2-methylpyridin-3-yl)-3-(3-methyl-1H-pyrazol-5-yl)-1H-pyrazolo[4,3-b]pyridin-5-yl]-3-methylmorpholine was prepared analogously to above examples and was isolated as yellow solid (2 mg, 15%);

LC/MS (Method F): Rt 2.049 min; [MH]+468.2.

Example 14

2-Methyl-5-((R)-3-methyl-morpholin-4-yl)-7-(6-methyl-pyridin-3-yl)-3-(1H-pyrazol-3-yl)-2H-pyrazolo[4,3-b]pyridine (14)

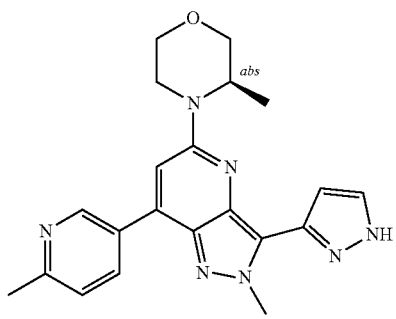 [SMILES: Cc1ccc(-c2cc(N3CCOC[C@H]3C)nc3c(-c4cc[nH]n4)n(C)nc23)cn1]

Building Block for Synthesis of Example 14: (3R)-3-methyl-4-[2-methyl-7-(6-methylpyridin-3-yl)-3-[1-(oxan-2-yl)-1H-pyrazol-3-yl]-2H-pyrazolo[4,3-b]pyridin-5-yl]morpholine

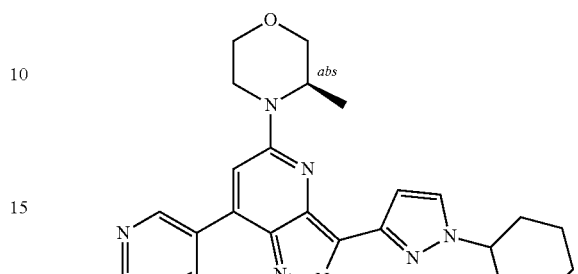

(3R)-3-Methyl-4-[7-(6-methylpyridin-3-yl)-3-[1-(oxan-2-yl)-1H-pyrazol-3-yl]-1H-pyrazolo[4,3-b]pyridin-5-yl]morpholine (75.000 mg, 0.15 mmol, 1. eq.), DMF (5 mL) and sodium hydride (8.812 mg, 0.22 mmol, 1.5 eq.) were combined and the solution stirred for 0.5 h at 0-5° C. To this was added CH₃I (32.919 mg, 0.22 mmol, 1.50 eq.). The resulting solution was stirred for 2 h at 25° C. The reaction was then quenched by the addition of NH₄Cl aq. The resulting mixture was concentrated under vacuum. The residue was purified by column chromatography (Method E). (3R)-3-Methyl-4-[2-methyl-7-(6-methylpyridin-3-yl)-3-[1-(oxan-2-yl)-1H-pyrazol-3-yl]-2H-pyrazolo[4,3-b]pyridin-5-yl]morpholine was isolated as a yellow solid (20 mg, 25%).

Example 14

2-Methyl-5-((R)-3-methyl-morpholin-4-yl)-7-(6-methyl-pyridin-3-yl)-3-(1H-pyrazol-3-yl)-2H-pyrazolo[4,3-b]pyridine (14)

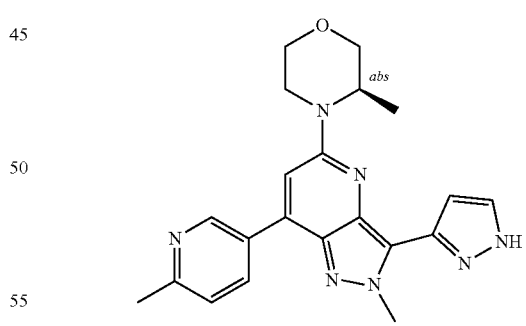

(3R)-3-Methyl-4-[2-methyl-7-(6-methylpyridin-3-yl)-3-[1-(oxan-2-yl)-1H-pyrazol-3-yl]-2H-pyrazolo[4,3-b]pyridin-5-yl]morpholine (20 mg, 0.04 mmol, 1.0 eq.) was dissolved in HCl in methanol (5 mL) and was stirred for 2 h at 25° C. The resulting mixture was concentrated under vacuum. The crude product was purified by Prep-HPLC (Method D). 2-Methyl-5-((R)-3-methyl-morpholin-4-yl)-7-(6-methyl-pyridin-3-yl)-3-(1H-pyrazol-3-yl)-2H-pyrazolo[4,3-b]pyridine was isolated as a yellow solid (6 mg, 38%); melting point 140-142° C.;

$^1$H NMR (400 MHz, DMSO-d$_6$); δ13.19 (s, 1H), 9.32 (d, J=2.4 Hz, 1H), 8.51 (dd, J=8.0, 2.5 Hz, 1H), 7.93 (s, 1H), 7.43 (d, J=8.1 Hz, 1H), 7.35 (s, 1H), 7.32 (s, 1H), 4.57 (d, J=7.6 Hz, 1H), 4.46 (s, 3H), 4.10 (d, J=13.2 Hz, 1H), 4.00 (dd, J=11.7, 3.6 Hz, 1H), 3.75 (q, J=11.0 Hz, 2H), 3.56 (t, J=10.9 Hz, 1H), 3.23 (dt, J=14.5, 7.2 Hz, 1H), 2.57 (s, 3H), 1.21 (d, J=6.6 Hz, 3H);

LC/MS (Method G): Rt 1.303 min, [MH]+390.2.

Example 15

1-Methyl-5-((R)-3-methyl-morpholin-4-yl)-3-(1H-pyrazol-3-yl)-7-(1H-pyrrolo[2,3-b]pyridin-4-yl)-1H-pyrazolo[4,3-b]pyridine (15)

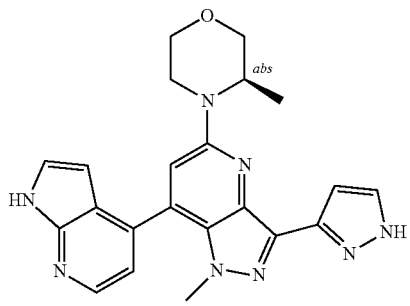 [SMILES: C[C@@H]1COCCN1c1cc(-c2ccnc3[nH]ccc23)c2c(n1)c(-c1cc[nH]n1)nn2C]

Building Block for Synthesis of Example 15: (3R)-3-methyl-4-(1-methyl-7-{1-[(4-methylbenzene)sulfonyl]-1H-pyrrolo[2,3-b]pyridin-4-yl}-3-(1H-pyrazol-3-yl)-1H-pyrazolo[4,3-b]pyridin-5-yl)morpholine

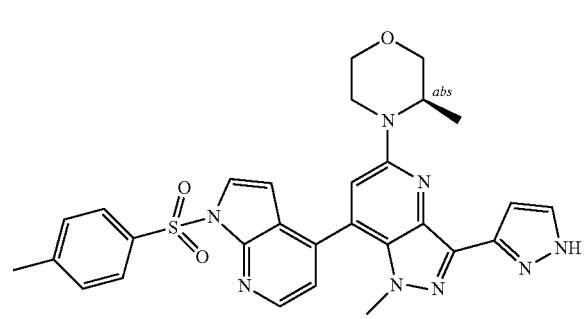 [SMILES: Cc1ccc(S(=O)(=O)n2ccc3c(-c4cc(N5CCOC[C@H]5C)nc5c(-c6cc[nH]n6)nn(C)c45)ccnc32)cc1]

(3R)-3-Methyl-4-(1-methyl-7-[1-[(4-methylbenzene)sulfonyl]-1H-pyrrolo[2,3-b]pyridin-4-yl]-3-(1H-pyrazol-3-yl)-1H-pyrazolo[4,3-b]pyridin-5-yl)morpholine was prepared analogously to above examples and was isolated as a yellow solid (100 mg, 83%).

Example 15

1-Methyl-5-((R)-3-methyl-morpholin-4-yl)-3-(1H-pyrazol-3-yl)-7-(1H-pyrrolo[2,3-b]pyridin-4-yl)-1H-pyrazolo[4,3-b]pyridine (15)

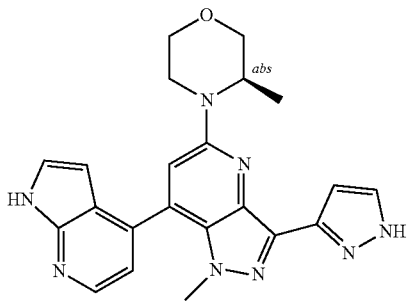 [SMILES: C[C@@H]1COCCN1c1cc(-c2ccnc3[nH]ccc23)c2c(n1)c(-c1cc[nH]n1)nn2C]

(3R)-3-Methyl-4-(1-methyl-7-[1-[(4-methylbenzene)sulfonyl]-1H-pyrrolo[2,3-b]pyridin-4-yl]-3-(1H-pyrazol-3-yl)-1H-pyrazolo[4,3-b]pyridin-5-yl)morpholine (50.000 mg, 0.08 mmol, 1.0 eq.) was dissolved in methanol (5 mL) and sodium hydroxide (9.995 mg, 0.24 mmol, 3.0 eq.) added. The resulting solution was stirred for 6 h at 25 degrees Celsius. The resulting solution was extracted with ethyl acetate and the organic layers combined and dried over anhydrous sodium sulfate and concentrated under vacuum. The crude product was purified by Prep-HPLC (Method E). 1-Methyl-5-((R)-3-methyl-morpholin-4-yl)-3-(1H-pyrazol-3-yl)-7-(1H-pyrrolo[2,3-b]pyridin-4-yl)-1H-pyrazolo[4,3-b]pyridine was isolated as a yellow solid (4 mg, 12%); melting point 200° C.;

$^1$H NMR (300 MHz, DMSO-d$_6$): δ13.09 (d, J=86.7 Hz, 1H), 11.97 (s, 1H), 8.39 (d, J=4.8 Hz, 1H), 7.57 (t, J=2.9 Hz, 2H), 7.25 (d, J=4.8 Hz, 1H), 7.04 (d, J=29.0 Hz, 2H), 6.18 (dd, J=3.4, 1.6 Hz, 1H), 4.44 (d, J=7.6 Hz, 1H), 4.21-3.86 (m, 2H), 3.85-3.63 (m, 2H), 3.54 (td, J=11.7, 2.9 Hz, 1H), 3.42 (s, 3H), 3.18 (td, J=12.7, 3.7 Hz, 1H), 1.19 (d, J=6.5 Hz, 3H);

LC/MS (Method H): Rt 1.258 min [MH]+415.3.

Example 16

2-Methyl-5-((R)-3-methyl-morpholin-4-yl)-3-(1H-pyrazol-3-yl)-7-(1H-pyrrolo[2,3-b]pyridin-4-yl)-2H-pyrazolo[4,3-b]pyridine (16)

Absolute

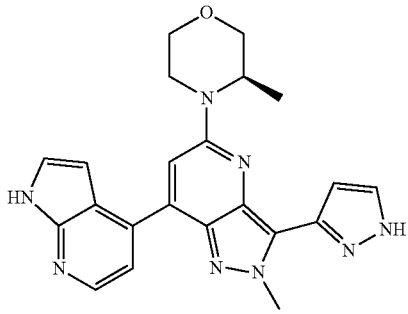

2-Methyl-5-((R)-3-methyl-morpholin-4-yl)-3-(1H-pyrazol-3-yl)-7-(1H-pyrrolo[2,3-b]pyridin-4-yl)-2H-pyrazolo[4,3-b]pyridine was prepared analogously to above examples and was isolated as a yellow solid (74 mg, 99%); melting point 280° C.; $^1$H NMR (300 MHz, DMSO-d$_6$): δ13.16 (s, 1H), 11.83 (s, 1H), 8.33 (d, J=4.9 Hz, 1H), 7.91 (s, 1H), 7.67 (d, J=4.9 Hz, 1H), 7.58 ? 7.44 (m, 1H), 7.30 (d, J=3.7 Hz, 2H), 6.55 (dd, J=3.5, 1.7 Hz, 1H), 4.39 (s, 4H), 4.10-3.83 (m, 2H), 3.73 (t, J=9.4 Hz, 2H), 3.54 (t, J=11.2 Hz, 1H), 3.19 (d, J=12.6 Hz, 1H), 1.21 (d, J=6.5 Hz, 4H); LC/MS (Method I): 2.41 min, [MH]+415.3.

Example 17

7-(6-Methanesulfonyl-4-methyl-pyridin-3-yl)-1-methyl-5-((R)-3-methyl-morpholin-4-yl)-3-(1H-pyrazol-3-yl)-1H-pyrazolo[4,3-b]pyridine (17)

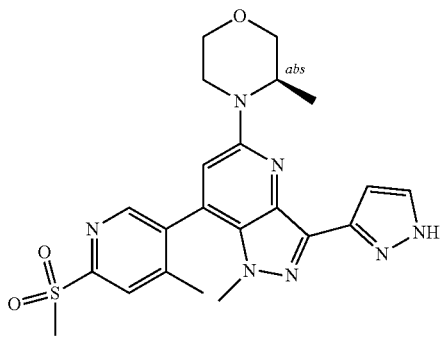 [SMILES: Cc1cc(S(C)(=O)=O)ncc1-c1cc(N2CCOC[C@H]2C)nc2c(-c3cc[nH]n3)nn(C)c12]

7-(6-Methanesulfonyl-4-methyl-pyridin-3-yl)-1-methyl-5-((R)-3-methyl-morpholin-4-yl)-3-(1H-pyrazol-3-yl)-1H-pyrazolo[4,3-b]pyridine was prepared analogously to above examples and was isolated as a yellow solid (30 mg, 22%); melting point 189-190° C.;
$^1$H NMR (300 MHz, DMSO-d$_6$): δ13.24 (m, 1H), 8.79 (s, 1H), 8.17 (s, 1H), 7.61 (m, 1H), 7.04 (d, J=11.1 Hz, 2H), 4.44 (s, 1H), 4.08-3.99 (m, 2H), 3.81-3.63 (m, 2H), 3.62-3.51 (m, 1H), 3.47 (s, 3H), 3.36 (s, 3H), 3.18 (m, 1H), 2.29 (s, 3H), 1.19 (t, J=6.4 Hz, 3H);
LC/MS (Method G): Rt 1.212 min, [MH]+468.3.

Example 18

7-(1-Isopropyl-1H-pyrazol-4-yl)-1-methyl-5-((R)-3-methyl-morpholin-4-yl)-3-(1H-pyrazol-3-yl)-1H-pyrazolo[4,3-b]pyridine (18)

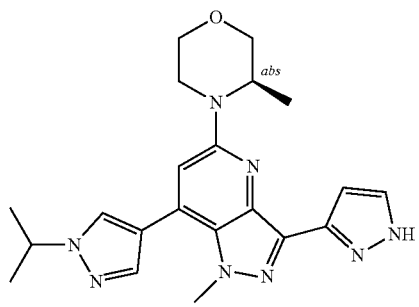 [SMILES: CC(C)n1cc(-c2cc(N3CCOC[C@H]3C)nc3c(-c4cc[nH]n4)nn(C)c23)cn1]

7-(1-Isopropyl-1H-pyrazol-4-yl)-1-methyl-5-((R)-3-methyl-morpholin-4-yl)-3-(1H-pyrazol-3-yl)-1H-pyrazolo[4,3-b]pyridine was prepared analogously to above examples and was isolated as a white solid (50 mg, 41%); melting point 114-115° C.;
$^1$H NMR (300 MHz, DMSO-d$_6$): δ13.22-13.14 (m, 1H), 8.27 (s, 1H), 7.84 (s, 1H), 7.58 (s, 1H), 7.01 (s, 1H), 6.87 (d, J=11.2 Hz, 1H), 4.70-4.56 (m, 1H), 4.56-4.44 (m, 1H), 4.09-3.93 (m, 2H), 3.80-3.65 (m, 2H), 3.88 (s, 3H), 3.53 (td, J=11.6, 2.9 Hz, 1H), 3.17 (td, J=12.7, 3.7 Hz, 1H), 1.50 (d, J=6.6 Hz, 6H), 1.17 (d, J=6.5 Hz, 3H); LC/MS (Method G): Rt 1.295 min [MH]+407.3.

Example 19

7-(1,3-Dimethyl-1H-pyrazol-4-yl)-1-methyl-5-((R)-3-methyl-morpholin-4-yl)-3-(1H-pyrazol-3-yl)-1H-pyrazolo[4,3-b]pyridine (19)

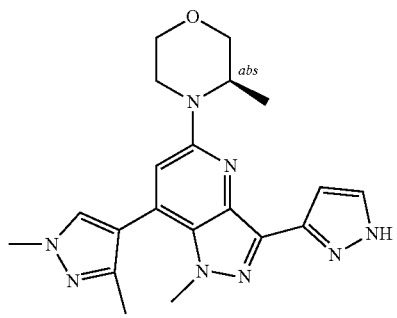 [SMILES: Cc1nn(C)cc1-c1cc(N2CCOC[C@H]2C)nc2c(-c3cc[nH]n3)nn(C)c12]

7-(1,3-Dimethyl-1H-pyrazol-4-yl)-1-methyl-5-((R)-3-methyl-morpholin-4-yl)-3-(1H-pyrazol-3-yl)-1H-pyrazolo[4,3-b]pyridine was prepared analogously to above examples and was isolated as a colorless solid (35 mg, 28%); melting point 139-140° C.;
$^1$H NMR (300 MHz, DMSO-d$_6$): δ13.17-12.90 (m, 1H), 7.95 (s, 1H), 7.79-7.61 (m, 1H), 7.02 (s, 1H), 6.80 (s, 1H), 4.42 (s, 1H), 4.09-3.95 (m, 2H), 3.89 (s, 3H), 3.77-3.70 (m, 5H), 3.54 (td, J=11.7, 3.0 Hz, 1H), 3.14 (td, J=12.7, 3.8 Hz, 1H), 2.12 (s, 3H), 1.16 (d, J=6.5 Hz, 3H); LC/MS (Method G): Rt 1.158 min [MH]+393.3.

Example 20

7-(3-Fluoro-pyridin-4-yl)-1-methyl-5-((R)-3-methyl-morpholin-4-yl)-3-(1H-pyrazol-3-yl)-1H-pyrazolo[4,3-b]pyridine (20)

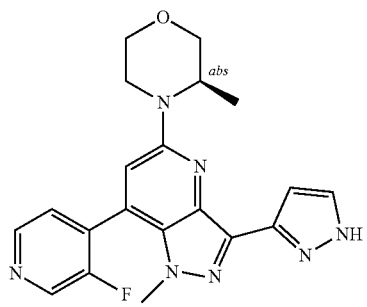 [SMILES: C[C@@H]1COCCN1c1cc(-c2ccncc2F)c2c(n1)c(-c1cc[nH]n1)nn2C]

7-(3-Fluoro-pyridin-4-yl)-1-methyl-5-((R)-3-methyl-morpholin-4-yl)-3-(1H-pyrazol-3-yl)-1H-pyrazolo[4,3-b]pyridine was prepared analogously to above examples and was isolated as yellow solid (33 mg, 40%); melting point 145-147° C.; ¹H NMR (300 MHz, DMSO-d₆): δ13.05 (s, 1H), 8.78 (d, J=1.4 Hz, 1H), 8.62 (dd, J=4.8, 1.2 Hz, 1H), 7.77-7.61 (m, 2H), 7.07-6.99 (m, 2H), 4.43 (q, J=7.0 Hz, 1H), 4.07-3.89 (m, 2H), 3.78-3.42 (m, 6H), 3.15 (td, J=12.7, 3.7 Hz, 1H), 1.15 (d, J=6.5 Hz, 3H);

LC/MS (Method E): Rt 1.285 min, [MH]+394.0.

Example 21

7-(6-Methanesulfonyl-4-methyl-pyridin-3-yl)-2-methyl-5-((R)-3-methyl-morpholin-4-yl)-3-(1H-pyrazol-3-yl)-2H-pyrazolo[4,3-b]pyridine (21)

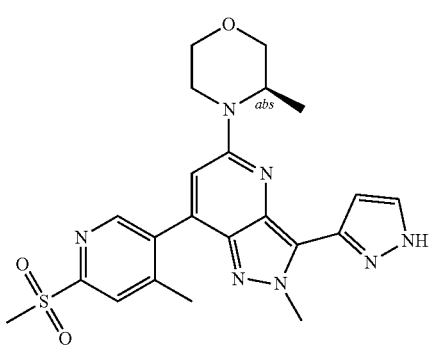 [SMILES: Cc1cc(S(C)(=O)=O)ncc1-c1cc(N2CCOC[C@H]2C)nc2c(-c3cc[nH]n3)n(C)nc12]

7-(6-Methanesulfonyl-4-methyl-pyridin-3-yl)-2-methyl-5-((R)-3-methyl-morpholin-4-yl)-3-(1H-pyrazol-3-yl)-2H-pyrazolo[4,3-b]pyridine was prepared analogously to above examples and was isolated as a yellow solid (2 mg, 4%); melting point 188-190° C.;

¹H NMR (300 MHz, CDCl₃): δ8.67 (s, 1H), 8.06 (s, 1H), 7.72 (d, J=2.0 Hz, 1H), 6.79 (d, J=14.0 Hz, 2H), 4.32 (s, 3H), 4.15-3.94 (m, 2H), 3.84 (d, J=2.2 Hz, 2H), 3.68 (td, J=11.8, 3.0 Hz, 1H), 3.40 (td, J=12.6, 3.7 Hz, 1H), 3.25 (s, 3H), 2.43 (s, 3H), 1.34 (d, J=6.7 Hz, 3H), 1.23 (s, 1H);

LC/MS (Method G): Rt 1.265 min, [MH]+468.0.

Example 22

7-(2,4-Dimethyl-pyridin-3-yl)-1-methyl-5-((R)-3-methyl-morpholin-4-yl)-3-(1H-pyrazol-3-yl)-1H-pyrazolo[4,3-b]pyridine (22)

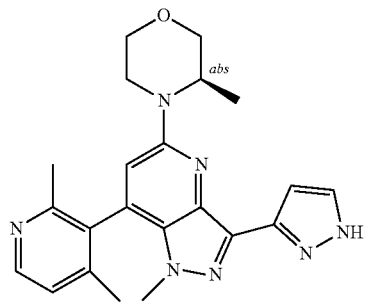

7-(2,4-Dimethyl-pyridin-3-yl)-1-methyl-5-((R)-3-methyl-morpholin-4-yl)-3-(1H-pyrazol-3-yl)-1H-pyrazolo[4,3-b]pyridine was prepared analogously to above examples and was isolated as yellow solid (11 mg, 18%); melting point 128-130° C.; ¹H NMR (300 MHz, DMSO-d₆): δ8.48 (d, J=5.1 Hz, 1H), 7.69 (s, 1H), 7.32 (d, J=5.1 Hz, 1H), 7.08 (s, 1H), 6.95 (s, 1H), 4.42 (d, J=7.5 Hz, 1H), 4.16-3.95 (m, 2H), 3.73 (d, J=4.6 Hz, 2H), 3.64-3.49 (m, 1H), 3.33 (s, 3H), 3.17 (td, J=12.7, 3.7 Hz, 1H), 2.23 (d, J=1.7 Hz, 3H), 2.06 (d, J=2.1 Hz, 3H), 1.28-1.14 (m, 3H); LC/MS (Method B): Rt 2.095 min, [MH]+404.0.

Example 23

1-Methyl-5-((R)-3-methyl-morpholin-4-yl)-7-(3-methyl-pyridin-4-yl)-3-(1H-pyrazol-3-yl)-1H-pyrazolo[4,3-b]pyridine (23)

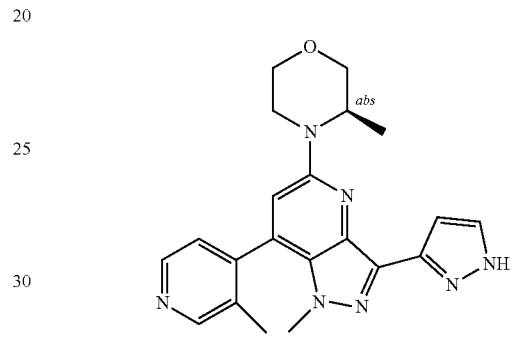

1-Methyl-5-((R)-3-methyl-morpholin-4-yl)-7-(3-methyl-pyridin-4-yl)-3-(1H-pyrazol-3-yl)-1H-pyrazolo[4,3-b]pyridine was prepared analogously to above examples and was isolated as a yellow solid (32 mg, 44%); melting point 145° C.; ¹H NMR (300 MHz, DMSO-d₆) δ13.15 (s, 1H), 8.64 (s, 1H), 8.57 (d, J=4.9 Hz, 1H), 7.67 (s, 1H), 7.44 (dd, J=5.0, 2.0 Hz, 1H), 7.06 (s, 1H), 6.90 (s, 1H), 4.55-4.33 (m, 1H), 4.02 (ddd, J=23.6, 11.5, 4.7 Hz, 2H), 3.83-3.61 (m, 2H), 3.53 (td, J=11.7, 3.0 Hz, 1H), 3.44 (d, J=1.1 Hz, 3H), 3.16 (td, J=12.6, 3.7 Hz, 1H), 2.11 (s, 3H), 1.17 (dd, J=6.6, 4.0 Hz, 3H);

LC/MS (Method E): RT 1.021 min, [MH]+390.1.

Example 24

[1-Methyl-5-((R)-3-methyl-morpholin-4-yl)-3-(1H-pyrazol-3-yl)-1H-pyrazolo[4,3-b]pyridin-7-yl]-methanol (24)

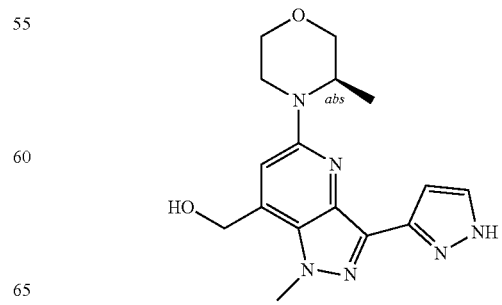

Building Block for Synthesis of Example 24:
methyl 1-methyl-5-[(3R)-3-methylmorpholin-4-yl]-
1H-pyrazolo[4,3-b]pyridine-7-carboxylate

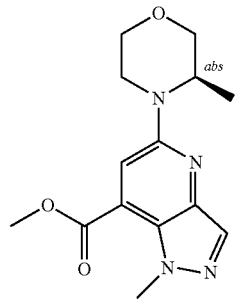

7-Chloro-1-methyl-5-((R)-3-methyl-morpholin-4-yl)-1H-pyrazolo[4,3-b]pyridine (2.95 g, 11.06 mmol), Pd(dppf)Cl$_2$·CH$_2$Cl$_2$ (271 mg, 0.332 mmol, 0.03 eq.), 1,1-bis-(diphenylphosphino)-ferrocen (184 mg, 0.332 mmol), triethylamine (1.5 g, 14.4 mmol, 1.3 eq.), THF (30 ml) and methanol (30 mL) were combined and stirred under a CO atmosphere at 6.3 bar and for 16 h at 100° C. The resulting solution was concentrated under vacuum and purified by column chromatography. 1-Methyl-5-[(3R)-3-methylmorpholin-4-yl]-1H-pyrazolo[4,3-b]pyridine-7-carboxylate was isolated as a yellow solid (3.1 g, 96%); LC/MS (Method K): RT 0.872 min, [MH]+291.1.

Building Block for Synthesis of Example 24:
methyl 3-bromo-1-methyl-5-[(3R)-3-methylmorpholin-4-yl]-1H-pyrazolo[4,3-b]pyridine-7-carboxylate

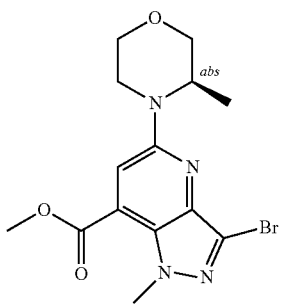 [SMILES: COC(=O)c1cc(N2CCOC[C@H]2C)nc2c(Br)nn(C)c12]

Methyl 1-methyl-5-[(3R)-3-methylmorpholin-4-yl]-1H-pyrazolo[4,3-b]pyridine-7-carboxylate (200 mg, 0.62 mmol, 1.0 eq.), NBS (147.13 mg, 0.74 mmol, 1.20 eq.) and MeCN (20 mL) were combined and stirred for 1 h at 25° C. The resulting mixture was concentrated under vacuum. The residue was purified by column chromatography (Method E). Methyl 3-bromo-1-methyl-5-[(3R)-3-methylmorpholin-4-yl]-1H-pyrazolo[4,3-b]pyridine-7-carboxylate was isolated as a yellow solid (120 mg, 43%). LC/MS (Method J): RT 1.238 min, [MH]+369.0.

Building Block for Synthesis of Example 24:
methyl 1-methyl-5-[(3R)-3-methylmorpholin-4-yl]-
3-[1-(oxan-2-yl)-1H-pyrazol-3-yl]-1H-pyrazolo[4,3-b]pyridine-7-carboxylate

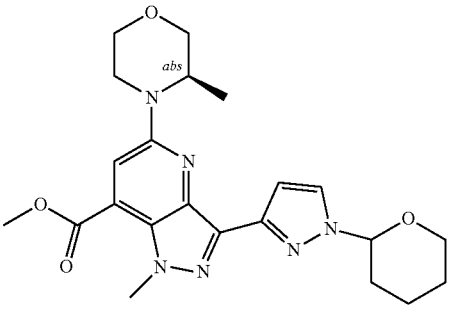 [SMILES: COC(=O)c1cc(N2CCOC[C@H]2C)nc2c(-c3ccn(C4CCCCO4)n3)nn(C)c12]

Methyl 3-bromo-1-methyl-5-[(3R)-3-methylmorpholin-4-yl]-1H-pyrazolo[4,3-b]pyridine-7-carboxylate (110 mg, 0.27 mmol, 1.0 eq.), 1-(oxan-2-yl)-3-(tetramethyl-1,3,2-dioxaborolan-2-yl)-1H-pyrazole (235.53 mg, 0.80 mmol, 3 eq.), Pd(pph$_3$)$_4$ (34.43 mg, 0.03 mmol, 0.10 eq.), sodium carbonate (89.75 mg, 0.80 mmol, 3.0 eq.), tetrahydrofuran (17.60 mL) and water (4.40 mL) were combined and stirred 1 h at 80° C. in the microwave. The resulting solution was extracted with ethyl acetate and concentrated under vacuum. The residue was purified by column chromatography (Method E). Methyl 1-methyl-5-[(3R)-3-methylmorpholin-4-yl]-3-[1-(oxan-2-yl)-1H-pyrazol-3-yl]-1H-pyrazolo[4,3-b]pyridine-7-carboxylate was isolated as a yellow solid (80 mg, 61%); LC/MS (Method J): RT 1.242 min, [MH]+441.0.

Building Block for Synthesis of Example 24:
{1-methyl-5-[(3R)-3-methylmorpholin-4-yl]-3-[1-(oxan-2-yl)-1H-pyrazol-3-yl]-1H-pyrazolo[4,3-b]pyridin-7-yl}methanol

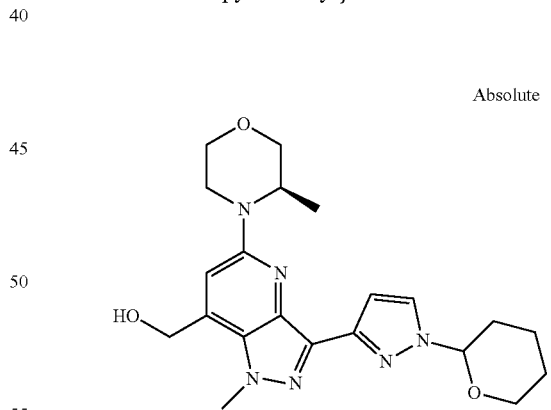

To a stirred mixture of methyl 1-methyl-5-[(3R)-3-methylmorpholin-4-yl]-3-[1-(oxan-2-yl)-1H-pyrazol-3-yl]-1H-pyrazolo[4,3-b]pyridine-7-carboxylate (16 g, 32.69 mmol) in THF (400 mL) was added LiBH$_4$ (1117 mg, 48.71 mmol, 1.5 eq. 95%) dropwise at 0° C. under nitrogen atmosphere. The resulting mixture was stirred for 2 h at room temperature under nitrogen atmosphere. The reaction was quenched with saturated NH$_4$Cl (aq.) at 0° C. The resulting mixture was concentrated under reduced pressure. The aqueous layer was extracted with CH$_2$Cl$_2$. The resulting mixture was concentrated under reduced pressure. The residue was purified by column chromatography (Method O) to afford [1-methyl-5-[(3R)-3-methylmorpholin-4-yl]-3-[1-(oxan-2-yl)-1H-pyrazol-3-yl]-1H-pyrazolo[4,3-b]pyridin-7-yl]methanol (13 g, 87%) as a yellow solid.

Example 24

[1-Methyl-5-((R)-3-methyl-morpholin-4-yl)-3-(1H-pyrazol-3-yl)-1H-pyrazolo[4,3-b]pyridin-7-yl]-methanol

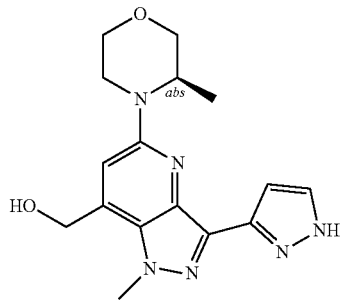 [SMILES: C[C@@H]1COCCN1c1cc(CO)c2c(n1)c(-c1cc[nH]n1)nn2C]

[1-Methyl-5-[(3R)-3-methylmorpholin-4-yl]-3-[1-(oxan-2-yl)-1H-pyrazol-3-yl]-1H-pyrazolo[4,3-b]pyridin-7-yl]methanol (50 mg, 0.11 mmol, 1 eq.) was dissolved in HCl in methanol (3.000 mL). The resulting solution was stirred for 1 h at 25° C. The pH value of the solution was adjusted to 9 with sodium bicarbonate (0.5 mL). The resulting solution was extracted with dichloromethane and the organic layers combined and concentrated under vacuum. The crude product was purified by Prep-H PLC (Method F). [1-Methyl-5-[(3R)-3-methylmorpholin-4-yl]-3-(1H-pyrazol-3-yl)-1H-pyrazolo[4,3-b]pyridin-7-yl]methanol was isolated as a colorless solid (30 mg, 82%); melting point 195-197° C.;
$^1$H NMR (300 MHz, DMSO-$d_6$): δ13.09 (s, 1H), 7.55 (s, 1H), 6.99 (d, J=14.7 Hz, 2H), 5.59 (t, J=5.5 Hz, 1H), 4.90 (d, J=4.4 Hz, 2H), 4.36 (d, J=10.8 Hz, 1H), 3.96 (dd, J=11.1, 3.6 Hz, 2H), 3.79-3.60 (m, 2H), 3.50 (td, J=11.7, 3.0 Hz, 1H), 3.28 (s, 2H), 3.12 (td, J=12.8, 3.8 Hz, 1H), 1.12 (d, J=6.6 Hz, 3H).
LC/MS (Method E): RT 0,932 min, [MH]+329.1.

Example 25

2-[1-Methyl-5-((R)-3-methyl-morpholin-4-yl)-3-(1H-pyrazol-3-yl)-1H-pyrazolo[4,3-b]pyridin-7-yl]-propan-2-ol (25)

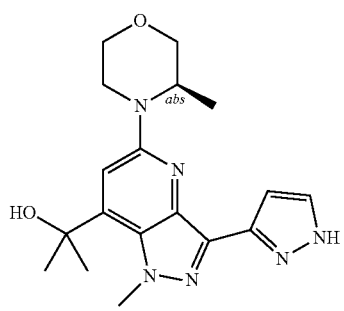

Building Block for Synthesis of Example 25: 2-{1-methyl-5-[(3R)-3-methylmorpholin-4-yl]-3-[1-(oxan-2-yl)-1H-pyrazol-3-yl]-1H-pyrazolo[4,3-b]pyridin-7-yl}propan-2-ol

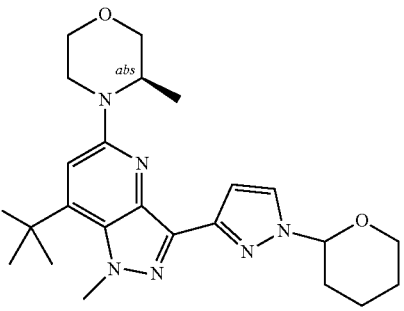

Methyl 1-methyl-5-[(3R)-3-methylmorpholin-4-yl]-3[1-(oxan-2-yl)-1H-pyrazol-3-yl]-1H-pyrazolo[4,3-b]pyridine-7-carboxylate (700 mg, 1.43 mmol) and a solution of CH$_3$MgBr (575.11 mg, 4.58 mmol, 3.0 eq.) in tetrahydrofuran (20 mL) were combined and stirred 2 h at 25° C. The reaction was quenched by the addition of NH$_4$Cl. The resulting solution was extracted with ethyl acetate and the organic layers combined and concentrated under vacuum. 2-[1-Methyl-5-[(3R)-3-methylmorpholin-4-yl]-3-[1-(oxan-2-yl)-1H-pyrazol-3-yl]-1H-pyrazolo[4,3-b]pyridin-7-yl]propan-2-ol was isolated as a yellow solid (600 mg, 86%).

Example 25

2-[1-Methyl-5-((R)-3-methyl-morpholin-4-yl)-3-(1H-pyrazol-3-yl)-1H-pyrazolo[4,3-b]pyridin-7-yl]-propan-2-ol

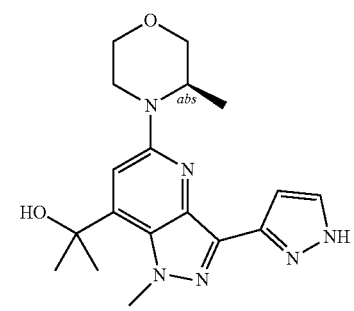 [SMILES: C[C@@H]1COCCN1c1cc(C(C)(C)O)c2c(n1)c(-c1cc[nH]n1)nn2C]

2-[1-Methyl-5-[(3R)-3-methylmorpholin-4-yl]-3-(1H-pyrazol-3-yl)-1H-pyrazolo[4,3-b]pyridin-7-yl]propan-2-ol was prepared analogously to above examples and was isolated as a colorless solid (80 mg, 18%); melting point 123-125° C.; $^1$H NMR (300 MHz, DMSO-$d_6$): δ13.11 (s, 1H), 12.85 (s, 0H), 7.75 (s, 0H), 7.53 (s, 1H), 7.08 (s, 0H), 6.96 (s, 1H), 6.81 (s, 1H), 5.70 (s, 1H), 4.38 (s, 4H), 3.95 (dd, J=11.1, 3.5 Hz, 2H), 3.79-3.60 (m, 2H), 3.50 (td, J=11.7, 2.9 Hz, 1H), 3.12 (td, J=12.6, 3.8 Hz, 1H), 2.04 (s, 0H), 1.62 (d, J=3.5 Hz, 5H), 1.12 (d, J=6.6 Hz, 3H);
LC/MS (Method D): Rt 0.867 min, [MH]+357.2.

Example 26

7-(1-Methanesulfonyl-cyclopropyl)-1-methyl-5-((R)-3-methyl-morpholin-4-yl)-3-(1H-pyrazol-3-yl)-1H-pyrazolo[4,3-b]pyridine (26)

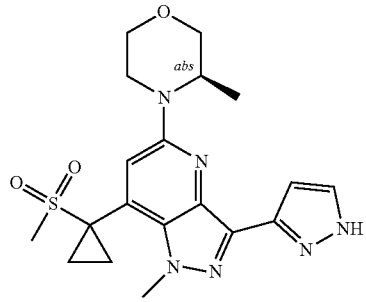 [SMILES: C[C@@H]1COCCN1c1cc(C2(S(C)(=O)=O)CC2)c2c(n1)c(-c1cc[nH]n1)nn2C]

Building Block for Synthesis of Example 26: {1-methyl-5-[(3R)-3-methylmorpholin-4-yl]-3-[1-(oxan-2-yl)-1H-pyrazol-3-yl]-1H-pyrazolo[4,3-b]pyridin-7-yl}methyl methanesulfonate

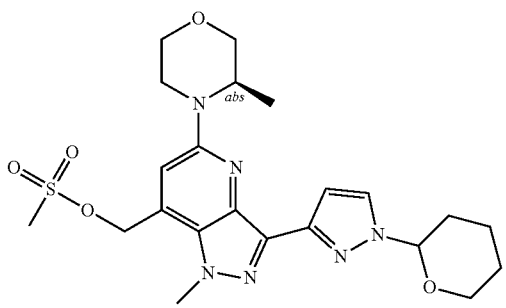 [SMILES: C[C@@H]1COCCN1c1cc(COS(C)(=O)=O)c2c(n1)c(-c1ccn(C3CCCCO3)n1)nn2C]

[1-Methyl-5-[(3R)-3-methylmorpholin-4-yl]-3[1-(oxan-2-yl)-1H-pyrazol-3-yl]-1H-pyrazolo[4,3-b]pyridin-7-yl]methanol (700 mg, 1.53 mmol, 1.0 eq.) was dissolved in dichloromethane (34.48 mL) and stirred for 0.5 h at 0° C. To this was added triethylamine (700 mg, 6.57 mmol, 3 eq.), MsCl (340 mg, 2.82 mmol, 1.30 eq.). The resulting solution was stirred for 1 h at 25° C. The reaction was then quenched by the addition of 2 mL of NH₄Cl solution. The resulting solution was extracted with dichloromethane and the organic layers combined and concentrated under vacuum. The residue was purified by column chromatography (Method E). [1-Methyl-5-[(3R)-3-methylmorpholin-4-yl]-3-[1-(oxan-2-yl)-1H-pyrazol-3-yl]-1H-pyrazolo[4,3-b]pyridin-7-yl] methyl methanesulfonate was isolated as a yellow solid (1 g, quant). LC/MS (Method J): RT 1.165 min, [MH]+491.0.

Building Block for Synthesis of Example 26: (3R)-4-[7-(methanesulfonylmethyl)-1-methyl-3-[1-(oxan-2-yl)-1H-pyrazol-3-yl]-1H-pyrazolo[4,3-b]pyridin-5-yl]-3-methylmorpholine

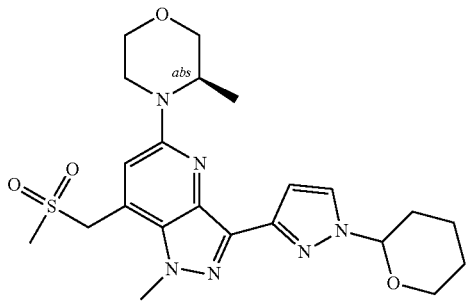 [SMILES: C[C@@H]1COCCN1c1cc(CS(C)(=O)=O)c2c(n1)c(-c1ccn(C3CCCCO3)n1)nn2C]

[1-Methyl-5-[(3R)-3-methylmorpholin-4-yl]-3-[1-(oxan-2-yl)-1H-pyrazol-3-yl]-1H-pyrazolo[4,3-b]pyridin-7-yl] methyl methanesulfonate (900 mg, 1.65 mmol, 1 eq.), sodium methanesulfinate (230.66 mg, 2.15 mmol, 1.30 eq.), triethylamine (527.61 mg, 4.95 mmol, 3.0 eq.), CH₃CN (90 mL) and DMF (9 mL) were combined and stirred for 16 h at 120° C. The resulting solution was extracted with ethyl acetate and the organic layers combined and concentrated under vacuum. The residue was purified by column chromatography (Method E). (3R)-4-[7-(Methanesulfonylmethyl)-1-methyl-3-[1-(oxan-2-yl)-1H-pyrazol-3-yl]-1H-pyrazolo[4,3-b]pyridin-5-yl]-3-methylmorpholine was isolated as a yellow solid (700 mg, 80%); LC/MS (Method L): RT 0.788 min, [MH]+413.1.

Building Block for Synthesis of Example 26: (3R)-4-[7-(1-methanesulfonylethenyl)-1-methyl-3-[1-(oxan-2-yl)-1H-pyrazol-3-yl]-1H-pyrazolo[4,3-b]pyridin-5-yl]-3-methylmorpholine

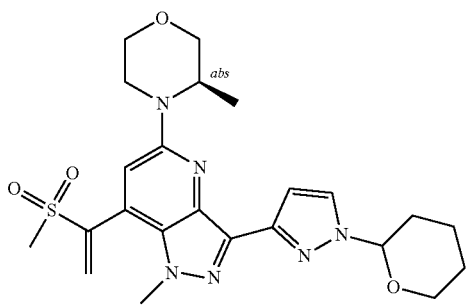 [SMILES: C=C(c1cc(N2CCOC[C@H]2C)nc2c(-c3ccn(C4CCCCO4)n3)nn(C)c12)S(C)(=O)=O]

(3R)-4-[7-(Methanesulfonylmethyl)-1-methyl-3-[1-(oxan-2-yl)-1H-pyrazol-3-yl]-1H-pyrazolo[4,3-b]pyridin-5-yl]-3-methylmorpholine (100 mg, 0.19 mmol, 1. eq.), [(dimethylamino)methyl]dimethylamine (44.87 mg, 0.42 mmol, 2.20 eq.), acetic anhydride (44.83 mg, 0.42 mmol, 2.20 eq.) and DMF (20 mL) were combined and stirred for 16 h at 60° C. The resulting solution was extracted with dichloromethane and the organic layers combined and concentrated under vacuum. The residue was purified by column chromatography (Method E). (3R)-4-[7-(1-Methanesulfonylethenyl)-1-methyl-3-[1-(oxan-2-yl)-1H-pyrazol-3-yl]-1H-pyrazolo[4, 3-b]pyridin-5-yl]-3-methylmorpholine was isolated as a yellow solid (60 mg, 58%); LC/MS (Method J): Rt 1.119 min [MH]+487.2.

Building Block for Synthesis of Example 26: (3R)-4-[7-(1-methanesulfonyl-cyclopropyl)-1-methyl-3-[1-(oxan-2-yl)-1H-pyrazol-3-yl]-1H-pyrazolo[4,3-b]pyridin-5-yl]-3-methylmorpholine

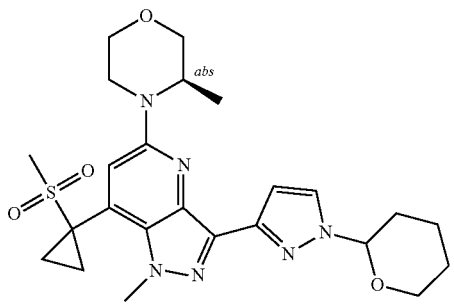 [SMILES: C[C@@H]1COCCN1c1cc(C2(S(C)(=O)=O)CC2)c2c(n1)c(-c1ccn(C3CCCCO3)n1)nn2C]

Methanesulfonyl iodide (24.06 mg, 0.11 mmol, 1.20 eq.) and DMSO (10 mL) were combined and stirred for 30 min at 0° C. To this was added sodium hydride (4.40 mg, 0.11 mmol, 1.19 equiv, 60%) and (3R)-4-[7-(1-methane-sulfonylethenyl)-1-methyl-3-[1-(oxan-2-yl)-1H-pyrazol-3-yl]-1H-pyrazolo[4,3-b]pyridin-5-yl]-3-methylmorpholine (50 mg, 0.09 mmol, 1.0 eq.). The mixture was stirred for 1 h at 25° C. in the microwave. The reaction was then quenched by the addition of $NH_4Cl$. The resulting solution was extracted with ethyl acetate and the organic layers combined and concentrated under vacuum. (3R)-4-[7-(1-Methanesulfonylcyclopropyl)-1-methyl-3-[1-(oxan-2-yl)-1H-pyrazol-3-yl]-1H-pyrazolo[4,3-b]pyridin-5-yl]-3-methylmorpholine was isolated as a yellow solid (40 mg, 80%); LC/MS (Method L): RT: 0.887 min, [MH]+501.0.

Example 26

7-(1-Methanesulfonyl-cyclopropyl)-1-methyl-5-((R)-3-methyl-morpholin-4-yl)-3-(1H-pyrazol-3-yl)-1H-pyrazolo[4,3-b]pyridine

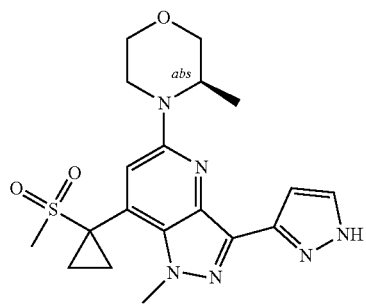 [SMILES: C[C@@H]1COCCN1c1cc(C2(S(C)(=O)=O)CC2)c2c(n1)c(-c1cc[nH]n1)nn2C]

(3R)-4-[7-(1-Methanesulfonylcyclopropyl)-1-methyl-3-[1-(oxan-2-yl)-1H-pyrazol-3-yl]-1H-pyrazolo[4,3-b]pyridin-5-yl]-3-methylmorpholine (30 mg, 0.05 mmol, 1. eq.) was dissolved in hydrogen chloride in methanol (3 mL). The resulting solution was stirred for 1 h at 25° C. The resulting solution was extracted with dichloromethane and the organic layers combined and concentrated under vacuum. The crude product was purified by Prep-HPLC (Method G). (3R)-4-[7-(1-Methanesulfonylcyclopropyl)-1-methyl-3-(1H-pyrazol-3-yl)-1H-pyrazolo[4,3-b]pyridin-5-yl]-3-methylmorpholine was isolated as a light yellow solid (5 mg, 24%); melting point 180-182° C.;

$^1$H NMR (400 MHz, Methanol-$d_4$): δ7.64 (s, 1H), 7.25 (s, 2H), 7.06 (s, 1H), 4.51 (d, J=7.1 Hz, 2H), 4.38 (s, 5H), 4.07 (d, J=12.5 Hz, 4H), 3.86 (s, 3H), 3.76-3.65 (m, 2H), 3.05 (s, 4H), 2.28 (dd, J=10.7, 5.6 Hz, 2H), 1.82 (p, J=5.1 Hz, 2H), 1.70 (q, J=6.7, 5.9 Hz, 4H), 1.30 (t, J=6.0 Hz, 7H); LC/MS (Method E): Rt 1.235 min [MH]+417.0.

Example 26 can be synthesized via an alternative synthesis route.

Building block for alternative synthesis route to Example 26: 3-Bromo-7-chloromethyl-1-methyl-5-((R)-3-methyl-morpholin-4-yl)-1H-pyrazolo[4,3-b]pyridine

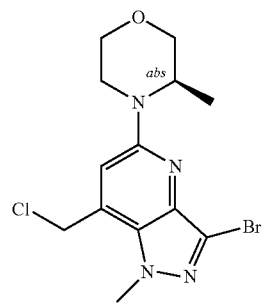 [SMILES: C[C@@H]1COCCN1c1cc(CCl)c2c(n1)c(Br)nn2C]

[3-Bromo-1-methyl-5-((R)-3-methyl-morpholin-4-yl)-1H-pyrazolo[4,3-b]pyridin-7-yl]-methanol (500 mg, 1.46 mmol), dichloromethane (3.72 ml) and thionyl chloride (0.32 ml; 4.37 mmol; 3 eq.) were combined and stirred at room temp. for 14 h. The reaction mixture was concentrated under reduced pressure and extracted with saturated $NaHCO_3$ solution and DCM. The combined organic layers were concentrated under reduced pressure. 3-Bromo-7-chloromethyl-1-methyl-5-((R)-3-methyl-morpholin-4-yl)-1H-pyrazolo[4,3-b]pyridine was isolated as brown solid (519 mg, 99%); LC/MS (Method F): Rt 2.798 min; [MH]+359.0.

Building block for alternative synthesis route to Example 26: 3-Bromo-7-methanesulfonylmethyl-1-methyl-5-((R)-3-methyl-morpholin-4-yl)-1H-pyrazolo[4,3-b]pyridine

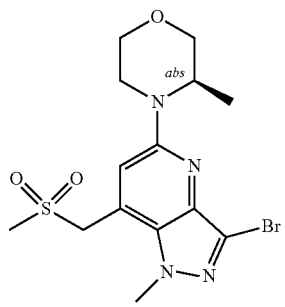 [SMILES: C[C@@H]1COCCN1c1cc(CS(C)(=O)=O)c2c(n1)c(Br)nn2C]

3-Bromo-7-chloromethyl-1-methyl-5-((R)-3-methyl-morpholin-4-yl)-1H-pyrazolo[4,3-b]pyridine (518.70 mg; 1.44 mmol; 1 eq.), 2-propanol (3.86 ml) and sodium methanesulfinate (250 mg; 2.45 mmol; 1.70 eq.) were combined and stirred at 80° C. for 14 h. The reaction suspension was concentrated under reduced pressure. The residue was treated with water and the resulting precipitate was filtered and washed with water and dried for 5 days. 3-Bromo-7-methanesulfonylmethyl-1-methyl-5-((R)-3-methyl-morpholin-4-yl)-1H-pyrazolo[4,3-b]pyridine was isolated as yellow solid (484 mg, 83%); LC/MS (Method F): Rt 2.339 min; [MH]+403.1.

Building block for alternative synthesis route to Example 26: 3-Bromo-7-(1-methanesulfonyl-cyclopropyl)-1-methyl-5-((R)-3-methyl-morpholin-4-yl)-1H-pyrazolo[4,3-b]pyridine

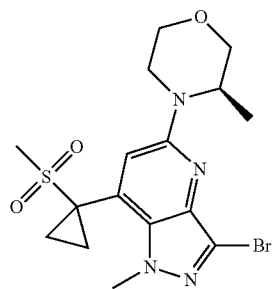 [SMILES: C[C@@H]1COCCN1c1cc(C2(S(C)(=O)=O)CC2)c2c(n1)c(Br)nn2C]

3-Bromo-7-methanesulfonylmethyl-1-methyl-5-((R)-3-methyl-morpholin-4-yl)-1H-pyrazolo[4,3-b]pyridine (800 mg; 1.9 mmol; 1.0 eq.), cesium carbonate (12.63 g; 38.8 mmol; 20 eq.) and tetrabutylammonium bromide (126 mg; 0.39 mmol; 0.2 eq.) were combined. Under nitrogen atmosphere dry dimethyl sulfoxide (20 ml) and 1,2-dibromethane (506 µl; 5.8 mmol; 3.0 eq.) were added and the reaction suspension was stirred at 60° C. 2 days. The reaction mixture was poured into water and the solid was filtered off, washed with water and dried under reduced pressure.

The aqueous layer was extracted with DCM, the combined organic layers were dried over MgSO₄, filtered and concentrated under reduced pressure. 3-Bromo-7-(1-methanesulfonyl-cyclopropyl)-1-methyl-5-((R)-3-methyl-morpholin-4-yl)-1H-pyrazolo[4,3-b]pyridine was isolated as brown solid (311 mg, 37.4%);

LC/MS (Method K), RT: 0.967 min [MH]+429.1.

Building block for alternative synthesis route to Example 26: 7-(1-Methanesulfonyl-cyclopropyl)-1-methyl-5-((R)-3-methyl-morpholin-4-yl)-3-[2-(2-trimethylsilanyl-ethoxymethyl)-2H-pyrazol-3-yl]-1H-pyrazolo[4,3-b]pyridine

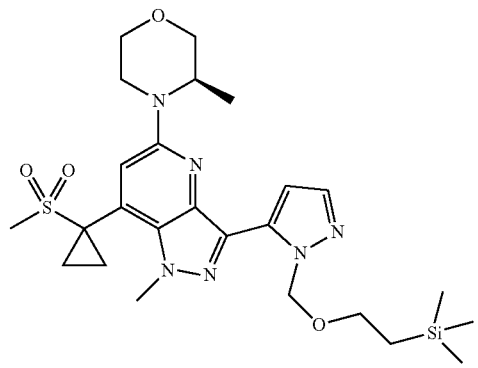

1-(2-Trimethylsilylethoxy)methylpyrazole-5-boronic acid, pinacol ester (421 mg; 1.2 mmol; 1.5 eq.), sodium carbonate (264 mg; 2.5 mmol; 3.0 eq.) and tetrakis(triphenylphosphine)-palladium(0) (116 mg; 0.1 mmol; 0.1 eq.) were added. Then 3-bromo-7-(1-methanesulfonyl-cyclopropyl)-1-methyl-5-((R)-3-methyl-morpholin-4-yl)-1H-pyrazolo[4,3-b]pyridine (357 mg; 0.8 mmol; 1.0 eq.) in tetrahydrofuran (7 ml) and water (0.65 ml) were added while flushing with nitrogen. The reaction suspension was stirred at 90° C. for 3 h. The reaction mixture was filtered and concentrated under reduced pressure. The residue was dissolved in DCM and purified by column chromatography (Method M). 7-(1-Methanesulfonyl-cyclopropyl)-1-methyl-5-((R)-3-methyl-morpholin-4-yl)-3-[2-(2-trimethylsilanyl-ethoxymethyl)-2H-pyrazol-3-yl]-1H-pyrazolo[4,3-b]pyridine was isolated as yellow solid (364; 80.1%); LC/MS (Method K): Rt 1.176 min, [MH]+547.2.

Alternative synthesis route to Example 26: 1-(1-Methanesulfonyl-cyclopropyl)-1-methyl-5-((R)-3-methyl-morpholin-4-yl)-3-(1H-pyrazol-3-yl)-1H-pyrazolo[4,3-b]pyridine

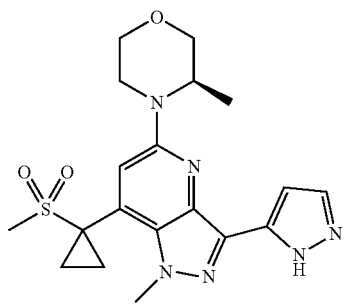 [SMILES: C[C@@H]1COCCN1c1cc(C2(S(C)(=O)=O)CC2)c2c(n1)c(-c1ccn[nH]1)nn2C]

7-(1-Methanesulfonyl-cyclopropyl)-1-methyl-5-((R)-3-methyl-morpholin-4-yl)-3-[2-(2-trimethylsilanyl-ethoxymethyl)-2H-pyrazol-3-yl]-1H-pyrazolo[4,3-b]pyridine (364 mg; 0.666 mmol; 1 eq) was dissolved in HCl in MeOH (10.7 ml, 1.25 M). The solution was stirred at room temp. for 14 h. The reaction solution was concentrated under reduced pressure and diluted with 1M NaOH and the resulting precipitate was filtered off, washed with water and dried at 50° C. under reduced pressure for 14 h. 7-(1-Methanesulfonyl-cyclopropyl)-1-methyl-5-((R)-3-methyl-morpholin-4-yl)-3-(1H-pyrazol-3-yl)-1H-pyrazolo[4,3-b]pyridine was isolated as yellow solid (230 mg, 83%); LC/MS (Method K), RT: 0.843 min [MH]+417.2.

Example 27

5-((R)-3-Methyl-morpholin-4-yl)-3-(1H-pyrazol-3-yl)-1H-pyrazolo[4,3-b]pyridine-7-carboxylic acid dimethylamide (27)

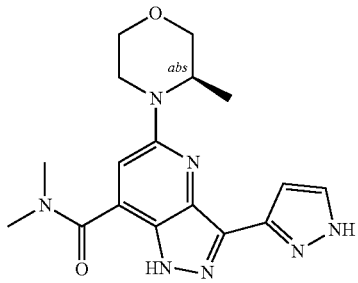 [SMILES: C[C@@H]1COCCN1c1cc(C(=O)N(C)C)c2[nH]nc(-c3cc[nH]n3)c2n1]

Building Block for Synthesis of Example 27:
methyl 5-[(3R)-3-methylmorpholin-4-yl]-1-{[2-(trimethylsilyl)ethoxy]methyl}-1H-pyrazolo[4,3-b]pyridine-7-carboxylate

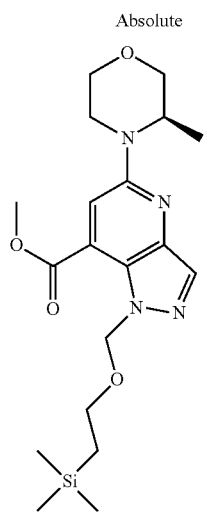 [SMILES: COC(=O)c1cc(N2CCOC[C@H]2C)nc2cnn(COCC[Si](C)(C)C)c12]

5-[(3R)-3-methylmorpholin-4-yl]-1-[[2-(trimethylsilyl)ethoxy]methyl]-1H-pyrazolo[4,3-b]pyridin-7-yl trifluoromethanesulfonate (2 g, 3.6 mmol, 1.0 eq., 90%), Pd(dppf)Cl₂·CH₂Cl₂ (165 mg, 0.18 mmol, 0.05 equiv, 90%), methanol (20 ml) and triethylamine (1.5 g, 3.9 eq.) were combined and purged with nitrogen for 2 min and then pressurized to 10 atm with carbon monoxide at 80° C. for 14 h. The resulting solution was extracted with ethyl acetate and the organic layers combined and dried over sodium sulfate and concentrated under vacuum. The residue was purified by column chromatography (Method P). Methyl 5-[(3R)-3-methylmorpholin-4-yl]-1-[[2-(trimethylsilyl)ethoxy]methyl]-1H-pyrazolo[4,3-b]pyridine-7-carboxylate was isolated as a yellow solid (1.5 g, 92%).

Building Block for Synthesis of Example 27:
methyl 3-iodo-5-[(3R)-3-methylmorpholin-4-yl]-1H-pyrazolo[4,3-b]pyridine-7-carboxylate

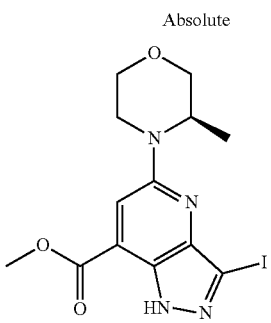 [SMILES: COC(=O)c1cc(N2CCOC[C@H]2C)nc2c(I)n[nH]c12]

Methyl 5-[(3R)-3-methylmorpholin-4-yl]-1H-pyrazolo[4,3-b]pyridine-7-carboxylate (350 mg, 1.14 mmol, 1.0 eq.), methanol (4 mL), potassium carbonate (261 mg, 1.8 mmol, 1.6 eq.) and I2 (481 mg, 1.8 mmol, 1.6 eq.) were combined. The resulting solution was stirred for 1 h at 25° C. and extracted with ethyl acetate and the organic layers combined and dried over anhydrous sodium sulfate and concentrated under vacuum. Methyl 3-iodo-5-[(3R)-3-methylmorpholin-4-yl]-1H-pyrazolo[4,3-b]pyridine-7-carboxylate was isolated as a yellow solid (130 mg, 26%).

Building Block for Synthesis of Example 27:
methyl 3-iodo-5-[(3R)-3-methylmorpholin-4-yl]-1-{[2-(trimethylsilyl)ethoxy]methyl}-1H-pyrazolo[4,3-b]pyridine-7-carboxylate

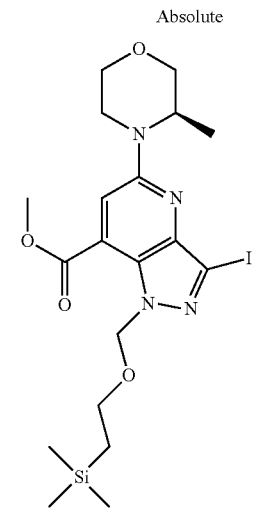 [SMILES: COC(=O)c1cc(N2CCOC[C@H]2C)nc2c(I)nn(COCC[Si](C)(C)C)c12]

Methyl 3-iodo-5-[(3R)-3-methylmorpholin-4-yl]-1H-pyrazolo[4,3-b]pyridine-7-carboxylate (75 mg, 0.17 mmol, 1.0 eq.), tetrahydrofuran (10 mL) and sodium hydride (8.06 mg, 0.20 mmol, 1.2 eq., 60%) were combined and stirred for 0.5 h at 0-5° C. in a water/ice bath. To this was added SEMCl (32.37 mg, 0.20 mmol, 1.20 eq.). The resulting solution was stirred for 1 h at 25° C. The reaction was then quenched by the addition of NH₄Cl aq. The resulting mixture was concentrated under vacuum and extracted with ethyl acetate and the organic layers combined and concentrated under vacuum. Methyl 3-iodo-5-[(3R)-3-methylmorpholin-4-yl]-1-[[2-(trimethylsilyl)ethoxy]methyl]-1H-pyrazolo[4,3-b]pyridine-7-carboxylate as was isolated as a yellow solid (90 mg, 91%).

Building Block for Synthesis of Example 27:
Methyl 5-[(3R)-3-methylmorpholin-4-yl]-3-[1-(oxan-2-yl)-1H-pyrazol-3-yl]-1-{[2-(trimethylsilyl)ethoxy]methyl}-1H-pyrazolo[4,3-b]pyridine-7-carboxylate

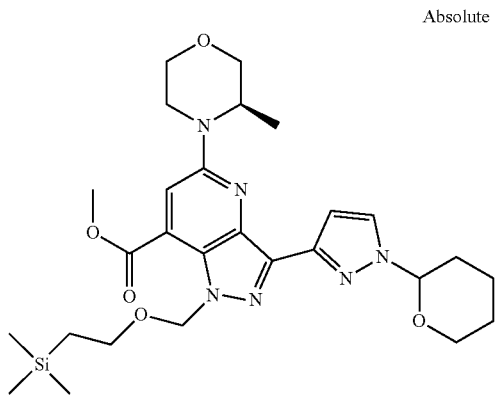 [SMILES: COC(=O)c1cc(N2CCOC[C@H]2C)nc2c(-c3ccn(C4CCCCO4)n3)nn(COCC[Si](C)(C)C)c12]

Methyl 3-iodo-5-[(3R)-3-methylmorpholin-4-yl]-1-[[2-(trimethylsilyl)ethoxy]-methyl]-1H-pyrazolo[4,3-b]pyridine-7-carboxylate (90 mg, 0.15 mmol, 1.0 eq.), 1-(oxan-2-yl)-3-(tetramethyl-1,3,2-dioxaborolan-2-yl)-1H-pyrazole (67 mg, 0.23 mmol, 1.50 eq.), Pd(PPh₃)₄ (18.50 mg, 0.02 mmol, 0.10 eq.), sodium carbonate (50.92 mg, 0.46 mmol, 3 eq.), tetrahydrofuran (18 mL) and water (4.50 mL) were combined and stirred for 2 h at 80° C. The resulting mixture was concentrated under vacuum and the residue purified by column chromatography (Method O). Methyl 5-[(3R)-3-methylmorpholin-4-yl]-3-[1-(oxan-2-yl)-1H-pyrazol-3-yl]-1-[[2-(trimethylsilyl)ethoxy]methyl]-1H-pyrazolo[4,3-b]pyridine-7-carboxylate was isolated as a yellow solid (90 mg, 96%).

Building Block for Synthesis of Example 27:
5-[(3R)-3-methylmorpholin-4-yl]-3-[1-(oxan-2-yl)-1H-pyrazol-3-yl]-1-{[2-(trimethylsilyl)ethoxy]methyl}-1H-pyrazolo[4,3-b]pyridine-7-carboxylic acid

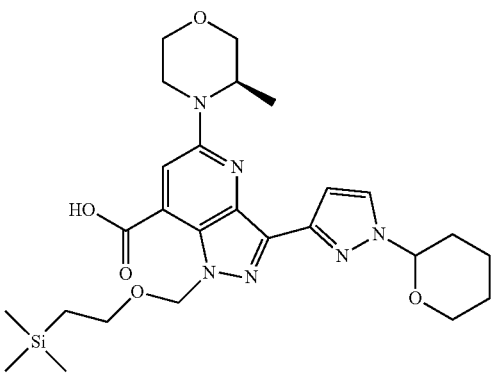

5-[(3R)-3-Methylmorpholin-4-yl]-3-[1-(oxan-2-yl)-1H-pyrazol-3-yl]-1-[[2-(trimethylsilypethoxy]methyl]-1H-pyrazolo[4,3-b]pyridine-7-carboxylate (85 mg, 0.14 mmol), tetrahydrofuran (17 mL, 199 mmol), water (4.25 mL) and LiOH (17.3 mg, 0.69 mmol, 5.0 eq.) were combined. The resulting solution was stirred for 14 h at 25° C. The pH value of the solution was adjusted to 5 with hydrogen chloride. The resulting solution was extracted with ethyl acetate and the organic layers combined and concentrated under vacuum. 5-[(3R)-3-methylmorpholin-4-yl]-3-[1-(oxan-2-yl)-1H-pyrazol-3-yl]-1-[[2-(trimethylsilyl)-ethoxy]methyl]-1H-pyrazolo[4,3-b]pyridine-7-carboxylic acid was isolated as a yellow solid (60 mg, 72%).

Building Block for Synthesis of Example 27: N,N-dimethyl-5-[(3R)-3-methylmorpholin-4-yl]-3-[1-(oxan-2-yl)-1H-pyrazol-3-yl]-1-{[2-(trimethylsilypethoxy]methyl}-1H-pyrazolo[4,3-b]pyridine-7-carboxamide

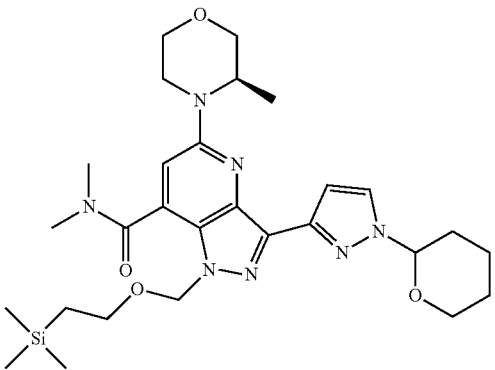

5-[(3R)-3-methylmorpholin-4-yl]-3-[1-(oxan-2-yl)-1H-pyrazol-3-yl]-1-[[2-(trimethylsilyl)ethoxy]methyl]-1H-pyrazolo[4,3-b]pyridine-7-carboxylic acid (10 mg, 0.02 mmol, 1.0 eq.) was dissolved in dichloromethane (2 mL) and N,N-dimethylformamide (0.5 mL) and HATU (7.965 mg, 0.02 mmol, 1.2 eq.), dimethylamine hydrochloride (2.847 mg, 0.03 mmol) and DIEA (6.768 mg, 0.05 mmol, 3.0 eq.) were added. The resulting solution was stirred for 2 h at 25° C. The resulting mixture was concentrated under vacuum to obtain N,N-dimethyl-5-[(3R)-3-methylmorpholin-4-yl]-3-[1-(oxan-2-yl)-1H-pyrazol-3-yl]-1-[[2-(trimethylsilyl)ethoxy]methyl]-1H-pyrazolo[4,3-b]pyridine-7-carboxamide as a yellow solid (5 mg, 48%).

Example 27

5-((R)-3-Methyl-morpholin-4-yl)-3-(1H-pyrazol-3-yl)-1H-pyrazolo[4,3-b]pyridine-7-carboxylic acid dimethylamide

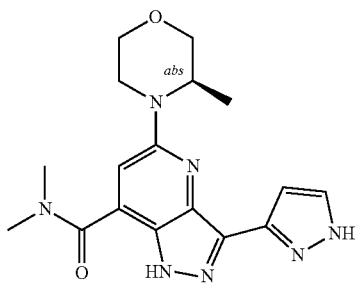 [SMILES: C[C@@H]1COCCN1c1cc(C(=O)N(C)C)c2[nH]nc(-c3cc[nH]n3)c2n1]

N,N-dimethyl-5-[(3R)-3-methylmorpholin-4-yl]-3-[1-(oxan-2-yl)-1H-pyrazol-3-yl]-1-[[2-(trimethylsilyl)ethoxy]methyl]-1H-pyrazolo[4,3-b]pyridine-7-carboxamide (50 mg, 0.08 mmol, 1 eq.) was dissolved in HCl in methanol (5 mL). The resulting solution was stirred for 5 h at 25° C. The resulting mixture was concentrated under vacuum. The crude product was purified by Prep-HPLC (Method K) to obtain 5-((R)-3-methyl-morpholin-4-yl)-3-(1H-pyrazol-3-yl)-1H-pyrazolo[4,3-b]pyridine-7-carboxylic acid dimethylamide as a yellow solid (5 mg, 17%); melting point 168-170° C. 1H NMR (400 MHz, methanol-$d_4$): δ 7.70 (m, 1H), 7.06 (m, 2H), 4.46 (d, J=7.2 Hz, 1H), 4.05 (dd, J=11.8, 4.8 Hz, 2H), 3.83 (d, J=2.3 Hz, 2H), 3.67 (td, J=11.7, 3.1 Hz, 1H), 3.34 (dd, J=12.8, 3.2 Hz, 1H), 3.01 (s, 3H), 1.28 (d, J=6.6 Hz, 3H); LC/MS (Method B): Rt 2.075 min, [MH]+ 356.0.

Example 28

5-((R)-3-Methyl-morpholin-4-yl)-3-(1H-pyrazol-3-yl)-1H-pyrazolo[4,3-b]pyridine-7-carboxylic acid methylamide (28)

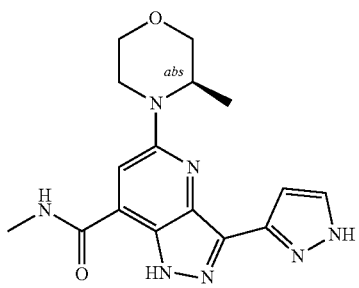 [SMILES: CNC(=O)c1cc(N2CCOC[C@H]2C)nc2c(-c3cc[nH]n3)n[nH]c12]

5-((R)-3-Methyl-morpholin-4-yl)-3-(1H-pyrazol-3-yl)-1H-pyrazolo[4,3-b]pyridine-7-carboxylic acid methylamide was prepared analogously to above examples and isolated as light yellow solid (8 mg, 38%); melting point 186-188° C.; $^1$H NMR (300 MHz, methanol-$d_4$): δ 7.68 (d, J=2.1 Hz, 1H), 7.39 (s, 1H), 7.09 (d, J=2.1 Hz, 1H), 4.47 (d, J=6.9 Hz, 1H), 4.03 (dd, J=11.4, 3.3 Hz, 2H), 3.82 (d, J=2.2 Hz, 2H), 3.66 (td, J=11.4, 2.9 Hz, 1H), 3.36 (dd, J=13.1, 3.8 Hz, 1H), 2.99 (s, 3H), 1.27 (d, J=6.7 Hz, 3H); LC/MS (Method M): Rt 0.824 min, [MH]+342.1.

Example 29

5-((R)-3-Methyl-morpholin-4-yl)-3-(1H-pyrazol-3-yl)-1H-pyrazolo[4,3-b]pyridine-7-carboxylic acid amide (29)

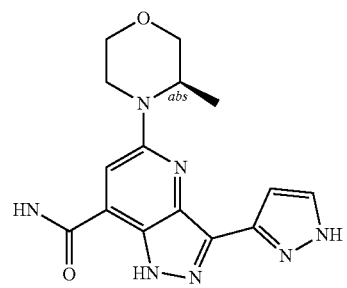 [SMILES: C[C@@H]1COCCN1c1cc(C(N)=O)c2[nH]nc(-c3cc[nH]n3)c2n1]

5-((R)-3-Methyl-morpholin-4-yl)-3-(1H-pyrazol-3-yl)-1H-pyrazolo[4,3-b]pyridine-7-carboxylic acid amide was prepared analogously to above examples and isolated as a yellow solid (2 mg, 10%); melting point >280° C.; $^1$H NMR (300 MHz, methanol-$d_4$): δ 7.68 (s, 1H), 7.48 (s, 1H), 7.11 (s, 1H), 4.52 (d, J=7.1 Hz, 1H), 4.14-3.99 (m, 2H), 3.85 (d, J=2.2 Hz, 2H), 3.69 (t, J=10.4 Hz, 1H), 3.44-3.35 (m, 1H), 1.30 (d, J=6.7 Hz, 3H); LC/MS (Method N) Rt 2.694 min, [MH]+327.9.

Example 30

1-Methyl-5-((R)-3-methyl-morpholin-4-yl)-3-(1H-pyrazol-3-yl)-1H-pyrazolo[4,3-b]pyridine-7-carboxylic acid dimethylamide (30)

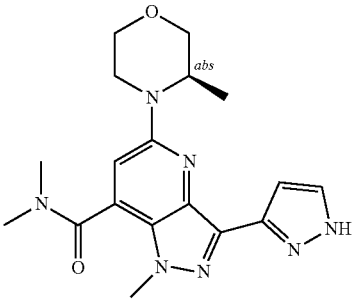 [SMILES: C[C@@H]1COCCN1c1cc(C(=O)N(C)C)c2c(n1)c(-c1cc[nH]n1)nn2C]

1-Methyl-5-((R)-3-methyl-morpholin-4-yl)-3-(1H-pyrazol-3-yl)-1H-pyrazolo[4,3-b]pyridine-7-carboxylic acid dimethylamide was prepared analogously to above examples and isolated as a yellow solid (10 mg, 29%); melting point 128-130° C. $^1$H NMR (400 MHz, DMSO-$d_6$):

δ13.23 (s, 1H), 7.58 (s, 1H), 7.14-6.88 (m, 2H), 4.44 (s, 1H), 4.12-3.94 (m, 2H), 3.88 (d, J=9.3 Hz, 3H), 3.80-3.66 (m, 2H), 3.54 (td, J=11.9, 3.0 Hz, 1H), 3.11 (m, 4H), 2.90 (d, J=2.1 Hz, 3H), 1.16 (d, J=6.5 Hz, 3H); LC/MS (Method O): Rt 1.045 min, [MH]+370.3.

Example 31

1-Methyl-5-((R)-3-methyl-morpholin-4-yl)-3-(1H-pyrazol-3-yl)-1H-pyrazolo[4,3-b]pyridine-7-carboxylic acid methylamide (31)

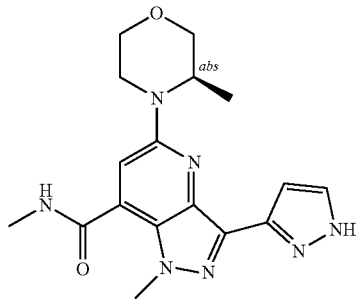 [SMILES: CNC(=O)c1cc(N2CCOC[C@H]2C)nc2c(-c3cc[nH]n3)nn(C)c12]

1-Methyl-5-((R)-3-methyl-morpholin-4-yl)-3-(1H-pyrazol-3-yl)-1H-pyrazolo[4,3-b]pyridine-7-carboxylic acid methylamide was prepared analogously to above examples and isolated as a yellow solid (10 mg, 31%); melting point 146-148° C.; $^1$H NMR (400 MHz, DMSO-d$_6$): δ13.22 (s, 1H), 8.82 (d, J=5.8 Hz, 1H), 7.57 (s, 1H), 7.20-6.91 (m, 2H), 4.46 (s, 1H), 3.99 (d, J=10.3 Hz, 5H), 3.82-3.64 (m, 2H), 3.53 (td, J=11.9, 3.0 Hz, 1H), 3.18 (t, J=11.6 Hz, 1H), 2.86 (d, J=4.6 Hz, 3H), 1.18 (d, J=6.6 Hz, 3H); LC/MS (Method 0): Rt 0.983 min, [MH]+356.3.

Example 32

1-Methyl-5-((R)-3-methyl-morpholin-4-yl)-3-(1H-pyrazol-3-yl)-1H-pyrazolo[4,3-b]pyridine-7-carboxylic acid amide (32)

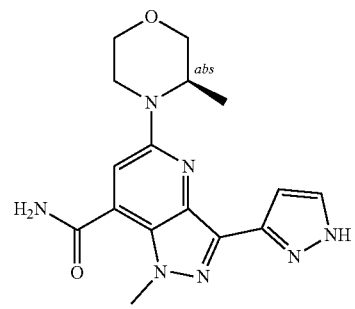 [SMILES: C[C@@H]1COCCN1c1cc(C(N)=O)c2c(n1)c(-c1cc[nH]n1)nn2C]

1-Methyl-5-((R)-3-methyl-morpholin-4-yl)-3-(1H-pyrazol-3-yl)-1H-pyrazolo[4,3-b]pyridine-7-carboxylic acid amide was prepared analogously to above examples and isolated as a yellow solid (5 mg, 15%); melting point 228-230° C.; $^1$H NMR (400 MHz, DMSO-d$_6$): δ13.23 (s, 1H), 8.34 (m, J=10.1 Hz, 1H), 8.09-7.53 (m, 2H), 7.21-6.89 (m, 2H), 4.48 (d, J=8.0 Hz, 1H), 4.15-3.92 (m, 4H), 3.84-3.66 (m, 2H), 3.54 (td, J=11.7, 2.9 Hz, 1H), 3.26-3.12 (m, 1H), 1.19 (d, J=6.6 Hz, 3H); LC/MS (Method 0): Rt 0.920 min, [MH]+342.3.

Example 33

1-Methyl-5-((R)-3-methyl-morpholin-4-yl)-7-(6-methyl-pyridin-2-yl)-3-(1H-pyrazol-3-yl)-1H-pyrazolo[4,3-b]pyridine (33)

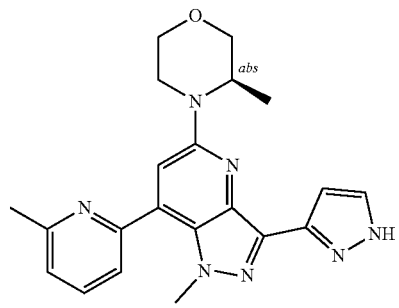 [SMILES: Cc1cccc(-c2cc(N3CCOC[C@H]3C)nc3c(-c4cc[nH]n4)nn(C)c23)n1]

1-Methyl-5-((R)-3-methyl-morpholin-4-yl)-7-(6-methyl-pyridin-2-yl)-3-(1H-pyrazol-3-yl)-1H-pyrazolo[4,3-b]pyridine was prepared analogously to above examples and isolated as a yellow solid (14 mg, 33%); melting point 115° C.;

$^1$H NMR (400 MHz, DMSO-d$_6$): δ13.21 (s, 1H), 7.92 (t, J=7.7 Hz, 1H), 7.66 (d, J=7.7 Hz, 2H), 7.43 (d, J=7.8 Hz, 1H), 7.06 (d, J=11.8 Hz, 2H), 4.50 (s, 1H), 4.11-3.94 (m, 2H), 3.73 (s, 5H), 3.56 (td, J=11.7, 3.0 Hz, 1H), 3.20 (td, J=12.9, 3.7 Hz, 1H), 2.60 (s, 3H), 1.19 (d, J=6.6 Hz, 3H); LC/MS (Method E): RT1.190 min, [MH]+390.1.

Example 34

7-[1-(2-Fluoro-ethyl)-1H-pyrazol-3-yl]-1-methyl-5-((R)-3-methyl-morpholin-4-yl)-3-(1H-pyrazol-3-yl)-1H-pyrazolo[4,3-b]pyridine (34)

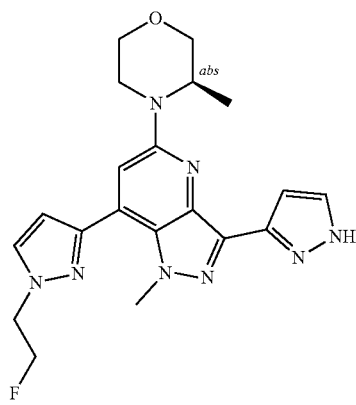 [SMILES: C[C@@H]1COCCN1c1cc(-c2ccn(CCF)n2)c2c(n1)c(-c1cc[nH]n1)nn2C]

Building Block for Synthesis of Example 34: (3R)-3-methyl-4-[1-methyl-7-(1H-pyrazol-5-yl)-1H-pyrazolo[4,3-b]pyridin-5-yl]morpholine

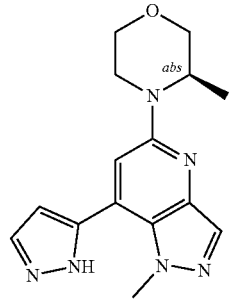 [SMILES: C[C@@H]1COCCN1c1cc(-c2ccn[nH]2)c2c(cnn2C)n1]

(3R)-3-Methyl-4-[1-methyl-7-[1-(oxan-2-yl)-1H-pyrazol-5-yl]-1H-pyrazolo[4,3-b]pyridin-5-yl]morpholine (340 mg, 0.84 mmol, 1.0 eq. 95%) was dissolved in a solution of hydrogen chloride in methanol (10 mL) and stirred for 2 h at room temperature. The resulting mixture was concentrated under vacuum. The pH value of the solution was adjusted to 7-8 with sodium bicarbonate. The resulting solution was extracted with dichloromethane and the organic layers combined and concentrated under vacuum. (3R)-3-Methyl-4-[1-methyl-7-(1H-pyrazol-5-yl)-1H-pyrazolo[4,3-b]pyridin-5-yl]morpholine was isolated as yellow oil (250 mg, 96%); LC/MS (Method P): Rt 0.566 min, [MH]+299.2.

Building Block for Synthesis of Example 34.: (3R)-4-{7-[1-(2-fluoroethyl)-1H-pyrazol-3-yl]-1-methyl-1H-pyrazolo[4,3-b]pyridin-5-yl}-3-methylmorpholine

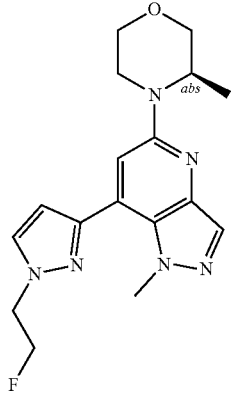 [SMILES: C[C@@H]1COCCN1c1cc(-c2ccn(CCF)n2)c2c(cnn2C)n1]

(3R)-3-Methyl-4-[1-methyl-7-(1H-pyrazol-5-yl)-1H-pyrazolo[4,3-b]pyridin-5-yl]morpholine (150 mg, 0.48 mmol, 1.0 eq. 96%), DMF (5 mL), sodium hydride (80.3 mg, 2 mmol, 4.2 equiv. 60%) and 1-fluoro-2-iodoethane (174.6 mg, 0.95 mmol, 1.98 eq.) were combined and stirred for 2 h at room temperature. The reaction was then quenched by the addition of NH₄Cl. The resulting solution was extracted with dichloromethane and the organic layers combined and dried over anhydrous sodium sulfate and concentrated under vacuum. The residue was purified by column chromatography (Method K). (3R)-4-[7-[1-(2-Fluoroethyl)-1H-pyrazol-3-yl]-1-methyl-1H-pyrazolo[4,3-b]pyridin-5-yl]-3-methylmorpholine was isolated as yellow oil (110 mg, 66%); LC/MS (Method P): Rt 0.667 min, [MH]+345.3.

Example 34

7-[1-(2-Fluoro-ethyl)-1H-pyrazol-3-yl]-1-methyl-5-((R)-3-methyl-morpholin-4-yl)-3-(1H-pyrazol-3-yl)-1H-pyrazolo[4,3-b]pyridine

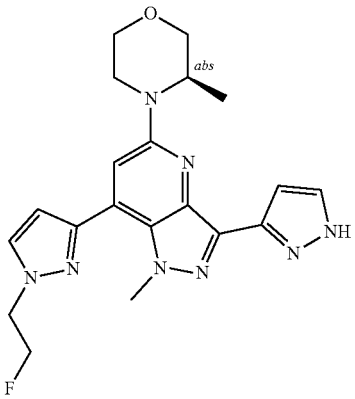 [SMILES: C[C@@H]1COCCN1c1cc(-c2ccn(CCF)n2)c2c(n1)c(-c1cc[nH]n1)nn2C]

7-[1-(2-Fluoro-ethyl)-1H-pyrazol-3-yl]-1-methyl-5-((R)-3-methyl-morpholin-4-yl)-3-(1H-pyrazol-3-yl)-1H-pyrazolo[4,3-b]pyridine was prepared analogously to above examples and isolated as light yellow solid (8 mg, 21%); melting point 106-107° C.; light yellow solid;
¹H NMR (300 MHz, methanol-$d_4$): δ 7.86 (d, J=2.4 Hz, 1H), 7.63 (s, 1H), 7.04 (s, 2H), 6.71 (d, J=2.3 Hz, 1H), 4.91 (t, J=4.7 Hz, 2H), 4.75 (t, J=4.7 Hz, 1H), 4.62 (t, J=4.7 Hz, 1H), 4.53 (t, J=4.7 Hz, 1H), 4.04 (d, J=11.9 Hz, 2H), 3.95 (s, 3H), 3.83 (d, J=2.2 Hz, 2H), 3.68 (td, J=11.7, 3.1 Hz, 1H), 1.29 (d, J=6.7 Hz, 3H); LC/MS (Method E): Rt 1.238 min, [MH]+411.2.

Example 35

(3R)-3-Methyl-4-[7-(2-methylphenyl)-3-(1H-pyrazol-3-yl)-1H-pyrazolo[4,3-b]pyridin-5-yl]morpholine (35)

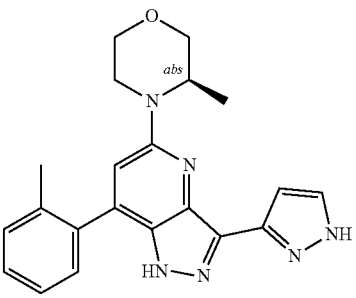 [SMILES: Cc1ccccc1-c1cc(N2CCOC[C@H]2C)nc2c(-c3cc[nH]n3)n[nH]c12]

(3R)-3-Methyl-4-[7-(2-methylphenyl)-3-(1H-pyrazol-3-yl)-1H-pyrazolo[4,3-b]pyridin-5-yl]morpholine was prepared analogously to above examples and isolated as yellow solid (17 mg, 64%); ¹H NMR (400 MHz, DMSO-$d_6$): δ d 7.74 (d, J=1.9 Hz, 1H), 7.47-7.34 (m, 5H), 7.08 (d, J=1.9 Hz, 1H), 6.91 (s, 1H), 4.49-4.42 (m, 1H), 4.10-4.04 (m, 1H), 4.02-3.96 (m, 1H), 3.77-3.73 (m, 1H), 3.70 (dd, J=11.1, 2.9 Hz, 1H), 3.56 (td, J=11.7, 3.0 Hz, 1H), 3.21 (td, J=12.5, 3.6 Hz, 1H), 2.20 (s, 3H), 1.20 (d, J=6.6 Hz, 3H); LC/MS (Method F): Rt 2.102 min; [MH]+375.2.

Example 36

7-[2-(2-Fluoro-ethyl)-2H-pyrazol-3-yl]-1-methyl-5-((R)-3-methyl-morpholin-4-yl)-3-(1H-pyrazol-3-yl)-1H-pyrazolo[4,3-b]pyridine (36)

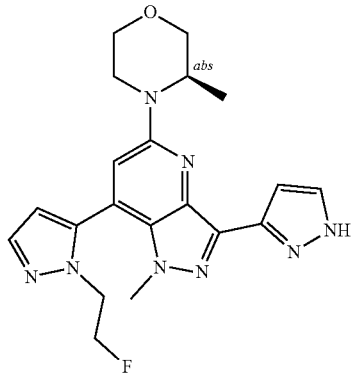 [SMILES: C[C@@H]1COCCN1c1cc(-c2ccnn2CCF)c2c(n1)c(-c1cc[nH]n1)nn2C]

Building Block for Synthesis of Example 36: (3R)-4-{7-[1-(2-fluoroethyl)-1H-pyrazol-5-yl]-1-methyl-1H-pyrazolo[4,3-b]pyridin-5-yl}-3-methylmorpholine

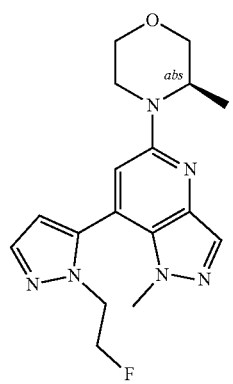 [SMILES: C[C@@H]1COCCN1c1cc(-c2ccnn2CCF)c2c(cnn2C)n1]

(3R)-3-Methyl-4-[1-methyl-7-(1H-pyrazol-5-yl)-1H-pyrazolo[4,3-b]pyridin-5-yl]morpholine (450 mg, 1.49 mmol, 1.0 eq. 99%), DMF (10 mL), sodium hydride (240.8 mg, 6.02 mmol, 4.03 equiv, 60%) and 1-fluoro-2-iodoethane (523.7 mg, 2.86 mmol, 1.92 eq.) were combined and stirred for 2 h at room temperature. The reaction was then quenched by the addition of NH$_4$Cl. The resulting solution was extracted with dichloromethane and the organic layers combined and dried over anhydrous sodium sulfate and concentrated under vacuum. The crude product was purified by Prep-HPLC (Method H). (3R)-4-{7-[1-(2-fluoroethyl)-1H-pyrazol-5-yl]-1-methyl-1H-pyrazolo[4,3-b]pyridin-5-yl}-3-methylmorpholine was isolated as yellow oil (60 mg, 12%); LC/MS (Method P): Rt 0.668 min, [MH]+345.3

Example 36

7-[2-(2-Fluoro-ethyl)-2H-pyrazol-3-yl]-1-methyl-5-((R)-3-methyl-morpholin-4-yl)-3-(1H-pyrazol-3-yl)-1H-pyrazolo[4,3-b]pyridine

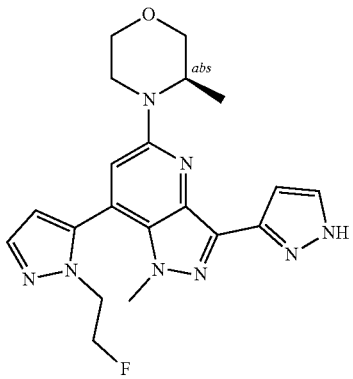 [SMILES: C[C@@H]1COCCN1c1cc(-c2ccnn2CCF)c2c(n1)c(-c1cc[nH]n1)nn2C]

7-[2-(2-Fluoro-ethyl)-2H-pyrazol-3-yl]-1-methyl-5-((R)-3-methyl-morpholin-4-yl)-3-(1H-pyrazol-3-yl)-1H-pyrazolo[4,3-b]pyridine was prepared analogously to above examples and isolated as light yellow solid (15 mg, 30%); melting point 120-121° C.; $^1$H NMR (300 MHz, DMSO-d$_6$): δ12.93-13.24 (m, 1H), 7.89-7.59 (m, 2H), 7.13-6.94 (m, 2H), 6.66 (s, 1H), 4.77 (s, 1H), 4.61 (s, 1H), 4.39 (dd, J=27.7, 16.9 Hz, 3H), 4.04 (dd, J=29.2, 12.1 Hz, 2H), 3.79-3.64 (m, 2H), 3.62-3.42 (m, 4H), 3.17 (t, J=13.0 Hz, 1H), 1.18 (d, J=6.5 Hz, 3H);
LC/MS (Method B): Rt 2.294 min, [MH]+411.2.

Example 37

2-{3-[1-Methyl-5-((R)-3-methyl-morpholin-4-yl)-3-(1H-pyrazol-3-yl)-1H-pyrazolo[4,3-b]pyridin-7-yl]-pyrazol-1-yl}-ethanol (37)

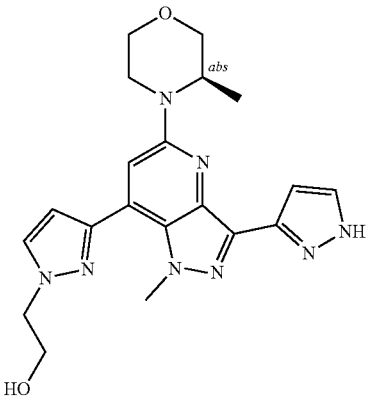 [SMILES: C[C@@H]1COCCN1c1cc(-c2ccn(CCO)n2)c2c(n1)c(-c1cc[nH]n1)nn2C]

2-{3-[1-Methyl-5-((R)-3-methyl-morpholin-4-yl)-3-(1H-pyrazol-3-yl)-1H-pyrazolo[4,3-b]pyridin-7-yl]-pyrazol-1-yl}-ethanol was prepared analogously to above examples and isolated as light yellow solid (60 mg, 33%); melting point 110-111° C.; $^1$H NMR (300 MHz, DMSO-d$_6$): δ13.18 (s, 1H), 7.91 (d, J=2.3 Hz, 1H), 7.65 (s, 1H), 7.04 (d, J=11.3 Hz, 2H), 6.78 (d, J=2.3 Hz, 1H), 4.95 (t, J=5.4 Hz, 1H), 4.54-4.41 (m, 1H), 4.28 (t, J=5.6 Hz, 2H), 4.05-3.97 (m, 5H), 3.88-3.64 (m, 4H), 3.55 (td, J=11.8, 3.0 Hz, 1H), 3.18 (td, J=12.7, 3.7 Hz, 1H), 1.17 (d, J=6.6 Hz, 3H); LC/MS (Method E): Rt 1.073 min, [MH]+409.2.

Example 38

(3R)-3-Methyl-4-[3-(1H-pyrazol-3-yl)-7-(pyridin-2-yl)-1H-pyrazolo[4,3-b]pyridin-5-yl]morpholine (38)

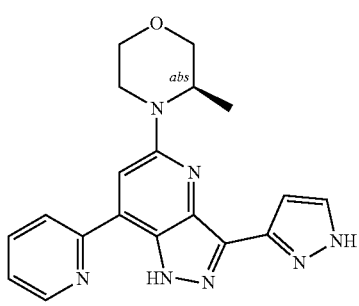 [SMILES: C[C@@H]1COCCN1c1cc(-c2ccccn2)c2[nH]nc(-c3cc[nH]n3)c2n1]

Building Block for Synthesis of Example 38: [5-[(3R)-3-methylmorpholin-4-yl]-1-(2-trimethylsilylethoxymethyl)pyrazolo[4,3-b]pyridin-7-yl]boronic acid

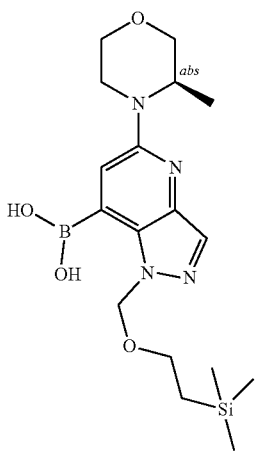 [SMILES: C[C@@H]1COCCN1c1cc(B(O)O)c2c(cnn2COCC[Si](C)(C)C)n1]

5-((R)-3-Methyl-morpholin-4-yl)-1-(2-trimethylsilanyl-ethoxymethyl)-1H-pyrazolo[4,3-b]pyridin-7-yl ester (50 mg; 0.101 mmol; 1.0 eq.) was dissolved in 1,4-dioxane (2 ml), potassium acetat (19.764 mg; 0.201 mmol; 2.0 eq.), bis(pinacolato)diboron (38.353 mg; 0.151 mmol; 1.50 eq.) and (1,1'-bis(diphenylphosphino)ferrocene)-dichloropalladium(II) (7.067 mg; 0.010 mmol; 0.10 eq.) were added and stirred at 110° C. for 4 hours. The reaction solution was used without further purification in next reaction step.

Building Block for Synthesis of Example 38: 5-((R)-3-Methyl-morpholin-4-yl)-7-pyridin-2-yl-1-(2-trimethylsilanyl-ethoxymethyl)-1H-pyrazolo[4,3-b]pyridine

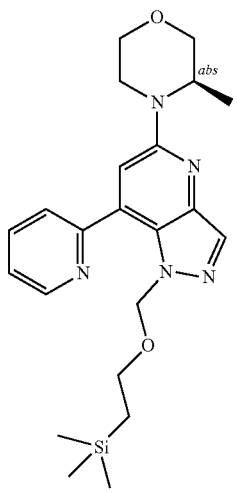 [SMILES: C[C@@H]1COCCN1c1cc(-c2ccccn2)c2c(cnn2COCC[Si](C)(C)C)n1]

To the reaction mixture of [5-[(3R)-3-methylmorpholin-4-yl]-1-(2-trimethylsilyl-ethoxymethyl)pyrazolo[4,3-b]pyridin-7-yl]boronic acid was added 2-bromo-pyridine (19.149 mg; 0.121 mmol; 1.20 eq.), potassium carbonat (42.038 mg; 0.304 mmol; 3.01 eq.), water (0.300 ml) and 1,1'-bis(diphenylphosphino)-ferrocendichlorpalladium-(II) *DCM (8.248 mg; 0.010 mmol; 0.10 eq.) were added and stirred at 100° C. for 2 hours. The reaction mixture was concentrated and the crude product purified by column chromatography (Method L). 5-((R)-3-Methyl-morpholin-4-yl)-7-pyridin-2-yl-1-(2-trimethylsilanyl-ethoxymethyl)-1H-pyrazolo[4,3-b]pyridine was isolated as brown resin (64 mg, 79%); LC/MS (Method F): Rt 2.464 min; [MH]+426.2.

Example 38

(3R)-3-Methyl-4-[3-(1H-pyrazol-3-yl)-7-(pyridin-2-yl)-1H-pyrazolo[4,3-b]pyridin-5-yl]morpholine

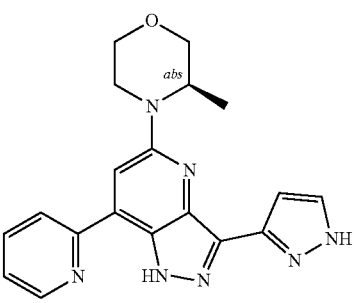 [SMILES: C[C@@H]1COCCN1c1cc(-c2ccccn2)c2[nH]nc(-c3cc[nH]n3)c2n1]

(3R)-3-Methyl-4-[3-(1H-pyrazol-3-yl)-7-(pyridin-2-yl)-1H-pyrazolo[4,3-b]pyridin-5-yl]morpholine was prepared analogously to above examples and isolated as yellow solid (7 mg, 38%); $^1$H NMR (400 MHz, DMSO-$d_6$): δ8.86-8.83 (m, 1H), 8.49-8.44 (m, 1H), 8.03 (td, J=7.8, 1.9 Hz, 1H), 7.69 (d, J=1.8 Hz, 1H), 7.66 (s, 1H), 7.55-7.51 (m, 1H), 7.09 (d, J=1.9 Hz, 1H), 4.65-4.57 (m, 1H), 4.15-4.10 (m, 1H), 4.03 (dd, J=11.3, 3.5 Hz, 1H), 3.83-3.78 (m, 1H), 3.75 (dd, J=11.2, 3.0 Hz, 1H), 3.63-3.55 (m, 1H), 3.28-3.20 (m, 1H), 1.21 (d, J=6.6 Hz, 3H); LC/MS (Method F): Rt 2.026 min; [MH]+362.2.

Example 39

(3R)-3-Methyl-4-[7-(3-methylpyridin-2-yl)-3-(1H-pyrazol-3-yl)-1H-pyrazolo[4,3-b]pyridin-5-yl]morpholine (39)

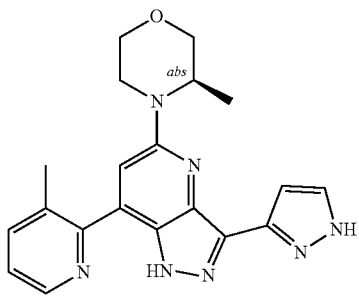 [SMILES: Cc1cccnc1-c1cc(N2CCOC[C@H]2C)nc2c(-c3cc[nH]n3)n[nH]c12]

(3R)-3-Methyl-4-[7-(3-methylpyridin-2-yl)-3-(1H-pyrazol-3-yl)-1H-pyrazolo[4,3-b]pyridin-5-yl]morpholine was prepared analogously to above examples and isolated as yellow solid (11 mg, 50%); ¹H NMR (400 MHz, DMSO-d₆) δ13.28-13.10 (m, 1H), 12.99-12.78 (m, 1H), 8.63-8.58 (m, 1H), 7.88-7.83 (m, 1H), 7.68-7.53 (m, 1H), 7.45 (dd, J=7.7, 4.7 Hz, 1H), 7.11-7.03 (m, 2H), 4.48-4.42 (m, 1H), 4.11-4.03 (m, 1H), 4.00 (dd, J=11.4, 3.5 Hz, 1H), 3.79-3.74 (m, 1H), 3.71 (dd, J=11.4, 2.9 Hz, 1H), 3.57 (td, J=11.7, 2.9 Hz, 1H), 3.19 (td, J=12.7, 3.7 Hz, 1H), 2.34 (s, 3H), 1.19 (d, J=6.6 Hz, 3H); LC/MS (Method F): Rt 1.836 min; [MH]+376.

Example 40

(3R)-3-Methyl-4-[1-methyl-3-(1H-pyrazol-5-yl)-1H-pyrazolo[4,3-b]pyridin-5-yl]morpholine (40)

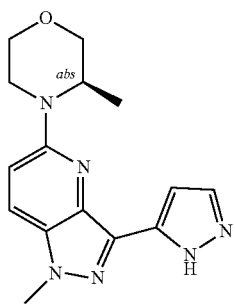 [SMILES: C[C@@H]1COCCN1c1ccc2c(n1)c(-c1ccn[nH]1)nn2C]

Building Block for Synthesis of Example 40:
1-Methyl-5-((R)-3-methyl-morpholin-4-yl)-1H-pyrazolo[4,3-b]pyridine

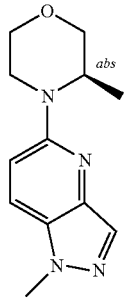 [SMILES: C[C@@H]1COCCN1c1ccc2c(cnn2C)n1]

Trifluoro-methanesulfonic acid 1-methyl-5-((R)-3-methyl-morpholin-4-yl)-1H-pyrazolo[4,3-b]pyridin-7-yl ester (350 mg; 0.810 mmol; 1 eq.), dioxane (7.00 ml), triethylamine (354.48 μl; 2.429 mmol; 3 eq.), palladium(II) acetate (18.18 mg; 0.081 mmol; 0.1 eq.), 1,1'-bis-(diphenylphosphino)-ferrocen (47.12 mg; 0.081 mmol; 0.1 eq.) and formic acid (61.10 μl; 1.620 mmol; 2 eq.) were combined and stirred at 80° C. for 45 min. The reaction mixture was evaporated to dryness and the crude product purified by column chromatography (Method M). 1-Methyl-5-((R)-3-methyl-morpholin-4-yl)-1H-pyrazolo[4,3-b]pyridine was isolated as yellow solid (104 mg, 55%); LC/MS (Method C): Rt 0.662 min; [MH]+233.1.

Example 40

(3R)-3-Methyl-4-[1-methyl-3-(1H-pyrazol-5-yl)-1H-pyrazolo[4,3-b]pyridin-5-yl]morpholine

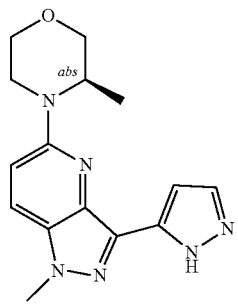 [SMILES: C[C@@H]1COCCN1c1ccc2c(n1)c(-c1ccn[nH]1)nn2C]

(3R)-3-Methyl-4-[1-methyl-3-(1H-pyrazol-5-yl)-1H-pyrazolo[4,3-b]pyridin-5-yl]morpholine was prepared analogously to above examples and isolated as yellow solid (52 mg, 82%); ¹H NMR (700 MHz, DMSO-d₆): δ7.99 (d, J=9.3 Hz, 1H), 7.66 (d, J=1.9 Hz, 1H), 7.12 (d, J=9.4 Hz, 1H), 7.01 (d, J=1.9 Hz, 1H), 4.60-4.27 (m, 1H), 4.07-3.95 (m, 5H), 3.76 (d, J=11.1 Hz, 1H), 3.70 (dd, J=11.2, 3.1 Hz, 1H), 3.54 (td, J=11.8, 3.1 Hz, 1H), 3.15 (td, J=12.8, 3.9 Hz, 1H), 1.15 (d, J=6.7 Hz, 3H); LC/MS (Method C): Rt 0.832 min; [MH]+299.1.

Example 41

(3R)-4-[7-(4-Methanesulfonylphenyl)-1-(propan-2-yl)-3-(1H-pyrazol-3-yl)-1H-pyrazolo[4,3-b]pyridin-5-yl]-3-methylmorpholine (41)

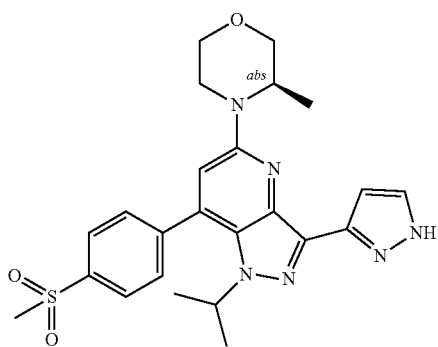 [SMILES: CC(C)n1nc(-c2cc[nH]n2)c2nc(N3CCOC[C@H]3C)cc(-c3ccc(S(C)(=O)=O)cc3)c21]

(3R)-4-[7-(4-Methanesulfonylphenyl)-1-(propan-2-yl)-3-(1H-pyrazol-3-yl)-1H-pyrazolo[4,3-b]pyridin-5-yl]-3-methylmorpholine was prepared analogously to above examples and isolated as yellow solid (21 mg, 34%); $^1$H NMR (400 MHz, DMSO-d$_6$): δ8.13-8.09 (m, 2H), 7.91-7.86 (m, 2H), 7.70 (d, J=1.9 Hz, 1H), 7.08 (d, J=2.0 Hz, 1H), 6.87 (s, 1H), 4.50-4.43 (m, 1H), 4.12-4.01 (m, 2H), 3.98 (dd, J=11.3, 3.5 Hz, 1H), 3.75 (d, J=11.2 Hz, 1H), 3.68 (dd, J=11.3, 3.1 Hz, 1H), 3.57-3.53 (m, 1H), 3.33 (s, 3H), 3.18 (td, J=12.6, 3.6 Hz, 1H), 1.30-1.25 (m, 6H), 1.19 (d, J=6.7 Hz, 3H); LC/MS (Method F): Rt 2.273 min; [MH]+481.2.

Example 42

1-Methyl-7-(3-methyl-3H-imidazol-4-yl)-5-((R)-3-methyl-morpholin-4-yl)-3-(1H-pyrazol-3-yl)-1H-pyrazolo[4,3-b]pyridine (42)

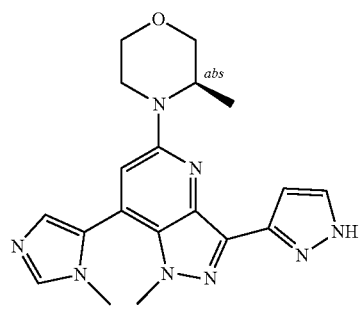 [SMILES: C[C@@H]1COCCN1c1cc(-c2cncn2C)c2c(n1)c(-c1cc[nH]n1)nn2C]

Building Block for Synthesis of Example 42:
1-Methyl-7-(3-methyl-3H-imidazol-4-yl)-5-((R)-3-methyl-morpholin-4-yl)-3-[2-(2-trimethylsilanyl-ethoxymethyl)-2H-pyrazol-3-yl]-1H-pyrazolo[4,3-b]pyridine

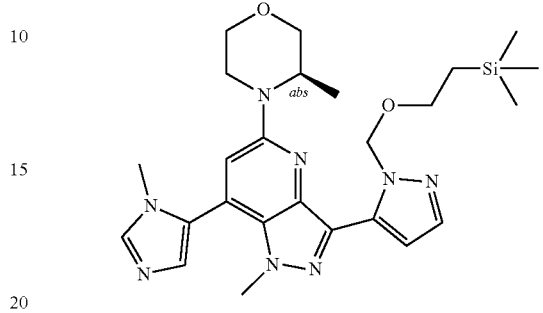

3-Bromo-1-methyl-7-(3-methyl-3H-imidazol-4-yl)-5-((R)-3-methyl-morpholin-4-yl)-1H-pyrazolo[4,3-b]pyridine (63 mg; 0.161 mmol; 0.694 eq.), 1-(2-trimethyl-silyl) ethoxymethyl-1H-pyrazole-5-boronic acid pinacol ester (158.45 mg; 0.464 mmol; 2 eq.), sodium carbonate (73.80 mg; 0.696 mmol; 3 eq.), tetrakis(tri-phenylphosphine)-palladium(0) (32.51 mg; 0.028 mmol; 0.120 eq.) were combined and THF (1.90 ml) and water (190.00 µl.) were added and stirred at 90° C. for 1.5 h. The reaction mixture was filtered and concentrated under reduced pressure. The crude product was purified by column chromatography (Method N). 1-Methyl-7-(3-methyl-3H-imidazol-4-yl)-5-((R)-3-methyl-morpholin-4-yl)-3-[2-(2-trimethylsilanyl-ethoxymethyl)-2H-pyrazol-3-yl]-1H-pyrazolo[4,3-b]pyridine was isolated as brown solid (61.50 mg; 52.1%);

LC/MS (Method Q): Rt 0.946 min; [MH]+509.8.

Example 42

1-Methyl-7-(3-methyl-3H-imidazol-4-yl)-5-((R)-3-methyl-morpholin-4-yl)-3-(1H-pyrazol-3-yl)-1H-pyrazolo[4,3-b]pyridine

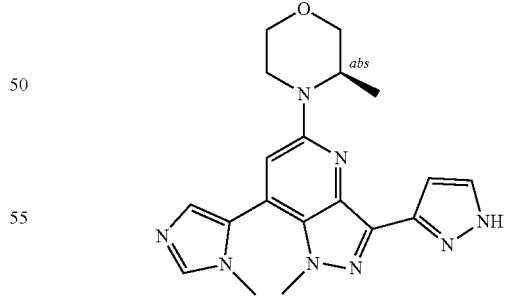

1-Methyl-7-(3-methyl-3H-imidazol-4-yl)-5-((R)-3-methyl-morpholin-4-yl)-3-[2-(2-trimethylsilanyl-ethoxymethyl)-2H-pyrazol-3-yl]-1H-pyrazolo[4,3-b]pyridine (61.50 mg; 0.121 mmol; 1 eq.) was added and dissolved in HCl in MeOH (1.93 ml) and stirred at room temp for 21 h. The reaction solution was concentrated under reduced pressure. The crude product was purified by column chromatography (Method O). 1-Methyl-7-(3-methyl-3H-imidazol-4-yl)-5-

((R)-3-methyl-morpholin-4-yl)-3-(2H-pyrazol-3-yl)-1H-pyrazolo[4,3-b]pyridine was isolated as yellow solid (35 mg; 75.0%); $^1$H NMR (500 MHz, DMSO-d$_6$): δ13.27-12.88 (m, 1H), 7.93-7.53 (m, 2H), 7.30-6.94 (m, 3H), 4.47 (s, 1H), 4.08 (d, J=13.7 Hz, 1H), 3.99 (dd, J=11.3, 3.6 Hz, 1H), 3.75 (d, J=11.2 Hz, 1H), 3.69 (dd, J=11.3, 3.1 Hz, 1H), 3.61 (s, 3H), 3.56-3.50 (m, 4H), 3.17 (td, J=12.7, 3.8 Hz, 1H), 1.18 (d, J=6.6 Hz, 3H); LC/MS (Method R): Rt 0.399 min; [MH]+379.2.

Example 43

7-Cyclopropyl-1-methyl-5-((R)-3-methyl-morpholin-4-yl)-3-(2H-pyrazol-3-yl)-1H-pyrazolo[4,3-b]pyridine (43)

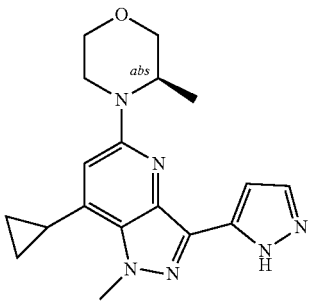 [SMILES: C[C@@H]1COCCN1c1cc(C2CC2)c2c(n1)c(-c1ccn[nH]1)nn2C]

7-Cyclopropyl-1-methyl-5-((R)-3-methyl-morpholin-4-yl)-3-(2H-pyrazol-3-yl)-1H-pyrazolo[4,3-b]pyridine hydrochloride was prepared analogously to above examples and isolated as yellow solid (5 mg, 26%); melting point 234-235° C.;

$^1$H NMR (300 MHz, methanol-d$_4$): δ7.88 (d, J=2.4 Hz, 1H), 6.95-6.84 (m, 2H), 4.46 (s, 4H), 4.12 (d, J=9.3 Hz, 1H), 3.96-3.84 (m, 3H), 3.73 (q, J=12.5, 12.0 Hz, 2H), 2.65 (p, J=5.9, 4.8 Hz, 1H), 1.45 (d, J=6.5 Hz, 3H), 1.40-1.31 (m, 2H), 1.19 (q, J=4.5, 3.8 Hz, 2H); LC/MS (Method S): Rt 1.340 min [MH]+339.3.

Example 44

7-Isopropoxy-1-methyl-5-((R)-3-methyl-morpholin-4-yl)-3-(2H-pyrazol-3-yl)-1H-pyrazolo[4,3-b]pyridine (44)

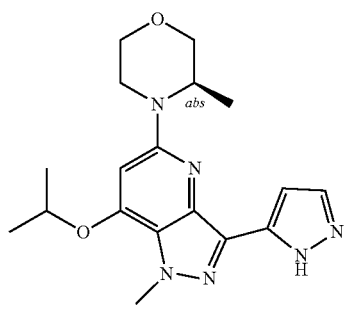 [SMILES: CC(C)Oc1cc(N2CCOC[C@H]2C)nc2c(-c3ccn[nH]3)nn(C)c12]

Building Block for Synthesis of Example 44: (3R)-3-methyl-4-[1-methyl-7-(propan-2-yloxy)-1H-pyrazolo[4,3-b]pyridin-5-yl]morpholine

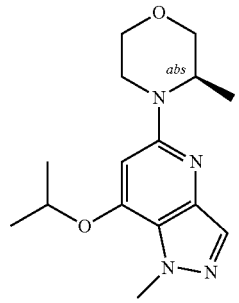 [SMILES: CC(C)Oc1cc(N2CCOC[C@H]2C)nc2cnn(C)c12]

1-Methyl-5-[(3R)-3-methylmorpholin-4-yl]-1H-pyrazolo[4,3-b]pyridin-7-ol (500 mg, 1.81 mmol, 1 eq.), DMF (50 mL), potassium carbonate (545.1 mg, 3.75 mmol, 2.07 eq.) and 2-iodopropane (450 mg, 2.51 mmol, 1.39 eq.) were combined and stirred for 2 h at room temperature. The reaction mixture was filtered and concentrated under vacuum. The crude product was purified by column chromatography (Method E). (3R)-3-Methyl-4-[1-methyl-7-(propan-2-yloxy)-1H-pyrazolo[4,3-b]pyridin-5-yl]morpholine was isolated as yellow oil (500 mg (89%); LC/MS (Method T): Rt 0.997 min, [MH]+291.3.

Example 44

7-Isopropoxy-1-methyl-5-((R)-3-methyl-morpholin-4-yl)-3-(2H-pyrazol-3-yl)-1H-pyrazolo[4,3-b]pyridine

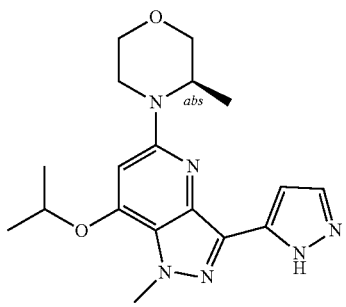 [SMILES: CC(C)Oc1cc(N2CCOC[C@H]2C)nc2c(-c3ccn[nH]3)nn(C)c12]

7-Isopropoxy-1-methyl-5-((R)-3-methyl-morpholin-4-yl)-3-(2H-pyrazol-3-yl)-1H-pyrazolo[4,3-b]pyridine was prepared analogously to above examples and isolated as a white solid (10 mg, 31%); melting point 134-135° C.;

$^1$H NMR (300 MHz, DMSO-d$_6$): δ12.72 (s, 1H), 7.54 (s, 1H), 6.90 (s, 1H), 6.41 (s, 1H), 4.96 (h, J=6.0 Hz, 1H), 4.39 (d, J=7.3 Hz, 1H), 4.12 (s, 3H), 3.97 (d, J=3.4 Hz, 1H), 3.93 (d, J=3.3 Hz, 1H), 3.71 (t, J=2.2 Hz, 2H), 3.54 (td, J=11.4, 3.0 Hz, 1H), 3.26-3.10 (m, 1H), 1.42 (d, J=6.0 Hz, 6H), 1.18 (d, J=6.6 Hz, 3H); LC/MS (Method E): Rt 1.219 min, [MH]+357.2.

Example 45

1-Methyl-5-((R)-3-methyl-morpholin-4-yl)-3-(2H-pyrazol-3-yl)-1H-pyrazolo[4,3-b]pyridin-7-ol (45)

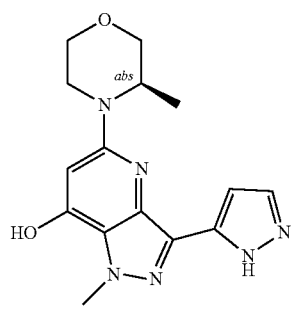 [SMILES: C[C@@H]1COCCN1c1cc(O)c2c(n1)c(-c1ccn[nH]1)nn2C]

Building Block for Synthesis of Example 45:
1-methyl-5-[(3R)-3-methylmorpholin-4-yl]-1H-pyrazolo[4,3-b]pyridin-7-yl acetate

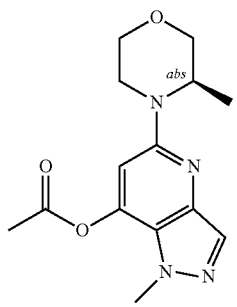 [SMILES: CC(=O)Oc1cc(N2CCOC[C@H]2C)nc2cnn(C)c12]

1-Methyl-5-[(3R)-3-methylmorpholin-4-yl]-1H-pyrazolo[4,3-b]pyridin-7-ol (300 mg, 1.09 mmol, 1. eq.), dichloromethane (10 mL), NEt$_3$ (366.8 mg, 3.44 mmol, 3.17 eq.) and acetyl chloride (189.7 mg, 2.30 mmol, 2.11 eq.) were combined and stirred for 2 h at room temperature. The resulting mixture was concentrated under vacuum. The pH value of the solution was adjusted to 7-8 with sodium bicarbonate. The resulting solution was extracted with of dichloromethane and the organic layers combined and dried over anhydrous sodium sulfate and concentrated under vacuum. The residue was purified by column chromatography (Method E). 1-Methyl-5-[(3R)-3-methylmorpholin-4-yl]-1H-pyrazolo[4,3-b]pyridin-7-yl acetate was isolated as yellow oil (310 mg, 88%); LC/MS (Method P): Rt 0.621 min, [MH]+291.3.

Example 45

1-Methyl-5-((R)-3-methyl-morpholin-4-yl)-3-(2H-pyrazol-3-yl)-1H-pyrazolo[4,3-b]pyridin-7-ol

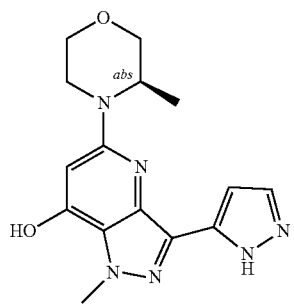 [SMILES: C[C@@H]1COCCN1c1cc(O)c2c(n1)c(-c1ccn[nH]1)nn2C]

1-Methyl-5-((R)-3-methyl-morpholin-4-yl)-3-(2H-pyrazol-3-yl)-1H-pyrazolo[4,3-b]pyridin-7-ol was prepared analogously to above examples and isolated as a colorless solid (20 mg, 70%); melting point 190-191° C.; $^1$H NMR (300 MHz, DMSO-d$_6$): δ7.67-7.59 (m, 1H), 6.80 (s, 1H), 5.94 (s, 1H), 4.16 (m, 4H), 3.93 (d, J=7.9 Hz, 1H), 3.70 (d, J=2.4 Hz, 2H), 3.65-3.47 (m, 3H), 3.20 (m, 1H), 1.17 (d, J=6.6 Hz, 3H); LC/MS (Method E): Rt 1.035 min, [MH]+ 315.1.

Example 46

1-(4-Methanesulfonyl-phenyl)-5-((R)-3-methyl-morpholin-4-yl)-3-(1H-pyrazol-3-yl)-1H-pyrazolo[4,3-b]pyridine (46)

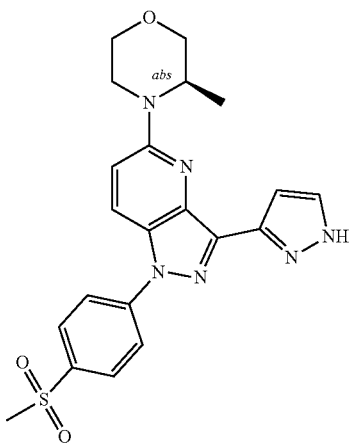 [SMILES: C[C@@H]1COCCN1c1ccc2c(n1)c(-c1cc[nH]n1)nn2-c1ccc(S(C)(=O)=O)cc1]

(3R)-4-[1-(4-Methanesulfonylphenyl)-3-[1-(oxan-2-yl)-1H-pyrazol-3-yl]-1H-pyrazolo[4,3-b]pyridin-5-yl]-3-methylmorpholine (200 mg, 0.34 mmol, 1. eq.) was dissolved in hydrogen chloride in methanol (10 mL) and stirred for 1 h at 25° C. The resulting solution was extracted with ethyl acetate and the organic layers combined and dried over anhydrous sodium sulfate and concentrated under vacuum. The crude product was purified by prep HPLC (Method I). 1-(4-Methanesulfonyl-phenyl)-5-((R)-3-methyl-morpholin-4-yl)-3-(1H-pyrazol-3-yl)-1H-pyrazolo[4,3-b]pyridine was isolated as a yellow solid (20 mg, 13%); melting point 155-157° C.; ¹H NMR (300 MHz, DMSO-d₆): δ13.22 (s, 1H), 8.37 (d, J=9.5 Hz, 1H), 8.22-8.07 (m, 4H), 7.80 (s, 1H), 7.29-7.19 (m, 2H), 4.54-4.43 (m, 1H), 4.15-3.97 (m, 2H), 3.86-3.66 (m, 2H), 3.57 (td, J=11.8, 2.8 Hz, 1H), 3.37-3.12 (m, 3H), 1.21 (d, J=6.6 Hz, 3H); LC/MS (Method E): Rt 1.396 min [MH]+439.1.

Example 47

1-(3-Methanesulfonyl-phenyl)-5-((R)-3-methyl-morpholin-4-yl)-3-(1H-pyrazol-3-yl)-1H-pyrazolo[4,3-b]pyridine (47)

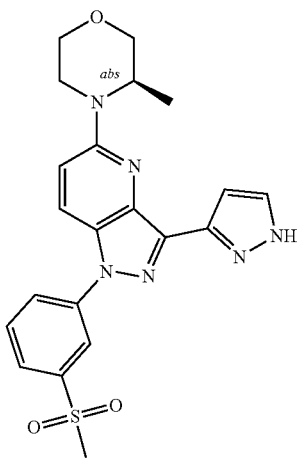 [SMILES: C[C@@H]1COCCN1c1ccc2c(n1)c(-c1cc[nH]n1)nn2-c1cccc(S(C)(=O)=O)c1]

1-(3-Methanesulfonyl-phenyl)-5-((R)-3-methyl-morpholin-4-yl)-3-(1H-pyrazol-3-yl)-1H-pyrazolo[4,3-b]pyridine was prepared analogously to above examples and isolated as a yellow solid (4 mg, 10%); melting point 133-135° C.; ¹H NMR (300 MHz, CD₃OD): δ8.46 (s, 2H), 8.22 (t, J=8.5 Hz, 4H), 8.00-7.80 (m, 4H), 7.71 (s, 1H), 7.37 (s, 1H), 7.28 (s, 1H), 7.18 (d, J=9.5 Hz, 2H), 4.52 (d, J=7.1 Hz, 2H), 4.09 (dd, J=12.4, 6.1 Hz, 4H), 3.86 (d, J=2.6 Hz, 3H), 3.70 (td, J=11.8, 3.2 Hz, 2H), 3.38 (dd, J=12.7, 3.9 Hz, 2H), 3.26 (s, 5H), 1.33 (d, J=6.7 Hz, 7H); LC/MS (Method E): Rt 1.395 min [MH]+439.2.

Example 48

3-{1-Methyl-5-[(3R)-3-methylmorpholin-4-yl]-3-(1H-pyrazol-3-yl)-1H-pyrazolo[4,3-b]pyridin-7-yl}benzonitrile (48)

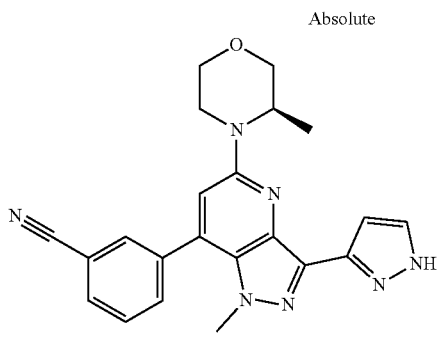 [SMILES: C[C@@H]1COCCN1c1cc(-c2cccc(C#N)c2)c2c(n1)c(-c1cc[nH]n1)nn2C]

3-{1-Methyl-5-[(3R)-3-methylmorpholin-4-yl]-3-(1H-pyrazol-3-yl)-1H-pyrazolo[4,3-b]pyridin-7-yl}benzonitrile was prepared analogously to above examples and isolated as yellow solid (34 mg, 25%); ¹H NMR (400 MHz, DMSO-d₆): δ8.16-8.14 (m, 1H), 8.03-8.00 (m, 1H), 7.98-7.94 (m, 1H), 7.79-7.73 (m, 1H), 7.68 (d, J=1.9 Hz, 1H), 7.07 (d, J=2.0 Hz, 1H), 6.96 (s, 1H), 4.53-4.46 (m, 1H), 4.09-4.03 (m, 1H), 4.01-3.96 (m, 1H), 3.78-3.74 (m, 1H), 3.68 (dd, J=11.4, 3.0 Hz, 1H), 3.60 (s, 3H), 3.54 (td, J=11.7, 3.0 Hz, 1H), 3.18 (td, J=12.7, 3.7 Hz, 1H), 1.19 (d, J=6.6 Hz, 3H); LC/MS (Method F): Rt 2.226 min; [MH]+400.2.

Example 49

(3R)-3-Methyl-4-[1-methyl-7-(2-methylphenyl)-3-(1H-pyrazol-5-yl)-1H-pyrazolo[4,3-b]pyridin-5-yl]morpholine (49)

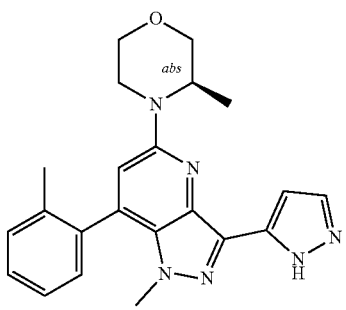 [SMILES: Cc1ccccc1-c1cc(N2CCOC[C@H]2C)nc2c(-c3ccn[nH]3)nn(C)c12]

(3R)-3-Methyl-4-[1-methyl-7-(2-methylphenyl)-3-(1H-pyrazol-5-yl)-1H-pyrazolo[4,3-b]pyridin-5-yl]morpholine was prepared analogously to above examples and isolated as beige solid (27 mg; 18%); ¹H NMR (500 MHz, DMSO-d₆): δ7.68 (d, J=1.9 Hz, 1H), 7.48-7.32 (m, 4H), 7.06 (dd, J=1.9, 0.9 Hz, 1H), 6.84 (s, 1H), 4.43 (t, J=7.6 Hz, 1H), 4.12-3.94 (m, 2H), 3.77-3.66 (m, 2H), 3.54 (td, J=11.8, 3.0 Hz, 1H), 3.40 (d, J=0.8 Hz, 3H), 3.17 (td, J=12.6, 3.8 Hz, 1H), 2.10 (s, 3H), 1.99 (s, 1H), 1.91 (s, 0H), 1.20-1.15 (m, 3H). LC/MS (Method C): Rt 1.116 min; [MH]+389.2.

Example 50

(3R)-4-[7-(4-Methanesulfonyl-2-methylphenyl)-1-methyl-3-(1H-pyrazol-3-yl)-1H-pyrazolo[4,3-b]pyridin-5-yl]-3-methylmorpholine (50)

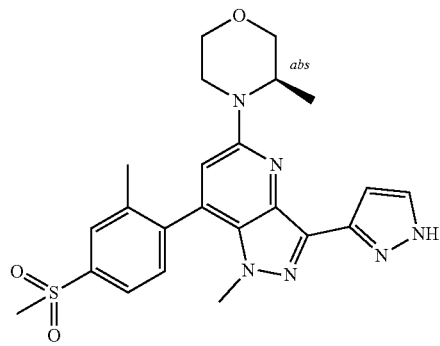 [SMILES: Cc1cc(S(C)(=O)=O)ccc1-c1cc(N2CCOC[C@H]2C)nc2c(-c3cc[nH]n3)nn(C)c12]

(3R)-4-[7-(4-Methanesulfonyl-2-methylphenyl)-1-methyl-3-(1H-pyrazol-3-yl)-1H-pyrazolo[4,3-b]pyridin-5-yl]-3-methylmorpholine was prepared analogously to above examples and isolated as yellow solid (41 mg, 31%); $^1$H NMR (400 MHz, DMSO-d$_6$): δ8.01-7.99 (m, 1H), 7.93-7.89 (m, 1H), 7.70-7.65 (m, 2H), 7.08-7.06 (m, 1H), 6.91 (s, 1H), 4.47-4.39 (m, 1H), 4.12-4.03 (m, 1H), 4.01-3.95 (m, 1H), 3.77-3.66 (m, 2H), 3.58-3.50 (m, 1H), 3.43-3.40 (m, 3H), 3.30 (s, 3H), 3.17 (td, J=12.7, 3.8 Hz, 1H), 2.21 (s, 3H), 1.21-1.16 (m, 3H); LC/MS (Method F): Rt 2.136 min; [MH]+467.1.

Example 51

(3R)-4-{7-[4-(Methoxymethyl)phenyl]-1-methyl-3-(1H-pyrazol-3-yl)-1H-pyrazolo[4,3-b]pyridin-5-yl}-3-methylmorpholine (51)

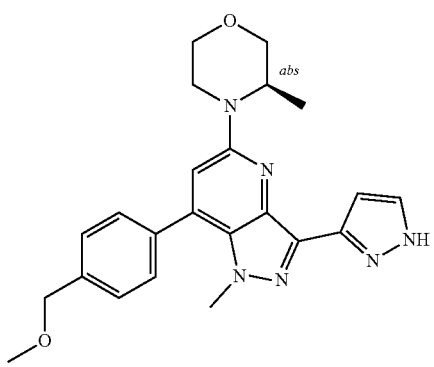 [SMILES: COCc1ccc(-c2cc(N3CCOC[C@H]3C)nc3c(-c4cc[nH]n4)nn(C)c23)cc1]

(3R)-4-{7-[4-(Methoxymethyl)phenyl]-1-methyl-3-(1H-pyrazol-3-yl)-1H-pyrazolo[4,3-b]pyridin-5-yl}-3-methylmorpholine was prepared analogously to above examples and isolated as yellow solid (104 mg, 74%);

$^1$H NMR (500 MHz, DMSO-d$_6$): δ7.68-7.67 (m, 1H), 7.59-7.56 (m, 2H), 7.51-7.48 (m, 2H), 7.06 (d, J=1.9 Hz, 1H), 6.87 (s, 1H), 4.53 (s, 2H), 4.50-4.44 (m, 1H), 4.07-4.02 (m, 1H), 3.98 (dd, J=11.4, 3.6 Hz, 1H), 3.77-3.73 (m, 1H), 3.69 (dd, J=11.3, 3.0 Hz, 1H), 3.60 (s, 3H), 3.54 (td, J=11.7, 3.0 Hz, 1H), 3.36 (s, 3H), 3.18 (td, J=12.7, 3.7 Hz, 1H), 1.19 (d, J=6.6 Hz, 3H);

LC/MS (Method F): Rt 2.259 min; [MH]+419.2.

Example 52

(4-{1-Methyl-5-[(3R)-3-methylmorpholin-4-yl]-3-(1H-pyrazol-3-yl)-1H-pyrazolo[4,3-b]pyridin-7-yl}phenyl)methanol (52)

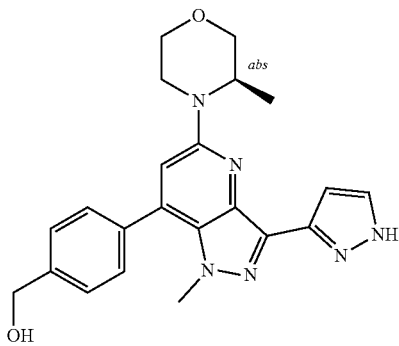 [SMILES: C[C@@H]1COCCN1c1cc(-c2ccc(CO)cc2)c2c(n1)c(-c1cc[nH]n1)nn2C]

(4-{1-Methyl-5-[(3R)-3-methylmorpholin-4-yl]-3-(1H-pyrazol-3-yl)-1H-pyrazolo[4,3-b]pyridin-7-yl}phenyl)methanol was prepared analogously to above examples and isolated as yellow solid (112 mg, 65%);
$^1$H NMR (400 MHz, DMSO-d$_6$): δ7.69 (d, J=1.9 Hz, 1H), 7.56-7.53 (m, 2H), 7.51-7.48 (m, 2H), 7.07 (d, J=2.0 Hz, 1H), 6.85 (s, 1H), 4.61 (s, 2H), 4.51-4.43 (m, 1H), 4.07-4.01 (m, 1H), 4.01-3.95 (m, 1H), 3.78-3.66 (m, 2H), 3.61 (s, 3H), 3.54 (td, J=11.8, 3.0 Hz, 1H), 3.19 (td, J=12.6, 3.7 Hz, 1H), 1.19-1.18 (m, 3H); LC/MS (Method F): Rt 1.997 min; [MH]+405.2.

Example 53

3-[5-((3R)-3-Methyl-morpholin-4-yl)-3-(1H-pyrazol-3-yl)-1H-pyrazolo[4,3-b]pyridin-1-yl]-benzonitrile (53)

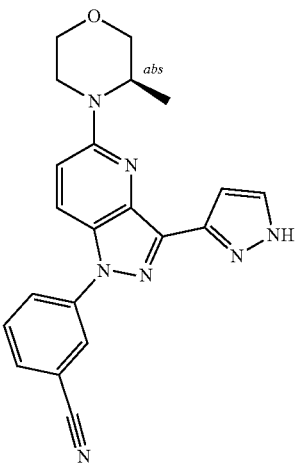 [SMILES: C[C@@H]1COCCN1c1ccc2c(n1)c(-c1cc[nH]n1)nn2-c1cccc(C#N)c1]

3-[5-((3R)-3-Methyl-morpholin-4-yl)-3-(1H-pyrazol-3-yl)-1H-pyrazolo[4,3-b]pyridin-1-yl]-benzonitrile was prepared analogously to above examples and isolated as a yellow solid (8 mg, 26%); melting point 115-117° C.;
$^1$H NMR (300 MHz, DMSO-d$_6$): δ13.50 (s, 1H), 13.15 (s, 1H), 8.37 (s, 4H), 8.24 (s, 3H), 7.84 (s, 5H), 7.68 (s, 1H), 7.22 (d, J=16.2 Hz, 4H), 4.50 (s, 2H), 4.03 (d, J=9.7 Hz, 3H), 3.86-3.67 (m, 4H), 3.65-3.50 (m, 2H), 3.29-3.14 (m, 2H), 1.21 (d, J=6.5 Hz, 7H); LC/MS (Method U): Rt 2.952 min [MH]+386.2.

Example 54

(3R)-4-[7-(3,6-Dihydro-2H-pyran-4-yl)-1-methyl-3-(1H-pyrazol-3-yl)-1H-pyrazolo[4,3-b]pyridin-5-yl]-3-methylmorpholine (54)

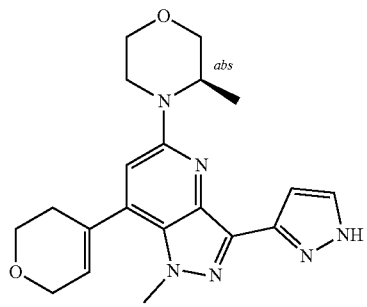 [SMILES: C[C@@H]1COCCN1c1cc(C2=CCOCC2)c2c(n1)c(-c1cc[nH]n1)nn2C]

(3R)-4-[7-(3,6-Dihydro-2H-pyran-4-yl)-1-methyl-3-(1H-pyrazol-3-yl)-1H-pyrazolo[4,3-b]pyridin-5-yl]-3-methylmorpholine was prepared analogously to above examples and isolated as yellow solid (35 mg, 65%);

$^1$H NMR (500 MHz, DMSO-d$_6$): δ13.19-12.86 (m, 1H), 7.82-7.53 (m, 1H), 7.11-6.95 (m, 1H), 6.86-6.77 (m, 1H), 6.01-5.96 (m, 1H), 4.50-4.39 (m, 1H), 4.29-4.25 (m, 2H), 4.04-3.95 (m, 5H), 3.90 (t, J=5.4 Hz, 2H), 3.75 (d, J=11.2 Hz, 1H), 3.68 (dd, J=11.2, 3.0 Hz, 1H), 3.52 (td, J=11.7, 3.0 Hz, 1H), 3.14 (td, J=12.7, 3.8 Hz, 1H), 2.50-2.45 (m, 2H), 1.16 (d, J=6.6 Hz, 3H); LC/MS (Method F): Rt 1.941 min; [MH]+381.2.

Example 55

1-Methyl-5-((R)-3-methyl-morpholin-4-yl)-3-(2H-pyrazol-3-yl)-7-(tetrahydro-pyran-4-yl)-1H-pyrazolo[4,3-b]pyridine (55)

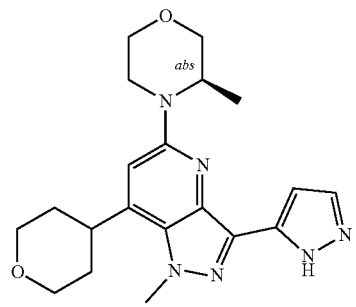 [SMILES: C[C@@H]1COCCN1c1cc(C2CCOCC2)c2c(n1)c(-c1ccn[nH]1)nn2C]

Building Block for Synthesis of Example 55: (3R)-3-methyl-4-[1-methyl-7-(oxan-4-yl)-1H-pyrazolo[4,3-b]pyridin-5-yl]morpholine

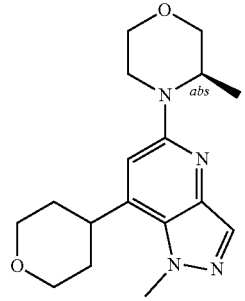 [SMILES: C[C@@H]1COCCN1c1cc(C2CCOCC2)c2c(cnn2C)n1]

(3R)-4-[7-(3,6-Dihydro-2H-pyran-4-yl)-1-methyl-1H-pyrazolo[4,3-b]pyridin-5-yl]-3-methylmorpholine (400 mg, 1.15 mmol, 1. eq.), methanol (30 mL) and Pd/C (2437.24 mg, 2.29 mmol, 2.0 eq. 10%) were combined and stirred for 5 h at 25 degrees Celsius. The reaction mixture was filtrated and concentrated under vacuum. (3R)-3-Methyl-4-[1-methyl-7-(oxan-4-yl)-1H-pyrazolo[4,3-b]pyridin-5-yl]morpholine was isolated as a yellow solid (300 mg 74%); LC/MS (Method J): Rt 0.752 min, [MH]+317.2.

Example 55

1-Methyl-5-((R)-3-methyl-morpholin-4-yl)-3-(2H-pyrazol-3-yl)-7-(tetrahydro-pyran-4-yl)-1H-pyrazolo[4,3-b]pyridine 1-Methyl-5-((R)-3-methyl-morpholin-4-yl)-3-(2H-pyrazol-3-yl)-7-(tetrahydro-pyran-4-yl)-1H-pyrazolo[4,3-b]pyridine was prepared analogously to above examples and isolated as colorless solid (20 mg (27%); melting point 240-242° C.; $^1$H NMR (300 MHz, methanol-d$_4$): δ7.62 (s, 1H), 7.01 (s, 1H), 6.84 (s, 1H), 4.43 (d, J=7.3 Hz, 1H), 4.25 (s, 3H), 4.15-4.03 (m, 2H), 4.07-3.91 (m, 2H), 3.80 (d, J=2.2 Hz, 2H), 3.64 (dtd, J=14.3, 11.1, 6.6 Hz, 2H), 3.32 (d, J=4.0 Hz, OH), 3.23 (d, J=3.7 Hz, OH), 2.04-1.85 (m, 4H), 1.23 (d, J=6.7 Hz, 3H);

LC/MS (Method E): Rt 1.150 min, [MH]+383.2.

Example 56

(3R)-3-Methyl-4-[3-(1H-pyrazol-3-yl)-1H-pyrazolo[4,3-b]pyridin-5-yl]morpholine (56)

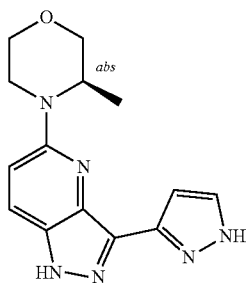 [SMILES: C[C@@H]1COCCN1c1ccc2[nH]nc(-c3cc[nH]n3)c2n1]

Building Block for Synthesis of Example 56:
3-Bromo-5-((R)-3-methyl-morpholin-4-yl)-1H-pyrazolo[4,3-b]pyridine

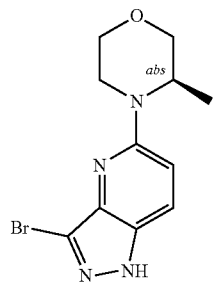 [SMILES: C[C@@H]1COCCN1c1ccc2[nH]nc(Br)c2n1]

3-Bromo-5-chloro-1H-pyrazolo[4,3-b]pyridine (2 g, 8.6 mmol), (R)-3-methyl-morpholine (957 mg, 9.5 mmol), XPhos-Pd-G2 (339 mg, 0.43 mmol), bis-cy-xPhos (205 mg, 0.43 mmol), LHMDS (3 g, 17 mmol) and dioxane (20 ml) were combined and stirred 3 hours at 60° C. The reaction was filtrated and concentrated under reduced pressure. The crude product was purified by column chromatography (n-Heptane/EtOAc-gradient). 3-Bromo-5-((R)-3-methyl-morpholin-4-yl)-1H-pyrazolo[4,3-b]pyridine was isolated as yellow solid (280 mg, 6%); LC/MS (Method V): Rt 2.802 min; [MH]+297.

Building Block for Synthesis of Example 56:
5-((R)-3-Methyl-morpholin-4-yl)-3-[1-(tetrahydro-pyran-2-yl)-1H-pyrazol-3-yl]-1H-pyrazolo[4,3-b]pyridine

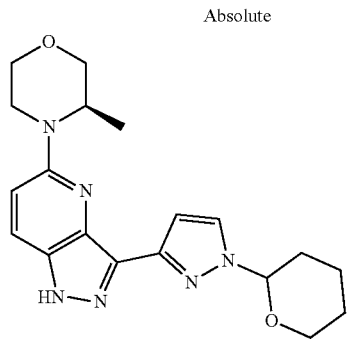 [SMILES: C[C@@H]1COCCN1c1ccc2[nH]nc(-c3ccn(C4CCCCO4)n3)c2n1]

3-Bromo-5-((R)-3-methyl-morpholin-4-yl)-1H-pyrazolo[4,3-b]pyridine (280 mg; 0.518 mmol; 1.0 eq.) was dissolved in THF (8 ml) and water (0.800 ml). 1-(Tetrahydro-pyran-2-yl)-3-(4,4,5,5-tetramethyl-[1,3,2]dioxaborolan-2-yl)-1H-pyrazole (294.194 mg; 1,037 mmol; 2.0 eq.), sodium carbonate (164.786 mg; 1.555 mmol; 3.0 eq.) and tetrakis(triphenylphosphine)-palladium(0) (72.591 mg; 0.062 mmol; 0.12 eq.) were combined and stirred at 90° C. for 3 h. 1-(Tetrahydro-pyran-2-yl)-3-(4,4,5,5-tetramethyl-[1,3,2]dioxaborolan-2-yl)-1H-pyrazole (294.194 mg; 1.037 mmol; 2.0 eq.) and tetrakis(triphenylphosphine)-palladium(0) (72.591 mg; 0.062 mmol; 0.12 eq.) was added and stirred at 90° C. for 14 h. The reaction mixture was concentrated under reduced pressure and the crude product was purified by column chromatography (n-heptane/EtOAc-gradient). 5-((R)-3-Methyl-morpholin-4-yl)-3-[1-(tetrahydro-pyran-2-yl)-1H-pyrazol-3-yl]-1H-pyrazolo[4,3-b]pyridine was isolated as yellow solid (131 mg, 61%); LC/MS (Method F): Rt 1.903 min; [MH]+369.2.

Example 56

(3R)-3-Methyl-4-[3-(1H-pyrazol-3-yl)-1H-pyrazolo[4,3-b]pyridin-5-yl]morpholine

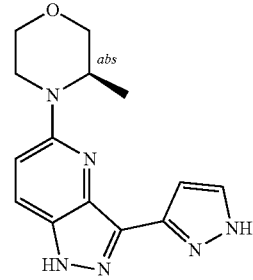 [SMILES: C[C@@H]1COCCN1c1ccc2[nH]nc(-c3cc[nH]n3)c2n1]

5-((R)-3-Methyl-morpholin-4-yl)-3-[1-(tetrahydro-pyran-2-yl)-1H-pyrazol-3-yl]-1H-pyrazolo[4,3-b]pyridine (131 mg; 0.316 mmol; 1.0 eq.) was dissolved in methanol (3.500 ml) and hydrogen chloride solution in dioxane (3.164 ml; 4.0 M). The reaction solution was stirred at RT for 2 hours. The reaction mixture was concentrated under reduced pressure and the crude product was purified by column chromatography (DCM/MeOH-gradient). (3R)-3-Methyl-4-[3-(1H-pyrazol-3-yl)-1H-pyrazolo[4,3-b]pyridin-5-yl]morpholine was isolated as yellow solid (90 mg, 99%); $^1$H NMR (400 MHz, DMSO-$d_6$): δ13.21-12.76 (m, 2H), 7.89-7.53 (m, 2H), 7.11-6.96 (m, 2H), 4.45-4.36 (m, 1H), 4.06-3.93 (m, 2H), 3.76 (d, J=11.2 Hz, 1H), 3.70 (dd, J=11.3, 3.0 Hz, 1H), 3.54 (td, J=11.7, 3.0 Hz, 1H), 3.15 (td, J=12.7, 3.8 Hz, 1H), 1.16 (d, J=6.6 Hz, 3H);

LC/MS (Method F): Rt 1.586 min; [MH]+285.1.

Example 57

(3R)-4-{1-[(3-Methanesulfonylphenyl)methyl]-3-(1H-pyrazol-3-yl)-1H-pyrazolo[4,3-b]pyridin-5-yl}-3-methylmorpholine (57)

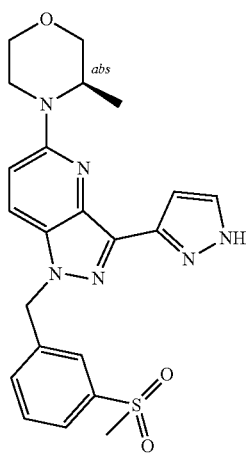 [SMILES: C[C@@H]1COCCN1c1ccc2c(n1)c(-c1cc[nH]n1)nn2Cc1cccc(S(C)(=O)=O)c1]

5-((R)-3-Methyl-morpholin-4-yl)-3-(1H-pyrazol-3-yl)-1H-pyrazolo[4,3-b]pyridine (56 mg; 0.197 mmol; 1.0 eq.), acetonitrile (2.8 ml), potassium carbonate (42.981 mg; 0.295 mmol; 1.50 eq.) and 1-bromomethyl-3-methanesulfonyl-benzene (51.651 mg; 0.197 mmol; 1.0 eq.) were combined and stirred at 80° C. for 2 hours. The reaction solution was extracted with EtOAc/water and the organic layer dried over sodium sulfate, filtered and the solvent removed in vacuo. The crude product was purified by prep HPLC. (3R)-4-{1-[(3-methane-sulfonylphenyl)methyl]-3-(1H-pyrazol-3-yl)-1H-pyrazolo[4,3-b]pyridin-5-yl}-3-methylmorpholine was isolated as yellow solid (27 mg, 28%); $^1$H NMR (700 MHz, DMSO-$d_6$): δ8.14 (d, J=9.4 Hz, 1H), 7.90-7.88 (m, 1H), 7.87-7.84 (m, 1H), 7.81 (d, J=1.9 Hz, 1H), 7.61 (t, J=7.8 Hz, 1H), 7.53-7.50 (m, 1H), 7.18 (d, J=9.5 Hz, 1H), 7.11 (d, J=1.9 Hz, 1H), 5.80 (s, 2H), 4.44-4.40 (m, 1H), 4.04-4.01 (m, 1H), 3.99 (dd, J=11.3, 3.7 Hz, 1H), 3.78-3.75 (m, 1H), 3.69 (dd, J=11.2, 3.1 Hz, 1H), 3.53 (td, J=11.7, 3.1 Hz, 1H), 3.20 (s, 3H), 3.19-3.15 (m, 1H), 1.16 (d, J=6.6 Hz, 3H); LC/MS (Method F): Rt 1.981 min; [MH]+453.1.

Example 58

(3R)-3-Methyl-4-[1-methyl-3-(1H-pyrazol-3-yl)-7-(pyridin-2-yl)-1H-pyrazolo[4,3-b]pyridin-5-yl]morpholine (58)

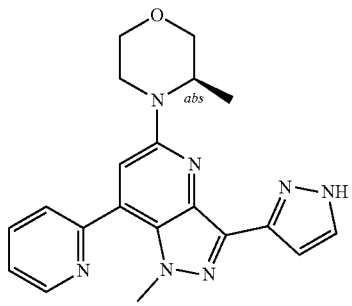 [SMILES: C[C@@H]1COCCN1c1cc(-c2ccccn2)c2c(n1)c(-c1cc[nH]n1)nn2C]

(3R)-3-Methyl-4-[1-methyl-3-(1H-pyrazol-3-yl)-7-(pyridin-2-yl)-1H-pyrazolo[4,3-b]pyridin-5-yl]morpholine was prepared analogously to above examples and isolated as orange solid (40 mg, 72.9%); $^1$H NMR (400 MHz, DMSO-$d_6$): δ8.82-8.79 (m, 1H), 8.07 (td, J=7.7, 1.8 Hz, 1H), 7.90-7.86 (m, 1H), 7.74 (d, J=2.0 Hz, 1H), 7.62-7.57 (m, 1H), 7.09 (d, J=1.9 Hz, 1H), 7.08 (s, 1H), 4.54-4.47 (m, 1H), 4.09-4.03 (m, 1H), 3.99 (dd, J=11.2, 3.5 Hz, 1H), 3.77 (d, J=11.3 Hz, 1H), 3.71 (s, 3H), 3.73-3.68 (m, 1H), 3.55 (td, J=11.8, 3.0 Hz, 1H), 3.26-3.17 (m, 1H), 1.20 (d, J=6.6 Hz, 3H);
LC/MS (Method C): Rt 0.947 min; [MH]+376.2.

Example 59

(3R)-4-[1-Benzyl-3-(1H-pyrazol-5-yl)-1H-pyrazolo[4,3-b]pyridin-5-yl]-3-methylmorpholine (59)

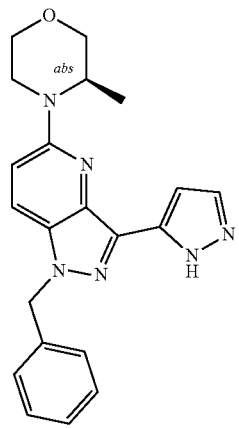

(3R)-4-[1-Benzyl-3-(1H-pyrazol-5-yl)-1H-pyrazolo[4,3-b]pyridin-5-yl]-3-methylmorpholine hydrochloride was prepared analogously to above examples and isolated as beige solid (120 mg; 52.3%); $^1$H NMR (500 MHz, DMSO-$d_6$): δ8.04 (d, J=9.4 Hz, 1H), 7.73 (d, J=2.0 Hz, 1H), 7.34-7.30 (m, 2H), 7.28-7.22 (m, 3H), 7.12 (d, J=9.5 Hz, 1H), 7.07 (d, J=2.0 Hz, 1H), 5.65 (s, 2H), 4.44-4.38 (m, 1H), 4.03-3.97 (m, 2H), 3.76 (d, J=11.2 Hz, 1H), 3.68 (dd, J=11.2, 3.1 Hz, 1H), 3.54-3.50 (m, 1H), 3.16 (td, J=12.8, 3.9 Hz, 1H), 1.16 (d, J=6.6 Hz, 3H); LC/MS (Method C): Rt 1.075 min; [MH]+375.2.

Example 60

4-[5-[(3R)-3-Methylmorpholin-4-yl]-3-(1H-pyrazol-3-yl)-1H-pyrazolo[4,3-b]pyridin-1-yl]benzonitrile (60)

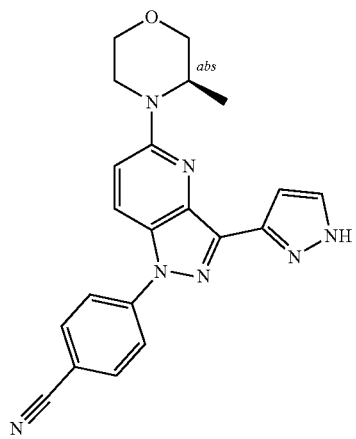 [SMILES: C[C@@H]1COCCN1c1ccc2c(n1)c(-c1cc[nH]n1)nn2-c1ccc(C#N)cc1]

4-[5-[(3R)-3-Methylmorpholin-4-yl]-3-(1H-pyrazol-3-yl)-1H-pyrazolo[4,3-b]pyridin-1-yl]benzonitrile was prepared analogously to above examples and isolated as a yellow solid (10 mg, 26%); melting point 140-142° C.; $^1$H NMR (300 MHz, DMSO-$d_6$): δ13.20 (s, 1H), 8.33 (d, J=9.5 Hz, 1H), 8.05 (q, J=8.9 Hz, 4H), 7.76 (s, 1H), 7.23-7.14 (m, 2H), 4.53-4.40 (m, 1H), 4.11-3.94 (m, 2H), 3.83-3.63 (m, 2H), 3.53 (td, J=11.8, 2.9 Hz, 1H), 3.26-3.09 (m, 1H), 1.17 (d, J=6.5 Hz, 3H); LC/MS (Method D): Rt 1.295 min [MH]+386.0.

Example 61

(3R)-3-Methyl-4-[1-methyl-7-(1-methyl-1H-pyrazol-5-yl)-3-(1H-pyrazol-3-yl)-1H-pyrazolo[4,3-b]pyridin-5-yl]morpholine (61)

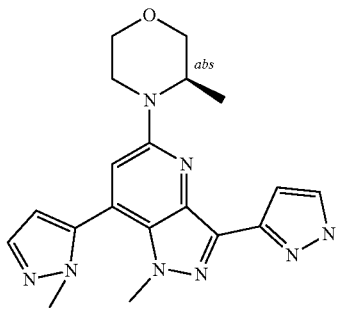 [SMILES: C[C@@H]1COCCN1c1cc(-c2ccnn2C)c2c(n1)c(-c1cc[nH]n1)nn2C]

(3R)-3-Methyl-4-[1-methyl-7-(1-methyl-1H-pyrazol-5-yl)-3-(1H-pyrazol-3-yl)-1H-pyrazolo[4,3-b]pyridin-5-yl]morpholine was prepared analogously to above examples and isolated as yellow solid (30 mg, 16%); $^1$H NMR (300 MHz, DMSO-$d_6$): δ13.11 (s, 1H), 7.85-7.51 (m, 2H), 7.06 (d, J=1.7 Hz, 2H), 6.61 (d, J=1.9 Hz, 1H), 4.47 (d, J=7.4 Hz, 1H), 4.22-3.88 (m, 2H), 3.72 (d, J=6.5 Hz, 5H), 3.32 (s, 4H), 3.25-3.01 (m, 1H), 1.18 (d, J=6.6 Hz, 3H);
LC/MS (Method K): Rt 1.177 min [MH]+379.3.

Example 62

(3R)-3-Methyl-4-[1-methyl-7-(3-methylpyridin-2-yl)-3-(1H-pyrazol-3-yl)-1H-pyrazolo[4,3-b]pyridin-5-yl]morpholine (62)

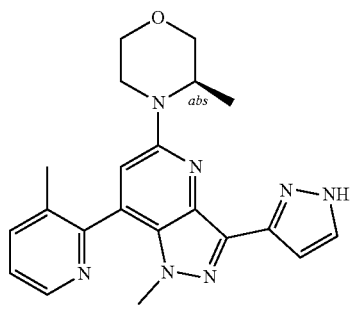 [SMILES: Cc1cccnc1-c1cc(N2CCOC[C@H]2C)nc2c(-c3cc[nH]n3)nn(C)c12]

(3R)-3-Methyl-4-[1-methyl-7-(3-methylpyridin-2-yl)-3-(1H-pyrazol-3-yl)-1H-pyrazolo[4,3-b]pyridin-5-yl]morpholine was prepared analogously to above examples and isolated as yellow solid (15.70 mg, 18.2%); $^1$H NMR (500 MHz, DMSO-$d_6$): δ13.24-12.88 (m, 1H), 8.59-8.57 (m, 1H), 7.89-7.86 (m, 1H), 7.84-7.56 (m, 1H), 7.49 (dd, J=7.7, 4.8 Hz, 1H), 7.15-6.92 (m, 2H), 4.49-4.40 (m, 1H), 4.13-4.01 (m, 1H), 3.99 (dd, J=11.4, 3.6 Hz, 1H), 3.76-3.72 (m, 1H), 3.70 (dd, J=11.4, 3.0 Hz, 1H), 3.55 (td, J=11.7, 3.0 Hz, 1H), 3.42-3.36 (m, 3H), 3.17 (td, J=12.7, 3.8 Hz, 1H), 2.20 (s, 3H), 1.17 (d, J=6.6 Hz, 3H); LC/MS (Method C): Rt 0.953 min; [MH]+390.2.

Example 63

(3R)-4-[1-(Cyclopropylmethyl)-3-(1H-pyrazol-3-yl)-1H-pyrazolo[4,3-b]pyridin-5-yl]-3-methylmorpholine (63)

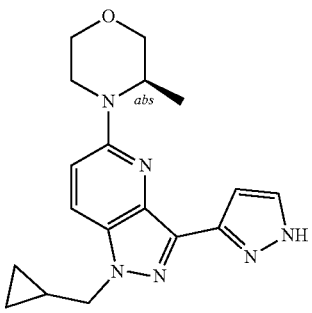 [SMILES: C[C@@H]1COCCN1c1ccc2c(n1)c(-c1cc[nH]n1)nn2CC1CC1]

(3R)-4-[1-(Cyclopropylmethyl)-3-(1H-pyrazol-3-yl)-1H-pyrazolo[4,3-b]pyridin-5-yl]-3-methylmorpholine was prepared analogously to above examples and isolated isolated as a colorless solid (20 mg, 43%); melting point 80° C.; $^1$H NMR (300 MHz, DMSO-$d_6$): δ13.07 (s, 1H), 8.05 (d, J=9.3 Hz, 1H), 7.67 (s, 1H), 7.11 (d, J=9.4 Hz, 1H), 7.04 (d, J=1.9 Hz, 1H), 4.43 (d, J=7.1 Hz, 1H), 4.29 (d, J=6.9 Hz, 2H), 4.10-3.90 (m, 2H), 3.83-3.62 (m, 2H), 3.62-3.47 (m, 1H), 3.23-3.08 (m, 1H), 1.29 (q, J=5.6 Hz, 1H), 1.17 (d, J=6.6 Hz, 3H), 0.58-0.45 (m, 2H), 0.4-0.33 (m, 2H);
LC/MS (Method A): RT 1.475 min, [MH]+339.3.

Example 64

5-((R)-3-Methyl-morpholin-4-yl)-1-phenethyl-3-(1H-pyrazol-3-yl)-1H-pyrazolo[4,3-b]pyridine (64)

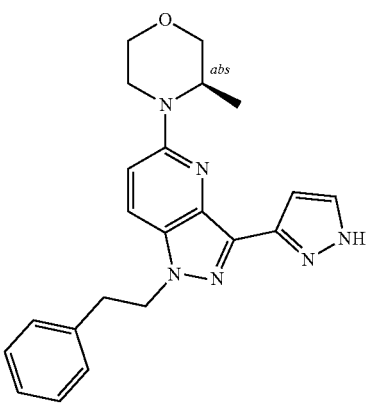 [SMILES: C[C@@H]1COCCN1c1ccc2c(n1)c(-c1cc[nH]n1)nn2CCc1ccccc1]

(3R)-3-methyl-4-[1-(2-phenylethyl)-3-(1H-pyrazol-3-yl)-1H-pyrazolo[4,3-b]pyridin-5-yl]morpholine was prepared analogously to above examples as colorless solid (27 mg, 52%); melting point 83° C.; ¹H NMR (300 MHz, DMSO-d₆): δ13.04 (d, J=86.7 Hz, 1H), 7.95-7.45 (m, 2H), 7.38-6.82 (m, 7H), 4.60 (s, 2H), 4.36 (s, 1H), 3.96 (d, J=10.0 Hz, 2H), 3.86-3.62 (m, 2H), 3.59-3.39 (m, 1H), 3.22-3.01 (m, 3H), 1.11 (d, J=6.6 Hz, 3H);

LC/MS (Method J): RT 1.030 min, [MH]+389.1.

Example 65

(3R)-3-Methyl-4-[1-methyl-3-(1H-pyrazol-3-yl)-7-[6-(trifluoro-methyl)pyridin-3-yl]-1H-pyrazolo[4,3-b]pyridin-5-yl]morpholine (65)

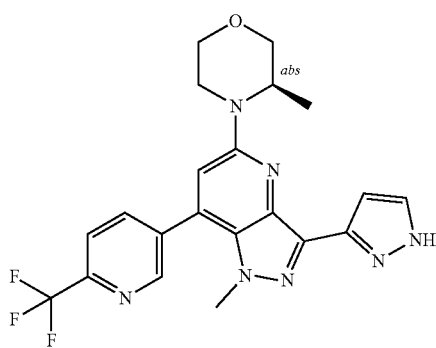 [SMILES: C[C@@H]1COCCN1c1cc(-c2ccc(C(F)(F)F)nc2)c2c(n1)c(-c1cc[nH]n1)nn2C]

(3R)-3-Methyl-4-[1-methyl-3-(1H-pyrazol-3-yl)-7-[6-(trifluoromethyl)pyridin-3-yl]-1H-pyrazolo[4,3-b]pyridin-5-yl]morpholine was prepared analogously to above examples and isolated as a yellow solid (26 mg, 93%);

¹H NMR (500 MHz, DMSO-d₆): δ13.29-12.89 (m, 1H), 9.05-9.03 (m, 1H), 8.41-8.37 (m, 1H), 8.12-8.09 (m, 1H), 7.85-7.54 (m, 1H), 7.13-7.00 (m, 2H), 4.55-4.45 (m, 1H), 4.08 (q, J=5.3 Hz, 1H), 3.99 (dd, J=11.4, 3.6 Hz, 1H), 3.76 (d, J=11.2 Hz, 1H), 3.69 (dd, J=11.3, 3.0 Hz, 1H), 3.63 (s, 3H), 3.54 (td, J=11.7, 3.1 Hz, 1H), 3.23-3.16 (m, 1H), 1.19 (d, J=6.6 Hz, 3H);

LC/MS (Method F): Rt 2.351 min; [MH]+444.1.

Example 66

(3R)-3-Methyl-4-[1-methyl-3-(1H-pyrazol-3-yl)-7-[2-(trifluoro-methyl)pyridin-3-yl]-1H-pyrazolo[4,3-b]pyridin-5-yl]morpholine (66)

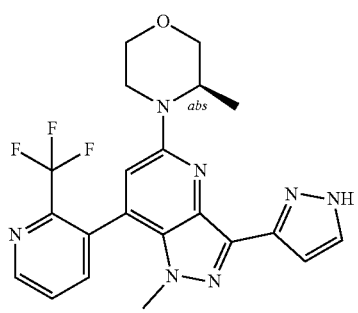 [SMILES: C[C@@H]1COCCN1c1cc(-c2cccnc2C(F)(F)F)c2c(n1)c(-c1cc[nH]n1)nn2C]

(3R)-3-Methyl-4-[1-methyl-3-(1H-pyrazol-3-yl)-7-[2-(trifluoromethyl)pyridin-3-yl]-1H-pyrazolo[4,3-b]pyridin-5-yl]morpholine hydrochloride was prepared analogously to above examples and isolated as orange solid (90 mg, quant);

¹H NMR (700 MHz, DMSO-d₆): δ8.95-8.93 (m, 1H), 8.24-8.21 (m, 1H), 7.93-7.91 (m, 1H), 7.71 (d, J=1.5 Hz, 1H), 7.08-7.06 (m, 1H), 7.03 (d, J=10.1 Hz, 1H), 4.41-4.35 (m, 1H), 4.08-4.03 (m, 1H), 4.01-3.96 (m, 1H), 3.75-3.66 (m, 2H), 3.54 (tt, J=11.7, 2.8 Hz, 1H), 3.41-3.39 (m, 3H), 3.16 (td, J=12.8, 3.9 Hz, 1H), 1.19-1.13 (m, 3H);

LC/MS (Method C): Rt 1.058 min; [MH]+444.2.

Example 67

1-Methyl-5-((R)-3-methyl-morpholin-4-yl)-3-(2H-pyrazol-3-yl)-7-(tetrahydro-pyran-3-yl)-1H-pyrazolo[4,3-b]pyridine (67) (diastereomeric mixture)

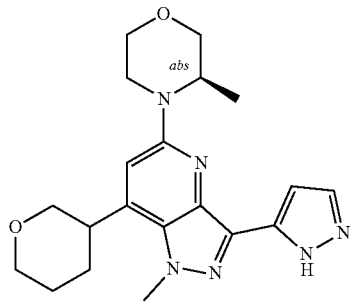

1-Methyl-5-((R)-3-methyl-morpholin-4-yl)-3-(2H-pyrazol-3-yl)-7-(tetrahydro-pyran-3-yl)-1H-pyrazolo[4,3-b]pyridine was prepared analogously to above examples and isolated as colorless solid (30 mg, 41%); melting point 198-200° C.; ¹H NMR (300 MHz, methanol-d4): δ7.60 (s, 1H), 6.99 (s, 1H), 6.90 (d, J=5.7 Hz, 1H), 4.42 (d, J=7.6 Hz, 1H), 4.25 (s, 3H), 4.08 (dd, J=10.1, 2.6 Hz, 1H), 4.07-3.90 (m, 3H), 3.80 (d, J=2.2 Hz, 2H), 3.71-3.50 (m, 4H), 3.32 (s, 0H), 3.23 (d, J=3.7 Hz, 0H), 2.16 (d, J=12.2 Hz, 1H), 2.04-1.71 (m, 2H), 1.27-1.18 (m, 3H); LC/MS (Method W): Rt 0.970 min, [MH]+383.1.

Example 68

1-Methyl-5-((R)-3-methyl-morpholin-4-yl)-3-(2H-pyrazol-3-yl)-7-(R)-tetrahydro-pyran-3-yl-1H-pyrazolo[4,3-b]pyridine (68)

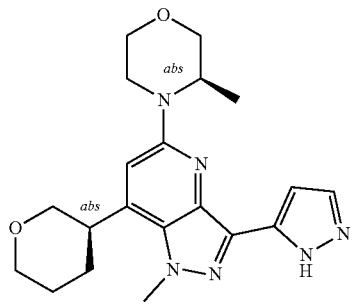

Diastereoisomer of 1-Methyl-5-((R)-3-methyl-morpholin-4-yl)-3-(2H-pyrazol-3-yl)-7-(tetrahydro-pyran-3-yl)-1H-pyrazolo[4,3-b]pyridine was separated by chiral SFC (ChiralCel OJ-H; CO$_2$: methanol+0.5% DEA 88:12). 1-Methyl-5-((R)-3-methyl-morpholin-4-yl)-3-(2H-pyrazol-3-yl)-7-(R)-tetrahydro-pyran-3-yl-1H-pyrazolo[4,3-b]pyridine was isolated as colorless solid (14 mg; 41.5%);

LC/MS (Method C): Rt 0.932 min; [MH]+383.3; Rt eluated from column first.

Example 69

1-Methyl-5-((R)-3-methyl-morpholin-4-yl)-3-(2H-pyrazol-3-yl)-7-(S)-tetrahydro-pyran-3-yl-1H-pyrazolo[4,3-b]pyridine (69)

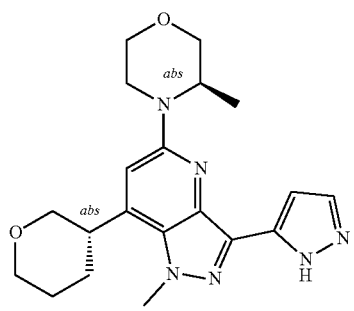

Diastereoisomer of 1-Methyl-5-((R)-3-methyl-morpholin-4-yl)-3-(2H-pyrazol-3-yl)-7-(tetrahydro-pyran-3-yl)-1H-pyrazolo[4,3-b]pyridine was separated by chiral SFC (ChiralCel OJ-H; CO$_2$:methanol+0.5% DEA 88:12). 1-Methyl-5-((R)-3-methyl-morpholin-4-yl)-3-(2H-pyrazol-3-yl)-7-(S)-tetrahydro-pyran-3-yl-1H-pyrazolo[4,3-b]pyridine was isolated as colorless solid (17.80 mg; 52.7%);

LC/MS (Method C): Rt 0.93 min; [MH]+383.3; Rt eluated from column second.

Example 70

1-Methyl-5-((R)-3-methyl-morpholin-4-yl)-3-(2H-pyrazol-3-yl)-7-(tetrahydro-furan-3-yl)-1H-pyrazolo[4,3-b]pyridine (70) (diastereomeric mixture)

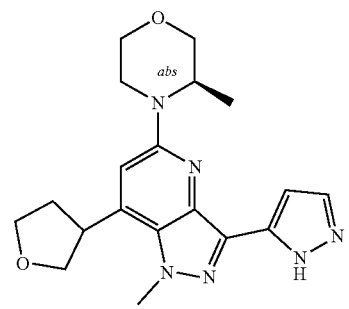

1-Methyl-5-((R)-3-methyl-morpholin-4-yl)-3-(2H-pyrazol-3-yl)-7-(tetrahydro-furan-3-yl)-1H-pyrazolo[4,3-b]pyridine was prepared analogously to above examples and isolated as colorless solid (40 mg; 53%); melting point 98-100° C.; $^1$H NMR (300 MHz, methanol-d4): δ7.59 (s, 1H), 7.14 (s, 0H), 6.98 (s, 1H), 6.87 (s, 1H), 4.25 (s, 3H), 4.24-3.88 (m, 7H), 3.79 (d, J=2.2 Hz, 2H), 3.78-3.54 (m, 2H), 3.35-3.18 (m, 1H), 2.52 (ddd, J=13.1, 8.1, 6.6 Hz, 1H), 2.19-2.05 (m, 1H), 1.52 (s, 0H), 1.22 (dd, J=6.7, 1.3 Hz, 3H);

LC/MS (Method W): Rt 0.870 min, [MH]+369.0.

Example 71

1-Methyl-5-((R)-3-methyl-morpholin-4-yl)-3-(2H-pyrazol-3-yl)-7-(S)-tetrahydro-furan-3-yl-1H-pyrazolo[4,3-b]pyridine (71)

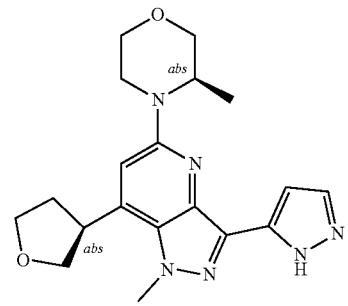 [SMILES: C[C@@H]1COCCN1c1cc([C@@H]2CCOC2)c2c(n1)c(-c1ccn[nH]1)nn2C]

Diastereoisomer of 1-Methyl-5-((R)-3-methyl-morpholin-4-yl)-3-(2H-pyrazol-3-yl)-7-(tetrahydro-furan-3-yl)-1H-pyrazolo[4,3-b]pyridine was separated by chiral SFC (ChiralCel OJ-H; CO$_2$: methanol+0.5% DEA 90:10). 1-Methyl-5-((R)-3-methyl-morpholin-4-yl)-3-(2H-pyrazol-3-yl)-7-(S)-tetrahydro-furan-3-yl-1H-pyrazolo[4,3-b]pyridine was isolated as colorless solid (7 mg; 41.2%);

LC/MS (Method C): Rt 0.867 min; [MH]+369.3; Rt eluated from column first.

Example 72

1-Methyl-5-((R)-3-methyl-morpholin-4-yl)-3-(2H-pyrazol-3-yl)-7-(R)-tetrahydro-furan-3-yl-1H-pyrazolo[4,3-b]pyridine (72)

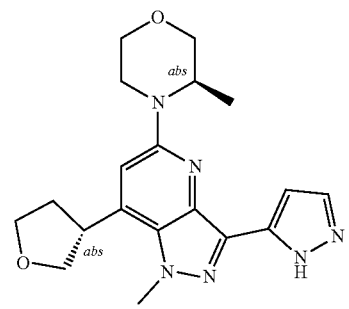 [SMILES: C[C@@H]1COCCN1c1cc([C@H]2CCOC2)c2c(n1)c(-c1ccn[nH]1)nn2C]

Diastereoisomer of 1-Methyl-5-((R)-3-methyl-morpholin-4-yl)-3-(2H-pyrazol-3-yl)-7-(tetrahydro-furan-3-yl)-1H-pyrazolo[4,3-b]pyridine was separated by chiral SFC (ChiralCel OJ-H; CO$_2$:methanol+0.5% DEA 90:10). 1-Methyl-5-((R)-3-methyl-morpholin-4-yl)-3-(2H-pyrazol-3-yl)-7-(R)-tetrahydro-furan-3-yl-1H-pyrazolo[4,3-b]pyridine was isolated as colorless solid (7 mg; 41.2%);

LC/MS (Method C): Rt 0.867 min; [MH]+369.2; Rt eluated from column second.

Example 73

(3R)-3-Methyl-4-[1-(propan-2-yl)-3-(1H-pyrazol-3-yl)-1H-pyrazolo[4,3-b]pyridin-5-yl]morpholine (73)

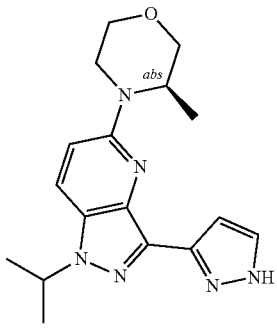 [SMILES: CC(C)n1nc(-c2cc[nH]n2)c2nc(N3CCOC[C@H]3C)ccc21]

(3R)-3-Methyl-4-[1-(propan-2-yl)-3-(1H-pyrazol-3-yl)-1H-pyrazolo[4,3-b]pyridin-5-yl]morpholine was prepared analogously to above examples as colorless solid (18 mg, 28%); melting point 94-95° C.; $^1$H NMR (400 MHz, DMSO-$d_6$): δ 12.99 (d, J=89.2 Hz, 1H), 8.05 (d, J=9.1 Hz, 1H), 7.68 (d, J=89.7 Hz, 1H), 7.03 (d, J=49.1 Hz, 2H), 4.98-4.89 (m, 1H), 4.41 (s, 1H), 3.99 (dd, J=11.2, 3.6 Hz, 2H), 3.76 (d, J=11.2 Hz, 1H), 3.69 (dd, J=11.2, 3.0 Hz, 1H), 3.54 (td, J=11.7, 3.0 Hz, 1H), 3.14 (td, J=12.7, 3.8 Hz, 1H), 1.51 (d, J=6.5 Hz, 6H), 1.15 (d, J=6.6 Hz, 3H); LC/MS (Method E): RT 1.241 min, [MH]+327.4.

Example 74

(3R)-4-[7-(6-Methanesulfonyl-2-methylpyridin-3-yl)-1-methyl-3-[3-(trifluoromethyl)-1H-pyrazol-5-yl]-1H-pyrazolo[4,3-b]pyridin-5-yl]-3-methyl-morpholine (74)

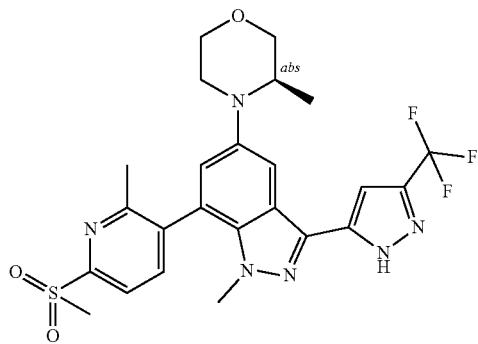 [SMILES: Cc1nc(S(C)(=O)=O)ccc1-c1cc(N2CCOC[C@H]2C)cc2c(-c3cc(C(F)(F)F)n[nH]3)nn(C)c12]

(3R)-4-[7-(6-Methanesulfonyl-2-methylpyridin-3-yl)-1-methyl-3-[3-(trifluoro-methyl)-1H-pyrazol-5-yl]-1H-pyrazolo[4,3-b]pyridin-5-yl]-3-methylmorpholine was prepared analogously to above examples and isolated as yellow solid (19 mg; 64%); $^1$H NMR (500 MHz, DMSO-$d_6$): δ14.14 (s, 1H), 8.22-8.19 (m, 1H), 8.07-8.04 (m, 1H), 7.33-7.31 (m, 1H), 7.12-7.10 (m, 1H), 4.48-4.39 (m, 1H), 4.15-4.07 (m, 1H), 4.00 (dd, J=11.4, 3.6 Hz, 1H), 3.76 (dd, J=11.3, 7.0 Hz, 1H), 3.69 (dd, J=11.3, 3.1 Hz, 1H), 3.58-3.51 (m, 1H), 3.52-3.50 (m, 3H), 3.36 (s, 3H), 3.19 (td, J=12.8, 3.8 Hz, 1H), 2.46-2.43 (m, 3H), 1.21-1.17 (m, 3H); LC/MS (Method C): Rt 1.146 min; [MH]+536.2.

Example 75

(3R)-4-[7-(5-Methanesulfonyl-2-methylphenyl)-1-methyl-3-(1H-pyrazol-5-yl)-1H-pyrazolo[4,3-b]pyridin-5-yl]-3-methylmorpholine (75)

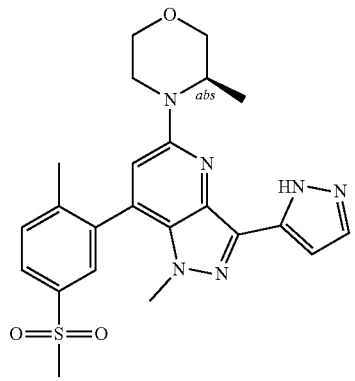 [SMILES: Cc1ccc(S(C)(=O)=O)cc1-c1cc(N2CCOC[C@H]2C)nc2c(-c3ccn[nH]3)nn(C)c12]

(3R)-4-[7-(5-Methanesulfonyl-2-methylphenyl)-1-methyl-3-(1H-pyrazol-5-yl)-1H-pyrazolo[4,3-b]pyridin-5-yl]-3-methylmorpholine was prepared analogously to above examples and isolated as yellow solid (144 mg; quant); $^1$H NMR (700 MHz, DMSO-$d_6$): δ8.00-7.97 (m, 1H), 7.92-7.90 (m, 1H), 7.76-7.74 (m, 1H), 7.72-7.70 (m, 1H), 7.11-7.09 (m, 1H), 6.98-6.96 (m, 1H), 4.48-4.44 (m, 1H), 4.09-4.04 (m, 1H), 4.00-3.96 (m, 1H), 3.77-3.73 (m, 1H), 3.72-3.65 (m, 1H), 3.54 (dd, J=11.6, 3.1 Hz, 1H), 3.42-3.40 (m, 3H), 3.29-3.27 (m, 3H), 3.22-3.16 (m, 1H), 2.22-2.20 (m, 3H), 1.21-1.16 (m, 3H);
LC/MS (Method C): Rt 0.991 min; [MH]+467.

Example 76

(3R)-4-[7-(3-Methanesulfonylphenyl)-1-methyl-3-(1H-pyrazol-5-yl)-1H-pyrazolo[4,3-b]pyridin-5-yl]-3-methylmorpholine (76)

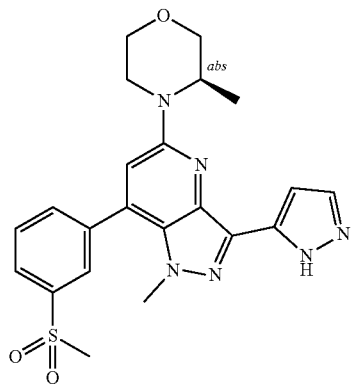 [SMILES: C[C@@H]1COCCN1c1cc(-c2cccc(S(C)(=O)=O)c2)c2c(n1)c(-c1ccn[nH]1)nn2C]

(3R)-4-[7-(3-Methanesulfonylphenyl)-1-methyl-3-(1H-pyrazol-5-yl)-1H-pyrazolo[4,3-b]pyridin-5-yl]-3-methylmorpholine was prepared analogously to above examples and isolated as yellow solid (47 mg; 30%); $^1$H NMR (700 MHz, DMSO-$d_6$): δ8.15-8.13 (m, 1H), 8.10-8.08 (m, 1H), 8.00-7.98 (m, 1H), 7.84 (t, J=7.7 Hz, 1H), 7.70-7.68 (m, 1H), 7.09-7.07 (m, 1H), 6.99 (s, 1H), 4.53-4.49 (m, 1H), 4.07-4.04 (m, 1H), 3.99 (dd, J=11.2, 3.8 Hz, 1H), 3.78-3.75 (m, 1H), 3.69 (dd, J=11.3, 3.1 Hz, 1H), 3.59 (s, 3H), 3.54 (td, J=11.6, 3.1 Hz, 1H), 3.33 (s, 3H), 3.19 (td, J=12.7, 3.8 Hz, 1H), 1.19 (d, J=6.7 Hz, 3H); LC/MS (Method C): Rt 0.992 min; [MH]+453.2.

Example 77: (3R)-3-Methyl-4-[3-(1H-pyrazol-3-yl)-1-[2-(pyridin-4-yl)ethyl]-1H-pyrazolo[4,3-b]pyridin-5-yl]morpholine (77)

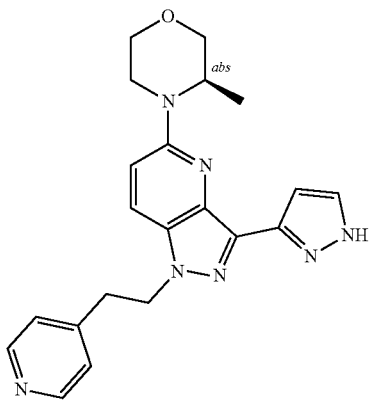

(3R)-3-Methyl-4-[3-(1H-pyrazol-3-yl)-1-[2-(pyridin-4-yl)ethyl]-1H-pyrazolo[4,3-b]pyridin-5-yl]morpholine was prepared analogously to above examples and isolated as yellow solid (10 mg, 20%); melting point 180-181° C.; $^1$H NMR (300 MHz, DMSO-$d_6$): δ13.18 (s, 1H), 8.41-8.32 (m, 2H), 7.84 (d, J=9.4 Hz, 1H), 7.23-7.14 (m, 2H), 7.00 (d, J=9.6 Hz, 2H), 4.65 (t, J=7.0 Hz, 2H), 4.37 (s, 1H), 4.02-3.91 (m, 2H), 3.79-3.60 (m, 2H), 3.57-3.42 (m, 1H), 3.24-3.02 (m, 3H), 1.11 (d, J=6.6 Hz, 3H); LC/MS (Method E): Rt 0.929 min, [MH]+390.0.

Example 78

(3R)-4-{7-[1-(Difluoromethyl)-1H-pyrazol-5-yl]-1-methyl-3-(1H-pyrazol-5-yl)-1H-pyrazolo[4,3-b]pyridin-5-yl}-3-methylmorpholine (78)

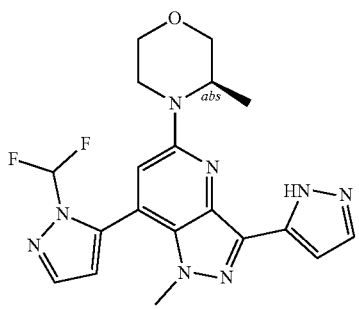 [SMILES: C[C@@H]1COCCN1c1cc(-c2ccnn2C(F)F)c2c(n1)c(-c1ccn[nH]1)nn2C]

(3R)-4-{7-[1-(Difluoromethyl)-1H-pyrazol-5-yl]-1-methyl-3-(1H-pyrazol-5-yl)-1H-pyrazolo[4,3-b]pyridin-5-yl}-3-methylmorpholine was prepared analogously to above examples and isolated as yellow solid (49 mg; 94%); $^1$H NMR (400 MHz, DMSO-$d_6$): δ13.27-12.85 (m, 1H), 8.02 (d, J=1.7 Hz, 1H), 7.90-7.57 (m, 1H), 7.16-6.98 (m, 2H), 6.94 (d, J=1.8 Hz, 1H), 4.53-4.28 (m, 1H), 4.12-3.95 (m, 2H), 3.80-3.49 (m, 6H), 3.24-3.10 (m, 2H), 1.18 (dd, J=6.8, 5.3 Hz, 3H); LC/MS (Method C): Rt 0.989 min; [MH]+ 415.3.

Example 79

(3R)-4-[7-(3,6-Dihydro-2H-thiopyran-4-yl)-1-methyl-3-(1H-pyrazol-5-yl)-1H-pyrazolo[4,3-b]pyridin-5-yl]-3-methylmorpholine (79)

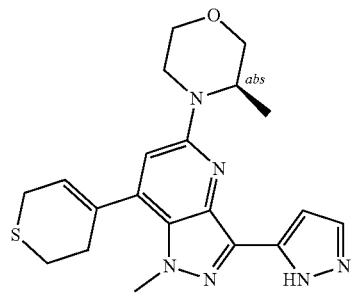 [SMILES: C[C@@H]1COCCN1c1cc(C2=CCSCC2)c2c(n1)c(-c1ccn[nH]1)nn2C]

(3R)-4-[7-(3,6-Dihydro-2H-thiopyran-4-yl)-1-methyl-3-(1H-pyrazol-5-yl)-1H-pyrazolo[4,3-b]pyridin-5-yl]-3-methylmorpholine was prepared analogously to above examples and isolated as yellow solid (10 mg, 18%); melting point 215-216° C.; $^1$H NMR (400 MHz, DMSO-$d_6$): δ13.05 (d, J=108.8 Hz, 1H), 7.60 (s, 1H), 7.02 (s, 1H), 6.79 (s, 1H), 6.05 (d, J=4.9 Hz, 1H), 4.44 (s, 1H), 4.01 (d, J=9.5 Hz, 5H), 3.75 (d, J=11.2 Hz, 1H), 3.68 (dd, J=11.3, 3.0 Hz, 1H), 3.52 (td, J=11.6, 3.1 Hz, 1H), 3.36 (d, J=3.7 Hz, 2H), 3.14 (td, J=12.6, 3.8 Hz, 1H), 2.92 (t, J=5.7 Hz, 2H), 2.61 (s, 2H), 1.16 (d, J=6.6 Hz, 3H);

LC/MS (Method D) Rt 1.129 min, [MH]+397.1.

Example 80

4-[1-Methyl-5-[(3R)-3-methylmorpholin-4-yl]-3-(1H-pyrazol-5-yl)-1H-pyrazolo[4,3-b]pyridin-7-yl]-3,6-dihydro-2H-1lambda4-thiopyran-1-one (80)

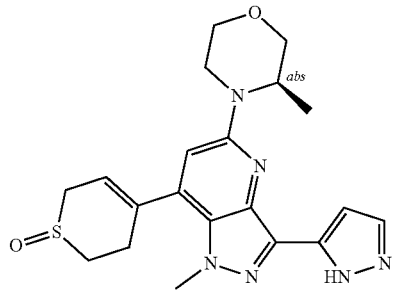 [SMILES: C[C@@H]1COCCN1c1cc(C2=CCS(=O)CC2)c2c(n1)c(-c1ccn[nH]1)nn2C]

Building Block for Synthesis of Example 80: 4-{1-methyl-5-[(3R)-3-methylmorpholin-4-yl]-3-[1-(oxan-2-yl)-1H-pyrazol-5-yl]-1H-pyrazolo[4,3-b]pyridin-7-yl}-3,6-dihydro-2H-1lambda4-thiopyran-1-one

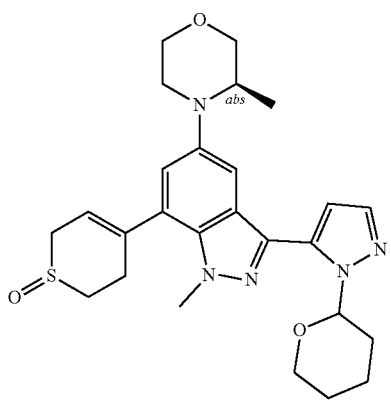 [SMILES: C[C@@H]1COCCN1c1cc(C2=CCS(=O)CC2)c2c(c1)c(-c1ccnn1C1CCCCO1)nn2C]

4-[3-Bromo-1-methyl-5-[(3R)-3-methylmorpholin-4-yl]-1H-pyrazolo[4,3-b]pyridin-7-yl]-3,6-dihydro-2H-1lambda4-thiopyran-1-one (100 mg, 0.21 mmol, 1.0 eq.), 1-(oxan-2-yl)-5-(tetramethyl-1,3,2-dioxaborolan-2-yl)-1H-pyrazole (123.91 mg, 0.42 mmol, 2.0 eq.), Pd(dppf)Cl$_2$·CH$_2$Cl$_2$ (19.20 mg, 0.02 mmol, 0.10 eq.), K$_3$PO$_4$ (141.83 mg, 0.63 mmol, 3.0 eq.), dioxane (12 mL) and water (3 mL) were combined and stirred for 1 h at 100° C. in the microwave. The resulting mixture was concentrated under vacuum. The residue was purified by column chromatography (Method E). 4-[1-Methyl-5-[(3R)-3-methyl-morpholin-4-yl]-3-[1-(oxan-2-yl)-1H-pyrazol-5-yl]-1H-pyrazolo[4,3-b]pyridin-7-yl]-3,6-dihydro-2H-1lambda4-thiopyran-1-one was isolated as yellow oil (70 mg, 60%); LC/MS (Method P): Rt 0.875 min, [MH]+425.2.

Example 80

4-[1-Methyl-5-[(3R)-3-methylmorpholin-4-yl]-3-(1H-pyrazol-5-yl)-1H-pyrazolo[4,3-b]pyridin-7-yl]-3,6-dihydro-2H-1lambda4-thiopyran-1-one

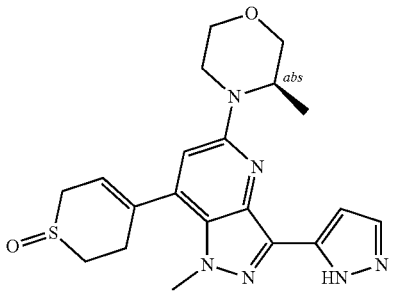 [SMILES: C[C@@H]1COCCN1c1cc(C2=CCS(=O)CC2)c2c(n1)c(-c1ccn[nH]1)nn2C]

4-[1-Methyl-5-[(3R)-3-methylmorpholin-4-yl]-3-[1-(oxan-2-yl)-1H-pyrazol-5-yl]-1H-pyrazolo[4,3-b]pyridin-7-yl]-3,6-dihydro-2H-1lambda4-thiopyran-1-one (60 mg, 0.11 mmol, 1.0 eq.), dichloromethane (5 mL) and trifluoroacetic acid (1 mL) were combined and stirred for 5 h at room temperature. The resulting mixture was concentrated under vacuum. The crude product was purified by Prep-HPLC (Method J). 20 mg 4-[1-Methyl-5-[(3R)-3-methylmorpholin-4-yl]-3-(1H-pyrazol-5-yl)-1H-pyrazolo[4,3-b]pyridin-7-yl]-3,6-dihydro-2H-1lambda4-thiopyran-1-one was obtained as red oil (20 mg, 32%); $^1$H NMR (400 MHz, methanol-d4): δ7.81 (s, 1H), 7.06 (d, J=14.8 Hz, 2H), 5.95 (d, J=4.6 Hz, 1H), 4.44 (d, J=7.6 Hz, 1H), 4.11 (d, J=26.7 Hz, 4H), 4.00 (d, J=13.0 Hz, 1H), 3.92-3.80 (m, 2H), 3.77-3.66 (m, 2H), 3.62 (dd, J=18.3, 5.1 Hz, 1H), 3.47 (td, J=12.5, 3.7 Hz, 1H), 3.39 (d, J=12.8 Hz, 1H), 3.19-2.97 (m, 2H), 2.79-2.65 (m, 1H), 1.37 (d, J=6.7 Hz, 3H);
LC/MS (Method X): Rt 0.953 min, [MH]+413.1.

Example 81

4-[1-Methyl-5-[(3R)-3-methylmorpholin-4-yl]-3-(1H-pyrazol-5-yl)-1H-pyrazolo[4,3-b]pyridin-7-yl]-3,6-dihydro-2H-1lambda6-thiopyran-1,1-dione (81)

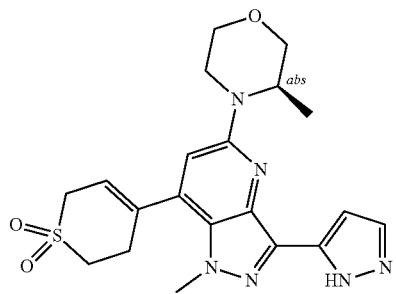 [SMILES: C[C@@H]1COCCN1c1cc(C2=CCS(=O)(=O)CC2)c2c(n1)c(-c1ccn[nH]1)nn2C]

Building Block for Synthesis of Example 81: 4-{1-methyl-5-[(3R)-3-methylmorpholin-4-yl]-1H-pyrazolo[4,3-b]pyridin-7-yl}-3,6-dihydro-2H-1lambda6-thiopyran-1,1-dione

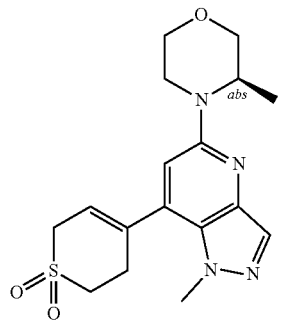 [SMILES: C[C@@H]1COCCN1c1cc(C2=CCS(=O)(=O)CC2)c2c(cnn2C)n1]

4-[1-Methyl-5-[(3R)-3-methylmorpholin-4-yl]-1H-pyrazolo[4,3-b]pyridin-7-yl]-3,6-dihydro-2H-1lambda4-thiopyran-1-one (500 mg, 1.30 mmol, 1.0 eq.), methanol (20 mL) and a solution of oxone (484 mg, 2.73 mmol, 2.10 eq.) in water (5 mL) were combined and stirred for 2 h at room temperature. The resulting mixture was concentrated under vacuum. The residue was purified by column chromatography (Method A). 4-[1-Methyl-5-[(3R)-3-methylmorpholin-4-yl]-1H-pyrazolo[4,3-b]pyridin-7-yl]-3,6-dihydro-2H-1lambda6-thiopyran-1,1-dione was isolated as yellow oil (500 mg, 96%);
LC/MS (Method T): Rt 0.833 min, [MH]+363.2.

Example 81

4-[1-Methyl-5-[(3R)-3-methylmorpholin-4-yl]-3-(1H-pyrazol-5-yl)-1H-pyrazolo[4,3-b]pyridin-7-yl]-3,6-dihydro-2H-1lambda6-thiopyran-1,1-dione

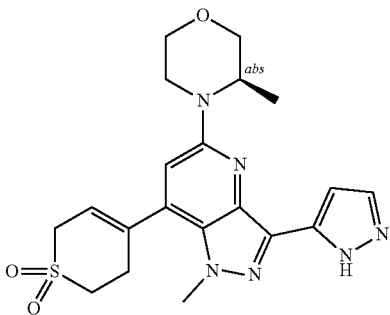 [SMILES: C[C@@H]1COCCN1c1cc(C2=CCS(=O)(=O)CC2)c2c(n1)c(-c1ccn[nH]1)nn2C]

4-[1-Methyl-5-[(3R)-3-methylmorpholin-4-yl]-3-(1H-pyrazol-5-yl)-1H-pyrazolo[4,3-b]pyridin-7-yl]-3,6-dihydro-2H-1lambda6-thiopyran-1,1-dione was prepared analogously to above examples and isolated as a yellow solid (15 mg, 25%); melting point 167-168° C.; $^1$H NMR (400 MHz, methanol-d4): δ7.87 (d, J=2.4 Hz, 1H), 7.10 (s, 1H), 7.04 (d, J=2.3 Hz, 1H), 6.00-5.92 (m, 1H), 4.43 (d, J=7.3 Hz, 1H), 4.16 (s, 3H), 4.09 (dd, J=11.6, 3.8 Hz, 1H), 3.98 (d, J=10.2 Hz, 3H), 3.89-3.81 (m, 2H), 3.73-3.66 (m, 1H), 3.53 (dd, J=12.6, 3.9 Hz, 1H), 3.45 (d, J=6.3 Hz, 2H), 3.15 (s, 2H), 1.38 (d, J=6.8 Hz, 3H);

LC/MS (Method D): Rt 0.869 min, [MH]+429.1.

Example 82

4-[1-Methyl-5-[(3R)-3-methylmorpholin-4-yl]-3-(1H-pyrazol-5-yl)-1H-pyrazolo[4,3-b]pyridin-7-yl]-2H-1lambda6-thiopyran-1,1-dione (82)

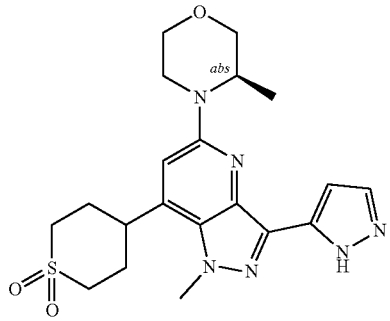 [SMILES: C[C@@H]1COCCN1c1cc(C2CCS(=O)(=O)CC2)c2c(n1)c(-c1ccn[nH]1)nn2C]

4-[1-Methyl-5-[(3R)-3-methylmorpholin-4-yl]-3-(1H-pyrazol-5-yl)-1H-pyrazolo[4,3-b]pyridin-7-yl]-2H-1lambda6-thiopyran-1,1-dione was prepared analogously to above examples and isolated as yellow solid (10 mg, 16%); melting point 189-190° C.; $^1$H NMR (400 MHz, methanol-d4): δ7.83 (d, J=2.3 Hz, 1H), 7.07 (s, 1H), 6.98 (d, J=2.2 Hz, 1H), 4.45 (d, J=7.3 Hz, 1H), 4.36 (s, 3H), 4.10 (dd, J=11.7, 3.7 Hz, 1H), 3.97 (d, J=12.4 Hz, 1H), 3.91-3.67 (m, 4H), 3.61-3.47 (m, 3H), 3.22 (d, J=13.9 Hz, 2H), 2.52-2.38 (m, 4H), 1.39 (d, J=6.8 Hz, 3H); LC/MS (Method D): Rt 0.831 min, [MH]+431.1.

Example 83

(3R)-3-Methyl-4-[3-(1H-pyrazol-3-yl)-1-[(pyridin-3-yl)methyl]-1H-pyrazolo[4,3-b]pyridin-5-yl]morpholine (83)

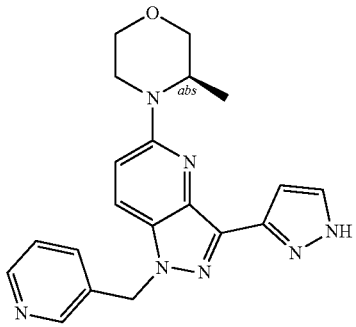 [SMILES: C[C@@H]1COCCN1c1ccc2c(n1)c(-c1cc[nH]n1)nn2Cc1cccnc1]

(3R)-3-Methyl-4-[3-(1H-pyrazol-3-yl)-1-[(pyridin-3-yl)methyl]-1H-pyrazolo[4,3-b]pyridin-5-yl]morpholine hydrochloride was prepared analogously to above examples and isolated as yellow solid (6 mg; 75%); $^1$H NMR (700 MHz, DMSO-d$_6$): δ8.82-8.80 (m, 1H), 8.76-8.74 (m, 1H), 8.16-8.13 (m, 2H), 7.82 (dd, J=8.1, 5.4 Hz, 1H), 7.72 (d, J=2.0 Hz, 1H), 7.16 (d, J=9.5 Hz, 1H), 7.07 (d, J=2.0 Hz, 1H), 5.83 (s, 2H), 4.44-4.40 (m, 1H), 4.02 (dd, J=13.4, 2.8 Hz, 1H), 3.99 (dd, J=11.3, 3.7 Hz, 1H), 3.76 (d, J=11.1 Hz, 1H), 3.68 (dd, J=11.2, 3.1 Hz, 1H), 3.53 (td, J=11.7, 3.1 Hz, 1H), 3.15 (td, J=12.7, 3.8 Hz, 1H), 1.16 (d, J=6.7 Hz, 3H);

LC/MS (Method R): Rt 0.483 min; [MH]+376.2.

Example 84

(3R)-4-[7-(1,5-Dimethyl-1H-1,2,3-triazol-4-yl)-1-methyl-3-(1H-pyrazol-3-yl)-1H-pyrazolo[4,3-b]pyridin-5-yl]-3-methylmorpholine (84)

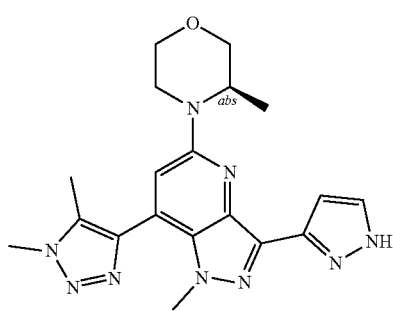 [SMILES: Cc1c(-c2cc(N3CCOC[C@H]3C)nc3c(-c4cc[nH]n4)nn(C)c23)nnn1C]

(3R)-4-[7-(1,5-Dimethyl-1H-1,2,3-triazol-4-yl)-1-methyl-3-(1H-pyrazol-3-yl)-1H-pyrazolo[4,3-b]pyridin-5-yl]-3-methylmorpholine was prepared analogously to above examples and isolated as yellow solid (34 mg; 85%); $^1$H NMR (500 MHz, DMSO-d$_6$): δ13.23-12.90 (m, 1H), 7.84-7.57 (m, 1H), 7.14-7.01 (m, 1H), 6.95-6.87 (m, 1H), 4.48-4.37 (m, 1H), 4.07 (s, 3H), 4.10-4.05 (m, 1H), 4.02-3.97 (m, 1H), 3.82-3.74 (m, 4H), 3.70 (dd, J=11.3, 3.0 Hz, 1H), 3.55 (td, J=11.7, 3.0 Hz, 1H), 3.21-3.13 (m, 1H), 2.40-2.37 (m, 3H), 1.18 (d, J=6.6 Hz, 3H); LC/MS (Method C): Rt 0.877 min; [MH]+394.3.

Example 85

2-Methyl-1-{5-[(3R)-3-methylmorpholin-4-yl]-3-(1H-pyrazol-3-yl)-1H-pyrazolo[4,3-b]pyridin-1-yl}propan-2-ol (85)

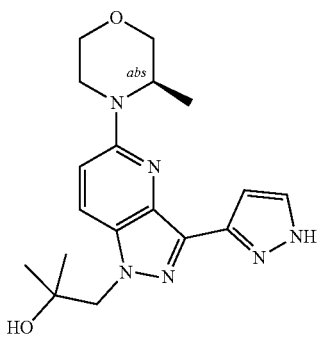 [SMILES: C[C@@H]1COCCN1c1ccc2c(n1)c(-c1cc[nH]n1)nn2CC(C)(C)O]

Building Block for Synthesis of Example 85: methyl 2-{3-iodo-5-[(3R)-3-methylmorpholin-4-yl]-1H-pyrazolo[4,3-b]pyridin-1-yl}acetate

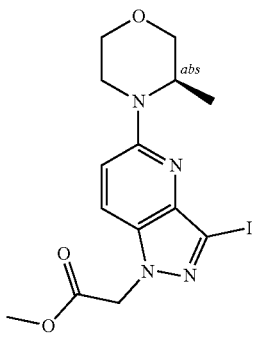 [SMILES: COC(=O)Cn1nc(I)c2nc(N3CCOC[C@H]3C)ccc21]

(3R)-4-[3-Iodo-1H-pyrazolo[4,3-b]pyridin-5-yl]-3-methylmorpholine (200 mg, 0.52 mmol, 1. eq.), DMF (2 mL), methyl 2-bromoacetate (126.33 mg, 0.78 mmol, 1.50 eq.) and Cs₂CO₃ (358.76 mg, 1.05 mmol, 2.0 eq.) were combined and stirred for 2 h at 25° C. The resulting mixture was concentrated under vacuum. The residue was purified by column chromatography (Method P). Methyl 2-[3-iodo-5-[(3R)-3-methylmorpholin-4-yl]-1H-pyrazolo[4,3-b]pyridin-1-yl]acetate was isolated as a yellow solid.

Building Block for Synthesis of Example 85: methyl 2-{5-[(3R)-3-methylmorpholin-4-yl]-3-[1-(oxan-2-yl)-1H-pyrazol-3-yl]-1H-pyrazolo[4,3-b]pyridin-1-yl}acetate

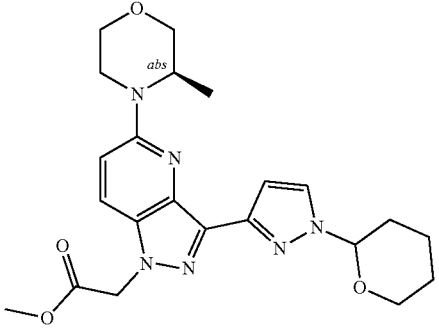 [SMILES: COC(=O)Cn1nc(-c2ccn(C3CCCCO3)n2)c2nc(N3CCOC[C@H]3C)ccc21]

Methyl 2-[3-iodo-5-[(3R)-3-methylmorpholin-4-yl]-1H-pyrazolo[4,3-b]pyridin-1-yl]acetate (200 mg, 0.43 mmol, 1.0 eq.), tetrahydrofuran (2 mL), sodium carbonate (96.50 mg, 0.86 mmol, 2. eq.), water (0.2 mL), 1-(oxan-2-yl)-3-(tetramethyl-1,3,2-dioxaborolan-2-yl)-1H-pyrazole (189.94 mg, 0.65 mmol, 1.50 eq.) and Pd(PPh₃)₄ (55.53 mg, 0.04 mmol, 0.10 eq.) were combined and stirred for 1 h at 80° C. in the microwave. The resulting mixture was concentrated under vacuum. The residue was purified by column chromatography (Method P). Methyl 2-[5-[(3R)-3-methylmorpholin-4-yl]-3-[1-(oxan-2-yl)-1H-pyrazol-3-yl]-1H-pyrazolo[4,3-b]pyridin-1-yl]acetate was isolated as a yellow solid (100 mg; 48%).

Building Block for Synthesis of Example 85: 2-methyl-1-{5-[(3R)-3-methylmorpholin-4-yl]-3-[1-(oxan-2-yl)-1H-pyrazol-3-yl]-1H-pyrazolo[4,3-b]pyridin-1-yl}propan-2-ol

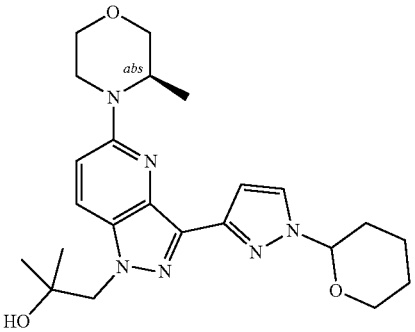 [SMILES: C[C@@H]1COCCN1c1ccc2c(n1)c(-c1ccn(C3CCCCO3)n1)nn2CC(C)(C)O]

Methyl 2-[5-[(3R)-3-methylmorpholin-4-yl]-3-[1-(oxan-2-yl)-1H-pyrazol-3-yl]-1H-pyrazolo[4,3-b]pyridin-1-yl]acetate (90 mg, 0.18 mmol, 1.0 eq.), tetrahydrofuran (1 mL) and bromo(methyl)magnesium (461.62 mg, 3.68 mmol, 20. eq.) were combined and stirred for 5 h at 25° C. The reaction was then quenched by the addition of water. The resulting mixture was concentrated under vacuum. The residue was purified by column chromatography (Method P). 2-Methyl-1-[5-[(3R)-3-methylmorpholin-4-yl]-3-[1-(oxan-2-yl)-1H-pyrazol-3-yl]-1H-pyrazolo[4,3-b]pyridin-1-yl]propan-2-ol was isolated as a brown solid (60 mg; 68%).

Example 85

2-Methyl-1-{5-[(3R)-3-methylmorpholin-4-yl]-3-(1H-pyrazol-3-yl)-1H-pyrazolo[4,3-b]pyridin-1-yl}propan-2-ol

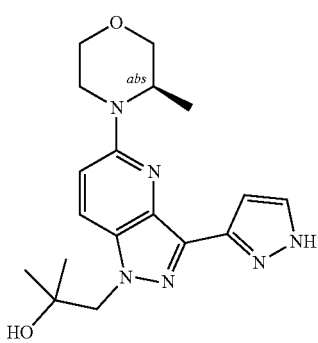 [SMILES: C[C@@H]1COCCN1c1ccc2c(n1)c(-c1cc[nH]n1)nn2CC(C)(C)O]

2-Methyl-1-{5-[(3R)-3-methylmorpholin-4-yl]-3-(1H-pyrazol-3-yl)-1H-pyrazolo[4,3-b]pyridin-1-yl}propan-2-ol was prepared analogously to above examples and isolated as colorless solid (8 mg, 22%); melting point 235-236° C.; $^1$H NMR (400 MHz, methanol-d4): δ7.93 (d, J=9.4 Hz, 1H), 7.66 (s, 1H), 7.07 (d, J=9.4 Hz, 2H), 4.46 (d, J=7.0 Hz, 1H), 4.35 (s, 2H), 4.10-3.99 (m, 2H), 3.84 (d, J=2.2 Hz, 2H), 3.68 (td, J=11.7, 3.1 Hz, 1H), 3.29 (d, J=3.7 Hz, 1H), 1.27 (d, J=10.4 Hz, 9H);

LC/MS (Method E): Rt 1.034 min, [MH]+357.2.

Example 86

2-Methyl-2-{5-[(3R)-3-methylmorpholin-4-yl]-3-(1H-pyrazol-3-yl)-1H-pyrazolo[4,3-b]pyridin-1-yl}propan-1-ol (86)

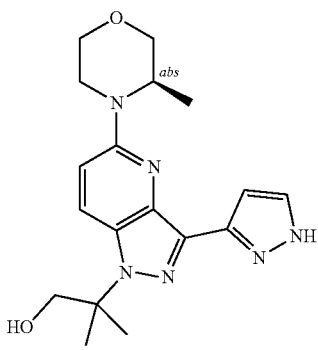 [SMILES: C[C@@H]1COCCN1c1ccc2c(n1)c(-c1cc[nH]n1)nn2C(C)(C)CO]

2-Methyl-2-{5-[(3R)-3-methylmorpholin-4-yl]-3-(1H-pyrazol-3-yl)-1H-pyrazolo[4,3-b]pyrid in-1-yl}propan-1-ol was prepared analogously to above examples and isolated as yellow solid (50 mg, 52%); melting point 210-212° C.; $^1$H NMR (400 MHz, methanol-d4): δ8.11 (d, J=9.5 Hz, 1H), 7.64 (s, 1H), 7.27-6.97 (m, 2H), 4.45 (d, J=13.1 Hz, 1H), 4.09-3.97 (m, 4H), 3.84 (d, J=2.2 Hz, 2H), 3.68 (td, J=11.7, 3.0 Hz, 1H), 3.36-3.25 (m, 1H), 1.75 (s, 6H), 1.27 (d, J=6.7 Hz, 3H); LC/MS (Method E): Rt 1.102 min, [MH]+357.2.

Example 87

(3R)-3-Methyl-4-[1-methyl-7-(4-methylpyrimidin-5-yl)-3-(1H-pyrazol-3-yl)-1H-pyrazolo[4,3-b]pyridin-5-yl]morpholine (87)

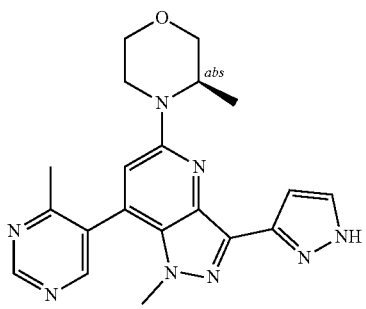 [SMILES: Cc1ncncc1-c1cc(N2CCOC[C@H]2C)nc2c(-c3cc[nH]n3)nn(C)c12]

(3R)-3-Methyl-4-[1-methyl-7-(4-methylpyrimidin-5-yl)-3-(1H-pyrazol-3-yl)-1H-pyrazolo[4,3-b]pyridin-5-yl]morpholine was prepared analogously to above examples and isolated as yellow solid (15 mg, 20%); melting point 140-142° C.; $^1$H NMR (300 MHz, DMSO-d$_6$): δ9.17 (s, 1H), 8.76 (s, 1H), 7.63 (s, 1H), 7.01 (s, 1H), 6.96 (s, 1H), 4.44 (s, 1H), 4.14-3.90 (m, 2H), 3.72 (s, 2H), 3.65-3.52 (m, 1H), 3.50 (s, 3H), 3.25 (d, J=10.7 Hz, 1H), 2.35 (s, 3H), 1.22 (d, J=6.6 Hz, 3H); LC/MS (Method A) Rt 1.146 min, [MH]+ 391.2.

Example 88

(3R)-3-Methyl-4-[3-(1H-pyrazol-3-yl)-1-[(pyridin-2-yl)methyl]-1H-pyrazolo[4,3-b]pyridin-5-yl]morpholine (88)

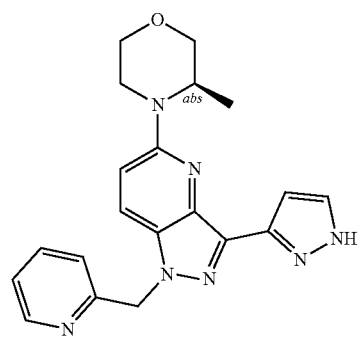 [SMILES: C[C@@H]1COCCN1c1ccc2c(n1)c(-c1cc[nH]n1)nn2Cc1ccccn1]

(3R)-3-Methyl-4-[3-(1H-pyrazol-3-yl)-1-[(pyridin-2-yl)methyl]-1H-pyrazolo[4,3-b]pyridin-5-yl]morpholine hydrochloride was prepared analogously to above examples and isolated as yellow solid (62 mg; 92%); $^1$H NMR (500 MHz, DMSO-d$_6$): δ8.60-8.57 (m, 1H), 8.06 (d, J=9.4 Hz, 1H), 7.88 (td, J=7.7, 1.8 Hz, 1H), 7.73 (d, J=2.0 Hz, 1H), 7.44-7.40 (m, 1H), 7.17-7.13 (m, 2H), 7.08 (d, J=2.0 Hz, 1H), 5.82 (s, 2H), 4.45-4.39 (m, 1H), 4.05-3.97 (m, 2H), 3.79-3.75 (m, 1H), 3.69 (dd, J=11.3, 3.1 Hz, 1H), 3.54 (td, J=11.4, 2.8 Hz, 1H), 3.17 (td, J=12.9, 3.8 Hz, 1H), 1.17 (d, J=6.6 Hz, 3H); LC/MS (Method C): Rt 0.875 min; [MH]+ 376.2.

Example 89

(3R)-4-[7-(1-Methanesulfonylethyl)-1-methyl-3-(1H-pyrazol-3-yl)-1H-pyrazolo[4,3-b]pyridin-5-yl]-3-methylmorpholine (89)

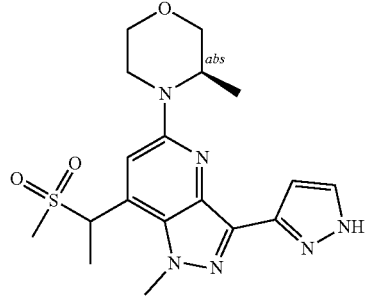 [SMILES: CC(c1cc(N2CCOC[C@H]2C)nc2c(-c3cc[nH]n3)nn(C)c12)S(C)(=O)=O]

Building Block for Synthesis of Example 89:
3-Bromo-7-(1-methanesulfonyl-ethyl)-1-methyl-5-((R)-3-methyl-morpholin-4-yl)-1H-pyrazolo[4,3-b]pyridine

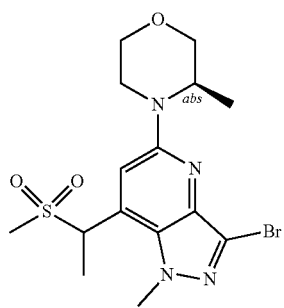 [SMILES: CC(c1cc(N2CCOC[C@H]2C)nc2c(Br)nn(C)c12)S(C)(=O)=O]

3-Bromo-7-methanesulfonylmethyl-1-methyl-5-((R)-3-methyl-morpholin-4-yl)-1H-pyrazolo[4,3-b]pyridine (100 mg; 0.25 mmol; 1, eq.), toluene (1523 µl), water (170 µl), sodium hydroxide (199 mg; 20.07 eq.), tetra-n-butylammonium iodide (8.24 mg; 0.02 mmol; 0.09 eq.), dichloromethane (170 µl) and iodomethane (30.99 µl; 0.50 mmol; 2, eq.) were combined and stirred at 80° C. for 3 h. The reaction mixture was extracted with water and DCM. The combined organic layer were concentrated under reduced pressure. 3-Bromo-7-(1-methanesulfonyl-ethyl)-1-methyl-5-((R)-3-methyl-morpholin-4-yl)-1H-pyrazolo[4,3-b]pyridine was isolated as yellow solid (130 mg, 55%); LC/MS (Method F): Rt 2.433 min; [MH]+417.1.

Example 89

(3R)-4-[7-(1-Methanesulfonylethyl)-1-methyl-3-(1H-pyrazol-3-yl)-1H-pyrazolo[4,3-b]pyridin-5-yl]-3-methylmorpholine

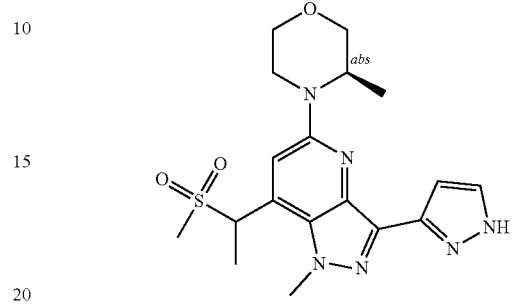

(3R)-4-[7-(1-Methanesulfonylethyl)-1-methyl-3-(1H-pyrazol-3-yl)-1H-pyrazolo[4,3-b]pyridin-5-yl]-3-methylmorpholine was prepared analogously to above examples and isolated as yellow solid (20 mg, 30%); $^1$H NMR (500 MHz, DMSO-$d_6$): δ13.42-12.64 (m, 1H), 7.68-7.62 (m, 1H), 7.04 (d, J=5.0 Hz, 1H), 7.02-6.99 (m, 1H), 5.29-5.22 (m, 1H), 4.45-4.38 (m, 1H), 4.28 (s, 3H), 4.04-3.97 (m, 2H), 3.79-3.75 (m, 1H), 3.73-3.69 (m, 1H), 3.59-3.52 (m, 1H), 3.20-3.12 (m, 1H), 3.13 (d, J=9.9 Hz, 3H), 1.85 (d, J=6.9 Hz, 3H), 1.18-1.13 (m, 3H); LC/MS (Method F): Rt 2.022 min; [MH]+405.2.

The following examples relate to medicaments:

Example A

Injection Vials

A solution of 100 g of an active ingredient of the formula I and 5 g of disodium hydrogenphosphate in 3 l of bidistilled water is adjusted to pH 6.5 using 2 N hydrochloric acid, sterile filtered, transferred into injection vials, lyophilised under sterile conditions and sealed under sterile conditions. Each injection vial contains 5 mg of active ingredient.

Example B

Suppositories

A mixture of 20 g of an active ingredient of the formula I with 100 g of soya lecithin and 1400 g of cocoa butter is melted, poured into moulds and allowed to cool. Each suppository contains 20 mg of active ingredient.

Example C

Solution

A solution is prepared from 1 g of an active ingredient of the formula I, 9.38 g of $NaH_2PO_4 \cdot 2H_2O$, 28.48 g of $Na_2HPO_4 \cdot 12 H_2O$ and 0.1 g of benzalkonium chloride in 940 ml of bidistilled water. The pH is adjusted to 6.8, and the solution is made up to 1 l and sterilised by irradiation. This solution can be used in the form of eye drops.

Example D

Ointment 500 mg of an active ingredient of the formula I are mixed with 99.5 g of Vaseline under aseptic conditions.

Example E

Tablets

A mixture of 1 kg of active ingredient of the formula I, 4 kg of lactose, 1.2 kg of potato starch, 0.2 kg of talc and 0.1 kg of magnesium stearate is pressed in a conventional manner to give tablets in such a way that each tablet contains 10 mg of active ingredient.

Example F

Dragees

Tablets are pressed analogously to Example E and subsequently coated in a conventional manner with a coating of sucrose, potato starch, talc, tragacanth and dye.

Example G

Capsules 2 kg of active ingredient of the formula I are introduced into hard gelatine capsules in a conventional manner in such a way that each capsule contains 20 mg of the active ingredient.

Example H

Ampoules

A solution of 1 kg of active ingredient of the formula I in 60 l of bidistilled water is sterile filtered, transferred into ampoules, lyophilised under sterile conditions and sealed under sterile conditions. Each ampoule contains 10 mg of active ingredient.

The invention claimed is:
1. A compound of formula Ia* or Ib*

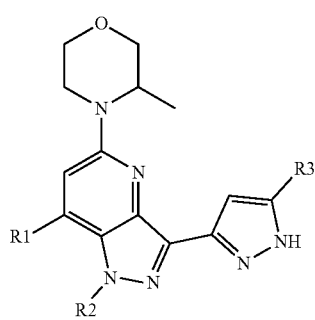

-continued

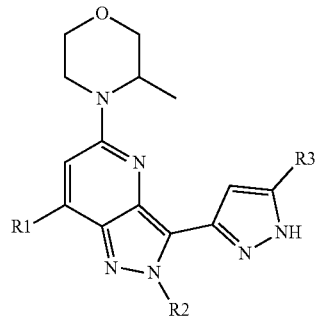

in which

R¹ denotes H, Het, Ar, (CH₂)ₙOH, 1-methylsulfonyl-cycloprop-1-yl, CONH₂, CONHA, CONA₂, Cyc, OA or CH(A)SO₂A, R² denotes H, A, (CH₂)ₙAr, (CH₂)ₙCyc or (CH₂)ₙHet, R³ denotes H or A, Het denotes 1H-pyrrolo[2,3-b]pyridinyl, 1H-pyrrolo[2,3-c]pyridinyl, indolyl, benzimidazolyl, imidazolyl, 1,2,3,4-tetrahydroisoquinolyl, pyridyl, pyrimidinyl, triazolyl, pyrazolyl, quinolyl, isoquinolyl, quinazolinyl, furanyl, tetrahydrofuranyl, pyranyl, 3,6-dihydro-2H-pyranyl, tetrahydropyranyl, 3,6-dihydro-2H-thiopyranyl or hexahydro-thiopyranyl, each of which is unsubstituted or mono-, di- or trisubstituted by A, SOA, SO₂A, Hal and/or =O, Ar denotes phenyl, napthyl or biphenyl, each of which is unsubstituted or mono-, di- or trisubstituted by NH₂, NHA, NA₂, COOH, COOA, CONH₂, CONHA, CONA₂, NHCOA, CHO, COA, SO₃H, SO₂NH₂, O(CH₂)ₚNH₂, (CH₂)ₙHet¹, O(CH₂)ₙHet¹, (CH₂)ₙAr¹, O(CH₂)ₙAr¹, O(CH₂)ₚCONH₂, O(CH₂)ₚNHCOA, Hal, SOA, S(=O, =NH)A, SO₂A, A, CN and/or (CH₂)ₙOH, Ar¹ denotes phenyl which is unsubstituted or mono-, di- or trisubstituted by Hal, A, OH and/or OA, Het¹ denotes a mono- or bicyclic aromatic, unsaturated or saturated heterocycle having 1 to 4 N, O and/or S atoms, which may be unsubstituted or mono-, di- or trisubstituted by Hal, A, COOA, NH₂, NHA and/or NA₂, A denotes unbranched or branched alkyl having 1-6 C-atoms, in which 1-7H atoms may be replaced by OH, F, Cl and/or Br and/or in which one or two non-adjacent CH₂ groups may be replaced by O and/or NH groups, Cyc denotes cyclic alkyl with 3, 4, 5, 6 or 7 C-atoms, Hal denotes F, Cl, Br or I, n denotes 0, 1, 2, 3 or 4, and p denotes 1, 2, 3 or 4, with the proviso that R¹ denotes Het and/or R² denotes (CH₂)ₙHet, or a pharmaceutically acceptable salt, tautomer, stereoisomer or racemic mixture thereof, or a non-racemic mixture thereof.

2. A compound of formula Ia* or Ib*

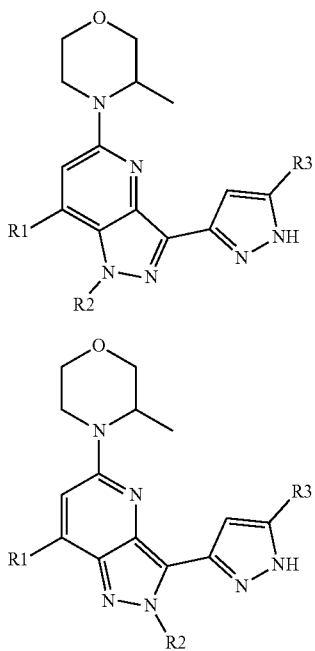

in which
R¹ denotes H, Het, Ar, $(CH_2)_n$OH, 1-methylsulfonyl-cycloprop-1-yl, $CONH_2$, CONHA, $CONA_2$, Cyc, OA or $CH(A)SO_2A$,
R² denotes H, A, $(CH_2)_n$Ar, $(CH_2)_n$Cyc or $(CH_2)_n$Het,
R³ denotes H or A,
Het denotes a mono- or bicyclic aromatic, unsaturated or saturated heterocycle having 1 to 4 N, O and/or S atoms, which may be unsubstituted or mono-, di- or trisubstituted by $NH_2$, NHA, $NA_2$, COOH, COOA, $CONH_2$, CONHA, $CONA_2$, CONHAr, CN, OH, $(CH_2)_n$ Ar¹, $O(CH_2)_n$Ar¹, A, SOA, $SO_2$A, Hal, =NH and/or =O,
Ar denotes phenyl, which is unsubstituted or mono-, di- or trisubstituted by SOA, S(=O, =NH)A, $SO_2$A, A, CN and/or $(CH_2)_n$OH,
Ar¹ denotes phenyl which is unsubstituted or mono-, di- or trisubstituted by Hal, A, OH and/or OA,
Het¹ denotes a mono- or bicyclic aromatic, unsaturated or saturated heterocycle having 1 to 4 N, O and/or S atoms, which may be unsubstituted or mono-, di- or trisubstituted by Hal, A, COOA, $NH_2$, NHA and/or $NA_2$,
A denotes unbranched or branched alkyl having 1-6 C-atoms, in which 1-7H atoms may be replaced by OH, F, Cl and/or Br and/or in which one or two non-adjacent $CH_2$ groups may be replaced by O and/or NH groups,
Cyc denotes cyclic alkyl with 3, 4, 5, 6 or 7 C-atoms,
Hal denotes F, Cl, Br or I,
n denotes 0, 1, 2, 3 or 4,
p denotes 1, 2, 3 or 4,
with the proviso that R¹ denotes Ar and/or R² denotes $(CH_2)_n$Ar,
or a pharmaceutically acceptable salt, tautomer, stereoisomer or racemic mixture thereof, or a non-racemic mixture thereof.

3. The compound according to claim 1, in which
R¹ denotes H, Het, Ar, $(CH_2)_n$OH, 1-methylsulfonyl-cycloprop-1-yl, $CONH_2$, CONHA, $CONA_2$, Cyc, OA or $CH(A)SO_2A$,
R² denotes H, A, $(CH_2)_n$Ar, $(CH_2)_n$Cyc or $(CH_2)_n$Het,
R³ denotes H or A,
Ar denotes phenyl, which is unsubstituted or mono-, di- or trisubstituted by SOA, S(=O, =NH)A, $SO_2$A, A, CN and/or $(CH_2)_n$OH,
A denotes unbranched or branched alkyl having 1-6 C-atoms, in which 1-7H atoms may be replaced by OH, F, C and/or Br and/or in which one or two non-adjacent $CH_2$ groups may be replaced by O and/or NH groups,
Cyc denotes cyclic alkyl with 3, 4, 5, 6 or 7 C-atoms, Hal denotes F, Cl, Br or I,
n denotes 0, 1, 2, 3 or 4,
with the proviso that R¹ denotes Het and/or R² denotes $(CH_2)_n$Het,
or a pharmaceutically acceptable salt, tautomer, stereoisomer or racemic mixture thereof, or a non-racemic mixture thereof.

4. A compound, which is one of the following compounds

| No. | Structure |
|---|---|
| (1) | 1-Methyl-5-((R)-3-methyl-morpholin-4-yl)-7-(6-methyl-pyridin-3-yl)-3-(1H-pyrazol-3-yl)-1H-pyrazolo[4,3-b]pyridine |
| (2) | 5-((R)-3-Methyl-morpholin-4-yl)-7-(6-methyl-pyridin-3-yl)-3-(1H-pyrazol-3-yl)-1H-pyrazolo[4,3-b]pyridine |
| (3) | (3R)-3-Methyl-4-[3-(3-methyl-1H-pyrazol-5-yl)-7-(6-methylpyridin-3-yl)-1H-pyrazolo[4,3-b]pyridin-5-yl]morpholine |
| (4) | 1-Methyl-5-((R)-3-methyl-morpholin-4-yl)-7-(2-methyl-pyridin-3-yl)-3-(1H-pyrazol-3-yl)-1H-pyrazolo[4,3-b]pyridine |
| (5) | 7-(4-Methanesulfinyl-phenyl)-1-methyl-5-((R)-3-methyl-morpholin-4-yl)-3-(1H-pyrazol-3-yl)-1H-pyrazolo[4,3-b]pyridine |
| (6) | Imino(methyl)(4-{1-methyl-5-[(3R)-3-methylmorpholin-4-yl]-3-(1H-pyrazol-3-yl)-1H-pyrazolo[4,3-b]pyridin-7-yl}phenyl)-lambda6-sulfanone |
| (7) | 7-(4-Methanesulfonyl-phenyl)-1-methyl-5-((R)-3-methyl-morpholin-4-yl)-3-(1H-pyrazol-3-yl)-1H-pyrazolo[4,3-b]pyridine |
| (8) | 7-(6-Methanesulfinyl-2-methyl-pyridin-3-yl)-1-methyl-5-((R)-3-methyl-morpholin-4-yl)-3-(1H-pyrazol-3-yl)-1H-pyrazolo[4,3-b]pyridine |
| (9) | (3R)-4-(7-{6-[(S)-Methanesulfinyl]-2-methylpyridin-3-yl}-1-methyl-3-(1H-pyrazol-3-yl)-1H-pyrazolo[4,3-b]pyridin-5-yl)-3-methylmorpholine |
| (10) | (3R)-4-(7-{6-[(R)-Methanesulfinyl]-2-methylpyridin-3-yl}-1-methyl-3-(1H-pyrazol-3-yl)-1H-pyrazolo[4,3-b]pyridin-5-yl)-3-methylmorpholine |
| (11) | (3R)-4-[7-(6-Methanesulfonyl-2-methylpyridin-3-yl)-1-methyl-3-(1H-pyrazol-3-yl)-1H-pyrazolo[4,3-b]pyridin-5-yl]-3-methylmorpholine |
| (12) | 7-(6-Methanesulfonyl-2-methyl-pyridin-3-yl)-5-((R)-3-methyl-morpholin-4-yl)-3-(1H-pyrazol-3-yl)-1H-pyrazolo[4,3-b]pyridine |
| (13) | (3R)-4-[7-(6-Methanesulfonyl-2-methylpyridin-3-yl)-3-(3-methyl-1H-pyrazol-5-yl)-1H-pyrazolo[4,3-b]pyridin-5-yl]-3-methylmorpholine |
| (14) | 2-Methyl-5-((R)-3-methyl-morpholin-4-yl)-7-(6-methyl-pyridin-3-yl)-3-(1H-pyrazol-3-yl)-2H-pyrazolo[4,3-b]pyridine |
| (15) | 1-Methyl-5-((R)-3-methyl-morpholin-4-yl)-3-(1H-pyrazol-3-yl)-7-(1H-pyrrolo[2,3-b]pyridin-4-yl)-1H-pyrazolo[4,3-b]pyridine |
| (16) | 2-Methyl-5-((R)-3-methyl-morpholin-4-yl)-3-(1H-pyrazol-3-yl)-7-(1H-pyrrolo[2,3-b]pyridin-4-yl)-2H-pyrazolo[4,3-b]pyridine |
| (17) | 7-(6-Methanesulfonyl-4-methyl-pyridin-3-yl)-1-methyl-5-((R)-3-methyl-morpholin-4-yl)-3-(1H-pyrazol-3-yl)-1H-pyrazolo[4,3-b]pyridine |
| (18) | 7-(1-Isopropyl-1H-pyrazol-4-yl)-1-methyl-5-((R)-3-methyl-morpholin-4-yl)-3-(1H-pyrazol-3-yl)-1H-pyrazolo[4,3-b]pyridine |
| (19) | 7-(1,3-Dimethyl-1H-pyrazol-4-yl)-1-methyl-5-((R)-3-methyl-morpholin-4-yl)-3-(1H-pyrazol-3-yl)-1H-pyrazolo[4,3-b]pyridine |
| (20) | 7-(3-Fluoro-pyridin-4-yl)-1-methyl-5-((R)-3-methyl-morpholin-4-yl)-3-(1H-pyrazol-3-yl)-1H-pyrazolo[4,3-b]pyridine |
| (21) | 7-(6-Methanesulfonyl-4-methyl-pyridin-3-yl)-2-methyl-5-((R)-3-methyl-morpholin-4-yl)-3-(1H-pyrazol-3-yl)-2H-pyrazolo[4,3-b]pyridine |

| No. | Structure |
|---|---|
| (22) | 7-(2,4-Dimethyl-pyridin-3-yl)-1-methyl-5-((R)-3-methyl-morpholin-4-yl)-3-(1H-pyrazol-3-yl)-1H-pyrazolo[4,3-b]pyridine |
| (23) | 1-Methyl-5-((R)-3-methyl-morpholin-4-yl)-7-(3-methyl-pyridin-4-yl)-3-(1H-pyrazol-3-yl)-1H-pyrazolo[4,3-b]pyridine |
| (24) | [1-Methyl-5-((R)-3-methyl-morpholin-4-yl)-3-(1H-pyrazol-3-yl)-1H-pyrazolo[4,3-b]pyridin-7-yl]-methanol |
| (25) | 2-[1-Methyl-5-((R)-3-methyl-morpholin-4-yl)-3-(1H-pyrazol-3-yl)-1H-pyrazolo[4,3-b]pyridin-7-yl]-propan-2-ol |
| (26) | 7-(1-Methanesulfonyl-cyclopropyl)-1-methyl-5-((R)-3-methyl-morpholin-4-yl)-3-(1H-pyrazol-3-yl)-1H-pyrazolo[4,3-b]pyridine |
| (27) | 5-((R)-3-Methyl-morpholin-4-yl)-3-(1H-pyrazol-3-yl)-1H-pyrazolo[4,3-b]pyridine-7-carboxylic acid dimethylamide |
| (28) | 5-((R)-3-Methyl-morpholin-4-yl)-3-(1H-pyrazol-3-yl)-1H-pyrazolo[4,3-b]pyridine-7-carboxylic acid methylamide |
| (29) | 5-((R)-3-Methyl-morpholin-4-yl)-3-(1H-pyrazol-3-yl)-1H-pyrazolo[4,3-b]pyridine-7-carboxylic acid amide |
| (30) | 1-Methyl-5-((R)-3-methyl-morpholin-4-yl)-3-(1H-pyrazol-3-yl)-1H-pyrazolo[4,3-b]pyridine-7-carboxylic acid dimethylamide |
| (31) | 1-Methyl-5-((R)-3-methyl-morpholin-4-yl)-3-(1H-pyrazol-3-yl)-1H-pyrazolo[4,3-b]pyridine-7-carboxylic acid methylamide |
| (32) | 1-Methyl-5-((R)-3-methyl-morpholin-4-yl)-3-(1H-pyrazol-3-yl)-1H-pyrazolo[4,3-b]pyridine-7-carboxylic acid amide |
| (33) | 1-Methyl-5-((R)-3-methyl-morpholin-4-yl)-7-(6-methyl-pyridin-2-yl)-3-(1H-pyrazol-3-yl)-1H-pyrazolo[4,3-b]pyridine |
| (34) | 7-[1-(2-Fluoro-ethyl)-1H-pyrazol-3-yl]-1-methyl-5-((R)-3-methyl-morpholin-4-yl)-3-(1H-pyrazol-3-yl)-1H-pyrazolo[4,3-b]pyridine |
| (35) | (3R)-3-Methyl-4-[7-(2-methylphenyl)-3-(1H-pyrazol-3-yl)-1H-pyrazolo[4,3-b]pyridin-5-yl]morpholine |
| (36) | 7-[2-(2-Fluoro-ethyl)-2H-pyrazol-3-yl]-1-methyl-5-((R)-3-methyl-morpholin-4-yl)-3-(1H-pyrazol-3-yl)-1H-pyrazolo[4,3-b]pyridine |
| (37) | 2-{3-[1-Methyl-5-((R)-3-methyl-morpholin-4-yl)-3-(1H-pyrazol-3-yl)-1H-pyrazolo[4,3-b]pyridin-7-yl]-pyrazol-1-yl}-ethanol |
| (38) | (3R)-3-Methyl-4-[3-(1H-pyrazol-3-yl)-7-(pyridin-2-yl)-1H-pyrazolo[4,3-b]pyridin-5-yl]morpholine |
| (39) | (3R)-3-Methyl-4-[7-(3-methylpyridin-2-yl)-3-(1H-pyrazol-3-yl)-1H-pyrazolo[4,3-b]pyridin-5-yl]morpholine |
| (40) | (3R)-3-Methyl-4-[1-methyl-3-(1H-pyrazol-5-yl)-1H-pyrazolo[4,3-b]pyridin-5-yl]morpholine |
| (41) | (3R)-4-[7-(4-Methanesulfonylphenyl)-1-(propan-2-yl)-3-(1H-pyrazol-3-yl)-1H-pyrazolo[4,3-b]pyridin-5-yl]-3-methylmorpholine |
| (42) | 1-Methyl-7-(3-methyl-3H-imidazol-4-yl)-5-((R)-3-methyl-morpholin-4-yl)-3-(1H-pyrazol-3-yl)-1H-pyrazolo[4,3-b]pyridine |
| (43) | 7-Cyclopropyl-1-methyl-5-((R)-3-methyl-morpholin-4-yl)-3-(2H-pyrazol-3-yl)-1H-pyrazolo[4,3-b]pyridine |
| (44) | 7-lsopropoxy-1-methyl-5-((R)-3-methyl-morpholin-4-yl)-3-(2H-pyrazol-3-yl)-1H-pyrazolo[4,3-b]pyridine |
| (45) | 1-Methyl-5-((R)-3-methyl-morpholin-4-yl)-3-(2H-pyrazol-3-yl)-1H-pyrazolo[4,3-b]pyridin-7-ol |
| (46) | 1-(4-Methanesulfonyl-phenyl)-5-((R)-3-methyl-morpholin-4-yl)-3-(1H-pyrazol-3-yl)-1H-pyrazolo[4,3-b]pyridine |
| (47) | 1-(3-Methanesulfonyl-phenyl)-5-((R)-3-methyl-morpholin-4-yl)-3-(1H-pyrazol-3-yl)-1H-pyrazolo[4,3-b]pyridine |
| (48) | 3-{1-Methyl-5-[(3R)-3-methylmorpholin-4-yl]-3-(1H-pyrazol-3-yl)-1H-pyrazolo[4,3-b]pyridin-7-yl}benzonitrile |
| (49) | (3R)-3-Methyl-4-[1-methyl-7-(2-methylphenyl)-3-(1H-pyrazol-5-yl)-1H-pyrazolo[4,3-b]pyridin-5-yl]morpholine |
| (50) | (3R)-4-[7-(4-Methanesulfonyl-2-methylphenyl)-1-methyl-3-(1H-pyrazol-3-yl)-1H-pyrazolo[4,3-b]pyridin-5-yl]-3-methylmorpholine |
| (51) | (3R)-4-{7-[4-(Methoxymethyl)phenyl]-1-methyl-3-(1H-pyrazol-3-yl)-1H-pyrazolo[4,3-b]pyridin-5-yl}-3-methylmorpholine |
| (52) | (4-{1-Methyl-5-[(3R)-3-methylmorpholin-4-yl]-3-(1H-pyrazol-3-yl)-1H-pyrazolo[4,3-b]pyridin-7-yl}phenyl)methanol |
| (53) | 3-[5-((R)-3-Methyl-morpholin-4-yl)-3-(1H-pyrazol-3-yl)-1H-pyrazolo[4,3-b]pyridin-1-yl]-benzonitrile |
| (54) | (3R)-4-[7-(3,6-Dihydro-2H-pyran-4-yl)-1-methyl-3-(1H-pyrazol-3-yl)-1H-pyrazolo[4,3-b]pyridin-5-yl]-3-methylmorpholine |
| (55) | 1-Methyl-5-((R)-3-methyl-morpholin-4-yl)-3-(2H-pyrazol-3-yl)-7-(tetrahydro-pyran-4-yl)-1H-pyrazolo[4,3-b]pyridine |
| (57) | (3R)-4-{1-[(3-Methanesulfonylphenyl)methyl]-3-(1H-pyrazol-3-yl)-1H-pyrazolo[4,3-b]pyridin-5-yl}-3-methylmorpholine |
| (58) | (3R)-3-Methyl-4-[1-methyl-3-(1H-pyrazol-3-yl)-7-(pyridin-2-yl)-1H-pyrazolo[4,3-b]pyridin-5-yl]morpholine |
| (59) | (3R)-4-[1-Benzyl-3-(1H-pyrazol-5-yl)-1H-pyrazolo[4,3-b]pyridin-5-yl]-3-methylmorpholine |
| (60) | 4-[5-[(3R)-3-Methylmorpholin-4-yl]-3-(1H-pyrazol-3-yl)-1H-pyrazolo[4,3-b]pyridin-1-yl]benzonitrile |
| (61) | (3R)-3-Methyl-4-[1-methyl-7-(1-methyl-1H-pyrazol-5-yl)-3-(1H-pyrazol-3-yl)-1H-pyrazolo[4,3-b]pyridin-5-yl]morpholine |
| (62) | (3R)-3-Methyl-4-[1-methyl-7-(3-methylpyridin-2-yl)-3-(1H-pyrazol-3-yl)-1H-pyrazolo[4,3-b]pyridin-5-yl]morpholine |
| (63) | (3R)-4-[1-(Cyclopropylmethyl)-3-(1H-pyrazol-3-yl)-1H-pyrazolo[4,3-b]pyridin-5-yl]-3-methylmorpholine |
| (64) | 5-((R)-3-Methyl-morpholin-4-yl)-1-phenethyl-3-(1H-pyrazol-3-yl)-1H-pyrazolo[4,3-b]pyridine |
| (65) | (3R)-3-Methyl-4-[1-methyl-3-(1H-pyrazol-3-yl)-7-[6-(trifluoro-methyl)pyridin-3-yl]-1H-pyrazolo[4,3-b]pyridin-5-yl]morpholine |
| (66) | (3R)-3-Methyl-4-[1-methyl-3-(1H-pyrazol-3-yl)-7-[2-(trifluoro-methyl)pyridin-3-yl]-1H-pyrazolo[4,3-b]pyridin-5-yl]morpholine |
| (67) | 1-Methyl-5-((R)-3-methyl-morpholin-4-yl)-3-(2H-pyrazol-3-yl)-7-(tetrahydro-pyran-3-yl)-1H-pyrazolo[4,3-b]pyridine |
| (68) | 1-Methyl-5-((R)-3-methyl-morpholin-4-yl)-3-(2H-pyrazol-3-yl)-7-(R)-tetrahydro-pyran-3-yl-1H-pyrazolo[4,3-b]pyridine |
| (69) | 1-Methyl-5-((R)-3-methyl-morpholin-4-yl)-3-(2H-pyrazol-3-yl)-7-(S)-tetrahydro-pyran-3-yl-1H-pyrazolo[4,3-b]pyridine |
| (70) | 1-Methyl-5-((R)-3-methyl-morpholin-4-yl)-3-(2H-pyrazol-3-yl)-7-(tetrahydro-furan-3-yl)-1H-pyrazolo[4,3-b]pyridine |
| (71) | 1-Methyl-5-((R)-3-methyl-morpholin-4-yl)-3-(2H-pyrazol-3-yl)-7-(S)-tetrahydro-furan-3-yl-1H-pyrazolo[4,3-b]pyridine |
| (72) | 1-Methyl-5-((R)-3-methyl-morpholin-4-yl)-3-(2H-pyrazol-3-yl)-7-(R)-tetrahydro-furan-3-yl-1H-pyrazolo[4,3-b]pyridine |
| (73) | (3R)-3-Methyl-4-[1-(propan-2-yl)-3-(1H-pyrazol-3-yl)-1H-pyrazolo[4,3-b]pyridin-5-yl]morpholine |
| (74) | (3R)-4-[7-(6-Methanesulfonyl-2-methylpyridin-3-yl)-1-methyl-3-[3-(trifluoromethyl)-1H-pyrazol-5-yl]-1H-pyrazolo[4,3-b]pyridin-5-yl]-3-methylmorpholine |
| (75) | (3R)-4-[7-(5-Methanesulfonyl-2-methylphenyl)-1-methyl-3-(1H-pyrazol-5-yl)-1H-pyrazolo[4,3-b]pyridin-5-yl]-3-methylmorpholine |
| (76) | (3R)-4-[7-(3-Methanesulfonylphenyl)-1-methyl-3-(1H-pyrazol-5-yl)-1H-pyrazolo[4,3-b]pyridin-5-yl]-3-methylmorpholine |
| (77) | (3R)-3-Methyl-4-[3-(1H-pyrazol-3-yl)-1-[2-(pyridin-4-yl)ethyl]-1H-pyrazolo[4,3-b]pyridin-5-yl]morpholine |
| (78) | (3R)-4-{7-[1-(Difluoromethyl)-1H-pyrazol-5-yl]-1-methyl-3-(1H-pyrazol-5-yl)-1H-pyrazolo[4,3-b]pyridin-5-yl}-3-methylmorpholine |
| (79) | (3R)-4-[7-(3,6-Dihydro-2H-thiopyran-4-yl)-1-methyl-3-(1H-pyrazol-5-yl)-1H-pyrazolo[4,3-b]pyridin-5-yl]-3-methylmorpholine |
| (80) | 4-[1-Methyl-5-[(3R)-3-methylmorpholin-4-yl]-3-(1H-pyrazol-5-yl)-1H-pyrazolo[4,3-b]pyridin-7-yl]-3,6-dihydro-2H-1lamdba4-thiopyran-1-one |
| (81) | 4-[1-Methyl-5-[(3R)-3-methylmorpholin-4-yl]-3-(1H-pyrazol-5-yl)-1H-pyrazolo[4,3-b]pyridin-7-yl]-3,6-dihydro-2H-1lamdba6-thiopyran-1,1-dione |
| (82) | 4-[1-Methyl-5-[(3R)-3-methylmorpholin-4-yl]-3-(1H-pyrazol-5-yl)-1H-pyrazolo[4,3-b]pyridin-7-yl]-2H-1lambda6-thiopyran-1,1-dione |
| (83) | (3R)-3-Methyl-4-[3-(1H-pyrazol-3-yl)-1-[(pyridin-3-yl)methyl]-1H-pyrazolo[4,3-b]pyridin-5-yl]morpholine |
| (84) | (3R)-4-[7-(1,5-Dimethyl-1H-1,2,3-triazol-4-yl)-1-methyl-3-(1H-pyrazol-3-yl)-1H-pyrazolo[4,3-b]pyridin-5-yl]-3-methylmorpholine |
| (85) | 2-Methyl-1-{5-[(3R)-3-methylmorpholin-4-yl]-3-(1H-pyrazol-3-yl)-1H-pyrazolo[4,3-b]pyridin-1-yl}propan-2-ol |
| (86) | 2-Methyl-2-{5-[(3R)-3-methylmorpholin-4-yl]-3-(1H-pyrazol-3-yl)-1H-pyrazolo[4,3-b]pyridin-1-yl}propan-1-ol |
| (87) | (3R)-3-Methyl-4-[1-methyl-7-(4-methylpyrimidin-5-yl)-3-(1H-pyrazol-3-yl)-1H-pyrazolo[4,3-b]pyridin-5-yl]morpholine |
| (88) | (3R)-3-Methyl-4-[3-(1H-pyrazol-3-yl)-1-[(pyridin-2-yl)methyl]-1H-pyrazolo[4,3-b]pyridin-5-yl]morpholine |
| (89) | (3R)-4-[7-(1-Methanesulfonylethyl)-1-methyl-3-(1H-pyrazol-3-yl)-1H-pyrazolo[4,3-b]pyridin-5-yl]-3-methylmorpholine | or a pharmaceutically acceptable salt, tautomer, stereoisomer or racemic mixture thereof, or a non-racemic mixture thereof.

5. A pharmaceutical composition comprising at least one compound of formula Ia* or Ib* according to claim 1 and/or a pharmaceutically acceptable salt, tautomer, stereoisomer or racemic mixture thereof, or a non-racemic mixture thereof, and a pharmaceutically acceptable carrier, excipient or vehicle.

6. A method for the treatment of cancer selected from the group consisting of lung cancer, breast cancer, ovarian cancer, colon cancer, cancer of the blood, cancer of the bone and blood-borne tumors, comprising administering to a subject in need thereof an effective amount of the pharmaceutical composition according to claim 5.

7. The pharmaceutical composition according to claim 5, further comprising an additional pharmaceutically active ingredient.

8. A kit, comprising separate packs of
(a) an effective amount of the compound of formula Ia* or Ib* according to claim 1 and/or a pharmaceutically acceptable salt, solvate, tautomer, stereoisomer or racemate thereof, or a mixture thereof,
and
(b) an effective amount of a further medicament active ingredient.

9. A method for the treatment of cancer selected from the group consisting of lung cancer, breast cancer, ovarian cancer and colon cancer, comprising administering to a subject in need thereof an effective amount of the pharmaceutical composition according to claim 5.

10. A pharmaceutical composition comprising at least one compound of the formula Ia* or Ib* according to claim 2 and/or a pharmaceutically acceptable salt, tautomer, stereoisomer or racemic mixture thereof, or a non-racemic mixture thereof, and a pharmaceutically acceptable carrier, excipient or vehicle.

11. A method for the treatment of cancer selected from the group consisting of lung cancer, breast cancer, ovarian cancer, colon cancer, cancer of the blood, cancer of the bone and blood-borne tumors, comprising administering to a subject in need thereof an effective amount of the pharmaceutical composition according to claim 10.

12. A pharmaceutical composition comprising at least one compound of claim 4 and/or a pharmaceutically acceptable salt, tautomer, stereoisomer or racemic mixture thereof, or a non-racemic mixture thereof, and a pharmaceutically acceptable carrier, excipient or vehicle.

13. A method for the treatment of cancer selected from the group consisting of lung cancer, breast cancer, ovarian cancer, colon cancer, cancer of the blood, cancer of the bone and blood-borne tumors, comprising administering to a subject in need thereof an effective amount of the pharmaceutical composition according to claim 12.

14. The compound according to claim 2, in which
$R^1$ denotes H, Het, Ar, $(CH_2)_nOH$, 1-methylsulfonyl-cycloprop-1-yl, $CONH_2$, CONHA, $CONA_2$, Cyc, OA or $CH(A)SO_2A$,
$R^2$ denotes H, A, $(CH_2)_nAr$, $(CH_2)_nCyc$ or $(CH_2)_nHet$,
$R^3$ denotes H or A,
Het denotes 1H-pyrrolo[2,3-b]pyridinyl, 1H-pyrrolo[2,3-c]pyridinyl, indolyl, benzimidazolyl, imidazolyl, 1,2,3,4-tetrahydroisoquinolyl, pyridyl, pyrimidinyl, triazolyl, pyrazolyl, quinolyl, isoquinolyl, quinazolinyl, furanyl, tetrahydrofuranyl, pyranyl, 3,6-dihydro-2H-pyranyl, tetrahydropyranyl, 3,6-dihydro-2H-thiopyranyl or hexahydro-thiopyranyl, each of which is unsubstituted or mono-, di- or trisubstituted by A, SOA, $SO_2A$, Hal and/or =O, A denotes unbranched or branched alkyl having 1-6 C-atoms, in which 1-7H atoms may be replaced by OH, F, Cl and/or Br and/or in which one or two non-adjacent $CH_2$ groups may be replaced by O and/or NH groups,
Cyc denotes cyclic alkyl with 3, 4, 5, 6 or 7 C-atoms,
Hal denotes F, Cl, Br or I,
n denotes 0, 1, 2, 3 or 4,
with the proviso that $R^1$ denotes Ar and/or $R^2$ denotes $(CH_2)_nAr$,
or a pharmaceutically acceptable salt, tautomer, stereoisomer or racemic mixture thereof, or a non-racemic mixture thereof.

15. The compound according to claim 1 or a pharmaceutically acceptable salt thereof.

16. The compound according to claim 2 a pharmaceutically acceptable salt thereof.

17. The compound according to claim 4 a pharmaceutically acceptable salt thereof.

18. A compound of formula Ia* or Ib* according to claim 1, which are respectively of formula Ia or Ib

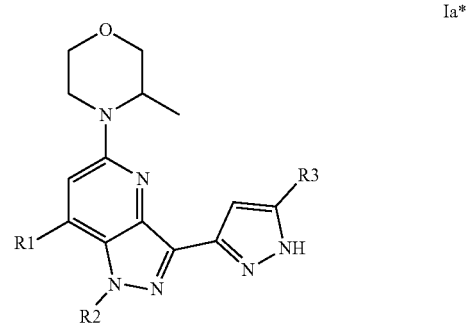

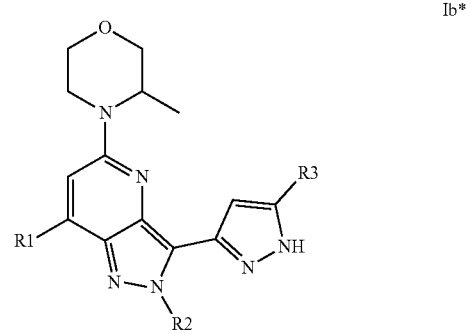

in which
$R^1$ denotes H, Het, Ar, $(CH_2)_nOH$, 1-methylsulfonyl-cycloprop-1-yl, $CONH_2$, CONHA, $CONA_2$, Cyc, OA or $CH(A)SO_2A$,
$R^2$ denotes H, A, $(CH_2)_nAr$, $(CH_2)_nCyc$ or $(CH_2)_nHet$,
$R^3$ denotes H or A,
Het denotes 1H-pyrrolo[2,3-b]pyridinyl, 1H-pyrrolo[2,3-c]pyridinyl, indolyl, benzimidazolyl, imidazolyl, 1,2,3,4-tetrahydroisoquinolyl, pyridyl, pyrimidinyl, triazolyl, pyrazolyl, quinolyl, isoquinolyl, quinazolinyl, furanyl, tetrahydrofuranyl, pyranyl, 3,6-dihydro-2H-pyranyl, tetrahydropyranyl, 3,6-dihydro-2H-thiopyranyl or hexahydro-thiopyranyl, each of which is unsubstituted or mono-, di- or trisubstituted by A, SOA, $SO_2A$, Hal and/or =O,
Ar denotes phenyl, napthyl or biphenyl, each of which is unsubstituted or mono-, di- or trisubstituted by $NH_2$, NHA, $NA_2$, COOH, COOA, $CONH_2$, CONHA, CONA$_2$, NHCOA, CHO, COA, SO$_3$H, SO$_2$NH$_2$, O(CH$_2$)$_p$NH$_2$, (CH$_2$)$_n$Het$^1$, O(CH$_2$)$_n$Het$^1$, (CH$_2$)$_n$Ar$^1$, O(CH$_2$)$_n$Ar$^1$, O(CH$_2$)$_p$CONH$_2$, O(CH$_2$)$_p$NHCOA, Hal, SOA, S(=O, =NH)A, SO$_2$A, A, CN and/or (CH$_2$)$_n$OH, Ar$^1$ denotes phenyl which is unsubstituted or mono-, di- or trisubstituted by Hal, A, OH and/or OA, Het$^1$ denotes a mono- or bicyclic aromatic, unsaturated or saturated heterocycle having 1 to 4 N, O and/or S atoms, which may be unsubstituted or mono-, di- or trisubstituted by Hal, A, COOA, NH$_2$, NHA and/or NA$_2$, A denotes unbranched or branched alkyl having 1-6 C-atoms, in which 1-7H atoms may be replaced by OH, F, Cl and/or Br and/or in which one or two non-adjacent CH$_2$ groups may be replaced by O and/or NH groups, Cyc denotes cyclic alkyl with 3, 4, 5, 6 or 7 C-atoms, Hal denotes F, Cl, Br or I, n denotes 0, 1, 2, 3 or 4, and p denotes 1, 2, 3 or 4, with the proviso that R$^1$ denotes Het and/or R$^2$ denotes (CH$_2$)$_n$Het, or a pharmaceutically acceptable salt thereof.

19. A compound of formula Ia* or Ib* according to claim 2, which are respectively of formula Ia or Ib

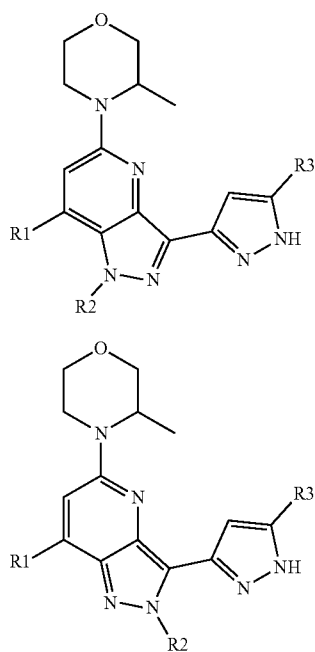

in which

R$^1$ denotes H, Het, Ar, (CH$_2$)$_n$OH, 1-methylsulfonyl-cycloprop-1-yl, CONH$_2$, CONHA, CONA$_2$, Cyc, OA or CH(A)SO$_2$A, R$^2$ denotes H, A, (CH$_2$)$_n$Ar, (CH$_2$)$_n$Cyc or (CH$_2$)$_n$Het, R$^3$ denotes H or A, Het denotes a mono- or bicyclic aromatic, unsaturated or saturated heterocycle having 1 to 4 N, O and/or S atoms, which may be unsubstituted or mono-, di- or trisubstituted by NH$_2$, NHA, NA$_2$, COOH, COOA, CONH$_2$, CONHA, CONA$_2$, CONHAr, CN, OH, (CH$_2$)$_n$Ar$^1$, O(CH$_2$)$_n$Ar$^1$, A, SOA, SO$_2$A, Hal, =NH and/or =O, Ar denotes phenyl, which is unsubstituted or mono-, di- or trisubstituted by SOA, S(=O, =NH)A, SO$_2$A, A, CN and/or (CH$_2$)$_n$OH, Ar$^1$ denotes phenyl which is unsubstituted or mono-, di- or trisubstituted by Hal, A, OH and/or OA, Het$^1$ denotes a mono- or bicyclic aromatic, unsaturated or saturated heterocycle having 1 to 4 N, O and/or S atoms, which may be unsubstituted or mono-, di- or trisubstituted by Hal, A, COOA, NH$_2$, NHA and/or NA$_2$, A denotes unbranched or branched alkyl having 1-6 C-atoms, in which 1-7H atoms may be replaced by OH, F, Cl and/or Br and/or in which one or two non-adjacent CH$_2$ groups may be replaced by 0 and/or NH groups, Cyc denotes cyclic alkyl with 3, 4, 5, 6 or 7 C-atoms, Hal denotes F, Cl, Br or I, n denotes 0, 1, 2, 3 or 4, p denotes 1, 2, 3 or 4, with the proviso that R$^1$ denotes Ar and/or R$^2$ denotes (CH$_2$)$_n$Ar, or a pharmaceutically acceptable salt thereof.

20. A method for the treatment of cancer selected from the group consisting of lung cancer, breast cancer, ovarian cancer, colon cancer, cancer of the blood, cancer of the bone and blood-borne tumors, comprising administering to a subject in need thereof an effective amount of the pharmaceutical composition comprising at least one compound of claim 18 and/or a pharmaceutically acceptable salt thereof and a pharmaceutically acceptable carrier, excipient or vehicle.

* * * * *